(12) United States Patent
Schaefer et al.

(10) Patent No.: US 9,198,890 B2
(45) Date of Patent: *Dec. 1, 2015

(54) COMPOSITIONS AND METHODS FOR TREATING AND PREVENTING CORONARY HEART DISEASE

(71) Applicant: Boston Heart Diagnostics Corporation, Framingham, MA (US)

(72) Inventors: Ernst J. Schaefer, Natick, MA (US); Eliana Polisecki, Framingham, MA (US)

(73) Assignee: Boston Heart Diagnostics Corporation, Framingham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/265,862

(22) Filed: Apr. 30, 2014

(65) Prior Publication Data

US 2014/0235607 A1 Aug. 21, 2014

Related U.S. Application Data

(63) Continuation of application No. 13/650,948, filed on Oct. 12, 2012, now Pat. No. 8,765,377.

(60) Provisional application No. 61/546,802, filed on Oct. 13, 2011.

(51) Int. Cl.
| | |
|---|---|
| C12Q 1/68 | (2006.01) |
| C12Q 1/60 | (2006.01) |
| A61K 31/22 | (2006.01) |
| A61K 31/397 | (2006.01) |

(52) U.S. Cl.
CPC .............. *A61K 31/22* (2013.01); *A61K 31/397* (2013.01); *C12Q 1/6883* (2013.01); *C12Q 1/6827* (2013.01); *C12Q 2600/106* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 3,703,591 A | 11/1972 | Bucolo | |
| 4,245,041 A | 1/1981 | Denney | |
| 4,330,299 A | 5/1982 | Cerami | |
| 4,495,279 A | 1/1985 | Karpetsky et al. | |
| 4,683,195 A | 7/1987 | Mullis et al. | |
| 4,683,202 A | 7/1987 | Mullis | |
| 4,800,159 A | 1/1989 | Mullis et al. | |
| 4,999,289 A | 3/1991 | Akiba et al. | |
| 5,223,392 A | 6/1993 | Cohen | |
| 5,436,149 A | 7/1995 | Barnes | |
| 5,843,663 A | 12/1998 | Stanley et al. | |
| 5,849,481 A | 12/1998 | Urdea et al. | |
| 5,849,486 A | 12/1998 | Heller et al. | |
| 5,851,772 A | 12/1998 | Mirzabekov et al. | |
| 5,888,827 A | 3/1999 | Kayahara et al. | |
| 5,900,481 A | 5/1999 | Lough et al. | |
| 5,919,626 A | 7/1999 | Shi et al. | |
| 5,955,351 A | 9/1999 | Gerdes et al. | |
| 6,194,164 B1 | 2/2001 | Matsui et al. | |
| 6,316,196 B1 | 11/2001 | Morten | |
| 6,410,309 B1 | 6/2002 | Barbera-Guillem et al. | |
| 6,582,908 B2 | 6/2003 | Fodor et al. | |
| 7,417,039 B2 | 8/2008 | Davis | |
| 7,435,541 B2 | 10/2008 | Olson et al. | |
| 7,608,405 B2 | 10/2009 | Ebinuma et al. | |
| 7,659,107 B2 | 2/2010 | Smith et al. | |
| 7,700,277 B2 | 4/2010 | Ambrose et al. | |
| 7,871,789 B2 | 1/2011 | Yonehara et al. | |
| 8,003,795 B2 | 8/2011 | Liu et al. | |
| 8,026,345 B2 | 9/2011 | Burghardt et al. | |
| 8,093,222 B2 | 1/2012 | Freier et al. | |
| 8,470,541 B1 | 6/2013 | Asztalos et al. | |
| 2003/0143223 A1 | 7/2003 | Cabezas et al. | |
| 2004/0131658 A1 | 7/2004 | Kaput | |
| 2004/0259179 A1 | 12/2004 | Assmann et al. | |
| 2005/0054005 A1 | 3/2005 | Ellis et al. | |
| 2005/0059581 A1 | 3/2005 | Mantzoros | |
| 2005/0281868 A1 | 12/2005 | Lane | |
| 2006/0293225 A1 | 12/2006 | Dialynas et al. | |

(Continued)

FOREIGN PATENT DOCUMENTS

| | | |
|---|---|---|
| EP | 1 186 672 A2 | 3/2002 |
| EP | 1 651 774 B1 | 9/2007 |

(Continued)

OTHER PUBLICATIONS

Ahern et al., Biochemical, Reagent Kits Offer Scientists Good Return on Investment, The Science, vol. 9, pp. 1-5, 1995.

(Continued)

*Primary Examiner* — Chris R Tate
*Assistant Examiner* — Douglas F White
(74) *Attorney, Agent, or Firm* — Brown Rudnick LLP

(57) ABSTRACT

The invention pertains to a method of determining a statin dosage for an individual in need of treatment with a statin, comprising determining a SLCO1B1 genotype from a nucleic acid sample of the individual, said genotype comprising the presence or absence of the SLCO1B1-056 polymorphism, and determining an ApoE genotype or phenotype identifying an ApoE polymorphism selected from the group consisting of ApoE2, ApoE3, ApoE4, and any combination thereof, wherein the combination of a SLCO1B1 genotype identifying the presence of the SLCO1B1-056 C polymorphism and the ApoE genotype or phenotype identifying one of the ApoE3/4 or ApoE4/4 genotypes indicates the statin dosage.

17 Claims, 37 Drawing Sheets

(56) References Cited

U.S. PATENT DOCUMENTS

| | | | |
|---|---|---|---|
| 2007/0003600 A1 | 1/2007 | Moore et al. | |
| 2007/0015291 A1 | 1/2007 | Smith | |
| 2007/0031838 A1 | 2/2007 | Ambrose et al. | |
| 2007/0059722 A1 | 3/2007 | Salonen et al. | |
| 2007/0196841 A1 | 8/2007 | Ruano et al. | |
| 2007/0218519 A1 | 9/2007 | Urdea et al. | |
| 2008/0227210 A1 | 9/2008 | Smith | |
| 2008/0269188 A1* | 10/2008 | Chapman et al. | 514/210.02 |
| 2008/0293054 A1 | 11/2008 | Medina et al. | |
| 2008/0300170 A1 | 12/2008 | Gelber et al. | |
| 2009/0197242 A1 | 8/2009 | Kaddurah-Daouk et al. | |
| 2009/0246801 A1 | 10/2009 | Smith | |
| 2010/0063153 A1 | 3/2010 | Chatterjee et al. | |
| 2010/0076787 A1 | 3/2010 | Naylor et al. | |
| 2010/0120136 A1 | 5/2010 | Larsen et al. | |
| 2010/0167306 A1 | 7/2010 | Smith | |
| 2010/0190172 A1 | 7/2010 | Cargill et al. | |
| 2010/0204557 A1 | 8/2010 | Kiaie et al. | |
| 2011/0112186 A1 | 5/2011 | Link et al. | |
| 2011/0250618 A1 | 10/2011 | Nelson et al. | |
| 2011/0269735 A1 | 11/2011 | Shiffman et al. | |
| 2012/0065514 A1 | 3/2012 | Naghavi et al. | |

FOREIGN PATENT DOCUMENTS

| | | |
|---|---|---|
| WO | 02/48715 | 6/2002 |
| WO | 2004/050898 A2 | 6/2004 |
| WO | 2005/012566 A2 | 2/2005 |
| WO | 2006/008656 A2 | 1/2006 |
| WO | 2006/072654 A1 | 7/2006 |
| WO | 2007/012884 A1 | 2/2007 |
| WO | 2007/061995 A2 | 5/2007 |
| WO | 2007/128884 A1 | 11/2007 |
| WO | 2008/131224 A2 | 10/2008 |
| WO | 2009/106838 A1 | 9/2009 |
| WO | 2011/058232 A1 | 5/2011 |
| WO | 2013/056087 A2 | 4/2013 |
| WO | 2013/078122 A1 | 5/2013 |

OTHER PUBLICATIONS

Anderson, 2010, The Clinical Plasma Proteome: A Survey of Clinical Assays for Proteins in Plasma and Serum, Clinical Chemistry 56(2):177-185.
Armitage, J., "The safety of statins in clinical practice," Lancet, 2007, pp. 1781-90, vol. 370.
Assmann G, Kannenberg F, Ramey DR, Musliner TA, Gutkin SW, Veltri EP. Effects of ezetimibe, simvastatin, atorvastatin, and ezetimibe-statin therapies on non-cholesterol sterols in patients with primary hypercholesterolemia. Curr Med Res Opin 2008;24:249-59.
Asztalos B F et al: "LpA-I, LpA-I:A-II HDL and CHD-risk: The Framingham Offspring Study and the Veterans Affairs HDL Intervention Trial", Atherosclerosis, vol. 188, No. 1, Sep. 1, 2006, pp. 59-67, XP028071474, Elsevier Ireland Ltd, Dublin ISSN: 0021-9150, DOI: 10.1016/J. Atherosclerosis.2005.10.018.
Asztalos, B.F., et al., "Distribution of ApoA-I-containing HDL Subpopulations in Patients with Coronary Heart Disease," Arterioscler Thromb Vasc Biol., Dec. 2000; 20(12)2670-6.
Asztalos, B.F., et al., "High-density Lipoprotein Subpopulation Profile and Coronary Heart Disease Prevalence in Male Participants of the Framingham Offspring Study," Arterioscler Thromb Vasc Biol., Nov. 2004; 24(11)2181-7.
Asztalos, B.F., et al., "Two-dimensional electrophoresis of plasma lipoproteins: recognition of new apoA-I-containing subpopulations," Biochim Biophys Acta., Sep. 8, 1993; 1169(3):291-300.
Asztalos, B.F., et al., "Value of High-Density Lipoprotein (HDL) Subpopulations in Predicting Recurrent Cardiovascular Events in the Veterans Affairs HDL Intervention Trial," Arterioscler Thromb Vasc Biol., Oct. 2005; 25 (10):2185-2191.
Ballantyne et al. Effect of ezetimibe coadministered with atorvastatin in 628 patients with primary hypercholesterolemia: a prospective, randomized, double-blind trial. Circulation 2003;107:2409-15.
Ballantyne, C.M., et al., "Risk for myopathy with statin therapy in high-risk patients," Arch Intern Med, 2003, pp. 553-564, vol. 163.
Barrett, J.C., et al., Haploview: analysis and visualization of LD and haplotype maps, Bioinformatics, 2005, pp. 263-265, vol. 21.
Bland et al., "Multiple significance tests: the Bonferroni method," BMJ, vol. 310, p. 170, Jan. 21, 1995.
Brambilla et al., 2011, Normal Fasting Plasma Glucose and Risk of Type 2 Diabetes, Diabetes Care 34:1372-1374.
Burke et al.,Mechanisms of the Liebermann-Burchard and Zak Color Reactions for Cholesterol, Clin. Chem .20(7), 794-801, 1974.
Burke, J. P., et al., "Rapid Rise in the Incidence of Type 2 Diabetes From 1987 to 1996," (1999) Arch Intern Med. 159:1450-1456.
Camont et al: "Biological activities of HDL subpopulations and their relevance to cardiovascular disease", Trends in Molecular Medicine, vol. 17, No. 10, Oct. 1, 2011.
Carlton et al., "Functional single nucleotide polymorphism-based association studies," Human Genomics, 2(6): 391-402 (2006).
Catapano AL, Reiner Z, De Backer G, et al. ESC/EAS Guidelines for the management of dyslipidaemias The Task Force for the management of dyslipidaemias of the European Society of Cardiology (ESC) and the European Atherosclerosis Society (EAS). Atherosclerosis 2011;217:3-46.
Cholesterol Treatment Trialists' (CTT) Collaborators, Efficacy and safety of cholesterol-lowering treatment: prospective meta-analysis of data from 90,056 participants in 14randonnised trials of statins, Lancet, 2005, pp. 1267-1278, vol. 366.
Corsini, A., et al., "Pharmacokinetic interactions between statins and fibrates," Am J. Cardiol, 2005,pp. 44K-49K, vol. 96.
Cruz et al., 2004, Low Adiponectin Levels Predict Type 2 Diabetes in Mexican Children, Diabetes Care 27 (6):1451-1453.
Cuyper et al., Determination of changes in serum lathosterol during treatment with simvastatin to evaluate the role of lathosterol as a parameter for whole body cholesterol synthesis. Clin Chim Acta 1993;219:123-30.
Davidson MH, Ballantyne CM, Kerzner B, et al. Efficacy and safety of ezetimibe coadministered with statins: randomised, placebo-controlled, blinded experience in 2382 patients with primary hypercholesterolemia. Int J Clin Pract 2004;58:746-55.
Davidson MH, McGarry T, Bettis R, et al. Ezetimibe coadministered with simvastatin in patients with primary hypercholesterolemia. J Am Coll Cardiol 2002;40:2125-34.
Davis, H et al. Zetia: Inhibition of Niemann-Pick C1 Like 1 (NPC1L1) To Reduce Intestinal Cholesterol Absorption and Treat Hyperlipidemia. Journal of Atherosclerosis and Thrombosis. May 2007, vol. 14; pp. 99-108.
De Cuyper I, Wolthers BG, van Doormaal JJ, Wijnandts PN. Determination of changes in serum lathosterol during treatment with simvastatin to evaluate the role of lathosterol as a parameter for whole body cholesterol synthesis. Clin Chim Acta 1993;219:123-30.
Deepak Voora et al., The SLCO1B18*5 Genetic Variant is Associated with Statin-Induced Side Effects, Journal of the American College of Cardiology, vol. 54, No. 17, 2009, pp. 1609-1616.
Degn et al., 2004, One Week's Treatment With the Long-Acting Glucagon-Like Peptide 1 Derivative Liraglutide (NN2211) Markedly Improves 24-h Glycemia and-and-Cell Function and Reduces Endogenous Glucose Release in Patients with Type 2 Diabetes, Diabetes 53:1187-1194.
Devlin, B., et al., "Genomic control for association studies," Biometrics, 1999, pp. 997-1004, vol. 55.
Eddy et al., 2003, A trial-validated model of diabetes, Diabetes Care 26(11):3093-3101.
Eddy et al., 2003, Validation of the Archimedes Diabetes Model, Diabetes Care 26(11):3102-3110.
Espy et al (2006) Clin Microbiol Rev. Jan. 2006; 19(1): 165-256.
Farnier, M et al. Lipid-Altering Eficacy Of Ezetimibe/Simvastatin 10/20 mg Compared With Rosuvastatin 10 mg in High-Risk Hypercholesterolaemic Patients Inadequately Controlled With Prior Statin Monotherapy—The IN-CROSS Study. The International Journal of Clinical Practice. Apr. 2009, vol. 63; pp. 547-559.
Fiegenbaum et al., "The role of common variants of ABCB1, CYP3A4, and CYP3A5 genes in lipidlowering efficacy and safety of simvastatin treatment," Clin. Pharmacol. Ther., vol. 78, pp. 551-558, 2005.

(56) References Cited

OTHER PUBLICATIONS

Friedewald WT, Levy RI, Fredrickson DS. Estimation of the concentration of low-density lipoprotein cholesterol in plasma, without use of the preparative ultracentrifuge. Clin Chem 1972;18:499-502.

Frudakis et al., "CYP2D6*4 polymorphism is associated with statin-induced muscle effects,"Pharmacogenetics and Genomics, vol. 17, pp. 695-707, 2007.

Fumeron et al., 2004, Adiponectin Gene Polymorphisms and Adiponectin Levels Are Independently Associated With the Development of Hyperglycemia During a 3-Year Period; The Epidemiologic Data on the Insulin Resistance Syndrome Prospective Study, Diabetes 53:1150-1157.

Gagne et al., Efficacy and safety of ezetimibe coadministered with atorvastatin or simvastatin in patients with homozygous familial hypercholesterolemia. Circulation 2002;105:2469-75.

Goh et al., HPLC analysis of desmosterol, 7-dehydrocholesterol, and cholesterol. Lipids 24.7 (1989): 652-655.

Gordon, D.J. et al., "High-density Lipoprotein Cholesterol and Cardiovascular Disease. Four Prospective American Studies," Circulation, Jan. 1989; 79(1):8-15.

Gouni et al. Effects of ezetimibe and/or simvastatin on LDL receptor protein expression and on LDL receptor and HMG-CoA reductase gene expression: a randomized trial in healthy men. Atherosclerosis 2008;198:198-207.

Grundy et al. Implications of recent clinical trials for the National Cholesterol Education Program Adult Treatment Panel III guidelines. Circulation 2004;110:227-39.

Grundy et al., "Plasma Non-Cholesterol Sterols as Indicators of Cholesterol Absorption." Journal of lipid research (2013) V54 873-875.

Gunderson, K.L., et al., "Whole-genome genotyping of haplotype tag single nucleotide polymorphisms," Pharmacogenomics, 2006, pp. 641-648, vol. 7.

Harder et al., 2004, The Effect of Liraglutide, a Long-Acting Glucagon-Like Peptide 1 Derivative, on Glycemic Control, Body Composition, and 24-h Energy Expenditure in Patients; With Type 2 Diabetes, Diabetes Care 27(8):1915-1921.

Havekes LM et al. A rapid micro method for apolipoprotein E phenotyping directly in serum. J Lipid Res (1987) 28:455-63.

Heart Protection Study Collaborative Group, "MRC/BHF Heart Protection Study of cholesterol lowering with simvastatin in 20,536 high-risk individuals: a randomised placebo-controlled trial," Lancet, 2002, pp. 7-22, vol. 360.

Hermann et al., "Pharmacokinetics and Drug Disposition: Exposure of atorvastatin is unchangedbut lactone and acid metabolites are increased several-fold in patients with atorvastatin-induced myopathy," Clinical Pharmacology & Therapeutics, vol. 79, No. 6, pp. 532-539, 2006.

Himbergen et al., Comparison of the effects of maximal dose atorvastatin and rosuvastatin therapy on cholesterol synthesis and absorption markers. J Lipid Res 2009;50:730-9.

Xu et al., "Organic anion transporting polypeptide-1B1 haplotypes in Chinese patients," Acta Pharmacologica Sinica, vol. 28, No. 10, pp. 1693-1697, Oct. 28, 2007.

Zocor datasheet, 2007.httD://www.emc.medicines.ora.uk/emc/assets/c/htmlIDisDlavDoc.asD?DocumentID=120.

Zuccaro et al.t "Tolerability of statins is not linked to CYP450 polymorphisms, but reduced CYP2D6 metabolism improves cholesteraemic response to simvastatin and fluvastatin,"Pharmacological Research, vol. 55, pp. 310-317, 2007.

Hironobu Akao et al., Genetic Variation at the SLC01B1 Gene Locus and Low Density Lipoprotein Cholesterol Lowering Response to Pravastatin in the Elderly, Atherosclerosis, 220, 2012, pp. 413-417.

Ho et al., "Drug and Bile Acid Transporters in Rosuvastatin Hepatic Uptake: Function, Expression, and Pharmacogenetics," Gastroenterology, 130(6): 1793-1806 (2006).

Hsiang et al., "A Novel Human Hepatic Organic Anion Transporting Polypeptide (OATP2): Identification of a liver-specific human organic anion transporting polypeptide and identification of rat and human hydroxymethylglutaryl-CoA reductase inhibitor transporters," J. Biol. Chem., 274(52): 37161-37168 (1999).

International Hapmap Consortium, "A haplotype map of the human genome," Nature, 2005,pp. 1299-1320, vol. 437.

International Search Report for PCT/GB2009/000547, May 11, 2009, 4 pages.

International Search Report and Written Opinion for PCT/US2013/066860 mailed Jan. 20, 2014, 14 pages.

International Search Report and Written Opinion for PCT/US2013/62241 mailed Jan. 17, 2014, 16 pages.

Isbell et al: "Reproducibility and Reliability of Atherosclerotic Plaque Volume Measurements in Peripheral Arterial Disease with Cardiovascular Magnetic Resonance", Journal of Cardiovascular Magnetic Resonance, vol. 9, No. 1, Jan. 1, 2007, p. 1-15.

Jakulj et al. Baseline cholesterol absorption and the response to ezetimibe/simvastatin therapy: a post-hoc analysis of the Enhance trial. J Lipid Res 2010;51:755-62.

Jones et al. Comparison of the efficacy and safety of rosuvastatin versus atorvastatin, simvastatin, and pravastatin across doses (STELLAR* Trial). Am J Cardiol 2003;92:152-60.

Juraschek et al., Alternative Markers of Hyperglycemia and Risk of Diabetes, vol. 35 No. 11, Aug. 8, 2012, p. 1-6.

Kajinami, K., et al., "CYP3A4 genotypes and plasma lipoprotein levels before and after treatment with atorvastatin in primary hypercholesterolemia," Am J Cardiol, 2004, pp. 104-107, vol. 93.

Kameyama et al., "Functional characterization of SLC01B1 (OATP-C) variants, SLC01B1*5,SLC01B1*15 and SCL01B1*15+C1007G, by using transient expression systems of HeLa and HEK293 cells," Pharmacogenetics and Genomics, vol. 15, No. 7, pp. 513-522. Jul. 2005.

Kaput et al., 2004, Nutritional genomics: the next frontier in the postgenomic era, Physiol Genomics 16:166-177.

Kaput et al., 2007, Application of nutrigenomic concepts to Type 2 diabetes mellitus, Nutrition, Metabolism & Cardiovascular Diseases 17:89-103.

Kaput, 2004, Diet-Disease Gene Interactions, Nutrition 20:26-31.

Kim et. al., "3-Hydroxy-3-methylglutaryl-coenzyme A reductase inhibitors (statins) and genetic variability(single nucleotide polymorphisms) in a hepatic drug uptake transporter: What's it all about?," Clinical Pharmacology & Therapeutics, vol. 75, No. 5, pp. 381-385, 2004.

Kim, K.T, et al., "Increased systemic exposure to rosuvastatin in Asian subjects residing in the United States compared to Caucasian subjects," Clinical Pharmacology and Therapeutics, 2008, p. S 14,vol. 83.

Kivistö et al: "Influence of Drug Transporter Polymorphisms on Pravastatin Pharmacokinetics in Humans" Pharmaceutical Research, Kluwer Academic Publishers-Plenum Publishers, NE, vol. 24, No. 2, Dec. 20, 2006, pp. 239-247.

Kolberg et al., 2009, Development of a Type 2 Diabetes Risk Model From a Panel of Serum Biomarkers From the Inter99 Cohort, Diabetes Care 32(7):1207-1212.

Konig, J., et al., Pharmacogenomics of human OATP transporters, Naunyn Schmiedebergs Arch Pharmacol2006, pp. 432-43, vol. 372.

Krakoff et al., 2003, Inflammatory Markers, Adiponectin, and Risk of Type 2 Diabetes in the Pima Indian, Diabetes Care 26(6):1745-1751.

Lakoski SG, Xu F, Vega GL, et al. Indices of Cholesterol Metabolism and Relative Responsiveness to Ezetimibe and Simvastatin. J Clin Endocrinol Metab 2010;95:800-9.

Lamon-Fava S, Diffenderfer MR, Barrett PH, et al. Effects of different doses of atorvastatin on human apolipoprotein B-100, B-48, and A-I metabolism. J Lipid Res 2007;48:1746-53.

Law, M., et al., "Statin safety: a systematic review," Am J. Cardiol, 2006, pp. S52-S60, vol. 97.

Lindstrom et al., 2003, The Diabetes Risk Score, Diabetes Care 26(3):725-731.

Link et al., "SLC01B1 Variants and Statin-Induced Myopathy—A Genomewide Study," N. Engl. J. Med., 359: 789-799 (2008).

Lund, E., et al. "Determination of serum levels of unesterified lathosterol by isotope dilution-mass spectrometry." Scandinavian journal of clinical & laboratory investigation 49.2 (1989): 165-171.

(56) References Cited

OTHER PUBLICATIONS

Luzón-Toro et al., "Gas chromatographic-mass spectrometric determination of brain levels of ?-cholest-8-en-3?-ol (lathosterol)." Journal of Chromatography B 850.1 (2007): 177-182.

Lyssenko et al., 2005, Genetic Prediction of Future Type 2 Diabetes, PLoS Medicine 2(12):e345.

Madsbad et al., 2004, Improved Glycemic Control With No Weight Increase in Patients With Type 2 Diabetes After Once-Daily Treatment With the Long-Acting Glucagon-Like Peptide 1 Analog Liraglutide (NN2211), Diabetes Care 27 (6):1335-1342.

Mangravite, L.M., et al., "Clinical implications of pharmacogenomics of statin treatment,"Pharmacogenomics J, 2006, pp. 360-374, vol. 6.

Mann, D. M., et al., "The Multi-Ethnic Study of Atherosclerosis," (MESA) (2010) Am J Epidemiol 171(9):980-988. Jan. 2010.

Matthan NR et al., Impact of simvastatin, niacin, and/or antioxidants on cholesterol metabolism in CAD patients with low HDL. J Lipid Res. 2003;44:800-806.

Matthan NR et al., "Deuterium uptake and plasma cholesterol precursor levels correspond as methods for measurement of endogenous cholesterol synthesis in hypercholesterolemic women.", Lipids. 2000;35:1037-1044.

Matthan, N. et al. Cholesterol Absorption and Synthesis Markers in Individuals With and Without a CHD Event During Pravastatin Therapy: Insights From the Prosper Trial. Journal of Lipid Research. Jul. 3, 2009, vol. 51; pp. 202-209.

Miettinen et al., Serum plant sterols and cholesterol precursors reflect cholesterol absorption and synthesis in volunteers of a randomly selected male population. Am J Epidemiol 1990;131:20-31.

Miettinen TA, Gylling H, Lindbohm N, Miettinen TE, Rajaratnam RA, Relas H. Serum noncholesterol sterols during inhibition of cholesterol synthesis by statins. J Lab Clin Med 2003;141:131-7.

Miettinen TA, Strandberg TE, Gylling H. Noncholesterol sterols and cholesterol lowering by long-term simvastatin treatment in coronary patients: relation to basal serum cholestanol. Arterioscler Thromb Vasc Biol 2000;20:1340-6.

Mikko Niemi et al., Organic Anion Transporting Polypeptide 1B1: a Genetically PolymorphicTransporter of Major Impotance for Hepatic Drug Uptake, Pharmacological Reviews, vol. 63, No. 1, 2011, pp. 157-181.

Molden, E., "Variability in Cytochrome P450-Mediated Metabolism of Cardiovascular Drugs: Clinical Implications and Practical Attempts to Avoid Potential Problems," Heart Drug, 2004, pp. 55-79, vol. 4.

Morimoto et al., "Candidate gene approach for the study of genetic factors involved in HMG-CoA reductase inhibitor-induced rhabdomyolysis," Eighteenth JSSX Annual Meeting, 8PE-32 (2003).

Morimoto et al; A Novel Variant Allele of OATP-C (SLCO1B1) Found in a Japan Patient with Pravastatin-induced Myopathy, Drug Metab. Pharmocokinet. vol. 19, pp. 453-455; 2004.

Morimoto, K, et al., "OATP-C(OATP01B1)*15 is associated with statin-induced myopathy in hypercholesterolemia patients," Clinical Pharmacology & Therapeutics, 2005, pp. P21-P21 vol. 77.

Morrone D, Weintraub WS, Toth PP, Hanson ME, Lowe RS, Lin J, Shah AK, and Tershakovec AM. Lipid-altering efficacy of ezetimibe plus statin and statin monotherapy and identification of factors associated with treatment response: A pooled analysis of over 21,000 subjects from 27 clinical trials. Atherosclerosis , in press. 2012.223, 251-261.

Mulder et al., "Association of polymorphism in the cytochrome CYP2D6 and the efficacy and tolerability of simvastatin," Clin. Pharmacol. Ther., vol. 70, pp. 546-551, 2001.

Márk, L et al., Change in the cholesterol metabolism associated with the combined inhibition of synthesis and absorption. Orvosi hetilap 148.14 (2007): 627.

Nauck et al., Clinical Chemistry Feb. 2002 vol. 48 No. 2 236-254.

Niemi et al., "Acute effects of pravastatin on cholesterol synthesis are associated with SLC01B1(encoding OATP1B1) haplotype *17," Pharmacogenet. Genomics, vol. 15, No. 5, pp. 303-309, May 15, 2005.

Niemi et al., "High plasma pravastatin concentrations are associated with single nucleotide polymorphisms and haplotypes of organic anion transporting polypeptide-C (OATP-C, SCL01B1)," Pharmacogenetics, 14: 429-440 (2004).

Dullaart RPF et al, The Serum Lathosterol to Cholesterol Ratio, an Index of Cholesterol Synthesis,is Not Elevated in Patients With Glomerular Proteinuria and Is Not Associated With Improvement of Hyperlipidemia in Response to Antiproteinuric Treatment, Metabolism 45:723-730, 1996.

Couvert P et al, Association between a Frequent Allele of the Gene Encoding OATP1B1 and the Enhanced LDL-Lowering Response to Fluvastatin Therapy, Pharmacogenomics 9:1217-1227, 2008.

Gazi IF et al, Effect of Ezetimibe in Patients Who cannot Tolerate Statins or cannot Get to the Low Density Lipoprotein Cholesterol Target Despite Taking a Statin, Cur Med Res Opin 23:2183-2192, 2007.

Generaux GT et al, Impact of SLCOI B1 (OATP1 B1) and ABCG2 (BCRP) Genetic Polymorphisms and Inhibition on LDL-C Lowering and Myopathy of Statins, Xenobiot 41:639-651, 2011.

International Search Report and Written Opinion for PCT/US12/60014, dated Apr. 5, 2013, 9 pages.

Ordovas Jm et al, The APOE Locus and the Pharmacogenetics of Lipid Response, Cur Opin Lipidol 13:113-117, 2002.

Romaine SPR et al, The Influence of SLC01B1 (OATP1B1) Gene Polymorphisms on Response to Statin Therapy, Pharmacogenom J 10:1-11, 2010.

Uusitupa MIJ et al, Lathosterol and Other Noncholesterol Sterols During Treatment of Hypercholesterolemia With Lovastatin Alone and With Cholestyramine or Guar Gum, Arterioscler Thromb 12: 807-813, 1992.

Nishizato et al., "Polymorphisms of OATP-C (SLC21A6) and OAT3 (SLC22A8) genes: Consequences for pravastatir pharmacokinetics," Clin. Pharmacol. Ther., 73(6): 554-565 (2003).

Nissinen et. al., Applicability of non-cholesterol sterols in predicting response in cholesterol metabolism to simvastatin and fluvastatin treatment among hypercholesterolemic men. Nutr Metab Cardiovasc Dis 2010;20:308-16.

Nozawa et al.,"Genetic Polymorphisms of Human Organic Anion Transporters OATP-C(SLC21A6) and OATP-B(SLC21A9): Allele Frequiences in the Japanese Population and Functional Analysis," The Journal of Pharmacology and Experimental Therapeutics, vol. 302, No. 2, pp. 2002.

Oh, J., et al., "Genectic determinats of statin intolerance," Lipids Health Dis, 2007, pp. 6:7.

Ooi et. al., Dose-dependent effect of rosuvastatin on apolipoprotein B-100 kinetics in the metabolic syndrome. Atherosclerosis 2008;197:139-46.

Pasanen et al., "Different Effects of SLC01B1 Polymorphism on the Pharmacokinetics of Atorvastatin and Rosuvastatin," Clin. Pharmacol. Ther., 82(6): 726-733 (2007).

Pasanen et al., "Global analysis of genetic variation in SLC01B1," Pharmacogenomics, vol. 9, No. 1, pp. 19-33, Jan. 2008.

Pasanen et al.,"SLC01B1 polymorphism markedly affects the pharmacokinetics of simvastatinacid," Pharmacogenet. Genomics, vol. 16, No. 12, pp. 873-879, Dec. 2006.

Pasanen, M.K., et al., "Frequencies of single nucleotide polymorphisms and haplotypes of organic anion transporting polypeptide 1B1 SLC01B1 gene in a Finnish population," Eur J Clin Pharmacol, 2006, pp. 409-415, vol. 62.

Patent Examination Report No. 1 date of issue Jun. 11, 2014 for Patent Application No. AU 2011/261480.

Pearson et al., Effectiveness of ezetimibe added to ongoing statin therapy in modifying lipid profiles and low-density lipoprotein cholesterol goal attainment in patients of different races and ethnicities: a substudy of the Ezetimibe add-on to statin for effectiveness trial. Mayo Clin Proc 2006;81:1177-85.

Pearson et. al., A community-based, randomized trial of ezetimibe added to statin therapy to attain NCEP ATP III goals for LDL cholesterol in hypercholesterolemic patients: the ezetimibe add-on to statin for effectiveness (EASE) trial. Mayo Clin Proc 2005;80:587-95.

Perk et al. European Guidelines on cardiovascular disease prevention in clinical practice (version 2012): The Fifth Joint Task Force of the

(56) References Cited

OTHER PUBLICATIONS

European Society of Cardiology and Other Societies on Cardiovascular Disease Prevention in Clinical Practice Cardiovascular Prevention & Rehabilitation, Eur Heart J 2012;33:1635-701.
Pradhan et al., 2001, C-Reactive Protein, Interleukin 6, and Risk of Developing Type 2 Diabetes Mellitus, JAMA 286(3):327-334.
Price, A.L., et al., "Principal components analysis corrects for stratification in genome-wide association studies," Nat. Genet, 2006, pp. 904-909, vol. 38.
Programme for the Prevention of Type 2 Diabetes in Finland, Finnish Diabetes Association, 2003-2010, Published in 2003.
Purcell, S., et al., "PLINK: a tool set for whole-genome association and population-based linkage analyses," Am J. Hum Genet, 2007, pp. 559-575, vol. 81.
R Development Core Team, "R: A Language and Environment for Statistical Computing," Vienna, Austria: R Foundation for Statistical Computing, 2007.
Ravussin, 2002, Adiponectin enhances insulin action by decreasing ectopic fat deposition, The Pharmacogenomics Journal 2:4-7.
Reihnér E, Rudling M, Ståhlberg D, et al. Influence of pravastatin, a specific inhibitor of HMG-CoA reductase, on hepatic metabolism of cholesterol. N Engl J Med 1990;323:224-8.
Robinson, "Simvastatin: present and future perspectives," Expert Opin. Pharmacother., 8(13): 2159-2172 (2007).
Ruano et al., Physiogenomic Association of Statin-Related Myalgia to Serotonin Receptors, Muscle Nerve, vol. 36, pp. 329-335, 2007.
Schaefer et al., Association of Statin Potency with Markers of Cholesterol Absorption/Synthesis and LDL-C Lowering Efficacy of Ezetimibe Add on Therapy, J of Clinical Lipidology 6(3)286 abstract 160, Jun. 2012.
Schaffer, R., et al. "Comparison of two isotope dilution/mass spectrometric methods for determination of total serum cholesterol." Clinical chemistry 28.1 (1982): 5-8.
Schmidt, M. I., et al., "The Atherosclerosis Risk in Communities study," (2005) Diabetes Care 28(8):2013-2018.
Search Study Collaborative Group, "Study of the effectiveness of additional reductions in cholesterol and homocysteine (SEARCH): characteristics of a randomized trial among 12064 myocardial infarction survivors," Am Hear J, 2007, pp. 815-823, vol. 154, No. e6.
Shitara et al., "Pharmacokinetic and pharmacodynamic alterations of 3-hydroxy- 3-methylglutaryl coenzyme A (HMG-CoA) reductase inhibitors: drug-drug interactions and interindividual differences in transporter and metabolic enzyme functions," Pharmacol Ther, 2006, pp. 71-105, vol. 112.
Simonson, S.G., et al., "Rosuvastatin pharmacokinetics in heart transplant recipients administered an antirejection regimen including cyclosporine," Clin Pharmacol Ther, 2004, pp. 167-177, vol. 76.
Spranger et al., 2003, Adiponectin and protection against type 2 diabetes mellitus, Lancet 361:226-228.
Stern, M. P., et al., Predicting Diabetes, "Moving Beyond Impaired Glucose Tolerance," (1993) Diabetes 42:706-714.
Stern, M. P., et al., The San Antonio Heart Study, "Sex Difference in the Effects of Sociocultural Status on Diabetes and Cardiovascular Risk Factors in Mexican Americans," (1984) Am. J. Epidemiol. 120(6):834-851.
Streiner et al., "Correction for Multiple Testing, Is there a resolution?," Chest, vol. 140, No. 1, pp. 16-18, Jul. 2011.
Sturis et al., 2003, GLP-1 derivative liraglutide in rats with b-cell deficiencies: influence of metabolic state on b-cell mass dynamics, British Journal of Pharmacology 140:123-132.
Sudhop T, Lutjohann D, Kodal A, et al. Inhibition of intestinal cholesterol absorption by ezetimibe in humans. Circulation 2002;106:1943-8.
Sugiuchi et al., Clinical Chemistry 44:3 522-531 (1998).
The SEARCH Collaborative Group, The New England Journal of Medicine, SLC01B1 Variants and Statin-Induced Myopathy—A Genomewide Study, vol. 359, No. 8, Aug. 21, 2008, pp. 789-799.
Third Report of the National Cholesterol Education Program (NCEP) Expert Panel on Detection, Evaluation, and Treatment of High Blood Cholesterol in Adults (Adult Treatment Panel III) final report. Circulation 2002;106:3143-421.
Thompson, P.D., et al., "Statin-associated myopathy," JAMA, 2003, pp. 1681-1690, vol. 289.
Tirona, R.G., et al., "Polymorphisms in OATP-C: identification of multiple allelic variants associated with altered transport activity among European- and African-Americans," J Biol Chem, 2001, pp. 35669-35675, vol. 276.
Tobert, "Lovastatin and Beyond: The History of the HMG-CoA Reductase Inhibitors," Nat. Rev. Drug Discov., 2(7): 517-526 (2003).
Tyburczy et al., "Evaluation of low trans-fat edible oils by attenuated total reflection—Fourier transform infrared spectroscopy and gas chromatography: a comparison of analytical approaches." Analytical and bioanalytical chemistry 404.3 (2012): 809-819.
United Kingdom Search Report issued in application No. GB0803833.3 on Jun. 27, 2008.
van Himbergen TM, Matthan NR, Resteghini NA, et al. Comparison of the effects of maximal dose atorvastatin and rosuvastatin therapy on cholesterol synthesis and absorption markers. J Lipid Res 2009;50:730-9.
Vanhanen H, Miettinen TA. Pravastatin and lovastatin similarly reduce serum cholesterol and its precursor levels in familial hypercholesterolaemia. Eur J Clin Pharmacol 1992;42:127-30.
Vladutiu, et al., "Genetic risk factors associated with lipid-lowering drug-induced myopathies, Muscle Nerve," 2006, pp. 153-162, vol. 34.
Warnick et al., Clinical Chemistry Sep. 2001 vol. 47 No. 9 1579-1596.
Wellcome Trust Case Control Consortium, "Genome-wide association study of 14,000 cases of seven common diseases and 3,000 shared controls," Nature, 2007, pp. 661-678, vol. 447.
Weng et al., a systematic review and meta-analysis on the therapeutic equivalence of statins. J Clin Pharm Ther 2010;35:139-51.
Wilson et al., 2007, Prediction of Incident Diabetes Mellitus in Middle-aged Adults, Arch Intern Med 167:1068-1074.
International Search Report and Written Opinion for PCT/US2014/048022, with an International filing date of Jul. 24, 2014, and a mailing date of February 18, 2015, (17 pages).
Miettinen et al., 2000, Noncholesterol Sterols and Cholesterol Lowering by Long-Term Simvastatin Treatment in Coronary Patients: Relation to Basal Serum Cholestanol, Arteriosclerosis, Thrombosis, and Vascular Biology 20(3):1340-1346.
Thompson et al., 2002, Why some patients respond poorly to statins and how this might be remedied, European Heart Journal 23(3):200-206.
Thongtang et al, 2012, Effects of ezetimibe added to statin therapy on markers of cholesterol absorption and synthesis and LCL-C lowering in hyperlipidemic patients, Atherosclerosis 225(2):388:396.

* cited by examiner

FIG. 1 ApoE nucleic acid sequence (NCBI Accession No. NM_000041.2) (SEQ ID No. 68)

```
GGGATCCTTGAGTCCTACTCAGCCCCAGCGGAGGTGAAGGACGTCCTTCCCCAGGAGCCGACTGGCCAAT
CACAGGCAGGAAGATGAAGGTTCTGTGGGCTGCGTTGCTGGTCACATTCCTGGCAGGATGCCAGGCCAAG
GTGGAGCAAGCGGTGGAGACAGAGCCGGAGCCCGAGCTGCGCCAGCAGACCGAGTGGCAGAGCGGCCAGC
GCTGGGAACTGGCACTGGGTCGCTTTTGGGATTACCTGCGCTGGGTGCAGACACTGTCTGAGCAGGTGCA
GGAGGAGCTGCTCAGCTCCCAGGTCACCCAGGAACTGAGGGCGCTGATGGACGAGACCATGAAGGAGTTG
AAGGCCTACAAATCGGAACTGGAGGAACAACTGACCCCGGTGGCGGAGGAGACGCGGGCACGGCTGTCCA
AGGAGCTGCAGGCGGCGCAGGCCCGGCTGGGCGCGGACATGGAGGACGTGTGCGGCCGCCTGGTGCAGTA
CCGCGGCGAGGTGCAGGCCATGCTCGGCCAGAGCACCGAGGAGCTGCGGGTGCGCCTCGCCTCCCACCTG
CGCAAGCTGCGTAAGCGGCTCCTCCGCGATGCCGATGACCTGCAGAAGCGCCTGGCAGTGTACCAGGCCG
GGGCCCGCGAGGGCGCCGAGCGCGGCCTCAGCGCCATCCGCGAGCGCCTGGGGCCCCTGGTGGAACAGGG
CCGCGTGCGGGCCGCCACTGTGGGCTCCCTGGCCGGCCAGCCGCTACAGGAGCGGGCCCAGGCCTGGGGC
GAGCGGCTGCGCGCGCGGATGGAGGAGATGGGCAGCCGGACCCGCGACCGCCTGGACGAGGTGAAGGAGC
AGGTGGCGGAGGTGCGCGCCAAGCTGGAGGAGCAGGCCCAGCAGATACGCCTGCAGGCCGAGGCCTTCCA
GGCCCGCCTCAAGAGCTGGTTCGAGCCCCTGGTGGAAGACATGCAGCGCCAGTGGGCCGGGCTGGTGGAG
AAGGTGCAGGCTGCCGTGGGCACCAGCGCCGCCCCTGTGCCCAGCGACAATCACTGAACGCCGAAGCCTG
CAGCCATGCGACCCCACGCCACCCCGTGCCTCCTGCCTCCGCGCAGCCTGCAGCGGGAGACCCTGTCCCC
GCCCCAGCCGTCCTCCTGGGGTGGACCCTAGTTTAATAAAGATTCACCAAGTTTCACGCAAAAAAAAAAA
AAAAAAAAAAAAAAAAAAAAAAAAAAAAAAAA
```

FIG. 2: Wild-type ApoE nucleic acid sequence (NCBI Accession No.
NG_007084.2)(SEQ ID No. 69)

```
TGGAGAGCTGGTCTACCACCGGCGGCCTGGAGAGGAGGGCACTGTCATGTCTCTAGCTGGGAAATACACA
TGTGAGCCTGGCGCCTGGGTCCGAGGGTGGAGGGGCTGGGCCCCTGGACTCCTCCTGGGTCTGAGGGAGG
ACGGGCTAGGGCCCTGGACACTCAGGTCTGAGGGAGGAGGCCTGGGTTCCCAGATGCCCAAATCCCCTTG
GTAATGAGACCCCGCCTCCACCCCACTCTCTGACAGTGAACAACTGGTTGGCAACGGTAACGTTGGGCCA
GGCGGGCATGCACGCAACATACTACCACAAAGCCAGTGACCAGGTGAGTGGGTGCAGGGACTAGCTGGTG
CTGCCAGGGGCTGCTGGGCCTGGAAGTCCAGGTGGGCCACTTGCTAATTCTCATGTGTTGCTCCGGCCC
CTCCAGCTGCAGGTGGGTGTGGAGTTTGAGGCCAGCACAAGGATGCAGGACACCAGCGTCTCCTTCGGGT
ACCAGCTGGACCTGCCCAAGGCCAACCTCCTCTTCAAAGGTAAAGGTCTCGGTTCCCCTACGCGGGAAAC
AGGCAGGAGGTGACTCAACTCTGAGTGGATGTGTGGGCCACCACAGGTGCTGGAGGACAGTGTGCTGCCA
CCCTGTGGCCTCCACATTACCAGGGAACACTTGTTAAAAGGTAGGTGGGCCGGGTGCGGTGGCTCACG
CCTGTAATCCCAGCACTTTGGGAGGCCAAGGCGGGCGGACGTAAGGAGATTGAGACCATCCTGGCTAACA
CGGTGAAACTCCGTCTCTACTAAAAATACAAAAACAAAATTAGCCGGGTGTGGTTGCGGGTGCCTATAGT
CCCAACTACTGAGGCTGAGGCGGGAAAATGGTATGAACCCAGGAGGCGGAGCTTGCGGTGAGCCGAGATC
GTGCCACCGCACTCCAGCCTGGGTGACAGAGCAAGACTCCATCTCAAAAAAAAAAAAGTAGGTGGACAAC
CCTCTACTATGTTTTATGCTTGGAAAAAAAAAGTAGGTAGAGCAGCCAGGCGTGGTGACTCACGCCTGTA
ATCCCAGCATTTTGGGAGGCCAAGCCAGGTAGAATACTTGAGGCCAGGAGTTGGAGACCAGCCTGGCCAA
CGTGGTGAAATCCCCTCTCTACTAAAAGTACAAAAATTAGCCAGGTGTGGTAGCGTGCTGCAACTGTAGT
CCCCGCTACTTAGGAGGCTGAGGCACAAGAATCACTTGAACCTGGGAGGCGGAGGTTGCAGGGAGTTGAG
ACTGCACCACTGCACTCCAGCCTGGGTGACAGAGTGAGACTCCATCTCAAAAAAAATAAAATGAAATAA
ATAAATAAATGTTAAAAAAAATCTGGTGGAGCATCTGATGGGTGTTTGGGCCAAGCTGGAGCTTTGTCCA
TCCCCTCTTATTTTTCTGCACTTGACTCTCTTATTTTTCTGAGACTGGTCTCCCTCTGTCGCCCAGGCTA
GAGTGCAGCAGTGCAACTGCGGCTCACTGCAGCCTCCACCTCCCGGGCTCAAGCAGCCTTCCCACCTCAG
CCTCCTGAGTAGCTAGGACCACAGGTGTATGCCACCAGGCCCAGCTAATTTTTTTGATAGTTTTGGGAGA
CATGGGGGTTTCACCATGTTGCCCAGGCTGGTCTCGAACTCCTGGACTCAAGCCTTGGCCTCCCAAAGTG
CTGGGATTATAGGTGTGAGCCACCACACCCAGCCAGGGTAGAAGGCACTTTGGAAGCCTCGAGCCTGCCC
CATTCATCTTACGTTAGTGGAAACTGAGGCTTCCAGAGGGTTTCAAGGTCACAACTAAATCCAGAACCTCA
TCTCAGGCACACTGGTCGTAGTCCCAATGTCCAGTCTTAAGTCTTCTTGGATATCTGTGGCTCACAGATT
TTGGGTGTTTGAGCCTCCTGCTGAGCACTGCTGGGGCCACAGCGGTGACCAGCCCTGTCTTCACGGGACT
CAGTGAGAGGAACAGATTCATCCGCAGAGTGGGCAGGACTAGGTTGGGGGAACCCAGGGGTCTAGAGGGC
TTTTCAGAGGGCAGGGGTCACTGAGCGGAGAGCAGAGGAGGAGTGAGCCATTTGCTCCAGCGTGAAGTTG
TTGGTGTGATGGGGTTTCAGGGTGGCAGGAGCAGTGTGGTTAAAGGTCTGGAAGCTGTCGGCATGTGGCT
GGTATCCAAGGTGGCCAGGAACTCTGCATGGATATGGTGGGAAGCTGGCACGCCTCTCACCTCAGCTCTT
CCCTGCAGGCTCTGTGGATAGCAACTGGATCGTGGGTGCCACGCTGGAGAAGAAGCTCCCACCCCTGCCC
CTGACACTGGCCCTTGGGGCCTTCCTGAATCACCGCAAGAACAAGTTTCAGTGTGGCTTTGGCCTCACCA
TCGGCTGAGCCCTCCTGGCCCCCGCCTTCCACGCCCTTCCGATTCCACCTCCACCTCCACCTCCCCCTGC
CACAGAGGGGAGACCTGAGCCCCCCTCCCTTCCCTCCCCCTTGGGGGTCGGGGGGGACATTGGAAAGGA
GGGACCCCGCCACCCCAGCAGCTGAGGAGGGGATTCTGGAACTGAATGGCGCTTCGGGATTCTGAGTAGC
AGGGGCAGCATGCCCAGTGGGCCTGGGGTCCGGGAGGGATTCCGGAATTGAGGGGCACGCAGGATTCTG
AGCACCAGGGGCAGAGGCGGCCAGACAACCTCAGGGAGGAGTGTCCTGGCGTCCCCATCCTCCAAAGGGC
CTGGGCCCGCCCCGAGGGGCAGCGAGAGGAGCTTCCCCATCCCCGGTCAGTCCACCCTGCCCCGTCCAC
TTTCCCATCTCCTCGGTATAAATCATGTTTATAAGTTATGGAAGAACCGGGACATTTTACAGAAAAAAAA
CAAAAAACAACAAAAAATATACGTGGGAAAAAAAACGATGGGAGGCCTCCGTTTTCTCAAGTGTGTCTGG
CCTGTTTTGAGCATTTCATCCGGAGTCTGGCCGCCCTGACCTTCCCCCAGCCGCCTGCAGGGGCGCCAG
AGGGCCGGAGCACGGAAAGCAGCGGATCCTTGATGCTGCCTTAAGTCCGGCTCAGAGGGGCGCAGCGTGG
CCTGGGGTCGCTATCTTCCCATCCGGAACATCTGCCCTGCTGGGGGACACTACGGGCCTTCCCTTGCCTG
AGGGTAGGGTCTCAAGGTCACTTGCCCCCAGCTTGACCTGGCCGGAGTGGCTATAGAGGACTTTGTCCCT
GCAGACTGCAGCAGCAGAGATGACACTGTCTCTGAGTGCAGAGATGGGGGCAGGGAGCTGGGAGAGGGTT
CAAGCTACTGGAACAGCTTCAGAACAACTAGGGTACTAGGAACTGCTGTGTCAGGGAGAAGGGCTCAAG
GACTCGCAGGCCTGGGAGGAGGGGCCTAGGCCAGCCATGGGAGTTGGGTCACCTGTGTCTGAGGACTTGG
TGCTGTCTGGATTTTGCCAACCTAGGGCTGGGGTCAGCTGATGCCCACCACGACTCCCGAGCCTCCAGGA
ACTGAAACCCTGTCTGCCCCAGGGTCTGGGAAGGAGGCTGCTGAGTAGAACCAACCCCAGGTTACCAA
CCCCACCTCAGCCACCCCTTGCCAGCCAAAGCAAACAGGCCCGGCCCGGCACTGGGGGTTCCTTCTCGAA
CCAGGAGTTCAGCCTCCCCTGACCCGCAGAATCTTCTGATCCCACCCGCTCCAGGAGCCAGGAATGAGTC
```

FIG. 2 (continued)

```
CCAGTCTCTCCCAGTTCTCACTGTGTGGTTTTGCCATTCGTCTTGCTGCTGAACCACGGGTTTCTCCTCT
GAAACATCTGGGATTTATAACAGGGCTTAGGAAAGTGACAGCGTCTGAGCGTTCACTGTGGCCTGTCCAT
TGCTAGCCCTAACATAGGACCGCTGTGTGCCAGGGCTGTCCTCCATGCTCAATACACGTTAGCTTGTCAC
CAAACATACCCGTGCCGCTGCTTTCCCAGTCTGATGAGCAAAGGAACTTGATGCTCAGAGAGGACAAGTC
ATTTGCCCAAGGTCACACAGCTGGCAACTGGCAGAGCCAGGATTCACGCCCTGGCAATTTGACTCCAGAA
TCCTAACCTTAACCCAGAAGCACGGCTTCAAGCCCCTGGAAACCACAATACCTGTGGCAGCCAGGGGGAG
GTGCTGGAATCTCATTTCACATGTGGGGAGGGGGCTCCCCTGTGCTCAAGGTCACAACCAAAGAGGAAGC
TGTGATTAAAACCCAGGTCCCATTTGCAAAGCCTCGACTTTTAGCAGGTGCATCATACTGTTCCCACCCC
TCCCATCCCACTTCTGTCCAGCCGCCTAGCCCCACTTTCTTTTTTTTCTTTTTTTGAGACAGTCTCCCTC
TTGCTGAGGCTGGAGTGCAGTGGCGAGATCTCGGCTCACTGTAACCTCCGCCTCCCGGGTTCAAGCGATT
CTCCTGCCTCAGCCTCCCAAGTAGCTAGGATTACAGGCGCCCGCCACCACGCCTGGCTAACTTTTGTATT
TTTAGTAGAGATGGGGTTTCACCATGTTGGCCAGGCTGGTCTCAAACTCCTGACCTTAAGTGATTCGCCC
ACTGTGGCCTCCCAAAGTGCTGGGATTACAGGCGTGAGCTACCGCCCCCAGCCCCTCCCATCCCACTTCT
GTCCAGCCCCTAGCCCTACTTTCTTTCTGGGATCCAGGAGTCCAGATCCCCAGCCCCTCTCCAGATTA
CATTCATCCAGGCACAGGAAAGGACAGGGTCAGGAAAGGAGGACTCTGGGCGGCAGCCTCCACATTCCCC
TTCCACGCTTGGCCCCCAGAATGGAGGAGGGTGTCTGTATTACTGGGCGAGGTGTCCTCCCTTCCTGGGG
ACTGTGGGGGTGGTCAAAAGACCTCTATGCCCCACCTCCTTCCTCCCTCTGCCCTGCTGTGCCTGGGGC
AGGGGGAGAACAGCCCACCTCGTGACTGGGGGCTGGCCCAGCCCGCCCTATCCCTGGGGGAGGGGCGGG
ACAGGGGGAGCCCTATAATTGGACAAGTCTGGGATCCTTGAGTCCTACTCAGCCCCAGCGGAGGTGAAGG
ACGTCCTTCCCCAGGAGCCGGTGAGAAGCGCAGTCGGGGGCACGGGGATGAGCTCAGGGGCCTCTAGAAA
GAGCTGGGACCCTGGGAACCCCTGGCCTCCAGGTAGTCTCAGGAGAGCTACTCGGGGTCGGGCTTGGGA
GAGGAGGAGCGGGGTGAGGCAAGCAGCAGGGGACTGGACCTGGGAAGGGCTGGGCAGCAGAGACGACCC
GACCCGCTAGAAGGTGGGGTGGGGAGAGCAGCTGGACTGGGATGTAAGCCATAGCAGGACTCCACGAGTT
GTCACTATCATTTATCGAGCACCTACTGGGTGTCCCCAGTGTCCTCAGATCTCCATAACTGGGGAGCCAG
GGGCAGCGACACGGTAGCTAGCCGTCGATTGGAGAACTTTAAAATGAGGACTGAATTAGCTCATAAATGG
AACACGGCGCTTAACTGTGAGGTTGGAGCTTAGAATGTGAAGGGAGAATGAGGAATGCGAGACTGGGACT
GAGATGGAACCGGCGGTGGGGAGGGGGTGGGGGGATGGAATTTGAACCCCGGGAGAGGAAGATGGAATTT
TCTATGGAGGCCGACCTGGGGATGGGGAGATAAGAGAAGACCAGGAGGGAGTTAAATAGGGAATGGGTTG
GGGGCGGCTTGGTAAATGTGCTGGGATTAGGCTGTTGCAGATAATGCAACAAGGCTTGGAAGGCTAACCT
GGGGTGAGGCCGGGTTGGGGCCGGGCTGGGGGTGGGAGGAGTCCTCACTGCGGTTGATTGACAGTTTCT
CCTTCCCCAGACTGGCCAATCACAGGCAGGAAGATGAAGGTTCTGTGGGCTGCGTTGCTGGTCACATTCC
TGGCAGGTATGGGGCGGGGCTTGCTCGGTTCCCCCGCTCCTCCCCCTCTCATCCTCACCTCAACCTCC
TGGCCCCATTCAGGCAGACCCTGGGCCCCCTCTTCTGAGGCTTCTGTGCTGCTTCCTGGCTCTGAACAGC
GATTTGACGCTCTCTGGGCCTCGGTTTCCCCCATCCTTGAGATAGGAGTTAGAAGTTGTTTTGTTGTTGT
TGTTTGTTGTTGTTGTTTTGTTTTTTTGAGATGAAGTCTCGCTCTGTCGCCCAGGCTGGAGTGCAGTGGC
GGGATCTCGGCTCACTGCAAGCTCCGCCTCCCAGGTCCACGCCATTCTCCTGCCTCAGCCTCCCAAGTAG
CTGGGACTACAGGCACATGCCACCACACCCGACTAACTTTTTTGTATTTTCAGTAGAGACGGGGTTTCAC
CATGTTGGCCAGGCTGGTCTGGAACTCCTGACCTCAGGTGATCTGCCCGTTTCGATCTCCCAAAGTGCTG
GGATTACAGGCGTGAGCCACCGCACCTGGCTGGGAGTTAGAGGTTTCTAATGCATTGCAGGCAGATAGTG
AATACCAGACACGGGGCAGCTGTGATCTTTATTCTCCATCACCCCCACACAGCCCTGCCTGGGGCACACA
AGGACACTCAATACATGCTTTTCCGCTGGGCGCGGTGGCTCACCCCTGTAATCCCAGCACTTTGGGAGGC
CAAGGTGGGAGGATCACTTGAGCCCAGGAGTTCAACACCAGCCTGGGCAACATAGTGAGACCCTGTCTCT
ACTAAAAATACAAAAATTAGCCAGGCATGGTGCCACACACCTGTGCTCTCAGCTACTCAGGAGGCTGAGG
CAGGAGGATCGCTTGAGCCCAGAAGGTCAAGGTTGCAGTGAACCATGTTCAGGCCGCTGCACTCCAGCCT
GGGTGACAGAGCAAGACCCTGTTTATAAATACATAATGCTTTCCAAGTGATTAAACCGACTCCCCCCTCA
CCCTGCCCACCATGGCTCCAAAGAAGCATTTGTGGAGCACCTTCTGTGTGCCCCTAGGTACTAGATGCCT
GGACGGGGTCAGAAGGACCCTGACCCACCTTGAACTTGTTCCACACAGGATGCCCAAGGTGGAGCA
AGCGGTGGAGACAGAGCCGGAGCCCGAGCTGCCAGCAGACCGAGTGGCAGAGCGGCCAGCGCTGGGAA
CTGGCACTGGGTCGCTTTTGGGATTACCTGCGCTGGGTGCAGACACTGTCTGAGCAGGTGCAGGAGGAGC
TGCTCAGCTCCCAGGTCACCCAGGAACTGAGGTGAGTGTCCCCATCCTGGCCCTTGACCCTCCTGGTGGG
CGGCTATACCTCCCCAGGTCCAGGTTTCATTCTGCCCCTGTCGCTAAGTCTTGGGGGGCCTGGGTCTCTG
CTGGTTCTAGCTTCCTCTTCCCATTTCTGACTCCTGGCTTTAGCTCTCTGGAATTCTCTCTCTCAGCTTT
GTCTCTCTCTCTTCCCTTCTGACTCAGTCTCTCACACTCGTCCTGGCTCTGTCTCTGTCCTTCCCTAGCT
CTTTTATATAGAGACAGAGAGATGGGGTCTCACTGTTGCCCAGGCTGGTCTTGAACTTCTGGGCTCAA
GCGATCCTCCCGCCTCGGCCTCCCAAAGTGCTGGGATTAGAGGCATGAGCCACCTTGCCCGGCCTCCTAG
CTCCTTCTTCGTCTCTGCCTCTGCCCTCTGCATCTGCTCTCTGCATCTGTCTCTGTCTCCTTCTCTCGGC
CTCTGCCCCGTTCCTTCTCTCCCTCTTGGGTCTCTCTGGCTCATCCCCATCTCGCCCGCCCCATCCCAGC
```

FIG. 2 (continued)

```
CCTTCTCCCCGCCTCCCACTGTGCGACACCCTCCCGCCCTCTCGGCCGCAGGGCGCTGATGGACGAGACC
ATGAAGGAGTTGAAGGCCTACAAATCGGAACTGGAGGAACAACTGACCCCGGTGGCGGAGGAGACGCGGG
CACGGCTGTCCAAGGAGCTGCAGGCGGCGCAGGCCCGGCTGGGCGCGGACATGGAGGACGTGTGCGGCCG
CCTGGTGCAGTACCGCGGCGAGGTGCAGGCCATGCTCGGCCAGAGCACCGAGGAGCTGCGGGTGCGCCTC
GCCTCCCACCTGCGCAAGCTGCGTAAGCGGCTCCTCCGCGATGCCGATGACCTGCAGAAGCGCCTGGCAG
TGTACCAGGCCGGGGCCCGCGAGGGCGCCGAGCGCGGCCTCAGCGCCATCCGCGAGCGCCTGGGGCCCCT
GGTGGAACAGGGCCGCGTGCGGGCCGCCACTGTGGGCTCCCTGGCCGGCCAGCCGCTACAGGAGCGGGCC
CAGGCCTGGGGCGAGCGGCTGCGCGCGCGGATGGAGGAGATGGGCAGCCGGACCCGCGACCGCCTGGACG
AGGTGAAGGAGCAGGTGGCGGAGGTGCGCGCCAAGCTGGAGGAGCAGGCCCAGCAGATACGCCTGCAGGC
CGAGGCCTTCCAGGCCCGCCTCAAGAGCTGGTTCGAGCCCCTGGTGGAAGACATGCAGCGCCAGTGGGCC
GGGCTGGTGGAGAAGGTGCAGGCTGCCGTGGGCACCAGCGCCGCCCCTGTGCCCAGCGACAATCACTGAA
CGCCGAAGCCTGCAGCCATGCGACCCCACGCCACCCGTGCCTCCTGCCTCCGCGCAGCCTGCAGCGGGA
GACCCTGTCCCCGCCCCAGCCGTCCTCCTGGGGTGGACCCTAGTTTAATAAAGATTCACCAAGTTTCACG
CATCTGCTGGCCTCCCCCTGTGATTTCCTCTAAGCCCCAGCCTCAGTTTCTCTTTCTGCCCACATACTGG
CCACACAATTCTCAGCCCCCTCCTCTCCATCTGTGTCTGTGTGTATCTTTCTCTCTGCCCTTTTTTTTTT
TTTTAGACGGAGTCTGGCTCTGTCACCCAGGCTAGAGTGCAGTGGCACGATCTTGGCTCACTGCAACCTC
TGCCTCTTGGGTTCAAGCGATTCTGCTGCCTCAGTAGCTGGGATTACAGGCTCACACCACCACACCCGGC
TAATTTTTGTATTTTTAGTAGAGACGAGCTTTCACCATGTTGGCCAGGCAGGTCTCAAACTCCTGACCAA
GTGATCCACCCGCCGGCCTCCCAAAGTGCTGAGATTACAGGCCTGAGCCACCATGCCCGGCCTCTGCCCC
TCTTTCTTTTTTAGGGGGCAGGGAAAGGTCTCACCCTGTCACCCGCCATCACAGCTCACTGCAGCCTCCA
CCTCCTGGACTCAAGTGATAAGTGATCCTCCCGCCTCAGCCTTTCCAGTAGCTGAGACTACAGGCGCATA
CCACTAGGATTAATTTGGGGGGGGGGGTGGTGTGTGTGGAGATGGGGTCTGGCTTTGTTGGCCAGGCTGA
TGTGGAATTCCTGGGCTCAAGCGATACTCCCACCTTGGCCTCCTGAGTAGCTGAGACTACTGGCTAGCAC
CACCACACCCAGCTTTTTATTATTATTTGTAGAGACAAGGTCTCAATATGTTGCCCAGGCTAGTCTCAAA
CCCCTGGGCTCAAGAGATCCTCCGCCATCGGCCTCCCAAAGTGCTGGGATTCCAGGCATGGGGCTCCGAG
CCCGGCCTGCCCAACTTAATAATACTTGTTCCTCAGAGTTGCAACTCCAAATGACCTGAGATTGGTGCCT
TTATTCTAAGCTATTTTCATTTTTTTTCTGCTGTCATTATTCTCCCCCTTCTCTCCTCCAGTCTTATCTG
ATATCTGCCTCCTTCCCACCCACCCTGCACCCCATCCCACCCCTCTGTCTCTCCCTGTTCTCCTCAGGAG
ACTCTGGCTTCCTGTTTTCCTCCACTTCTATCTTTTATCTCTCCCTCCTACGGTTTCTTTTCTTTCTCCC
CGGCCTGCTTGTTTCTCCCCCAACCCCCTTCATCTGGATTTCTTCTTCTGCCATTCAGTTTGGTTTGAGC
TCTCTGCTTCTCCGGTTCCCTCTGAGCTAGCTGTCCCTTCACCCACTGTGAACTGGGTTTCCCTGCCCAA
CCCTCATTCTCTTTCTTTCTTTCTTTTTTTTTTTTTTTTTTTTTTTTTTGAGACAGAGTCTTGCT
CTGTTGCCCAGCCTGGAGTGCAGTGGTGCAATCTTGGTTCACTGCAACCTCCACTTCCCAGATTCAAGCA
ATTCTCCTGCCTCAGCCTCCAGAGTAGCTGGGATTACAGGCGTGTCCCACCACACCCGACTAATTTTTGT
ATTTTTGGTAGAGACAAGGCTTCGGCATTGTTGGCCAGGCAGGTCTCGAACTCCTGACCTCAAGTAATCT
GCCTGCCTCACCCTCCCAAAGTGCTGGGATTACAGGCATGAGCCACCTCACCCGGACCATCCCTCATTCT
CCATCCTTTCCTCCAGTTGTGATGTCTACCCCTCATGTTTCCCAACAAGCCTACTGGGTGCTGAATCCAG
GCTGGGAAGAGAAGGGAGCGGCTCTTCTGTCGGAGTCTGCACCAGGCCCATGCTGAGACGAGAGCTGGCG
CTCAGAGAGGGGAAGCTTGGATGGAAGCCCAGGAGCCGCCGGCACTCTCTTCTCCTCCCACCCCCTCAGT
TCTCAGAGACGGGGAGGAGGGTTCCCACCAACGGGGGACAGGCTGAGACTTGAGCTTGTATCTCCTGGGC
CAGCTGCAACATCTGCTTGTCCCTCTGCCCATCTTGGCTCCTGCACACCCTGAACTTGGTGCTTTCCCTG
GCACTGCTCTGATCACCCACGTGGAGGCAGCACCCCTCCCCT
```

FIG. 3  ApoE polypeptide wildtype sequence (NCBI Accession No. NP_000032.1)(SEQ ID No. 70)

```
MKVLWAALLVTFLAGCQAKVEQAVETEPEPELRQQTEWQSGQRWELALGRFWDYLRWVQTLSEQVQEELL
SSQVTQELRALMDETMKELKAYKSELEEQLTPVAEETRARLSKELQAAQARLGADMEDVCGRLVQYRGEV
QAMLGQSTEELRVRLASHLRKLRKRLLRDADDLQKRLAVYQAGAREGAERGLSAIRERLGPLVEQGRVRA
ATVGSLAGQPLQERAQAWGERLRARMEEMGSRTRDRLDEVKEQVAEVRAKLEEQAQQIRLQAEAFQARLK
SWFEPLVEDMQRQWAGLVEKVQAAVGTSAAPVPSDNH
```

FIG. 4    SLCO1B1 nucleic acid sequence (NCBI Accession No. NM_006446.4) (SEQ ID No. 71)

```
AAAGGGTGGACTTGTTGCAGTTGCTGTAGGATTCTAAATCCAGGTGATTGTTTCAAACTGAGCATCAACA
ACAAAAACATTTGTATGATATCTATATTTCAATCATGGACCAAAATCAACATTTGAATAAAACAGCAGAG
GCACAACCTTCAGAGAATAAGAAAACAAGATACTGCAATGGATTGAAGATGTTCTTGGCAGCTCTGTCAC
TCAGCTTTATTGCTAAGCACTAGGTGCAATTATTATGAAAAGTTCCATCATTCATATAGAACGGAGATT
TGAGATATCCTCTTCTCTTGTTGGTTTTATTGACGGAAGCTTTGAAATTGGAAATTTGCTTGTGATTGTA
TTTGTGAGTTACTTTGGATCCAAACTACATAGACCAAAGTTAATTGGAATCGGTTGTTTCATTATGGGAA
TTGGAGGTGTTTTGACTGCTTTGCCACATTTCTTCATGGGATATTACAGGTATTCTAAAGAAACTAATAT
CAATTCATCAGAAAATTCAACATCGACCTTATCCACTTGTTTAATTAATCAAATTTTATCACTCAATAGA
GCATCACCTGAGATAGTGGGAAAAGGTTGTTTAAAGGAATCTGGGTCATACATGTGGATATATGTGTTCA
TGGGTAATATGCTTCGTGGAATAGGGGAGACTCCCATAGTACCATTGGGGCTTTCTTACATTGATGATTT
CGCTAAAGAAGGACATTCTTCTTTGTATTTAGGTATATTGAATGCAATAGCAATGATTGGTCCAATCATT
GGCTTTACCCTGGGATCTCTGTTTTCTAAAATGTACGTGGATATTGGATATGTAGATCTAAGCACTATCA
GGATAACTCCTACTGATTCTCGATGGGTTGGAGCTTGGTGGCTTAATTTCCTTGTGTCTGGACTATTCTC
CATTATTTCTTCCATACCATTCTTTTTCTTGCCCCAAACTCCAAATAAACCACAAAAGAAAGAAAAGCT
TCACTGTCTTTGCATGTGCTGGAAACAAATGATGAAAAGGATCAAACAGCTAATTTGACCAATCAAGGAA
AAAATATTACCAAAAATGTGACTGGTTTTTTCCAGTCTTTTAAAAGCATCCTTACTAATCCCCTGTATGT
TATGTTTGTGCTTTTGACGTTGTTACAAGTAAGCAGCTATATTGGTGCTTTTACTTATGTCTTCAAATAC
GTAGAGCAACAGTATGGTCAGCCTTCATCTAAGGCTAACATCTTATTGGGAGTCATAACCATACCTATTT
TTGCAAGTGGAATGTTTTTAGGAGGATATATCATTAAAAAATTCAAACTGAACACCGTTGGAATTGCCAA
ATTCTCATGTTTTACTGCTGTGATGTCATTGTCCTTTTACCTATTATATTTTTCATACTCTGTGAAAAC
AAATCAGTTGCCGGACTAACCATGACCTATGATGGAAATAATCCAGTGACATCTCATAGAGATGTACCAC
TTTCTTATTGCAACTCAGACTGCAATTGTGATGAAAGTCAATGGGAACCAGTCTGTGGAAACAATGGAAT
AACTTACATCTCACCCTGTCTAGCAGGTTGCAAATCTTCAAGTGGCAATAAAAAGCCTATAGTGTTTTAC
AACTGCAGTTGTTTGGAAGTAACTGGTCTCCAGAACAGAAATTACTCAGCCCATTTGGGTGAATGCCCAA
GAGATGATGCTTGTACAAGGAAATTTTACTTTTTGTTGCAATACAAGTCTTGAATTTATTTTCTCTGC
ACTTGGAGGCACCTCACATGTCATGCTGATTGTTAAAATTGTTCAACCTGAATTGAAATCACTTGCACTG
GGTTTCCACTCAATGGTTATACGAGCACTAGGAGGAATTCTAGCTCCAATATATTTTGGGGCTCTGATTG
ATACAACGTGTATAAAGTGGTCCACCAACAACTGTGGCACACGTGGGTCATGTAGGACATATAATTCCAC
ATCATTTTCAAGGGTCTACTTGGGCTTGTCTTCAATGTTAAGAGTCTCATCACTTGTTTTATATATTATA
TTAATTTATGCCATGAAGAAAAAATATCAAGAGAAAGATATCAATGCATCAGAAATGGAAGTGTCATGG
ATGAAGCAAACTTAGAATCCTTAAATAAAAATAAACATTTTGTCCCTTCTGCTGGGGCAGATAGTGAAAC
ACATTGTTAAGGGGAGAAAAAAAGCCACTTCTGCTTCTGTGTTTCCAAACAGCATTGCATTGATTCAGTA
AGATGTTATTTTTGAGGAGTTCCTGGTCCTTTCACTAAGAATTTCCACATCTTTTATGGTGGAAGTATAA
ATAAGCCTATGAACTTATAATAAAACAAACTGTAGGTAGAAAAATGAGAGTACTCATTGTTACATTATA
GCTACATATTTGTGGTTAAGGTTAGACTATATGATCCATACAAATTAAAGTGAGAGACATGGTTACTGTG
TAATAAAAGAAAAAATACTTGTTCAGGTAATTCTAATTCTTAATAAAACAAATGAGTATCATACAGGTAG
AGGTTAAAAAGGAGGAGCTAGATTCATATCCTAAGTAAAGAGAAATGCCTAGTGTCTATTTTATTAAACA
AACAAACACAGAGTTTGAACTATAATACTAAGGCCTGAAGTCTAGCTTGGATATATGCTACAATAATATC
TGTTACTCACATAAAATTATATATTTCACAGACTTTATCAATGTATAATTAACAATTATCTTGTTTAAGT
AAATTTAGAATACATTTAAGTATTGTGGAAGAAATAAAGACATTCCAATATTTGCAAAAAAAAAAAAAAA
```

FIG. 5 Wildtype SLCOB1B1 nucleic acid molecule (NCBI Accession No. NG_011745.1)
(SEQ ID No. 72)

```
GATTCCTCTGCAGTGTAACTTCATGGTTTTTGAGGCAAAGGAAGGCTGGCAGTAAACAAAATATGTGAGT
AAAATTTATAGTATGATGGTGAGAGAATAAAAATTGAGTGTCAAAGGGAGTAATATTAAAAAATTGTTAG
AGAAGACTTCGCTGGGAAAGTGTCATTTGTTTGGGTACTAGAATATGGTGAGGGAGTAAGTTATGCAGCT
ATAGGGAAAGAACATTCCAGACAGAAAGAAAAATAGGAACAAAGATTCTCAGTAGAGGATCTATAACTTA
TAAGGCCTTAAAGCTGTTCTTTGGATTTTTGAGTGATATGTGAAGCCAATGGGGATTTGAGCAGAGCTA
TGACATGGTATGACCCTCACTTATATGTTAAGATTTACACAGGGGAAGGAGGTTGGGGAAGAGGGGCTGT
GAGTGGTCAGGAGGAAAGCTGAGATACAAGTATGAGGGTATTGCAATAATTCAGGACCAGCCTGAAAGTT
GTGGAGGAGGTAAGAAATCATCAGATTCTGGGTATATTTGGAAATTAGAGCCTAATGTGAGTGTGAGAAA
TAGGAGAAGAATGATTCTAATATTGTATGTGGCTGTGCATGTGCACGCATGTGTGCAACTGGAATGACAGA
ATTACAATGTATGGGGATTATTGTCTTCCCTGGACAATAATCCCTGGAAATGGGGATTATTACAAGAGGA
GAGGTTGGGGAAGGAAAGACAAAGATACCATGTTAGAAAATATTAAGTGTAAGATGCCTATTAGAGATAT
ATAGGAAGATGGTGAGAAGTCAATGGATAAATCTAGAGTTCATGAGTAACTTGGCTAGAGAAAAAATTTT
GGAATTATCAACGTATGGATAAGATTTAAAGACATGAAAATAGATGAGGTCACAAACACACACAGTAAGG
TTATTGTCTGACATGCTTCAATTTAGAAGACAAAGATAAAGAATTTAGAGTAAATGAAGTGTAAATAAGT
AAGTCAGTGAGTTAGAAGGCAAACCACAAAGGGTAGTGTCCTGCAAAGTTTTGCTTAGGGAGGGAATTCT
CAGTTCTGAAAAATGCTGCTAATAGTTCAAGTCAGATGAGGACTATTAGATGTAGCATTTAGGTAATTTA
TGACTTAGGAAAAGTAGTTTCAGTGGAAATTTGGGGGCAAAAGCCTGATAAGAGTGTGCTCAAGAGAGAA
TGTAGAGAGAGAGATTGAAAGCAATAATTAGACAAGCTATTTCTCTGTAAAAATAGCACAGAAATAGGGC
AATATTAGGAAAAAATGGGATCAAAAGAGAGATTTTTGGAAGATGAAAAAGTGACAGCATTCTTACATGC
TGATGGAAACATTTAAAAAGAGGATAGTGCTATCCTTAAAAACACAAGGGGAGGAGTCAATGTCATATGC
AAGTGGAGATTGGCCTTAGCTTAAACTTGGGTAGTTCACTAAGGCAGACCATGTGGTGGTACTGGGGCTT
TACATAGATAAATGTGGTCAAGGGAGCTTTTGAAGTTTCTTCTTTATTTATTTATTTTTTCAGTAAAATA
ATTCATCAGCTGAAGGTGGGGAAGGGATGTATTAGAATTTCAAAAAAAAAAAAAAAAGATGAAGGCACAA
AATGCTCAGAGTGCAAAATGGCGTGAATGATTTCTTGGCAAAATGAAAGGTCCATTTGGGCTTCCTAATC
ATACGTTTAAAGTCAGCATGGTTGAGAGATTTTCCTCAGTTACATTTAGCTTCATAAGGGAAATGTGCAG
AGTTATTTGAGAGTTAAATTTAATCAAGATTGTGGCTTTGACATGCAATTAAAATAATGCAAAACAGTCA
AAATTATATGAAGTTATATAGAAGAGAGTGATTACCGTGACCATTAAATTAACCCAGATGTATAGATAAG
GAACACCGAAATCTCTGGCAAAATCAAATTGTAGGTTATACATCCTGGTCAGTGGAAGCATGTGGATCTA
GGGTGTTACTGAGTGTGAGCTAGGAGTGATAAAGAGTGGTGCTCCAATCTTTGATATTATGGAGAGATTA
CAGTGGTGTGAAAAGCATAGGATATGCCCATAGCAGTAGGTAGAAGCCAAGATCATTGAGGAGAAGGCTA
AAAAATAAAAAGAAAATAAAAAGAAAACAGAGAATTAAAAAGATTCTCTTCATGGTCATTACCATCATGA
ATAATTAAAATAGTAGTAGCATTTTGAGAGAATGGCTTTGGATCGAGAGCTAAAATTGTCATGAAATGAG
TGGGAGTGACTGAGCGTTGATAGATGATTTCAACAAGAGGAATAAGTGATAGAGTCTTTCAATATGAGAT
CCAAAACTATGGATTATGAGTGTAAAGGGTGGGGAAATGTAAAGAAACTAGCAAAGTGAGGCACATTGGA
AACCAGCCCATCTGGTTTGCAGCAATATGGGGATAAGGCAACCCCTATGTATCACTGCTGCAGGAGAGG
GAGTGTCTCAGGGAAGACCAATTTTTAAGTTCAAGGCAGAAGTGAAGCAGAATAACTCAGAGAAGAGGTA
AAGGTAAGGGAGTTTCAGTCATGACTAGTGATGGGTTCCAGAAAACTCAAGAGAAGAATTTCAGTCCAG
GATTGGGAGAAAGAGAGAAGATGGGGGCAAACATAGGAATGTGCAGAGCCCTGTGGGGATTAGAGAAGAG
GTGATGAGTCATCAGGGAATCCCTACCTTCTTATGGTGGTCACTACCATAAGAGCGATAATTGCCATGGT
AATATTAGTCTTGATGATGCCAGAGCTTTGATCATTGGTGGGTATAGAAACATGTTTGGAGAATAATATG
TAGAATAGGAGTTCTTTCCAGGAGAGTGTAGCTTTCTGGAGCTGTCTCTTAATCAGCACCAACAGAAGTG
AAATGTTCGGGTAAGGGCGGATCTGCTTGGAGCCTGGAGGTGAAGCAGGGTGTGCCTGTGGTACACA
CCTGAGAACTCTGGGCTAAAACCTATTGGACATAGGTTTTACAGATCTACAGGATACAGATCTCAGAGA
TTTTATTTGTATTCATTAATATAAATTAACTGCTCTAAAATTTATAATATGCAAATATCATACAATTAA
TCTAATTAGGTGTTGAATCTATAATGTGCCAGGCATTATGTAAGGCACTTTACATACACTAAATCTTTAT
TCCAAATATAGACTTCTTACTTTATAGATGAGTGCACTGATGCTCAGAAATGGTAAATAACCTACTGATG
TTTATACTGCTGGCAGGTAGCAGAGACATATCGGCATTTAAGTCTTTCAGACTTCAAAGGCCATGATATT
TCATCAGAGCTGTGATAGCCGTTCCTGAAAAAAATATCAGCTGATTCTTTAAATCAATTTTTGTCATCTA
ACTGATGCGTGGCTGTTAGCATAATATTGATCTTGAAAGATGTTTTGCAACATCTTTCCCCTGGTGTACT
CTTGTTTTTCCATGATCCCACAAAATGAGCAGTCTAATTATTTACACAATTAGGAAGAGAAAAGGGGCAC
AGAGAATGCTCTTTGACCTCTGAAAATATTGGAGAATTTTACAACTGGCACCTTTAGCTCAGGATTATAA
AGGTTGTTAGTTAGTTTGTACTGTTTTATCTTCATTGTATATAATATATATATTAGTCTCCAAACATGTT
GATGTGTTTTCAATGAAATGGATGTCTGAGGAGAAAACCATTAGCCTGAGAAAACCCAAACTGTATTCCC
```

FIG. 5 (continued)

```
ATTGTGAATAAAAGGAAGTCCATAAAAATGATGGAAAATGTTCTGCATTCCTGTTATGATATCAAAATCT
GGCAGTACATGAAAATTTTTCAAAGTGCTTATTTAACAGGCATAATCTTTGGTCTCCTGAGCCAGAATCT
GCTGGGTATGGGACTGGATTGCTATTTTGACAACTCGCCAGTAGATTCTTACTCAGCAGAGTATTTGGAA
GCCTTACTCTAATATTTTGGCCTTGGGTCTACATTTCTCAGTTCTGCACAGTCATTCTTCCCCTCTACAC
TACTCTTTAGTTTGTCTCATGATTCCAATACTCTCAATAATTAACCAAGAATAGAACTAATCAATCAGAT
AACTGTGGCACAGACATCAAATACATTTTGCTGCAACCATATCAACAAATGTCCCATGAATGATAAGGGG
TAACCATATTCTCATATATGCATCCTCACATTACCACATATATATATGTGCATATGTGTATACAGGTAAA
AGTGTGTATATATGTATACATGTATGTTTGTGTATATACATACATATATCTTCACACTTTTCTGAAAT
ATATATATTTATGTGAGAGAAGGGTCTGTACTTTATTTCAGAAGAGAGCTTAATGTCCAAGGTATAATTG
AGAGTCTAAAATGTTTGAGTTATTGAATTAATTAAACTTCATCTCTACTCAAGAAAACTTTTAACTGAGT
TAAGCTCTTCCTTTCTCCACAAGTCAAGTCAATAAAAGGAAACTGTGATATTAATAATTCTTTCCTGTTT
TGATGTAAAGAATCTATCGCATAAAGCAGTCTTAATTTTCATCATTCAGAAAAATGGTCTTGCAGTTAAT
TGGGACTCTCTTATTCCAGGTGGTATCTCCAGTCTCCATACATACCACGTTAGAACCATACTTATGTACC
AAGCAAAGAGGGTATATTTAATTTTTAAATGCCAATGTAACCTGTAGGCATATTTTTATTTGTCTTAA
ATTATTTCCTATTTGGAAGTTTTAAATACCTGGAATAATTTATTGTACTCATATTTTTAAAGAAAAAAAT
CTTATGCCACCAACTTAATTGAATAAACAAGTAAAAGCCATTCCCAAAAGTAAGGTTTACTTGTTAAGAT
TAACAAAAAATAATGTGAGAATTCTGAGAAATATAATCTTTAAATATTGGCAACTGGAGTGAACTCTTAA
AACTAACTAGGTTTTATATGTTTGACTAGAGCAATGACATAATAAGGTGGTTAATCATCACTGGACTTGT
TTTCAAAAAGCCAACTACTTTAAGAGGAATAAAGGGTGGACTTGTTGCAGTTGCTGTAGGATTCTAAATC
CAGGTAAGAACCATTGAGATTCTCTAATTTTTACATATATTTTATGTAAGAAATTTTCACGGAAGAAGAT
TTTGATGGTCTTGAAAAATATTACGAATTTTATGCTCTGTGTCTTCCACACGCTTACATTCTGAGCCCTT
AAAACATAGTAAATATTCCTTCTGGGAGTAGAAGAGCCTCAGGTTTATATACTGTTAAAAATAAAGTAGA
GAAAATAATACCTTTATATATTTAAATATAAAGTTTCAAATCTTGGTCTTATTAATTTCCAAACAAATAA
AAATCAAGTCTCAAAAATGAAGCTCTAGTTACCTTCTTAAAATATGCTACAGGATAATTATTTTTGTCAA
CTACATTGACTGATCACACTAGACTCCTTATTTCTTTGATGTCTTCTTAACTGGATGAAGGCAGCCAAGG
GTGGGAGTAGAGGGAAGAGTTAATTGGCAAACATAAAAAACAGGTGTCTCAAAGTCACATAACCACCTCA
GTTTCCTTGTTTCAACTCAAGTTTGATACAGGGTGAAGGGAAATATATTTTCTAGATAATTTATCTCCAA
TTAAATAAGCAAAAAGTCTTCTCAGTACAGTTTTTTTCTTTTTTATTTCATTATTATTATACTTTAAGT
TTTAGGGTACATGTGCACAACATGCAGGTTTGTTACATATGTATACATGTGCCATGTTGGTGTGCTGCAC
CCATTAACTCATCATTTAACATTGGGCATATCTCCTAATGCTATCCCTCCCCTCTCCCCCACCCCACAAC
AGTCCCCGGTGTGTGATGTTCCCTTTCCTGTGTCCATGTGTTCTCATTGTTCAGTTCCCACCTATGAGTG
AGAACATGCGGTGTTTGGTTTTTTGTCCTTGCGATAGTTTGTTGAGAATGATGGTTTCCAGTTTCATCCA
TGTCCCTACAAAGGACATAAACTCATCATTTTTATGGCTGCATAGTATTCCATGGTGTATGTGTGCCACA
TTTTCTTAATCCACTCTATCGTTGTTGGACATTTAGGTTGGTTCCAAGTCTTTGCTACTGTGAATAGTGC
CGCTATAAACATACGTGTGCATGTGTCTTTATAGCAGCATGATTTATAATCCCTTGGGTATATATCCACT
TATGGGATGGCTGGGTCAAATGGTATTTCCAGTTCTAGATCCCTGAGGAATCGCCACACTGTCTTCCACA
ATGGTTGAACTAGTTTACAGTCCCACCAACAGTGTAAAAGTGTTCCTATTTCTCCACATCCTCTCCAGCA
CCTGTTGTTTCCTGACTTTTTAATGATCGCTATTCTAACTGGTGTGAGATAGTATCTCATTGTGGTTTTG
ATTTGCATTTCTCTGATGGCCAGTGATGATGAGCATTTTTTCACGTGTTTTTTGGCTGCATAAATGTCTT
CTGTTGAGAAGTGTCTGTTCATGTCCTTCACCCACTTCTTGATGGGGTCGTTTGTCTTTTGTAAATTTGT
TTGAGTTCATTGTAGATTTTGGGTATTAGCCTTTTGTCAGATGAGTAGGTTGCAAAAATTTTCTCCCATT
CTGTAGGTTGCCTGTTCACTCTGATGGTAGTTTCTTTTGCTGTGCAGAAGCTCTTTAGTTTAATTATATC
TCATTTGTCATTTTTGGCTTTTGTTGCCATTGCTTTTGGTGTTTTAGACATGAAGTCCTTGCCCATGCCT
ATGTCCTGAATGGTATTGCCTAGGTTTTCTTCTAGGGTTTTTATGGTTTTAGGTCTAACATTTAAGTCTT
TAATCCATCTTGAATTAATTTTTGTGTAAGGTGTAAGGAAGGGATCCAGTTTCAGCTTTCTACATATGGC
TTGCCAGTTTTCCCAGCATCATTTATTAAATAGGGAATCCTTTCCCCATTGCTTGTTTTCTCAGGTTTG
TCAAAGATCAGATAGTTGTAGATATGCGGCACTATTTCTGAGGGCTCTGTTCTGTTCCATTGGTCTATAT
CTCTGTTTTGGTACCAGTACCATGCTGTTTGGTTACTGTAGCCTTGTAGTATAGTTTGAAGTCAGGTAG
GGTGATGCCTCCAGCTTTGTTCTTTTCGCTTAGGATTGACTTGGTATGCGGGCTCTTTTTTGGTTCCATA
TGAACTTTAAAGTAGTTTTTTCCAATTCTGTGAAGAAAGTCATTGGTAGCTTGATGGGGATGGCATTGAA
TCTATAAATTACCTTGGACAGTATGGCCATTTTCATGATATTGATTCTTCCTGCCCATGAGCATGGAATG
TTCTTCTATTTGTTCGTATCCTCTTTTATTTCATTGAGCAGTGGTTTGTAGTTCTCCTTGAAGAGGTCCT
TCACATCCCTTGTAAGTTGGATTCCTAGGTATTTTATTCTCTTTGAAGCAATTGTGAATGGGAGTTCACT
CATGATTTGGCTCTCTGTTTGTCTGTTATTGGTGTATAAGAATGCTTGTGATTTTTATACATTGATTTG
TATTCTGAGACTTTGCTGAAGTTGCTTATCAACTTGAGGAAATTTTGGGCTGAGATGATGGGGTTTTCTA
GATATACAATCATGTGATCTGCAAACAGGGACAATTTGACTTCCTCTTTTCCTAATTGAATACCCTTTAT
TTTCTTCTCCTGCCTGATTGCCCTGGCCAGAACTTCCAACATTATGTTGAATAGGAGCAGTGAGAGAGGG
```

FIG. 5 (continued)

```
CATCCCTGTCTTGTGCCCGTTTTCAAAGGGAATGCTTCCAGTTTTTGCCCATTCAGTATCATATTGGCTG
CAGGTTTGTCATAGATAGCTCTTATTATTTTGAGATACATCCCATCAATACCTAATTTATTGAGAGTTTT
TAGCATGAAGGGTTGTTGAATTTTGTCAAAGGCCTTTTCTGCATCTATTGAGATGATCATGTAGTTTTTG
TCTTTGGTTCTGTTTATATGCTGGATTACATTTATTGATTTGCGTATGTTGAACCAGCCTTGCATCCCAG
GGATGAATCCCACTTGGTCATGTTGGATAAGCTTTTTGATGTGCTGTTGGATTTGGTTTGCCAGTATTTT
ATTGAGGATTTTTGCATCAATGTTCATCAAGGATATTGGTCTAAAATTCTCTTTTTTTGTTGTTTCTCTG
CCAGGCTTTGGTATCAGGATGATGCTGGCCTCATAAAATGAGTTAGGGAGGATTCCCTCTTTTTCTATTG
ATTGGAATAGTTTCAGAAGTATTGGTACCAGTTCCTCCTTGTACCTCTGGTAGAATTCGGCTGTGAATCC
ATCTGGTCCTGGACTTTTTTTTGTTGGTAAGCTATTGAGTATTGCCTCAATTTCAGAGCCTGTTATTGGT
CTATTCAGAGATGCAACTTCTTCCTGGTTTAGTCTTGGGAGGATGTATGTGTCAAGGAATTTATCCATTT
CTGCTAGATTTTCTAGTTTATTTGCCTAGAGGTGTTTATAGTATTCTCTGATGGTAGTTTGTATTTCTGT
GGGATCGGTGGTTATATCCTCTTTATCATTTTTATTGCATCTATTTGATTCTTCTCTGTTTTCTTCTTT
ATTAGTCTTGCTAGTGGTCTATCAATTTTGTTGATGCTTCAAAAAACCAGCTCCTGGATTCATTAATTT
TTTGAAGGGTTTTTTGTGTCTCTATTTCCTTCAGTTCTGCTCTGATGGTAGTTATTTCTTGCCTTCTGCT
AGCTTTTGAATGTGTTTGCTCTTGCTTTTCTAGTTCTTTTAATTGTGATGTTGGGGTGTCAATTTTGGAT
CTTTCCTGCTTTCTCTTGTGGGCATTTAGTGCTATAAATTTCCCTCTACACACTGCTTTAAATGTGTCCC
AGAGATTCTCGTATGTTGTGTGTTTGTTCTCATTGGTTTCAAAGAACATCTTTATTTATGCCTTCATTTC
ATTATGTACCCAGTAGTCATTCAGTAGCAGATTGTTCAGTTTCCATGCAGTTGAGCAGTTTTGAGTGAGT
TTCTTAATCCTGAGTTCTAGTTTGATTGCGCTGTGGTCTGAGAAACAGTTTGTTATAATTTCTGTTCTTT
TCCATTTGCTGAGGAGAGCTTTACTTCCAACTATGTGGTCAATTTCAGAGTAGGTGTGGTGTGGTGCTGA
AAAGAATGTATATTCTGTTGATTTGGGGTGGAGAGTTCTGTAGATGTCTATTAGGTCCGCTTGGTGCAGA
GCTGAGTTCAATTCCTGGGTATCCTTGTTAACTTTCTGTCTCATTGATCTGTCTAATGTTGACAGTGGGG
TGTTAAAGTCTCCCATTATTATTGAGTGGAATTCTAAGTCTCTTTGTAGGTCACTAAGGACTTGCTTTAT
GAATCTGGGTGCTCCTGTATTGGGTGCATATATATTTAGGATAGTTAGCGCTTCTTGTTGAATTGATCCC
TTTACCATTAGGTAATGGCCTTCTTTGTCTCTTTTGATCTTTGTTGGTATAAAGTCTGTTTTATCAGAGA
CTAGGATTGCAACCCCTGCCTTTTTTTGTTTTCCATTTGCTTGGTAGATCTTCCTCCATCCCTTTATTTT
GAGCCTATGTGTGTCTCTGCATGTGAGATGGATTTCCTGACTACAGTGCACTGATTGGTCTTGACTCTTT
ATCCAATTTGCCAGTCTGTGTCTTTTAATTGCAGCATTTAGCCCATTTACATTTAAAGTTAATATTGTTA
TGTGTGAATTTGATCCTGTCATTGTGATGTTAGCTGGTTATTTTGCTCATTAGTTGATGCAGTTTCTTCC
TAGCCTTGATGGTCTTTACAATTTGGCATGTTTTGCAGTGGCTGGTACCAGTTGTTCCTTTCCATGTTT
AGTGCTTCCTTCAGGAGCTCTTTTAGGGCAGGCCTGGTGGTGACAAAATCAGCATTTGCTTGTCTGTGAA
GGATTTTGTTTCTCCTTCACTTATGAAGCTTCGTTGGCTGGATATGAAATTCTGGGTTGAAAATTCTTT
TCTTTAAGAATGTTGAATATTGGTCCCCACTCTCTTCTGGCTTGTAGAGTTTCTGCCGAGAGATCAGCTG
TTAGTCTGATGGGCTTCCCTTTGTGGGTAACCCAACCTTTCTCTCTGGCTGCCCTTAATATTTTTTCCTT
CATTTCAACTTTGGTGAATCTGACAATTATGTGTCTTGGAGTTGCTCTTCTCGAGGAGTATCTTTGTGGC
GTACTCTGTATTTCCTGAATCTGAACGTTGGCCTGCCTTGCTAGATTGGGGAAGTTCTCCTGGATAATAT
CCTGCAGAGTGTTTTCCAACTTGGTTCCCTTCTCCCCATCACTTTCAGGTACACCAATCAGACGTAGATT
TGGTCTTTTCACATAGTCCCATATTTCTTGGAGGCTTTGTTCGTTTCTTTTTATTCTTTTTTCTCTAAAC
TTCTCTTCTCACTTCATTTCATTCATTTCGTCTTCCATCACTGATAACCTTTCTTCCAGTTGATCCTATC
AGCTACTGAGGCTTCTGCATTTGTCATGTGGCTCTCTTGCCTTGGTTTTCAGCTCCATCAAGTCCTTTAA
GAACTTCTCTGCATTGGTTATTCTAGTTATCCATTTGTCTGATTTTTTTTCAAAGCTTTTAACTTCTTTG
CCATTGGTTTGAATTTCCACCTGTAGCTCAGAGTAGTTTGATCATCTGAAGCCTTCTTCTCTCAACTTGT
CAAAGTCATTCTCCATCCAGCTTGTTCCGTTGCTGGTGAGGAGCTGCATTCCTTTGGAGGAGGAGAGGC
GCTCTGATCTTTAGAGTTTCCAGTTTTTCTGCTCTGTTTTTTTCTCATCTTTGTGGTTTCATCTATCTTT
GGTCTTTGATGATGGTGACGTACAGATGGGTTTTTGGTGCGGATGTCCTTTCTGTTTGTTAGTTTTCCTT
CTAACAGACAGGACCCTCAGCTGCAGGTCTGTTAGAGTTTGCTAGAGGTCCACTGCAGACCCTGTTTGCC
TGGGTTTCAGCCTCAGTGGCTGTAGAAGAGCGGATATTGGTGAACCACAAATGCTGCTGCCTGATCGTTC
CTCTGGAAGTTTTGTCTCAGAGGAGTACCCGACCGTGTGAGGTGTCAGTCCGCCCCTACTGGGGGGTGCC
TCCCAGTTAGGCTACTCGGGGTCAGGGACCCACTTGAGGAGGCAGTCTGCCTGTTCTCAGATCTCAAGC
TGCGTGCTGGGAGAACCACTGCTCTCTTCAAAGCTGTCAGAGAGGGACATTTAAGTCTGCAGAGGTTACT
GCTGTCTTTTTGTTTGTCTGTGCCCTGCCCCAGAGATGGAGCCTACAGAGGCAGGCAGGTGTCCTTGAG
CTGTGGTGGGCTCCACCCAGTTCGAGCTTCCCAGCCGCTTTGTTTACCTAATCAAACAACTAACTCAGCA
ATGGTGGCCGCCCCTCCCCCAGCCTCGCTGCCACCTTGCAGTTTGATCTTGGATGGCTGTGCTTGCAATG
AGCGAGACTCTGTGGGCATAGGACCCTCCAAGCCAGGTGCAGGATATAATCTCCTGGTGTGCTGTTTTTT
AAGCCGGTTGGAAAAGCACAGTATTAGGGTGGGAGTGACCCAATTTTCCAGGTGCCGTCTGTCACCCCTT
TCTCTGACTAGGAAAGGGAATTCCCTGACCCCTTGTGCTTCCCGGGTGAGGCAATGCCTCGCCCTGCTTT
GGCTTGCGCACGGTGCGCTTCACCCACTGTCCTGCACCTACTGTCTGGCACTCCCCAGTGAGATGAACCC
```

FIG. 5 (continued)

GGTACCTCAGTTGGAAATGCAGAAATCACCAGTCTTCTGTGTTGCTCATGCTGGGAGCTGTAGACCAGAG
CTGTTCCTATTTGGCCATCTTGGCTCCTCCCCTCAGCACAGTTTTTAGCATGAACTAAGGCCTCAATAAA
TATTAGTTCCCTTCTCCAATTCAGAAAGTTGTCTGCCTTGATAAGACAATTGTTTTTATTGTGAAAGTGA
GGTGGAGATGGGGGATTGTCTCTCCTATAAAAGGTCTAAGAAGTTAGCAAATGCTGTTTTTCCTTTTTGC
TCCTCAGTTGCATAAGTACATGGTAGAAATTGGGTCACTTTGCCTAAACCGGTTTTCTATAACCTATTAA
GTATTAAAAGCTTGACACAGATAAGTAGAGGCTGATAAGATTCTGTCCTGCACCCCACTCCTATCAAATT
TGGAAGAACTGACCTCTTCCGGGAAGAATTGCAATGCTAAATCCAAATGCCTATGGTTCTATCTTATAAA
CAAATGGTGTCCTCAAAATTCATTTATGTAAATCATTTGAAATTTAAGAAAAAAATATGTTCAGAGAAAA
ATATGTTAAATGTCAAGGTGAATTAGAAAGTGTGGCATTTAGTCAAGCATAAATTAATATTCCAACTTTC
TAGTTACTTTGTAGTAACTTATTTAACATTTTGGTGAAATGAGGAACAAAGTGTCCACCTTTTTTTCCTG
AATATTTTATCTGAAGATCTAGGAGAGAGATGTGAAATAGTATTTTTCTGGGGAAGTAGGGGAAATACAA
AGAAAAGTAATGACTTCAGGTATATTCTCCACTGGTACAGCAGGATGGGAGATATTATCAACAGGTGGTA
AGTATAAAAATATTGAAGAGGTACAATTTGGATCAGCATTACAACCAAGAATGGAGAATGACATTCAGGA
TTGAAAGAAACATACAAGAGGGCAGAAAGCTTTCTTCTTGGGACTGTGGTTTCATGTGTCTGCAGGTGCT
ATGGGTATATTGAGAATGGTTCTAAAAACAGGGGCTTGGTTTAGGTTGTGAAGACCATCAAATAGAAACT
GTGAATTTTATTTGTGTCGTTAAAGGGATCTTTGAAAGATTCTTAGGATAAATATGATATGCATAGGAT
AGAAAGAAAGGTGGGAGACAGGACAAACAGAAGTTAATCAATTGAAATAAACCAGGTTTGGAGTGGTGGG
ACAATAGCCTTCAAGACATCAAGAATATTTGTTAGTAGAAAGAAAATCGAAGCCTAAAACTAAAGGAAGA
CTATCCACCTTGCAAGTCATACAGAGATATTTGCTATTATATAATTTTTTTAAAAAAAGATTTCCTAATA
TTTAAATTATGAAGAAAGAGATAGAAACAGATATTCATGGAAAAAATGGGGTGAAATTAATCAAAGGGCA
GCTTATTACCTTGAGACTAAACAGCCATTGACTTTTTTCTTACCTCACTGAACCCAGAAACCCGACATAT
CTAGGTACAGGCATGCATAAAACATGTACACACACAAAATGTAATAATTGGAGTTCACTTAGAGGTACAC
ATGTATGGGTTTCTGTATTCAACCATATGTTGATATATACTCACATATATGTAAGTGATAATATCCTGTT
TGTTACTTCCACATTTATGCACTATCCCTTAAATATGTATTATATATATTTATATTATTCAGAATCCATC
AGCCCTTGTTGAATAAATTAGTGAATAAAATATAGAGTCGAGTCTCATTATTCACAGATTCTATATAAGA
AAATTTGTCTATTCACTAAAATTCCTTTGTAACACCAAAATCAATACTGCTGGACTTTCATGGGCATTCA
CATGCATGTGCAAAGTGGTGAAAAATTTGAGCTGCCATGTTCCCAACTAAGGTTGAACAAAATGAAGCTC
TGTCTTCTTGTTTCTGCTCACATATGATAAAGAAATATCCTTTCACACTGTATTTATTGCCACATTTTT
GGCATTTTTGTGTTTTGTGTTTCTGAGTTGAATGTTTCGAATGGGCCCCAAAGATAGTGCTGAAGTGCTC
TCCGGTGCACAAGAGTATCTGAGGGAAAAGATACATATGCTGTATAAGCTTCCTCCAGGCCTGAACTACA
GTGTTGTTGACAACTAATTCAATGTTAATGAATCAATAGTATGTATTAAATAAAGTGTCTTTAAACAAAA
CATACATAAAACACAGTTCTATATTGAACAATTTACCAAAATATTGTGACCAGAGGCAGACAGGCATATA
ACTAACCCCACATCTCTCCAAGGAACAATGGTTCAATATTTGCTAATTCAGTGTTCCCAGCAACTTTATA
AAACATAACTACTGCAACAAGTATCAACTGTACATATAATATATATTAGACATATTGTATAATTACTGCC
CTATTAAAAATCATGTATCTATGCTGTGTCTGCTTATATAGATATCTTAGATACATAAATATGTATTGTT
TACATACATAGGAGCAAGAATGTATTTCTAAAACTCCATGAAGAACACATTATATTCTATATAAAAGAGT
CAGTTGAAGTAAAAAGTTAACTCATTTTACTAGTCTTTAAAGTAGGACTTTAATGACTCTCAAAATAACA
ATTTCTCTCATACATTGACTCCAAAACTTTAGTTGTTGAATTTATTCTGCAGATATGGCCACATAAAACC
AAAATGGCATATGATATATTAAGAACATCTTTAATATGAAATGATTAGATACAACCTAAAAGCTGATGAA
TATGAACCAGTTGCATATATTATGGACAACTTAATACCCTGCTACCATAAGAAAAATGAGAAAGACTTA
TTAAGATTAAGTATATAGAAGATAAAAAGGTAGAGAATGATGTTTAAGGTATGCTACCATTTGCATTG
AAAAGGAAAATATTATGTACTTAATGAAAAATCCATATTATATTTCTGGATAATGGGACAAGAGTTAGAG
GAAGAATCTTTGTTTTATTTTTTTAATTTGCATTTTCAACTATATGCATTTTCTCTTGGAAAAGAAATGA
ACAAAATCAAAATAAAGTAACATCATGATGGTGGTAAGGTCAAGCAATACCAGAGTTGCTCTGAGAAGTA
CTTGGAGTACACTTTGCTCTTTTTAACAAATCCAAATTCTGTTTGCTTTTTGAGCCTGATTCCAGTGGTG
TCTCCTTTATAAAACTGAGGCCATTCTAATTTAATTCTTTATATTATTTTTGTATCTGTTTTGAATATCT
ACTCTGTGCAAGGGGCTAATAGGCACATTTTAAAACTAGAAGGATAAAGAAAACATATATTTGCTTTTAT
AAATTTTACAATATAGGTGTGTAGAAAAGATAATAATTTAAATTTCTATAATTTAAAATGTTCATGTAAT
CTGGTGTGTGATTCTATATTACTTACTTGTTTCAAATTTCTCTCCACAAATTTATTTTTCTATTTAAATTG
TAATCTCCTTAGGCTAGAATTTGTGTCTGTCTTTCCTACTTTTGTTTCCAGCATTGACCTAGCAGAGTGG
TAACGACATAGTAGACCCTGAGTGAATGTTAGTGAATGGTTGATTGATTGATGATGATCTTGTGGCTTTT
CTTATTTCTAAATTATATATTGTAAAAATAAAATAAACTATACTTTTTCTTCCTTAATAGGTGATTGTTT
CAAACTGAGCATCAACAACAAAACATTTGTATGATATCTATATTTCAATCATGGACCAAAATCAACATT
TGAATAAAACAGCAGAGGCACAACCTTCAGAGAATAAGAAAACAAGATACTGCAATGGATTGAAGGTAGA
ATAAGTTTTATGTTTTTGAGCTAAAATAAGTAAATAGGGAACTTTAATGTATAGAAAGCAAGTTGTTAA
AAAGAACATTATGTTTCAAATTATAATTTTCAATTGAAGCATATATTGAAATATTAACATAATGATTCAT
ACCTTGATTTAAACCAGTCTTTTAATCTGATTAAGTATTTCTTTGGCGAAATTTTTGATGCTTAATAGTT

FIG. 5 (continued)

```
TATCAATGTAGAAAATTTAGAAATATTTTGATAGCTTCTCTTTGGTTTTGGATTGATCACGACATATTTA
GGAATGTGATTAAAATAAAAAATGCATAATGAATAATATTTTAAAATTCTTAGAATTGACTTATAAACTT
AGAATATTAATGTCTTGAGACTCACTTTGTGATACTGACTTATTTAAAAATTCTTTTAAAAAAAAAAACA
AAAAACAGGATTTAAAAAAGTTCTGATAAGTAATTTAGGCTCATGGAACGGAGGTCTATGATAGTCAAAA
ACTTGGCCAAAAGACCTGTTTGACGATTTAGAAAAGCCATTTAATGTTTTCATTTGCCAGCTGGTAAAAG
TAATAATTCTGCTTTTTGCTTTTGGCACAAACTGTATTAAATGATACAGTTGAGGTATTAAGTGATGCTG
GCATTTTTATAAACAGGAATGAGTACTCCTAAGCACAATGCTAAATGAGAAGCCAAGACTCAGAAAAGTT
AAGAAATTTTCCTGAAGTCATCTACATTGTGAATTGAAAACCCTGGAACCCAAGACAAAGCCTTTAAATC
CCCATATGGAAGTCTTGAGGAAATCAAGAAATAAGGGTCACCTTTTATCAATGTTTTAACTTTTTTATTT
AGTCAAATTTGTAGTCTTATACAGCTGAATAAAGGCCACCAAGATTGGAGTCAATTACAATAATGTTATA
AAAGGTTCCTTTTAGCTCCTTCCAGGGAACATAAAATTTGTTTGTTTTCTGAGATTACTGATAAAGCCTT
CTCTGATGAAATATTTGAGTAACATTTAGGCCAAGTGGCAGTCATAAGGAAAAAGTATTGGTTAATGCAA
GTGAATTATGTTCTATATTCTAAGGATAATATAATGTACTGAATTGTTTTATTTTAAATACTGAGTGT
TACAGTAATTTCACTGACATGTGCATAGCAAAATGGCAGCAAACTGCCTGAAGCAATAAAATTTCCAGAG
TGATCCCTTATAGCATATCTGGAGAAGCTGGGAGTTAGGGAATTAGCAGTGTGTGGAAAGGACATTAACT
GCAGCCCAATAAAGAAGACTAGAGCTAGAGGAAGATACTGGGATAAGACTGGCATCCCTAATGCTGGTAT
TTCAGAAACATCGCTAAATTGGTTAATCATGTCTACAAGTGATATTTAAAATAATATTTTCACTCACTTA
AATTGTTAACATTGATATGTTGTTGATAAAGAATATTAAACTCAACAATCATTTTACAATAATTCTGTAA
AGACTTGCGTGCCTGTAGTTGAGGTTTGTTGCATTTCTGAGCTTACTTTTTATTCATGAGAAATGAAAAC
ATAATGGGAGAAAATTTTTAAATAAAGGGTATTTTAATTTTTTATGAAGTTTGGGACTTCAAAGTATTA
ACAAAAGTTGCTGAAAATATATTGACTTTTACTTTCATTAAATTACATTTTATCATCTAATTTCTTAATT
TTCTGTATTTGAAATATTATGATTTAGAGATATCTCTGTAGATAGAAAGATAATGAAAACAATAGTAAAA
CAAATGTAATTCAGGAGCATAAAAAAAGATGAGAGAAACCTTAATAATAGTAGCTAACATTTATCAAGCA
TTTACTATATGCCAGACATTGATTTAGTGTTTTACTTTTGCTAACAGATTTTTTCCTTACCATAATTCTA
TCAACTGGATGGTATTATCTCCCCTTTTCAGATGAAAAAACCTAGATATAGACAGGGCAAATGTCTTCTC
CTAGGTCTCAAAGTTGGTAATTGGTACACTGAAGGTCTGAACTCAGGCAATCTGATTCCAAATCCTATGC
TCTCAACTGTATTCCATATTGCTAAAATAAATGTGGATTTTTGTAATATTAGTACCCTCAAGATGTTATG
GCAAGCAGGCTTTTATAAGTGGTGTCTTTAATAACTTTCCTCATTCCATACTTCTAAAAAATTATCTTAA
GGTTAAATTATTGAGTGTCAAGCAACTGTGGATTCTAACACTTGCTAACATGCATGCACACACCCAAATA
TACATGTTGTTACTGACTTACATATACAGACACAGCAGGTGGCAATATATAAGTGCAAATTGATAATATA
TCCGTGGAAATACAAACAAAACTTTGAGAAATCAAATACTTGAATTCTTTTCTACCCCTTCTCCTCAATT
TTTGTACTGAACTAACTACATTACATAGAACCTGCTAGTATATGTTTCATCATTACACTTGTCATTTCTT
CTCTTCAAATTTAAACCCAACAAGATACAGGGGAAGATTTAAATGCAATCCAAAGAAAACAGGAAAACAA
TTCAAGAGTTTAAAGATGACATAGTCATTTTAAGAAAGAACCAAAATTAACTTCTGAAATTAAATATTTT
ACTACAGGAATTTCATAATACAATTATAGTAATTAACAACAAAATAGACCAAGCTTAAGAAAGAATCTCA
GAGTTTGAAGATTACCCCTTTGAATCAACACAAGCAGACAAAATTAAAGGAAAAATATTAATGAAAAAAA
CCTCTGAGAAATATGGGATTATGTAAAGAGACCAAGCCTGTGACTCATTGGCATTCCTGAAAGAGGAGAA
AGAGTAAGCAACTTGGAAAATGTCTTTGAGGATAAAGTCCATGAAAAATTTCCCAGTCTTGCTAGAGAGG
TGGATATGCAAGTTCAAAAAATTCAAAGAATCCCTTCAAGATACTATACAAGATGGTCATCCACAAGACA
CATAATCATCAGATTCTCCAAGGTAAACAAGAAAGAAAAAAACCTTAAAGGCAGCTAGAGAGAAGGGGCA
GGTCACTTACAAAAGGAGCCCCATCAGTCTAACAATAGATCTTTCAGCAGAAAGCTTACAAGCTAGAAGA
GATTGGGGACCTATTTTCACCATCCTTAAAGAAAAGAAATTGCAACTAAGAATTTTATATTCTGCCAAAC
TAAGCTTCATAAGTAAAGAAAAAATATTATTTTCGGTCAAGCAAATGCTAACAGAATTTGTTACCATTAG
ACCTGCCTTACCAGAGATGCTTAAGGGAGTCCTAAACATGAAAGAATGATACCTGTCACCACAA
AAATAGACTTAACTACAGAGCCCACAGACATTATAAAGCAATTATGCAATCAAGCCAACATAATAACCAG
CTAACAACACTATGACAGAATCAAATCCTCACATATCAGTATTAATCTTGAATGTAAATGGGTTAAATGC
CTACACTTAAAAGGCATAGAATAGCAAGTTGGATAAAGAAGCAAGACCCAACCGTTTTGTTGTCTTCATG
ACTCATGTATCATGACATCCATAAGATAGAAAATGAATAAATTGAAATAATATTTATCTCAGAGTTGTCA
GGATATTTATAAGGTGCTTAGCACAGTGTTACATAGAAACTCAATAAATTGGAAAGTTCCAACATAGTAG
CATTATAGTTGCTGCACTTTTTTGAGACAGGGCCTCTGTCACCCAGGCTGGAGTGCAGTGGCATAATCT
TGGCTCACTGCAAACTCCACCTCCCAGGCTCAAGTGATTCTCCCACCTCCTGAGTAGCTGGAACTACAGG
CACATGCCACTTCACCCAGCATTTTTTCATTTTTTTTTTTTTTTTTTTTTTTAGTAGAGATGAGGT
CTTACCTTGTTGCCAGGCTGGTCTTAAATTCCTAGGCTCAAGCAATCAGCCCGCCTTGGCCTCCTAAAGT
GCTGGAATTACAGGTATGAGCCATCACATCTGGAAGCTGTTTCTTTTTAAAGTGACTACATTAATTTACT
TGATCACGAGTAATACATAAATGAAAATTTGAGAATACATTCACTCCAATATTTGGAATTATGTGACTTC
TAGATTTTTGCAATTTAAGTAGGCATAAAATGGTACTTTGTTTTAGTATTTGTCTGTGCTCCTTGATTCT
TATAAATATTATATTTTGTGAAATCCATTGCTGAATGCAAGTGGTGCTGGTTACATTTGCCTATTTCCAA
```

FIG. 5 (continued)

```
GTTTTAGTACATTTATTTTTGAAATATATTTTATCAGTTTAAGGACTTACTTGTAATATCTTTGTGTGGT
CTTGGTATTAGGTTAATGTTGGCCTCAATAAATGAGATAGGAAGTATTTTTTCTGCTTCTAACCTCTGA
AAAAAACTGTAGAGAATTGATATAAATTAATTCTTAGGTATTTGGTAGAATTCAACAGTGAAACCATGTA
GGCCTGTTTCTTTCTGTTTTGGAAAGTTATTAAAATCAGTTCAATTTCTTAAACAGAAATAGTCCTTTTA
ATATTGTCTATTTATTCTTGTACAAAATTGGGTAGATCGTGTCTTTCAATATATTGGTCTATTTTATATA
GGTTATCATAGTTGTAGGCAGAGTGTTGCTTATAGTATTTCTTTATTATCCTTTTCATGTATATTGGATC
TGTAGTTATGTCCCCGCCTTTATTTCTGTTATTAGTAATTTGTGCCTTCCCTCATCTTCTTAGGTAACCT
GGCTGGGTCAATTTTATTAATCTTTCTAAAGAATTAACTTGTGGTTTTGTCAATTTCCTCTATTGATTTC
CTGTTTATGATTTAATTGATTTCAGGTCCAATTTTTATTCTATTTTTTCTTGTGCTTACTTAAAATTTAA
TTTGCTTTTCTTTTTGATTTTCCCAAGGTGGAAACTTAGATATTGATTTTAGCATTTTCTTGTTTTCTAA
CATATGCATTCAGTGCAATAAATCTCTAAGTCTTGATTTTGCTACCTTTCACAAATTTTGATCACTTGTA
TGTTTAATTTTATTTTTTTCAAGATGTTTTAAAATTTTTCTTCAGATTTCTTTTGACTCATAAGTTACTT
AAAAGTGTGGTAGTTAATCTCCACATATTTTGGTATTTTTCCAGTTATCTTTCTGTTATATTCTAGCTTA
ATTTCATTGTCATCTAAGAGAAGACATTATTAGTTTAAATGTGTTAAGGTGTGTTTTATGGCTTAGGCTG
TGGTATATATTGGTGAATATTCCATGTAAGCTTAAGAAGAATGTGTATTCTGTTGTTGTTGGATGAAATA
ACATATAGATGTTTATTATATCCAGTTAATTGATGATGTTGTTAAGGTCAATCATGTTCTTCCTGTTTTT
ACCTGCTGGATCTTTCCATTTCTAGAGAGATGTAGAGTCTCCAAATACCATAGTGTATTCATTTATTTCT
CCTTGTATTTCTACTGGCTTTTACTTCAGATAGTTTGCAGCTCTGTTGTTTGGTGCCTCTATGTTAAGAA
GTGTTATGTTTTCTTAAGAATTGACCCCTTTAACATTTTGTAATGCCCCGTTTTTACCTCTGTTAATTTC
CTTGCTTTAGAGTCTGCTGTGTCCAAAATTAATTTAGATTGTCTTGCTTTGTTTTGGTTATTGTTACCAT
GGAATGTTTTCTCCACTTCTTTACTTTTTAAAAAATTACACTTTAAGTTCTGGGATACATGTGCAGAA
TGTGCACATTTGTTACATAGGTAAACACATGCCATGGTGGTTTGCTGCACCCATCAACCCGTCATCTACA
TTAGGAATTTCTCCTAATGCTACTCCCTAGCCCCCCAACCCCCAACAGGTGCTGGTGTGTAATGTTCCCC
TCCCTGTGTCCATGTGTTCTCATTGTTCAACTCCCACTTATGAGTGGGAACATGCAGTGTTTGGATTTCT
GCTCCTATGTTAGTTTACTGAGAATGATGGTTTCCAGCTTCATCCATGTCCCTGCAAAGGACATAAACTC
ATTCTTTCTTTTGGCTGCATAGTATTCCATGGTGTATATGTGCCACATTTTATTTATCCATTCAATTATT
GATGGGCATTTGGGTTGGTTCCAAGTCTTTGCTATTGTGAATAGTGCTGCAATAAACATACATGTGCATG
TGTCTTTATAGTAGAATGATTTATAATCCTATGGATACATTCAACAATGGTTGAATTAATTTACACTCCC
ACCAACAGGGTAAAAGCATTCCTATTTCTCCACATCCTCTCCAGCATCTGTTGTTTCCTGACTTTTTAAT
GATCGCTTCCAACTGGCGTGAGATAGTATCTCATTGCAGTTTTGATTTGCATTCTCTAATGACCAGTGAT
GATGAGCTTTTTTAATATGTTTGTTGGCCACATAAATGTCTTATTTTGAGAAGTGTCTGTTCATATCCTT
GGCCCACTTTTTGATGGCATTGTTTGTTTCTTTCTTGTAAATTTGTTTAAGTTCCTTGTAGATTCTGGAT
ATTAGCTCTTTGTCAGATGGATAGATTGTAAAAATTTTCTCCCCATTCTGTAGGTTGCCTGTTCACTCTGA
TGATAGTTTCTTTTGCTATGCAGGAGCTTTTTAGTTTAATTAGATCCCATTTGTCAATCTGGGTTTTTGT
TGCCATTGCTTTTTGTGTTTAGTCATGAAGTATTTGTCCATGCCTATGTCCTGAATGGTATTGCCTAGG
TTTTGTTCTAGGGTTTTTATGGTGTTAGGTCTTACATTTAAGTCTTTAATCCATCTTGAGTTAATTTTTG
AATAAGGTGTAAGAAAGGGGTCCAGTTTCAATTTTCTGCATATGGCTAGCCAGTTTTCCCAACATCATAT
ATATTAAGAAGGGAATCCTTTTTCCATTGCTTTTTTGGTCAGACTTGTCAAAGATCGGATGGTTGTAGA
TATGTGGCATTATTTCTGAGGTCTCTGTTCTGTTCCATTGGTCTATATATCGTTTTGGTAAAAGTACCA
TGCTGTGTTGGTTACTGGAGGCTTGTAGTATCATTTAAAGTCAGGAAGCATGATGCCTCCAGCTTTGTTC
TTTTTGCTTAGGATTGTCTTGGCTATATGGGCTTTTTTTTTTTTTTTTTGGTTCCATATGAAATTTA
AAGTAGTTTTTTCCAATTCTGTGATGAAAGTCAATGGTAGCTTGATGGGGATAGCATTGAATCTATAAAT
TACTTTGGGCAGTATGGCCATTTTTACAATATTGATTCTTCCTATCCATGAGCATAGAATGTTTTCCAT
TTATTTGTGTCCTCTCTTATTTCATTGAGCAGTGGTTTGTAGTTCTCGTTGAAGAGGTCCCTCACACCCC
TTGTAAGTTGTATTCCTAGGTATTTTATTCTCATTGTAGCAATTGTGAATGGAAGTTCACTCATGATTTG
GCTCTCTGTTTGTCTATTATTGGTGTATAGGAATGCTTGTGATTTTTACACATTGATTTGTATCCTGAG
ACTTTGCTGAAGTTGCTTATCAGCTTAAGGAGATTTTGGGCTGAGACAATGGGGTTTTCTAAATATACAA
TCATATCATCTGCAAACAAAGACAATTTGACTTCCTCCTCCTTATTTGAGTATCTTTTATTTATTTCTC
TTGCCTGATTGCCCTGGCCAGAACTTCCAATACTATGTTGAATAGGAGTGGTGAGAGAGGGCATCCTTGT
CTTGTGCCGGTTTTCAAAGGGAATGCTTCCAGCTTTCACCCATTCAGTATGATATTGGCTGTGGGTTTGT
TATAGATAGCTCTTATTATTTTGAGATATATTCCATCAATACCTAGTTTATTGAGAGATTTTAGCACAGC
TCCAGTGTGCAGCTCCCAAAAAGATCAACGCAGAAGGTGGGTGATTTCTGCATTTCCAACTGAGGTACCC
AGCTCATCTCTTTGAGACTGGTTAGACAGTGGGTGCAGCCAACAGGGGCAAGCCGAAGCAGGGTAGGGT
GTCACCTAACCTGGGAAGTGCAAGTTGTCAGGAAACTTCCTCCCCTAGCCAAGGGAAGCCACGAGGGACT
GTGCCCTGAGGAAAAGTGCATTCTGGTCCAGATACTATGCTTTTCCCAGTCTTTGCCACTGGCAGACCAG
GAGATTCCCTCGGGTGCCTACACCACCAGGGCCCTGGGTTGCAAGCACAAAACTGGGTGGCTGTTTGGGC
AGACACTGAGATAGCTGCAGGATTTTCTTTTTAAACCCCAGTGGTGCCTGGGACACCAGCAAGACAGAAC
```

FIG. 5 (continued)

```
CCTTCACTCCCCTGGAAAAGGGGCTGAAGCTAGGGAACCAAGTGGTCTAGCTCAGTGGATCCCACCCCCA
TAGAGCCCAGCAAGCTGAGATCCACTGGCTTGAAATTCTCCTTGCCAGCCGAGCAGTCTGAAGTCAACCC
GGGATGCTCGAGCTTGGTAGGGGGAGGGGTGTCTGCCATTACTGAGGCTTGAGTAGGTGCTTTTCCCTCA
CAATGCAAACAAAGCCACTAGGAACTGGGTGGAGCCCACCGCAGCTCCACAAAGCCCCTGTAGCCAGACT
GCCTCTCTAGATTCCTCCTCTCTGGGCAGGGCATCTCTTAAAGAAAGGCAGCAGCCCCAGTCACGGGCTT
ATATATAAAATTCCCTCTATCTGGGACAGAGCACCTGGGAGAAGGGGCAGCTGTGGGCGCAGCTTCAGCA
GACTTAAACTATCCTGCCTGCTGGCTCTGAAGAGGGCAGTGGATCTCCTAGCACCATTCTCAAGCTCTGC
TAAGGGACAGACTGCCTCCTTAAGTGGGTCCCTGACTCCCGTGCCTCCTGACTGGGAGACACCTCACAGC
AGGGTTCAACAGACACCTCATGCAGGAGAGTTCTGGCTGGCATCTGGTGGGTGCCCCTCTGGAATGAAGC
TTCCAGAGGAAGGAACAGGCCGCAATCTCTGCTGTTCTGCAGCCACTGCTGGTGATACCTAGGCAAACAG
GGTCTGGAGTGGACCTCCAGCAAACTCCAGCAGACCTGCAGCTGAGGGGCCTGACTGTTAGAAGAAAAAC
CTACAAACAGAAAGGAATAGCATCAACATCAACAAAAAGGATGTCCACACAAAAACCCCATCTGAAAGGC
ACCAACATCAAAGACCAAAGGTAGATAAATCCACGAAGATGAGGAAAAACAAGTGCAAAAAGGCTGAAAA
TTCCAAAACCCAGAATGCCTCATCTCCTCCAAAGGATCATGTTTACTTTTAATCTATATGTGTTTATATA
TTTAAAGTGGGTTTCATGTAGACAACATATAGTTGGTTCTTGTTACTTGATCTACTGTGTCAATTTCAAT
CTTTTAATTAATACATTTAGATCATTTGCGTTAAAAGTGATTACTGATATATAGTCATGTGTCATTTAAC
AACAGGAATGCATTATGAGAAATGCATTGTTAGATAATTTTGTCATTGTGCAAACATCTTAGCGTGTACA
TACATAAACCTAGATATTATAGCCTACTACACACCTAAGCTTATGGTATAGGCTATTACTTTGATGCTAC
CAAAACCTGTACATTATTGTAGTTTACTAAATACTAATTACAACACAGTGATATTGGTGTATCTAAACAT
ATCTGAGCACAGAAAAGATAAAGTAAAAATATGGTATTATAATCTTATGGGACCATCATTGTATATGCTC
TCCAACATTGACTTAAATGTCATTATGACATGTGTGACTGTAGTTAGATTAGTATCTACCATAGCGGTTG
GGTTGCCTGGGTGTTTGCAAGATAAATTTACAAATAATTCAAGTCCACTTTCACGTGACGTCATACCACT
TCATGGGTAGTATGAGTACCTGATAATAGCAAATTATTTATAATACTTTCCTTCCATTTCTTGTATCATT
ATTGTCATTCATTTCAATTTTGTGTCAGCATACATAATCAAATACATTATAGATATTATTTTAAAAACAG
TTATGTCTTAGATTAAGAATAAGAAAAGTAATAATTTATATTTTATGCTCACTTATTTCTCCTCCAATGT
TTTCCTTGCTTTAAGTAGATCTGAGTTTCTGATTTATATTATTTTATCTTTCTGTAAAGAACTCCTTTTA
ACACCTTGCAAGGCTGATCTAAAGGCAAAACATTTCTTTCAGTTTCATTTCTCAGAGGAAGTTTTATTTC
TCCTTCATGTTAGATGGATAAATACACAGGGTATGGGGAAGGTATTTTTTCCTCTGTATTCTTTTGGGAT
TTTTTTCCTTTGTCTGTGATTTTCTATAGTTTTAAAATGACATGACTAGGTGTAACTTTTTGGGCATTTA
TACAACTTGTTATTCTATGGACTTCCAGGATCTGTGGTTTGTTGTCTGATACTAATTTGGGGAAATTCTC
GGTTGTTATTGTTTCAAATATTTCTTTAGTCTCTATTTCTCCTTCTAGTGATTCCATTATGTATATGCTA
TACCTTTTTTAGTTGGCCCACAGTTTTTTGATACTTTGTTCTGATTTTTTTTGTCTTTGTTATTTTTATTT
GCTTTTTAGTTTTGCAGATTTTAATTCATATATCTGAATCTCAGATATCCTGTTTTCAGTCTTGTGCAG
TATACTGATGTGTTTACCAAAGGCATTCTTCATTTCTGCTACGATGTTGTGACATTATAATTTTTTTAAT
GAAATTTTTATCTGTCTGCTTACATTGCTCTGTTCTTGTGTGCTTCTTTATTTTACCACTAGAACACTTA
GCATATTAATCACAGTTGTTTTAAATTCTCAGTCCAATAAATCCAACATCCTTTCTGTATCTGAGTTTGG
TTCTGATTCTTGCTCTGTCTCTTCAAAATTATATATATTTTTTTCTTTTAGATGACTGGTAATATATTC
TGGATATCCAGACATAATGTATTGAGTTTTGTAAAACCTGCTATACATAGGCCTTCAATAATTGTTGCTA
AGGTGTGGGAGAGGAGAGGCTTTTTTTTTTTTTTTGCCTCTGGACTGTAACCTTCACAAGTGTTTTT
TTAGTATTTTTTTCCTTCTTGGTCAGAATGGGTTTGGTAGAGTGAGATGGATTTGGTATTTTCCTTCT
GTCACATGGAAGACTAGAATTGGCTGGAGCTGGGTATTTCCTTTCCCTTCGGTCAGTTAGGCTCTAATAA
CACACCATCTTATGAGGCTCTGATAAACTAGTTCTGCCTAAGGGCAAGCACTAAAAGTCCTATTAAAAAC
AGAGGGCTCTAGTCTATTTCAAAAATGAGTCTTGTCTCCTCATGCTACTGAAAGAACAAGATAATTTTTC
TCCAACATTTACTATAAGAACCTGGTCAAGCTCCTGGAGGGAAAACTCAAAATGTGGAGGTCACCGACTG
GGTTCCCTTGGAGTGTTTAGTGCTCAGACTTAACCACACTGAGTGAGACTCTAGCAGTTTATCAATTATA
GTGAAGGTATTTCTACCTTGTCACTGGTTCCTGTGCAGTTTCTGTTCATGAGTCTCTACTGCTATAAGCT
GTGACACTTTGTAATCACCTATTTGTCTCTCCAATCTTGAAGGCAGTCGATTGCCATTGGTCCTCACCTC
TTTTACAGATCCAGAAAGAGTTGCTGCATTTAAATTGGTTCAGTGTTTTTCTTGTTGTTACTATAAAAT
GGCAAGCTCCAAGCTCCTTGAAGGTTTCCAGAGCCTAGAAACCAGAAATACCAGCATATATTTTTTATTG
TATTTTCTTATCTCATGTCTTACAGTTCTACATTTTACTTAAGAATTCATTGTGATTGCTTGATTAATAT
ACAAGTTATTTAAAATAACATTTTCTTCAAATATTTGGAGATTTTTCGTAATAAATTTTTGCCAGTAA
TATTTGTCATAATTGCATTGTGGAAGCTATGACAACTAATTTTTGAAATTAGTTGAGACTTCTCTATGTC
CTAGTACATCATTGATGTTTGTAAGTCTCCCTGATGTACTTAATAAAAATGCATATTCCATATTCTTTCA
ATTGTTGGATGTATAATTTTATATGTGTCTGAGAGGTCAGTCTTGTTAATTGTGTTATTCAGATCTTCTA
TGTCCTTGCTAATATTTTAACTATTTCACTTATCATAATTGAAAGAAAGATGTTGAATTTTTTCTTACA
AAAGCAGTTGTATTGATTTTTGCTTATATATTTTGCATCTACTAAGTGCATTATTATATAACCGTTTTAT
CTTTTAGGATGATATAATTCAATATATGGAGGACTTCTCTATCCTTAATGATGTTTCTATGTCTATTTGG
```

FIG. 5 (continued)

```
GCTATTATTTATACACCTATAAAATTTTCTCTAAGTGGTTATATTTTCTTATCATTTTACTATCACGAAG
AATTTCTTCGTGATTTAGGAATATCTCTTATAAAAAGCACAGAGGTAAATTTTGAAGAAAAATCCAAACT
AAAAATTATCTATCTTTAAACTAGCAATTTTCTACACTTATGTTTATTGTATCTATTGATATAGTTAGAC
TTGCTTTTACTATCTTACATTATTATGGTGATTTTCCCCTTTTTTAATGCTCCCTTAAAATTCTTTCTTA
TACTTTTTGAATGTATATGCCTATCTCTCTCATAACAAGACAAACATTCTAGCATGATTCTATGATCTGA
ATGTTTGTTTCCCCCCAAATTTGTATGTCGAGTCATAATCACCAAGGTGATTCTATTAGAAGGTGGAGAC
TTTGGAAAGTGATTAGTTCATGAAGGTAGAGTCCTCATGAACAAAATTAGTGTCCTTATGAAAGAGACCC
AATAGAGCTTCCTTGCCTCTTCTAACATGTGAGGTTACAGTGAGAAGATGGTTCTCACCAAATACCAAAT
ATGTTGGTGTCTTGATCTCAGACTTCCCAGGCTCCAGAGCTGCAAAAAGTAAATTTCTATTGTTTATAAA
GTACACAGTTTTCTTATATGCTATATTTGCTATATTTTCTTACAGCACCCCAAACAGACTGAGACATAT
GTTCACATACTCTTTTATATGCCTCTTTACCCTCTATACAATATGATGCTATCTGGATTTTCAATCTAAA
ATTTTAAATTCTAGACACTATGACTATTTTACCTCCTTTCCTGTTTTTAGTTTTTTTTTAAGACATTGAG
AAAATTTATCAAGTATTTTATTCACTTTGCTTTACAAATCTCATGCAACACCTTCAGAATTGGATTCTTC
TTTTATTTAAGCAATTCTTCCAAAATTGTTTCCAGTACGTGTTTGGTTGCAGTATTTTTGAGGCCTTATA
TGCTTGAGCATATATCTCTTTATAGCTGAGAGGCTGTTTATCTCAATGTAAAATTATGGGTTCAATGCTC
TTTTACTTCAGTACTTAAAAAATATATTTCTTTGTCTTTTGTGTACCCACTTTTGCTGTTAGAAAGTGAT
ATACTTTCTTTCCTGAAAGGCCTCAATTTTTTTCTTGTCTTTGATATTCATAAATTTTAATATACTTCT
TCCAAATATGTCTGTGTTCTTACTTATCTCTTGTGTTGAGCATTCAATGGGCACTCTCAACCTGCATTTT
TTGTTTTTTTAATCTTAGTAAATTATTTGAAAATTTTCATTTATTATTTCTTTAAATATTTCTCCTCTT
CAACTTATTTTTTCTCATTTTAAGGCATTAATAATTAAATTATTCTCAATTTTAGTTAAAAATTATGTAT
ATCTTAACCTTTTACCTATATATGCTTTCAATGTTTTAAATGAAATAACCAATTTTATTTTCCAATTCTT
TCTTGTTTTAAGCCCATATATTATTTTATACTATTTTACATCTTGTACTCCATATTTTCTACTTGTTCTT
TTTTGTTATCTTATTTTGCTTTTATTTCATTTTGCTAATATTCTTTTCTTATATATTTTGTGTATTTGTA
ATGCTTAAACTCCTGTTAAGTGTTTTGTAAAACAATTACTCCTTATGGTGTCTTCAAACCAGTTTACTTT
TTTCTTTCTCTTTTGAAATGTTTTCTCAAAGACATCACTATTTTGCCCTGAAGTCACATTTACTTAGTTA
TGATAGTTTCTTTTTTATAGTAATTGCACAGGGGAAGAGCTAAAGGATAGAACTCTGTCATTGTGAACCC
TGAAAGCTCAGAAAAAGGGGAGGGAAATGAGCCTCAAGGTGATGACCAGTAACCAATAAATCACGTCACT
CTGCCCTTTGACAAACATTTCTTTATCCATGGCTCCCTCAGTCCCCTGAATGCGAAATTGCTTTGAGGAG
ATTGTTAACTAGTACTGCAGAAATACTGAGGGGATTACCTGTAGAAGGGAATGCTCAAGGCTAGTCAGCC
TTTCCTCCTTTGCTCAGCTGCTCTGATTCAGAGCTACTCTGATTTTACTCTGGAGGACACATGCAACCAA
TGTCTGAACAGTCATACTCAATCCCTGCATTGAGGTAGAAAGCACTGATTCCTAGAGGCTGATCTGAATC
ATGCAACTGTATTGAAGGCAACAAAAAATAATAAAATAGCCATGTATTTAATAGGGAAAGTATATAGTA
ATTGAAAAGAAAAACCAAATCAATACAAGTAGTATTGTGACCGAGAGACAAAGGTAAATTTGAAGATAG
GTTTGTGATTTCATAATGGAGACCTTTGAATGCTAGAAGCTACCCCCTCCCTTTGTAAAGAACAACATTA
GGTAAATGATTAAAAAATTATGTCAAAGTCTATGATTTTGAAACTCTACCATATTTGAAAATATTATATT
AAAATAATGATACTAAACAAAGAATTTATGACAAATGTTCATCTTTTAAGTAAAAGAACCTTAAAATTTG
TAAGCAGCTAAATCTAATGATATAGGCAACTGCTAGGATATCACAAAAGAATGGGATTTTAATAGTGAAC
TTATACAATTTGCCTGAAATTAATCAAATCAGCACAGAAATGCACAGATGACAAACACTGTAAGATGTAA
GAGGAATTAATCATAAGAGGTTTATTTGGCTAAAGTGACAATTGTTAAAGATAGAATTGCCTAACGTTAG
TTAATAACAGAAAAAATATCAGAAATTTTAAAAAATGCTGTCTTAATCTATTAAAATTATATAAAGATAA
AGCAAAACAATGTAGGTTTATAAACAAGAACCTTTAAAAAAGCATAATACTGATGCTTATTACAAATTTA
TATCTTGAGCTGGGGTACATCATCCAATTTACGCATGAGAAAGTGTTTTATAATTTTTCACTCTGTAAT
TCATATTTTAAGTTCATCTGAAATGTATTTTACAGAGGTAAGAACAAGCAACTTGGTGCTCAACTCTCTT
CCTGCTCTTCGCCTAGTGCTAAAATAATTTGTGTAAATGAACTGTGAATGAATTTAAGTTTCAGAAATAA
AATTTATATTAATAGAGAGAAAGAAGGATAAATCAATAGTCTTCCAAATATGATACATGTACAATGCAAT
GATATTCACAAACATCTTCATGAACACACGAACATAATTTCTTTTGAATCTTACCATGACCTTCTAAAAT
AAGTAAGCTAAATATTCTATATTATACTACTATTTATGAGGAAACTACATTTCTGTGAATTGTGTAACTT
TTTCATCTTTATAAGGTTAGCAAGCAAAAACAAACAAATAACAAAATAAACAAAAAAACAAAAACTTGGC
CCAGATCTGACTTTAAAGTACCTTCACTTTTATTGTATCACATACGATCTCAGTCCACAGATGGGTTCCT
GATTTAGCCAAGAATATAGTAAAGTGAGTGTAAAGTAGAAGAAAAAGAAGGAAAATATTAGGTATAGAA
ACCTACATGAAATAAAATGAAATAAAGAGAGCCTACTCTTTCTGAAATGCACCAGTAAAATGTACTCCTA
TCTTGTGTATTAAGTTTATAATCATACATTCAATTCAAAATTTAACTAAAACTATGGAAACTGAGAGCTA
ATAATAAAATGATATACACAGCATTCTAACCAGAAAATCTTCTAAGCAATTGTACAATTCAGATAAGAAG
AAATAATTACAAATGTTCAGAAATTAAGATTAATTAAGACTGTAAAATTTTTTTTTTTTTTTTTTGAGA
CAGGGTCTCACTCTGTCACCCAGGCTGGAGTGCAGTGGCGCGATCTTGGCTCACTGCAAGCTCTGCCTCC
CAGGTTCACGCCATTCTCCTGCCTCAGCCTCCCAAGTAGCTGGGACTACAGGCGCCCACCACCACGCCCA
CTAATTTTTTGTATTTTTAGTAGAGACGGGGTTTCATCATGTTAGCCAGGATGGTCTCGATCTCCTGACC
```

FIG. 5 (continued)

```
TCGTGATCTGCCCACCTCGGCCTCCCACAGTGCTGGGATTACAGGCGTGAGCCACCGTGCCCGGCCAAGA
CTGTATAATTTGTTCCTGAAGGGCAGGGAAAATGTAGTGGTAATTTTTCAAGATGAATTGGAAGATAAAG
AAAGAGAGGTCACATTATTTGTGTTATTCAACTGAAATAGTTTTGAATTTCAATAAAACAAGCTAAGAAA
TGCCCTTTGTCATCAAATTGATGTGAAGAGTAAAAAAATTTTAAAAATGAAATTCTCTAAGATAATATGT
GAAAATAAGACTATTTAAATTTCAACAAACATTTAACAAGTGTATACCCATCCTATGTTCGTTTTATCCA
ACTTCTTATCATTCCTAAGTATATTAAGTAAAGTAATAGCTATTAATATGTTGACGTCATTAGCAGAAAA
ATAACTTTGCAAATGATTAAGTGATGACAGTTGTATATCCATGTTATTAGATGTTTAAAATTCAAAAAAT
AATTAATTCAATAAATTTTTGAAACAAATCCATAGAATAAAAACATAGTTTTTCAAAATGTATTTTTCAA
AGGTAAAAATTTCTCACATTAGGCTAGGTGCGTGGCTCATGCCTGTAATCCCAGCACTTTGGGAGGCCAA
GGCGGGCAGATCACGAGCTCAGGAGTTCAAGATGAGCCTGGCCAACATAGTGAAACCCCATCTCTACTAA
AAATACAAAAATTAGCCAGGTGTGGTGGTGCCTGCCTTTAGTCCCAGCTACTCAGGAGGCTGAGGTGAGA
GAATCGCTTGAACCCAGGAGGCAGAGGTTGCAGTGAGCCAAGACCACGCCATTGCACTCCAGCCTTGGGG
GAAGAGTAAGAGTCTGTCTCAAGAAAAAAAAAATTCTCACATTATTGTAAATACTATTACAATAGCTAAC
ATAAATTCAAGATTTATAATTATTTTTTTCTGATGCTCATACAAATACACATTTTACTGGATCTTGGGTG
TTGTAGTAAAAAACAATTTACTAAAACAAAAAAAAAGAATGTATACCTTAAATACATAGAATTTTATTTG
TCAATCATACCTTAATATGAGAAAATAATGTTCTTCTTTTCCAAAGTAAAAAGAAATTAATAGAGCAAAG
CTATATTTTACAACAATGTACATATAATCCATAATTCTGTCTAATACTTGATATTCTACTAACTGAATTG
AAGCAGTACTTGCCAACATTTACATATATATGAATAATTGAATTATAAAAGTTATGAGATGCTGATCTGA
ATTACAAAAGTCCCTCTGTGATAGTAAACACATGCATAAATTAATTCTATAAAGTGTTATTGCATTTTCT
CAAAATACATTGAAGTTCTGTAGTCAAAGTAATCAATAGAGAGCCAAAACTGTTTTTGAACAGTTTAGCA
TATTTTCATTATTAAAAACAAAACTTGCCAATAGATATAAGAAAAAGAGCTGACCAAATTAGAGTTTAAA
TAGCATAAAATAATAATTTTGAAATTCTAAAATTGTATTTTAGAAAATCATGACACGTAGAAAATTATT
TTAATACAGGTCTCATTTGAATTAGATAAACTTATATTCTATACCTGAATAAAAAGTAATTGAAAATACC
TATGACTTTGCAGCAATAAAAAATGGCAAATGATAAAAAATTCAAATTTTTCTTACATAAATATTTGTGA
AAAGGGGAAACTGAAGAGAGAAAATATGATAGTTTATTTAAAGTGAAACATTTACATAGTTTGATGTAGA
TAAAAGTAAATTGAGAAAATTCCTATTTGGCATTATTTGCTGTGAGTTTACCAAGATAATGTTTTTCTCC
ATTTTAAAAACAATGGTCTATGGTCAAAAAGTAAGTCAAACTATCCCTGTTTGCAGGTGACATGATTCTA
TATCTAGAAAACCCCAAAAGCTCCTTCAGCTGATAAACAACTTCAGCAAAGTTACAGGACACAAAATCAA
TGTACAAAAATCAGTAGCATTCCTATACACCAACAACAGCCAAACCGAGAGCCAAATCAGGAAGGCAATC
CCATTCACAATTGACACAAAAAGAATAAAATACTTTGAAATATAGCTAACTAGGGAGGTGAAAAATCTCT
ACAATGAGACTTATGAAACACTGCTCAAAGAAATTAGAGATGAAACAAACAAAGAGAAAAACATGCTTAT
AGATAGGAAGAATCAATATAATTAAAATGGTCATACTGCCCAAAGCAATTTATAGGTTCAGTGCTATTCC
TATTAAACTACCAGCAATATTCTTCACAGAACTAAAAAAAAAAAAAAAAAAACTATTTTGAAATTCATA
CAGAACCAAAATGGCCAAATAGCGAAGACAATCTAAGCAAAAAGAATAAAGCTAGAGACATCATGCCGTC
TGATTTCAAACTATACTACAGGACTATAGTAACCAAAACAGCATGGTACTAGTAGAAAAACAGACACATA
AACCAATGGAACAAAATAGAGAGCCCAGAAATTAGGCCGCATGCCTATGAACATTTGATCTTCAACAAAG
CTCACAAAAACAAGCAATGGGGAAAAAAAACCCTGTTCAATAAGTGATTCTGGGATAACTAGCTGGTCAT
ACACAGAAAATTGAAATTGGACCCCTTCCTTACACCATACATAAAAATTCTAAAAATTCAAATTATAAAA
AAGGAAAAAAAAAATCAACTCCAGGCAGACTAAAGACTTAAATCTAAAACCTCAAACTACAAAAACCCTG
GAAGACAACCTAGGCAATATCATCCTGGACATAGGAATGGCAAAGATTTCATGACAAATGACACCGAAAG
CAATCAAAACAAAAGCAAATATTGACAAATGAGATATAATTAAACTTAAGAGCTTCTGCACAGAAAAAGA
AACTGTCAACAGCATAAACAGACATCCTACAGAATGGGGAGAAAATATTTTACAAATATGCATCTAACAAAG
GTCTAATATCCAGCATCTATAAGAAACTTAAATTTACAAGAGAAAAACAAACGGCCTCATTAAAATGTAG
GCAAAGGGTATGAACAGACACTTTTCAAAAGAAGACATACACATGGCCAACAAGCACTTGAAAAAAAGGC
CAATATTACTGATCATTAGAGAAATTCAAATCAAAACCACAATGAGACATTATCTCACGCTAGTCAGATT
ATTATTATTAAAAAATAAAAAACTAACAGATGCCTGCAAGGTTGTGGAGAAAAGTGAACACTTATACAC
TGTTGGTGGGAGTGTAAATTAGTTCAACCATGTGCAAAGCAGTGTGGCAATTCCTCAAAGAGCTAAAACC
AGAACTACCATTCAACCCAGCAACCTCATCACTGTGTATATACACCCAGAGGAATATAAATCATTCTACT
ATAAAGACACAGGCATGTGAATGTTCATTGCAACATTATTCACAATAGCAAAGAAAGACATGGAATTAAC
CTATATGCCCATCAATGACAGATTGGATAAAGAAAATGTGGTACATACTATGGAATACTATGCAGCCATA
AAAGAACAAGATCATGTCTTTTGTGGAAACATGGATGGAGCTGGAAGCTATCATCTTTAGCAAACTAACA
CAGGAAGAGAAAACCAAATACTTCATGTTCTCACTTATAAGTGGGAGCTAAATGATGAGAACTCATAAAG
ACAAAAAGGGAATGACAAACACTGGGGTCTAGCTGAGGTTGGAGGGTGGAGGGTGGAAGAGAGAGAGA
AGCAGAAGAAATAACTATTGAGTACTAGGCTTAATACCTGAGTGATGAAATAATCTGTACCACAAACCCC
CGTGACACGTGTTTACCTGTACAATAAACCTTCACATGTACCTCTGAACATAAAAGTTAGAAAGAAAATA
TTAACAACTTTAAATTTAGTAATCATAAATGTCAAATTAAAAAAAAAAGATTTTAGACTCACACTTATAA
TCATAGCACTTTGGGATGCCGAGGTGGGCGAATCACTTGAGGTCGGGGGTTTGAGATCAGCCTGGCCAAC
```

FIG. 5 (continued)

```
ATGGTGAAACCCTGTCTCTACTGAAAATATAAAAATTAGCCAGGTGTGATGGCATGTGCCCATAGTCCTA
GCTATTCAGGAGGCCGAGGCAGGAAAATCTCTGGAACCTGGGAGGCAGAGGTTGCAGTGAGCCGAGATCA
CAACAGTGCACTTTAGCCTGGGTGACAAAGTGAGACTCTGCCTCAAAAAATACATATAAAATAAAAAAGA
TTTTAAATAATATTATAAATAAACTAAAATTTCTAGGAACAATTTTTAAAATCAGAAAAATAAGTCATA
TGATAATACAGATACTCTTAAGAAATGCATAAAATATATGAATATACATGTGTACTTATTGATGTGCATG
AAGATACACTAATATATCCAACAAGAATAAGCACATCCATTATTTTATAATATTAAAGTAAGCAATAAAA
GGAACACTTAAAAATATTTTCTTCAATTTAATTGACTATATTTTTTATTTGGAAAACAATTTTAACACA
TATTTTAAATAGTTTAAATAGAGAAAAATGTAAATAAAGCTGTATTACAAAGATATTCATTGATAAACAC
TTCAAAAAATTTTTCAACTTCCTTATTTTTATCACGTATTTTGCTCTAGAAAATTTCCATTCCACATGAT
ACATTTGTTGTATAAGAGATACAAAACAAATTCCTACTAGGGGAAATAAAGCTTCAGTAAGGAGGTGGCA
TTAAGCTGGGCTTTAAAATTCATGCAGAATTCCCGTTGCTTCAAATGGAGAGAAGCAGCAGTGTACCACA
GATAAATGAAGTGAGACGTAATAAGGGTTTGGCTCAAGATAATAAGGAGATGTATAATACTTTTTTATGT
ATAATACTTTTGTTCCAATTCCCTTTATGCTTTACTTCAGTTTTGTTTCTCTAGTTAAATAACTTTGCAT
CTCTAAACTTTATTATTCTTATTTGTATAATGAAGAGAGTAACTTATGCCAGGCAAAGATTTTACAGACA
CTAGAAATAATATATACAAAATAGTTGGAATAGTTCCTGAAAAATAGTAGGTTCCACATGATAACAAGAT
TTATGCTTGTGCTCTTTCTGTATTATTTGGAAAGAAATATGTGAAGTGCAGGAAAGTGGTGTGAAGTTAT
TTTTGTGGGATATCTGGTGTAATCTTTCTCTTTTATCTATGTTATCAAATATTTTTCAAAAGCTGTATTT
CTCATTAGTGCTTTTTGTGAATAAATTAACTAGGAAAATTAGAAGAATGGCAACAATATACATCATAGAA
AGGCATAGATTACAAAGAGAGTATATACACAATACCTGTCCAGAAGATGTGGTATAAGCCAATATTTTAA
TTATACTTATTTACTTCAGATATTGCAAATTTTTCTTATTTTTATACCTTCTTTCTTTTAATGACATTTC
CTATATTTTCATTCACTATGACATTGTTTTCTTTATATCAATACTTATGAAGAGAACTAACTATTCTAAC
TAGGGAGTAGTTAGACTAGTTATTTTAAAATACTTCATTAAAGGACTACAACGTGTGTACCATCTATGAC
TTAGTATTGATTGATTGTCATCTTTCATGTTCTTCATTAAGTGGGTAATTTTGAACACTGTTATATTATTT
CAAAGGGTGTTATTTGTTTGTTCAGATGTTTACAAAGTAATTAACTTTGTTGGCTTGAAATTGCAAACT
CTGTCTTCTTGGTGTCTTAGTCAATTCAGGCTGCTATGACAAAAATACCACAGACTGGGTAGCTTAAACA
ACAAACATTTATTTCTCACAGTTCAGTAGGCTGGGAGACCAAGATCAGGGTGCCAGTATGGTTAGCTTCT
GGTGACAGTTCTCTTCTTGCTTTCCTGACATGGCTAAAAGAGAAAGAGAATGGAAGTGAGTTCTCTTCTT
AAAAGGGTACAAATCTCATTCATGAGGGTTCCACAGCCATTATCTAATCACCCCCCAAAAGCTTCACCTC
CTGATACCATCACATTGGGTTAGGATTTGACATGCGCATTTGAGAGGGACACAAACATTCATTCTATGAC
AGATGGTAATCGAAGCAAAGACAATGAATGGGTTTGCCCAGCAAGAGTATGTAGAGTAAAAAGAGAAGAC
GGTATGAAACAAATCACTGAAAAAAAAAAAATGTAACAGCCAGAATAACATGATCTAAGGATACTTGGGA
GGAATTATGCAAAAAATAGGATTTGAGTCATGCAGGCAAACTCTTTAAATTTTTACTGGAAAAGACATGA
GAGACAGAGTTATGGAAAAGAAAGCATTTGGTGGAGGCAGATCCATTTTTTCTAATAAAATAAATTAATA
TGGATGAATTGTACAATCATTCCTTAGTAAATTTCAAAACTGCATCCAGGCAAATCTCTTATGCAACAGG
CCTGCCTTAGTTGTGTCTACTGGGTACTTGTTTATTTTAGGCATGTCAAATTCGACTTGTGAAAAGATG
ATTATATTGTCTTTAATGCTGTCTTCTTTTTCCCACCAAATGACAGTTATTCAAACCAGAAACTATAAAA
CAAACATACAGTTATCCGAACTAGAAAACAAAATCAGAATTTACATTTTCTATTTTCCCCACCTCCTGTT
GGTTCTCCTCTTAAACTTCTCCTTGTGTGTCTGTAAGCTTGTTATACACTTTTCATCTCTACTCTTTTTT
ATTTTCTGAAGTCAGCTTTCTAACAGATCTCTTTTTCCTAAGTTCTTCTTCTTCATGGCTGCCAGAATTA
ACCATCTAAAATTTAATTTTGTTATGTAACATTTTAAAGTGCATATTGACTCCTCAATGTTGAACATATT
TCTATCCTTACACTTCACCTACACAAATAATATTTCTGTTTTTCAAATAATCCGTGTTATTTCACTTCTT
AGGGGCTTTTCATGTGCTTCCTATTTTGTTTTAAGTATTTTGTGTCTTCAATATCTAAGCTTCTATAATC
AACTGAAGACTTAGCCCCAATGTCAACACATCTTTAAGAACTTTAACCTGTAAGGTCAGAATAGTCCCTT
TTTCCTATCTGCACATAACATTACAAACTTATGGCAATTATAAAACTCAATACATATTATACTGTCATTA
TTGGTTTATTGCTGCTGAAGATTATAATTTTCAGTGCATTGATTATGTCTTATTTGTTTTTACTGCCCTT
GTTCCTGTTCCTCTGTACCTGCCTCAACTACATAGCTTAGCAGACTAACTGCTATATTACAGTTGCTCAA
TGAATGTTTCTTGAGTAAATCAGTTGAGTTCCAAAGCTAATCCAAGTTGTGCGTTTGACAAATTAGAAGC
TTGGAACTGTCTTCTGACTTTAAGTTTAGAACTATTGCCATAATAAATTAATGACCGATCTGCCATGATT
GCAGGCAAGTAGAGACTTTATTTCTTATCTCAATGTCAGTTGTCTCTTTCTGCCAATGCACATTTTATTT
GATGATTGTGCACATTTATATCTCTGGTTTTTATTTAAATAAATTTAGAACATATAGCTGGAGACGGTAG
CTCAAACTGAGGATGAAAATAGACATTTATCAAGGTTATTATGTAGCTAGCACTGCATGTACACAGAGGT
ATTTAGGGAGCCACACATATGTCCAAGGCAAGACATATGCTCATAAAACGTCTGAGAAGATTGTATCCTT
TTACCTAATGCTAATCCCCAAGCTTAGAACAAGGCAAGTGAAAGGTCAAAGGGATAAAAAAATACAATAA
ACAAAATAAAAATTTACAAGAAGTTGTTATGGACTAAATATTTGTTCCCCTCTCCCCAAAATTGTGTATT
GAATTTCAAAATCCAATGTGATAGTATTTGGGAGTCTTTGGGAGCTAAAGAGATCATGAGAAATTTGCTC
TTATAATGTGAGTAGTGCCTTACAAGAAAATGCTGGAGAGCTCACTAGATTTTTTCCTCCATGTGAGAA
TACAAAGAGAAGTTAGCTGTTTGCAGCCTAGGAGAGGGCCCTCACCAGAAATTGACCATGCTGGCACCCT
```

FIG. 5 (continued)

```
TATCTCAGACTTCTCACCCTTCAGAACTGTGAGAAATAAATGTTTGTTGTTTAAGCCATCCGTTCCATCA
TAATTTGTGATAGCAGTCTGAACTGACTTAGACAAAAGTTCAACAGCAAATTTGAGCAGTTAGAACACAG
AATCCGCAAACTTGAAGATAAGACAATTGAAATGATTAGTCTGAGAAGCAGAAAGAAAAAAAAACGAAG
AAAAATTAACAAAACATACGGAACTGTGGGACACTATCAGGTGAACCAGCATAACAATTACAGTAGTTCT
AGAAAGAGAAGAGACAGAGAAAAGGGAAGAAATAATATTTGAAAAAAAAGTGGCCGAGAACGTCCCAAAT
TTGATAAAATATATGATCTCAATATCGTAGAAGCATAAGAAAATCCAAATAAACTCAGAGATCCACTTTG
AGGCACATTATGATCAAACTGTCAAAGGCCAAAAAAATAAAAATAAATTCAGAATCTTGACAGCAACAAG
AGTAGGAAATAATCATGGGCAAGAGTTCCTTAATAAGATTAACAACTGATTTCTCATCAGAGACCAGAAG
ACATTGAAATGATATATCCAATAAAGAACTGATATTCAAAAGTATGCAAAGAACATCTAAAACTCAATAA
TTAGAAAAATAACCCAATGATAAAATGAGGATGATATCTGAACAGATGCCTCACTGAAGAAGATATAGAG
ACAACAAATGAGCATGTGGAAAAATGCTCCACATCCCGTCATTAGGGAATTGTAAATTAAACAATAAGCT
ATGTCACTGTATACTTGTTAAAAGGACTAAAATTCCAAACACAAAAATATACCAAATACTGGCAAGAATG
TGGAGCGACAAGAACTCTTATTTACTGCCAGTGAGAATGCAAAATAGTGCAGCCACTTTGGAAAATATTC
TAATAGTTTCTTACAAATTTAAAGATAGGCTTACCATACAATCAAGCATTTGTAGTCCTTGGTATTTACT
GAAATAAGTATCAAGTGGAAAGCATGTCTACACAACAGCCTACAAAGAGGTGTTTATAGCAGCCTTATTG
ATAATTGCCATAAGTTAGAAGCAACCAAGGTGTCCTTCAATATGAGAATAGGTAAAGCGACCTTGGTACA
TTCATGCAATAGAATAAGAATATTTTTAGTGATTAACAAGAAATGAGACATAACCAATGAAAAGACATGA
AACATTAAAAGTATATTTATAAGTAAAAGAACGCAATATTAAAATGTTACCTACTATATGATTCCAACTA
TATGACAAATTTTATTTTATAAATGCTTTACCACAAAAGTTAATTCTAAAAATGTTTGCCACCAAAAAAC
AAACAAAAAACATGGTAGAGATCATCTTTATAGTTTTTTATAATAATCCTCTTGATAAAGATTATATCAT
AAGAAATCTTGACAGTTTACATTCAAGGATATGACATTTTATTTACAAATTAATGAAATCTAATAAAATG
TGACAATGAAAATTTAGCTGAGTATAAAAGAACCTAAATTAGTAGACAGTGAGAGAGGAATGGGGGAGGG
GATGTTTACAAGAAGTTCTACATCAGTACAGAACTTCATAAATTAGTGGATAAGAGCATGGTGAAGAGCA
ATTGTAAATCAAATGAAAATGTTGTGGAACTCTTATTAGTATCTGCAGCCACTCTGGCACTTTAAACATA
TCCAGTAGGAGAGGTTAATTCTCTCAGCAGGAGACCACTCACATTACTTTTTTCTCCCTATAAAATAATG
CATCGTTTTGTCATGCTGGTAAAAAACACATAACATTAAATGTACCTTTTCAACCAATTTTTAAGTGTAC
AATTAAAAAGTGTAAAGTACACTCACATTGATGAACAACAGATCTCTTGAACTTTTTCATTTTCCATTGC
TGAAACTTTGTATCCACTAAACTATCTTCTCCTCAGTTCTAAGTAAGTACCTTTCCACTTTCTGTTTCTA
ATTTTTTGACTACTTTAAATATTTCTTTCTTTTTTCTTTCTTTTCTTTTTTTTTTTTTTAAGATGGAG
TCTCGCACTGTCACCCAGGTTGGAGTGCAGTGGTGTGATCTCGTCTCACTGCAACCGCCGCCTCCTGGGT
TCAAGCGATTCTCCTGCCTCAGCCTCCCAAGTAGCTGGGATTACAGGTGACTACCACCATGCGCAGGTAA
TTTTTTTTTTTGTATTTTTAGTAGAGATGGGGTTTCACTATGTTGGCTAGGCTGGTCTCAAACTCCTGAC
CTCGTGATCCGCCCACCTTGGCCTCCAAAAGTGCTGGGATTACAAGTGTGAGCCACTATGCTTGGACTAC
TTTAAATATTTCATATGATAGAATCATACAGTATCTCTCCTTTCGTGACTGGCTTATTTAGCTTAGCATA
ATGTCCTTGAGGTTCATCCATATTGTAGCACATGATGTAATTTACTTATTTTTAAGTCTGCATAATATT
CCATTGTGTATGTATACCACATTTTCTTTATTCATTCATCAGTAGACATTTGGGTTGCTTCTACATCTTG
GCCGTTGTTAATAATGCTGCATGAATATGCATGTACAAATATCTCTGCTAGATCCTGTTTTGAATTACTT
TGACTATATACCCAGAAGAATAATTAATGGCTTGTATGGTGATTCTATTGTTTAGTATTTGTGGAACCTC
CAAACTCTTTTTCATGAAAGCTGAACCATTTTATATTTCCATCAACAAACATGAAGTTCCTAACTTCTCT
TACTCGTTATTTTCTATTCTTGAAATAGTGGCTTTTCTGATGGTTGTGGGGTGATATCTCATTGTGGTTT
TAATTTGCATTTCCCTGATAAGTAGAAAGTTGAGCATCTTTTAATGTGCTTATTGGCTCTTTGTATATCT
TCTTTGCAGAAATGTCTATGTAAGTCCTTGACCCATTTTTAAATTGGGTTGTTCTTTGTTGTTGTTTCCT
TGGAAAAGTCCATATATTCTAGATATTAACTCCTCATCACTTATATTATTTGCATTTATTCTGTGCCATT
CCATAGGTTATCTTTTCACCTGTTGTTTTCTTTTATGTGCAGATGATTTAAGTTTGATATAGTCTGATTT
GTGTATTTTTAATTTTGTTGCCTGTGCTTTTTGTATCACATTTTAAAAATTGCCAAATTGAATGTCCTGA
AGCTTTTCTTTTATTTTTTTCTGGAAGTTTAAGGTCTTACATTTAGGTATTTAGTTCATTTTGAGTTAAT
TTTTGCATATAGTATAGGGTAAGGGCCCAATTTCATTTCATTGCATGTGGGTATCCAGTTTCCCAAACAT
CATTTGAAGAGGCTGTCCGCTTCCTTGTACTAAATGAATGGTGTTTTGCTGCTTCTTTTAAGAGTCTCTG
TTTGTGTGTAACTTTTGACAGTTTGATTATACTGTGTCTTGGTATAGAGTTTTTTAGATTTATCTTATTT
GGAATTACTTGAGCTTCTTAAATGTTTAGGTTCCTTTATCTCTTAAGATTTAAAAAAAATGGGGTCCATAA
TTTACAAGTTTTCAGACCCTTTCTCATTTACTTCTCTTCTGGTATTCCCATAATGCATATGTTGCCCTGCT
GGATGGAGTCCCATAATTTCTTTAGGCTCTTCTTTTCTTTTTGCTCCTGTGACTCTAATTTTAGAAGTTC
TGTCTTTGATTTTCCTGATTTTTTCTTCTGCCTAGCCAAGTTACCTGTTGAGTCTTTCTAGTGAATTTTT
CAGTTCAGTTACTTTATAATTCAACTCCAGAATTTCTGTTTGGTTCTTCATAGTTTATAATCTGTTAATA
TTGCTATTTTGTTTATTTGTTATGTTCCTCATTTCATTTAATTGTCTGTTCATATTCTCTTTTAATTCAT
TGCACTACTTGACTAATTTCAAGTTCTATGTCTGGCAATTCCTATATCTTCATTTGTTTTTGGTCAGTTT
CTGGAGATGTAATTTTTTTTTCCTTTTAATGTGTGAGAATCCTTTCTTTCTTTTTATACTTTGTATTATT
```

FIG. 5 (continued)

```
TTGTTGTTGAGATTTTAACATTTAAAAAATCAGTCAACTCTCCCAGATTTTGTGAGATGATTTTCCATAA
GGAGAACTCTCCTCACTAATTCTGAATAGAGATTCTGTGGCCTACTCATGCTTTTTTCTAGTATGTTTT
CCTTTCTTTCTCCTTTAGGCTTGTGTGTGTGATCTGTTTGAAAAGGTTTGTTGGTTTCTATAGAAGACCC
TCCCCTGGGGCTTGAGGTACAGTGGCCTTTCTGGGGCTGCATTAAATTGTTGTACTGGTGCTCCACCTCG
TGTCTCTGTCTGGAACTGCAGTTTTTGGTGTACCTTTGCTTGCAAAGACCGCATTTTTATTAGTACTTGA
ATATAGGCAAGTCAGAAGCCTGTCCTTGGGCAACCTCCCTAAAAGTCAAAATATTGAACATAGGAGATTT
AAATGTTTCCTTCCAATTGCATTGCACAGGGTGGAGTGAGAAAGACTCTAGTGAGAGAGACTGGAAACAA
TCATGATTTTTCTTGCCAGGTTGTTTTCACGATAGCCTGGAGGTACAGAAACCTTGTAATTGGTTCTGAA
GTTCTCACAGAGGCATTTAGTACATATGTTGTTAATATTGTGTCTTGCTGTTGAGGTTCCAGGGCTGTTC
TGCTCTCTTGCTGATGTCACTCTCTTCCACATTTCTTAGTCCTTTTTAATAAAATGATTTTTTAATGATT
AGGACCTGAACAATTTTCATCACTATTCTATGGCACAAAGACTGCATACATTTTTACAAGATGTTAGAAT
TGACTATCTTTGAAGAAAATCTTCATAATTTTTGTCTAACTCTGTTGCCCCTTTCTCCTGTTTTATTATT
CCCATCATCAACTTAATACAACTAGTTTTGATACTCTTCTACATTTTATGCTGTTTCTTAGATAACTTTT
TACATTTTATTTTAAAACTTTTAGTTATCTCTATAAGTTGTATCATTTAATAAATCTTTTGAATTCCTTT
TATCTTCATTGATAGCATATATCATTTGATAGTTTCTTATGCAGAAAGGAACACACCCACATTTTGTCGG
CTATCAAAGAGTTTTGTTGGGCCTTTTATCTCTGTCCCCAAACATGGCCTAGGGCCAGACACAGAGTAG
GTTTTGGTTATATAAATGTTCACTCATTATTTCTTAAGCATCTTTGTGACAGACACTGTCCTAATCACTG
GGGACGGAGCAATGAACAAAACAGACAAAAACCTATGACTTGATGGGGCTAATATTCTGCTGTGGCAATA
TAAAATAAACTCATAAAGGAATAAATGTATTGTGAGCAGAAAAGGGGTGCAATTTTAAAGAGATTGATCAA
GGAAAACCTCACTGTGAAAGTTCCACTGAGCAAAACTCTTAAGGGTGTGAAGGAATGAATGATAGAAATA
CGACTATGGGGAAGAGCCTTTCATGTCAAGTGAAAAGCAAGAACAAAAAGCCTGGAGCAATATAATGAAT
CTGGAATGCTCAATATACAGCAACAAGGTCTAATGTAGCTGGAGAGGAATGACCAAGGACAAGAGTAACA
AAGTATAAGATTAGAAAGATAAAGAGGAATATTTGTGGGGAGGTGGGTGTAAAAAAGAGGATAGGTTGTT
TATGGTCTCATAGGTTATTGGAAAAACTTGATATGACTATAAGTTACATAGGAAAACAGAGGGGCAGCAT
GATCTATTTCTGATTTGTAAAGGACTTCTTTAGCTACTTTGTTGAGAAGAGACTGTTAGGCAGATGTGCA
CAGAAGTAGAAACATGGCTCAGGAGGCTCTTGCAATAATTGAAGCTAGGCATGGTGGTGGAAACCACTGG
GAAATATAGGAGGTAATTAGAAGAGGTCGTTTAGTCAGTTCAGGCTGACAGAATAGAATAGACTTGGTGA
CTTAAACAACAAATATTTGTCTCTCACATTTCCGGAGGCTGAGAATTCTGATATCAGGGTTCTGGCATAA
TTGAGTTCTGATAAGGGCCCTATTCCTGGTTTCCAGAAGGCCATATCCTCATTGTGTCATCACTTGGGGG
TAGGGGAGAGAGAGAGAGAAAGAGAGAAATAGAGGGAATCCCTAATTTCTTGTCTTATAAGGGCACTGAT
CTTATCAAGAGGGCTCCATTCTCATGACCTAATTTCCTCAAAAAGACCCTATCACCAAACATCAACACAC
TGGAAATTAGAGTTTCAACATATAAATTTGAGGTAGGGATATAAAGATGTAATACATAACAGGGTAAAT
ATTAATAGTAGAGAGCCCAAAGAAATTTGTTTATGGATATAAATGTGAGCTGTAATAGAAATGATTAATC
GATACATTTTATTAACATGAAATTGACAAATAAAACATCTATAACCACTGCATCTTACACTGGATGTCAG
TCACTTGTGTTGGTCATAGAATTTTTCTTTGCCTCTGCAAAGTTCTGTTTTTCAGCTGGCTTCCTGGAAA
TGCTGCCTTTGAGAATGTACTGCCACTCCCCTCCCAGTTAGCCAATGCTATTCATATGGAAATAAAGAAT
AGCTCACCATCATGGCCATCTGAGAACATGATGTAGCTTTCTATAAATCAGTTAATGAGATTAATTTAAA
AATAACAACCTTAACTGTAGTGCTCTAATATTTTGATATTATAACCAAATTAGAAATGATGCTTTATCAG
TGTAGTGATAATAACATTTAAATGGCTGAGTAGTAGTACCTGGTAAAAGGGAAAACTAAGTATGGTTTTT
AAGATACAAATAATGTTTTAAGTAAAGAAGAAAGCTATTATAATTCCATGTGCCTATTGACATTATATA
GTCCTTCGATTAACCATTTTCCCCCTTTCCTTCTGATTTTTCTTAGATGTTCTTGGCAGCTCTGTCACTC
AGCTTTATTGCTAAGACACTAGGTGCAATTATTATGAAAAGTTCCATCATTCATATAGAACGGAGATTTG
AGATATCCTCTTCTCTTGTTGGTTTATTGACGGAAGCTTTGAAATTGGTAACATTTATTTTCTATTTTA
ATAACCAAACTTGCAAAGTTAAAAAATATATATGCTTTACACCACTGGTTATCAACTGGGGTAAATTTAT
CTCTCACAGGCAATTTGGCAATAACTAAAAACATTTGTGGTTGTCATAACTGCACAGGGGTTGGGGGCAA
TGGAAGTGCTACTGGTATCTAAAGGTAGAGGTCAGGGGTACTGCTAAATATTCTATAATGCACAAAGAAT
GATGTAACTGAAAATGTTGATAGTGAGGATGTTCAGAAACCCTGATTCTACACAAATTCATTTTTTGCAA
ACTAACGCCATGTCATACTTTACCTCCCCTCTCAAGATGAAGAAACTTTGGGAGAGGACTGTTATTCT
TAAGGAGAAAGGAATCTTTTCAGAGCAACCTACGTTAGACCTCTATTGTTTCACTGAGCACACAAAAATC
TTTCCTTTGAAATACTGAAGATATTTTGTTGTCTTCATTTATGTTGGATTCTCCAATAACAGCTCAGG
GAAAACATTTTCTGGTTCATATTTGTGTTTTTCCCTATTAGTAATTTTTTCTAGATAATTTATAAGATG
AATATTAAATTTTCTGGGAATTTTTCTCTTTAAATTTTTTTCTTCTAAATTTCCATTGTTTTTCTTTATG
TTTCATTAATCTTTGATGCCATCATCCATCTTACCATATTAAGTTCTAATTTGTATATTTAATCTGTATT
TTATATTTACAACAGCACTTTATTATTCCCTTATTATTTTAGGCTGCCAGTTCTGATTTCATGGATGCA
ATGTGCCCTTGTACCCGTAAAGGTACTAAATTTTTTATAAAGTAAAAAAAAATTTACTCATTCATTTTG
GTGCTTTTATTCCAAATTATTTTATGCTATTTTTTTCAGAAGTGCTCAGTTATCCTTAACTGCTATTT
GTTTATTGTTATGCCTGAGGCTCCAGATGGATTAGAAGTGGTCATGACTTTTTTTTTTTTTTTTTGAG
```

FIG. 5 (continued)

ACGGAGTCTCGCTCTGTCGCCCAGGCTGTAGTGCAGTGGTGCGATCTCCCCTCACTGCAAGCTCTGCCTT
TCTCCTGCTTCATCCTCCCGAGTAGCTGGGACTACAGGCACCCGCCACTATGCCCGGCTAATTTTTTGTA
TTTTTAGTAGAGACGGGATTTCACTGTGTTAGCCAAGATGGTCTCGATTTCCTGACCTCGTGATCCACCC
ACCTCAGCCTCCTAAAGTGCTGGGATTACAGGTGTGAGCCACCATGCCTGGCCTCTGGAAGTTCTTAATT
AAGTTCCGCCTTTCTGTGGTTTAATAGCACCTCTGTCCATCTATTTTTATCGTTAGTATGAAACTTCTTG
AAGACAGATGCCATGGTTTATTCTTTTTCAAGTAACTTTCTTATTTCTGGCTCTGAGCTTCATGTCAGGT
TCATGTTAGAAATTTAAATAATATTAAGAATAAATAAAGAAACGCATGAAGGAGCACCTTACCCTCATCA
GGAAGATTCATCTCCATTTTTCTTCATTCCAGTATAATCCAGTCAACTCCAAATTTTTCAATAAAATTTT
ACTTCACTAATATTGCCAAGTAATTCAAGTGCTTTTTTTTGTATTTAAAACAACTTTTCAATGAGTGGT
CTAATGTAGGTGAATTCACCTTCTCAATTAAATCACATTGTCTTTGAGGGAAGGCACTATGTCTTGGACT
CTATTTGCATCCATTCTGGGGTTTTCAATTCTAGACGCAAAATTGAACTAAGCTGTATCAACATAATTTT
GTTCCCTTTCTAGGAAATTTGCTTGTGATTGTATTTGTGAGTTACTTTGGATCCAAACTACATAGACCAA
AGTTAATTGGAATCGGTTGTTTCATTATGGGAATTGGAGGTGTTTTGACTGCTTTGCCACATTTCTTCAT
GGGATAGTAAGTGTTAAAAAAAAAAAAAACCTCTGTGCCACTATCAGTACCTTGTAAATTAGGAGTAGAA
TTTTATTATTATCCCTTTAAATAGGCAGTTACCTTTTGAGAAGATACCCACTAAGTGTGTACAGAAATGA
AATAGTGTCTATTTGTCTACATAATCATTTTATTTATCGTAGCTTTCATATACTTTGAAATAACAAAAAG
ACTAAACTGTAGAGTTTCAAATGAAATAAATAGGCTTTTTATGAATTTTTAGTATAACGTATATACTGTA
CGTCTTTGCCTATAAGATTTTGATTATTTTTTATAAGACCTCAACACTTACACCTATACCCACTGAAGTA
TAGTTGTTCCCATCATTTCACTGAAGCTGTTATTCCTAAGGTCACTGTGTAGTTATAATTACAGTCAGAT
GCTCCTGAGAGAAAAGTTAAAATGGCACATGGGGGAGAAACTTATTTTTCACATTACAGTTAATGTAGCC
AGTTCAAGGATGATATGATTCTACCTCTTTCCATCATAGTGCTATGCCTTGCATGGTCTTGGCTTCATGA
TCCAAATTGTGGCAACGTATTTCCAGGCAACAAGATAGAAGAAGAAAAGAATAAGAAGCAACAAACAGTC
CACACAGGCTGAGGCTTAAGAAGCATTTTCAGAAGCAAAATATCTCTACTGACTTTACATTTACCAGATG
TTAGTTACATTTCACACATAGATATATAAATGCTGAAAAAAATAGACATTATTCCAAGTTACCAAGTTCC
CGGTTAAAAATCCCAAGTATAATTACTGTGGAAGGAAAGAAGAGAGGATATTAGGAGACAATGAGCAGTT
TCTGTTAGAGACACCAATTACTTACTCATTGCCAAATCCAGCAATGACATCATTTGCTCACCATATTAAA
TCCATTCACCCACCATATTTGGCCCTTATAGGAAGTTTCTTCTTAGTGGTACTGCTCTAGCTTGTTTTCA
TCATACTGCACTCTCTTGATTCATTTTCTATCTTTGTGTCTTCTTCATCATGTCCATTTTTTTTCATCTG
CTTTTGGCACCATACCGTCAGAGTCCTCTAATTTCCTTTTTAATCTTTATTTATGATTCTTCATGAGTTG
TATGGAAAATAAACCTTAAAGGCAAGTATCACAGCTTCATCTTCCATTCTACCCTAAAATTAAGGACCAC
AATCTAGATCAGCATTGCTCTAAATATGCCATAATATGTGACACTTTTGCACCTGGTATTTCTACAGCCT
TGAATACCTTTGTTTCTTTGTCTACCCTTCTATTCATCTTCCAGATTCGTTTTACCTGTCATTCTCATGT
TGATGTCTTCTCTGATCTATTCCCGCAACCTCCAAGCAAAGTTGATCATATCCTTTGTCTTTGTGACAAC
TCAGGACCTTATATATTAAACTTATAACTTTTATCATCTATGTTTATACTAGTGTGAAATTCCCTAAGTA
CAAAAACTGTGTGTTTTATTTCTAGCTCTTTGAAGCTTAGCATAATGCCTGGAATACAGTAGGCTGCCTT
TAGAGCTCACGTGGTACCTAATTATTTATGGATATTAACATCTCTGTTATTCCTATCAAGTTTTCTCTCA
TCTAGTTGAAATGGATTAGATTTTATTTTTACTACATTTTGAAGAGTCATACATTAGAGCGTGTGTGTGA
ATATGTGTCCATGAAAGAAAATCTGACAGACTGATCATCTTTGAAGATAATTCAAAAGGATGAATGGTTA
CACACAATTAATAATTACTTTTTAAAAAGGTGAAACTAGGATATTTCATATCTTGACCAAGATATAACCA
CTCCTAGGATAATAGCAAGGTGATAACCCACTTAGCCTGGGGTGTATTGAATTATCTTTCTTGCTGGACA
CTTCCATTTCACTTTTACCCATCACATCTCTTAAAACACATGCTGGGAAATTGACAGAAAGTACTCTGGT
AATTTGGGGAAGATAATGGTGCAAATAAAGGGGAATATTTCTCTGTATTTCTAGGAAAAGTGAAAATATT
CAGTAGATAAGCAAAATGTTTAATTCAGTGATGTTCTTACAGTTACAGGTATTCTAAAGAAACTAATATC
AATTCATCAGAAAATTCAACATCGACCTTATCCACTTGTTTAATTAATCAAATTTTATCACTCAATAGAG
CATCACCTGAGATAGTGGGAAAAGGTAAGAATTAATATTGACAGTAAAAAGTCTTCTAAAATGTATACAT
TTAATTACATCTCTAAAAATTGTTGTGATATTCATTAGCAAAATTTAATTAAGAATGAATAGGAAAAACA
TTTGACTCTTACAGACATAATTATAGTGTTAATATACACAGTTCGCCCATTAACAACACAGGTTTAAACT
ACGCGTTTTCACTTCTATGCAAATTTTGTCCATCTGAACTGGATGATAAACCTGCCGGTAAGAATATCTG
ACATTTTCTATATTTGGATTGAACAGGGCCAACTGCAGAACTTAAGTGTGCATGAATTTGAGAACACACA
GGCAGCCCTGTAACAAATTCCTTAATATACCAAGGGATGACTGTATTATATGTAAAAGCATTTAGAAGTA
GATCAGAAAAGAGAATATTTTCAATAGGAAATTGACAAAGAATATATGCATTAAAGTAAAACAGAAGGAA
ATGGTATAAATATGTAAATAATATAACTTTGCTTTCATTGCAAAAGGCAAACTATTATATCATTTAAAGA
CTTTTTGCCTATTATAACACAAATTATAAATTATAATTGCAAATTGTACTGCTAAAGATTTTTTTAACCT
ATTAAATAGAAAAGACTAAAAATACATAGAGACGAGGTAGAGGCAAAAAAGGATTTCACATTGTATATA
TTGCTGGAAGTGTATACGTTTGTAAATCTTTCTGGAGATTCATTATCAATATATGTTAAGAACAAAAATA
TACTTACCTACTTAGTCTGAAATTCTGCTATTATTGATTAATCTTAAGGAAATAACCAGGAAACTGCAAA
AGGACTTATTTACAGTTATAGTCATGATAAACCTAATAGAATAAAACAACAAAAAAGAAATTAAAACATA

FIG. 5 (continued)

AGATACTGAATAAACACATTTGGAAACTTATTCAGCACATTACTGTCCAGTCATTAAAGTTTTGATATTA
AAGAAATCTTAACAACATGGAACAATTGTTATAATATGGTGTTAACTGTGTATACCATTTAACAATATGA
ACTAGATTTTTAAATATATAATGGATATAATGAATATAATGTATATGTTTTGTGCAAATCTAGAAGATAT
ATAAAAAAGCTTGAGGTGATCTTCTGTGTGTAATGTGATTACAGATAATTTTTACTTGTTTGTGCTTTTC
TGTATGATATGGCTTGACTGTGTCCCCACTCAAATATCACCTTGATTGTAATAATCTCCACATGCCAAGA
GTGGGGCCAGGTAGAGATAATTGAATTTTGGGGGCGGTTTCCCCCATACTGTTCTCGTGGTAATGAAGAA
GTCTCACAAGATCTGATGATTTTATAAATGAGAGTTCCCCTGCAAAAGCTCTCTTGCCTGCCACCATGTA
AGACATGGCTTTGCTCTTCCTTCATCTTCCGCCATGATTGTGAGGCCCCCCAGCCATGAGGAACTATGAG
TCCATTAGACCCTTTTCCTTTATAAATTACCCAGTCTCAGGTATGTATTTATTAGCAGCATAAGAATGGA
CTAATACACCATATTGTCAAAGTTTGCAAAGTGAATATAAATTACTTGTACTTGTAAATTAAAAAAAAAT
AAGTAGAATAATTAAGAGTTTACAAGTAGTTAAATTTGTAATAGAAATGCTAAAATTAATGTTTAAAATG
AAACACTCTCTTATCTACATAGGTTGTTTAAAGGAATCTGGGTCATACATGTGGATATATGTGTTCATGG
GTAATATGCTTCGTGGAATAGGGGAGACTCCCATAGTACCATTGGGGCTTTCTTACATTGATGATTCGC
TAAAGAAGGACATTCTTCTTTGTATTTAGGTAATGTACACAAAATATTAAATTGTATGATCACTTTCCCT
TTGTCTACTTTTGAAATAGTAGAGTTACTAAACTTATTATTTTACCTATTAGAACATATATTTGGGTATA
TGTATTGTATCATATTTCTTTTAAAAACATGGTGAATAAGAACCATGCATTCTTGGCATCTAGTAAAATT
GCTTTATAATATTTTCAGGTATATTGAATGCAATAGCAATGATTGGTCCAATCATTGGCTTTACCCTGGG
ATCTCTGTTTTCTAAAATGTACGTGGATATTGGATATGTAGATCTAAGTAAGTACAACCAGAACAAGGTA
CCATGATAACGTCTTTCTAAGCACACATGCGAAAAACATTTTTTCAAATAACTGAATTCACTCTTTCAAT
AGTCCTTTGCTTAATATAATTAGAAAGTTACAAGTAGGAAATAAATGTATTACTAATCAGAATAAATATA
AAATCCAGCTCCTATTTATACTATCTTTATAACTAAGTGTAAAATGAGAGAATGTAAACAAATTTATTTT
CATGAGCTTGGTCCAAAATAACCAAATGTAAAATGTCTCCCTCCCAAACTGACTGTCCAGTCAAGTAAAT
TTTATTTTTCAGTTGATGGTGGCTTGGATGTTGATGTGTACAACTTAAAGTTTGGTTTGCTAAAGTCTTC
TTGTGGCTGCTGCATTGATTTATGGCTGGAGTCATTTGAGAGACTTCACTGTGTATTTTATGGTCATTTT
CCCTGGTCCTAGCAGAGGGCTTGGCGTATGGCAATGTTCAGTAAGTACTTGTTGAACAAAGGAATAAAGC
AGAGGACACATAAATAAAATCTATGATTTTCTTCTTCATTCTCAGAGCATACTTTCCTTCTTATCTCATA
GATGAAAGAGATGCCATGTTATAAAAACTGTCTCAACTTCAGGCCCTTTTCCCTAAAAATATTCTTGCAC
CATATCTATCTTTATCTTCTTTTTCTTTTTTGCAGCTCAGTGGAAAATATATACATCTGTATCCAATGTT
GATAGATCTAGCTGGAGCTTAGATTCTCCCTTCCCGCTTCTTTTATCTCCATCTTCTCTTTTATTCAGCAA
ACACACCAAGTATTTCCCATCTTTATATGTAGATACAGTTTTTTATACCCCCACACAACTTTCCAGCTG
AATCCTTTTTTTATTCCTCTTTAGAACCAAGCACCTAGGAAAATATCAGCTAAATTAGCTAAGATATCTC
ACCTTCTCACCTCCCATCCACTTCTAAATCCAGTATAATCTGCTTCTGTTATTAGTGAAACACAATCAAT
TTCTACCTACTTTACTATAGATTTGTAAATGGGTATATTTCTATCATTTGCGTTAATTGATATTTCCAGT
GCTTCTTCATCCATTTTCCCTCCTTAGATATCTTATTAGTACCTAAAGCACAATATGTCAAAATCTGATC
TCATCACCTTACCTCCAACCCCACTGTATTCCCTATATTCCTCCTTTTGATGAATATCCATACCTTATTC
AATTATTGACTGAGTTACTGTGCCCTGTAATCTCACATTTCTCTGCATTTACACTTGGTAAAACTTTTCC
CTCTTTTTCATTTGCATAGTTCTTGAAGCCTCTTCCAAAATGTGGATCCTCTTAGAGAAGCCTTACTTCA
CCACTTTCCATTAGTCTCAAATTAATAGCCAAGAGCATGCCTTTATTGTAACCCTTCTCACAATGAGCTA
TTAATATTTGTGTGCTTACTTGCCATCTCTTTACCACATGACAGAATGGCATGTTCTTAGCAAATAATAA
TTAGTTAAGTTTGTGAATAAATAAATATGATTTTCCACCTCATTAGGCCTTCAATAGATCATTCCAAAGA
GATCAAAGGATTCATTTCCAAGATGGGATAGACATCCAGTGGGCCAGCAACAGCCAAAAACTTGAAAGT
GTTTGCTAATCTAAAACTATAAAGAAAATACTTGATAAAATGTTTTACATGTTCAATTTTAGACATATGC
CTTAGAGTAGCTACACATTATGTACATTATTTCTACTCATTCAACTCCAGTTTCATCACTGCTTTATCAC
GAAGAGTACAGAAATACGTGGTAAATGTCCTTAGGTTAATTATTTTATAAGCTCTCTAAATAAGAAATTA
TTACATTATTTGAGAATTCATCACCATACAATTTCTAACATTGAATGTTCAGATATCATTATATCTTCTC
TTATTCAGTGATGAGTATGAGCTTCACTTACAAAGTATACTTTGGCAAACTCCAATGCCTAAAGGAGCTG
AAGACATAAAAATAAATGAGTAAAGAGTGCCAGGAACAGGAATTTAGGGTGTGATGGTTAGAATAGGAGA
ATTCTTTTGGTTGTGAACTGCTCTCCCCATGCATCCAAAAGCACTTGTGTTCCTCAGCTCTGGCCTATTC
TTTTAATGCACAAATTTAGGCCCTGCATTGGCAAGGACTTCTGATTGGTTTCCAAGAAAATCCAAACACC
AAAATTTTTGTGTAGAATTTTTCAATTTTTAAGACTGTGAGTGAGCCAAGAAAAACTTTTTCTCACGTCC
TATCTAGCGCGATTATGACCCTTAGTTACTATGTGTAGAACAGTGAAAGAACAGAAAAAAAAGTCATCAA
AATTACATTTGTCACAGGTGATGAATAAATACTTTGCATGTAGATGGAGTCACTGATTTAACCAATCATT
TCCTGAAGTCTGAGTTGTTGATTATGACATGGTATGATCATATAAATCAAATTTAAACCCAGATCTGTGC
ATACTTGAAAATAATTATTTCTAGGTAGTTTGTTATCAAGTCAATGTTATCTTATATTAGTGAGTTTTCT
TATAGATTAGAGTAATGGCACCATTTAATCGTGCCACAAACTTCTGTGGTGTGTGTTTCTGTATGCATAT
GCTTTTTTATTTCTTATTATTTTTCTTTTATTATGGTAAGAACAATTAAAATGACATCTACCTTCTTAAC
AGGTTTTGAAACATACAGTGGACCCATGAACAATAGGTTTAAATTATGCTCGTCCACTTATGCACAGACT

FIG. 5 (continued)

```
TTTTTCAATAAATATATTGAAAAAATTTGGGGAGATTTGTGAAAATTTGAGAAAATTTATAGATGAATTG
CATAGTGTAGAAGTAAAGGAAACCCTAAGAAAAAGGTATATCATGAGTGCATAAAGTATGTTTAGATACT
CCACTATTTTATCATTTACTACCATAAAATATACACAAATCTATTATAAGAAATTAAACTTATTAGAGGG
TACAAGATGGCCAACTAGACACACTCAGGAAGCACCACTTCCACTGAGGAAGCCCAAAATATTGAATAAA
CTAACATACTTCGAGCATATCTTTTGAGAGAAAACACTGAAAGTCAATAGAGAGGTGACACAGACACTGA
GGCTGAAGAGAGAGAAAGCTGGAAACCCAGTGCAGGGTTGTTGAACACCAGAGATAGTTTCCAGCCCTGA
GTGGCTCCTAGCTAAGGGGTGAGTAAAGTGGCAGTGGGACAGCCTACTCTCACTGTTGACATCTGGGATC
CTACCTACAAGAGAACCCACGACCCCCAGAGACATTGGAACAGGCAGGGGCATCTGCCCAGAGAGTAGGC
AGAAATAGAACTACAGCCAGCCTTGAACCCAGGGGGTTTTGCATGTTGGGTAGCTGCAGCAGAACGCAGC
CATAGGCGCCCAACATCCAAGGCTCTCTTTCTTCCACCAAGTAGCTCTCAACTCACCTGACTTCTGAGCG
AAGAGACAGCGGGGCCAACTTTCCTGTGAGCTGGGACACATCTGTATTGTAGGCCCTTCTGCCCGCCAGT
CCCTCCCAGTACTCCTGCCTGGCCACACCTGCAAGAATATGTGCACAGCACAGCCTCCACTGCTCAGCCT
GAGGGTTTTTTCAAGGACCCCCACCTGAGTACTTCCTCAGTATCCTTGGAGCACTTCAGATCCCCAGTG
TAGCTACTGCCTGAACCAGAGGGGCCAGACAGTGGAGACACAGGCTAGTCCCAAAACCCCAGGGCTGCAG
TGCATAGCTTGGGAGTGTGAGCTGAGATTGGTGCCCAGCACTCAAGCAGAGGAAGAATTCTGAATCTCAG
AACACTGAGAGGGGTGAGATGCACGGGTTCATGGGCCAGTGCAGAATGAGACATGCCTCATTTCATAGGC
CCAGTCCAGGAAGGCTGTGTCCTGTCTGCCAGCTGCTGCCTCTGCCTAAGGGAGCTCCATGGCTCAGAAC
AGTTTCCTAACAAAAGAAATGCAAGTGTGGCACCAGTGACCAGAGCGGGAGATTGGGGGGGTGTCCCCTA
TGGCCCAGGCACAGGCCTGTTAAGGGGGTCATCTCTCTTGCCCGCTGCCACAAGCACTGTTGTAAACACA
CTGAAAAACAAAAGAGTTATGTCCCCGAGTAACAGCTTATCTGCCAGCCATTACTCTTAAGCACCATTTA
CTGGATCACAGCTCAATTTAAAACATCTGCCTATATATTTGAGACTGTACCTCACTCTGTTACCCAGGCT
AGAGCGCAGAGAAGCAATCGTAGCTCACTGCAGCCTCAAGCTCCTAGGCTCAAGCCATTCTCCCACCTCA
GCCTTCTGAGTAGCTGGGACTACAGGCACACACCACTACACTTGGCTAATATGTGTTATTTTCTGTAAAG
ACAGGGTTTTCCATGTTGCCCAGGCTGATCTCAAACTTCTGGCCTCAAGTGATCCTCCCACCTTAGCCTG
GCAAAGTGCTGGAATTACAGGCTTGAGCCACTGTGCCTGACTTCAAAAATAGTTTGTCAGTATACATTGC
ATATGAAACTGAGAGCAAGAATCTAGCTATAAATAAAAATATTGTGCAGAGTCTTATCCCAGAAATTAAA
CCAACTGACCATACTCAACTTATACCACAGTTAAAGGAACACCATTCCTTCAAGATGAAAAAGAATCAAC
AAGAAATCTGGCAATTCAAAAAGTAAGAATGTACCTTAACCTTCAAATGGGTGCATTTGAGCTCTCCAGC
GATGGTTCTTAACCACATTGGAATGACTAAAATGACAGACAGGCAATTCGGAATCTGGATGGCAAGAAAG
CTCATTGAGATTCAGGAAAGTGCTGAAACACAATTTAAGGAATTCAATAATTCCAGTAGAATGATCCAAA
AGCTGAAAGACATAATAGCCATTAAAAAAACACTACTTCTGGAATTAAAAAAAATACTACATGGATTTGA
TAATACATCCAGACCTTTAGCAACAGAACATACCAAAGAGAGAAAAGAATCTCAGAGCTTAAAAACCAGT
TTTTATAATCCACTCCATCAGACAAAAAGAAAGAAAGAAAAAAAAACATAAAAATGAAGAAAACTTCTAG
GAATTTGGTTTCCTTCTGTAAAGAAACCAAGCCTATGATTCATTGGAATTCCTGAGAGAGAAAAAGAGAG
AGTAAACAACTTGTAAAACGTATTTGCAGATATAGTCCATGAAAATATCCTCAAACTTGCTAGAGAGATT
GATATGCAAATTCCTAAATTACAGAGAACCCCTTTGAGATGCTATAAAGATGACAATCCCCAAGGCATCT
ACTCATTAGATTCCCCAAAGTCCACATGAAAGAAATAAATATTTTAAGATTTTTTTGGGGGGCAGCTAGA
GAGATGGATCAAGTCACTGTCAAGGGGAACCCCATCAATCTTGCAGAACACCTTTGAGCAAAACCATAC
AAGCCAGAAGAGATTGGGGACCTATTTTCAGCACCCTTAAAGAAAAGAAATTTCAACCAAAAATTTAATA
TCCCACCAAATTAATTTTGTAAGTGAAAGAGAACTAAACTCCTTCTCATACAAGCAAACATTGAGGAAAT
TTCTTATCACTAAACCAGCCTTATAACAGGTCTCTAGAAGAGTGCTAAACATGGAAACAAAAGATTAATA
CTTGCCACAACAAATACTCACTTAAATAGGTAGCCCAGACACATAAAGCAACTATACAACCAAGTCTATG
AAACAACCAGCTAACAACATGATGCCATGATCAAAATCTCACGTATCAATAATAACCCTGAATGTAAACA
GGCTAAATGCCCCAAGTAAAAGACACTGAGTGACAAGCTTCATAAGTAGACAAAACTTAGCCTTCTGTTG
TCTTTAAAAGACACATCTTACATGTACAATACCCACAGGATCAAAGTAAAGGAACGGAAAGAGATCTATC
CATGCAAACAGAAAACAAAACAGGGCAGTAATCACTATTCTTATATCAGATAAAACAGACATTAAACCAA
AAACCATCAAGAAGGACAAAGAAGGGTATTACATAAGGATAAAGTGTTCCATTAAACGAGAAGACTTAAC
TATTCTAAATATATATGCAGTCAAAAGTGGAGGACCCAGATTTACAAAAAAGATTCTTAGAGACCTAAGG
AAACTAAAAACAGACAGCCACACCATGATAGTGGAAGACTTCAACAACTCACTGACAGTGTTAGATATCG
AAGCAGAAAATTAAAATGTAAATTTTGGACTTAAACTCAACTCTCAACCAACTGGATCCAAAACATCCT
ACAGAATACTCCACCCAGCACTATCAGAATATGCTTTCTTCTCATCTGCATATAGATTGTATTCTAAAAT
CAATCATATGCTCAGTCATAAAGTCTCAATACATTCAAAAAATTAAAAGATTTTGAGTACATTCTTGAAC
AAAAGTGCAATAAAAATAGAAATCAATACCAAAAAGATTTCTTAAAACCACCCAAAAGTATGGTAATTCA
ACAACTTTTCCTGAATAATTCTTGGTTTAAGAATGAAAGTAAAACCGTTTTTGACATTAAATAAAATAGA
GACACACCTCACTAAAATCTTTGGGATCTATCTAAAGCAGTGTTAAGAGGAAGTTTACAATGCTAAAGGC
CTTCATCAAGAAGGCAGAGAGATTTCAAATTAACAATTTAACATTGCACTTACACTAACTAGAAAAAAAA
AGGACAACCCCAAAGCAAACTGAAAATAAATAACGAAAATCAGAATGAAATTGTGATGCAAAATGTATAC
```

FIG. 5 (continued)

```
AAAAGATAAATAAAACCAAGAGTTTGTTATTCAAAAGAATACAAAAAGATTAATAGACTGTTAACTAGAT
TAACAAGGAAAAAAAGGAGACCCAATTAAGCACAATCGGAAATGACAAAGATCACATTACAACTCCCATA
GAAATGCATTACAAATGCCCCTCTGCACACAAATTAGAAAATCTAGAGGAAGTAGAGTCATTCTTGGAAA
CAACCTCCAAAGATTAAACCAGAAAAAAAGTGAAAACCTGAACAGACCGATAACAAGTTATCAAATTGAA
TTAGTAATAAAAAACCTACTGACCAAAAAAAAAGCCCTGGACCAGATGGATTCTCAGCCAAATTCTACTA
ATTCTAATTTTATTCTAACATAAAAGTTCGCTTTTTTAAAGTTAAACTTCAAATTTAAGCACAGAAACAC
ATATGTACCTCATATTATCTCATCTACAGTCAAGAGAAGTGAAAACAAATGTGAAGATGTACTATTAAAG
CATAACTTTATACAATTGACTGTAATATATACGTTACTGCTGTAATAATTTCATAGCACCTCCTGTAATT
GTAGTAATAAGGTTGTGTTGAAAGCACCTGCTTAAAACACCATGTGACACTAATTATCTCCACATGAACA
GTTCCTCTCTCCAATAAATTGCGGATTGCAGCAAAATCTGATTGTGATTCTTGTGCGTTTTTATACTGTT
TAGTGCAATACTGTCAACTTTGAATAACACCGTTGGAGCCATATGAATTGCCACTAGTGATGCTGAAACT
GCTCCTAAGAAACTGAGAAAAGTCACGACATTACAAGAAAAAGTTGTATTGCTTGATATATAATGCAGAT
TGAGGTCTTCAGCTGCCCATTGTTTCAATACAAATGAATCCAGCATAAAGATCATTGTAAAAAACAAAAA
AAGGGAAAAAAAAAGGAAATTCATGATGGCATTGCTGAGTCTATGCCAGCAGGCACAAAATCTTGCACTT
TTAGTAATATACCGTCTTATCTCATATTGAAAATGAAATTGTTATATGGCTGCAAACTTTTATAAGAAAG
GCATAACCACAGACTTTAATGTGATTTGAGAAAAAGTGAAGTTATTATATGACCATTTAAAGCAAAGGAA
GGTGAGGGATCTAAAACTGGAGAAACTAATGCAAGCAAAGGATGGTTTGATAATTTTAGAAAATGATTTG
GGTTTAAAAATTTTCAAAATAACAGAAGCAGCAGCTTCTGCCAAATGAGAGAAAGTGAACAAGTTTTCAG
ATTCCACTAAGAAAATCATTGAGAAAGCATATCTGCATGAGCAGGTTTTTAATGCAGATGAAAGTGTCCT
ATCCTGGGGAAAAGAAAGCCACGAAGGACGTTTATTAATAAAGAAGAGAAGTGAGCACCAGGATTTAAGG
CAGGAAGGGATGAGGTAAGTCTACTATTCTGTACAAATAAGGTCAGGCTTATTATCAAAACTGCTAGTAT
CTACAAAGTTGATAAGTCCCAAACCTTGAAGGCAAAAGATAAAAATCAACTGCTAGTCTTCCAGTCATAC
AAAAGGAAGGTCTGAACAATTAGTACTCTTTTTCAGAATTGTTTCCATCAATGCCTTGTTCCTGAAGACA
GGAAGTAGCTTGACAGTAAGGGACTGCCTTTACAGTTCTTTTCATATCAGTCGATGCCCCTGGTCACCTA
GAAAGCCCATAAGTTCAACATCAAAGGCATTGTAGTGATCTATTTCTTCCACCACAACATCTCTAATTCA
GCCTCTAGATCATGGAGTCATAAGAAACTTTAAAGGATCATTACAGATGATACTCTAACGAAAGGATTAT
CAGTGCTATCAAAGAAATCCTGATAGGCAGAACATCATAAAAGACTAGAAGAATTACACCATTTAAGAT
GCTATTGTTATAGGGAAAAAAAAAGTGAAAGTCATTAAGTGCAAAACAATACATTTCTACCAGAGAAAA
TTTTGTTCAGATGTTGTGCATAAATTCATAGGATTAACAACATGGCCAATCAAGAAAATTATGAAAGAGA
TTATGGATATGGAAGAAAAAGTGAGGAGTAAAGAATTTCAAGATATCGGTATTGGAGAAATTCAAGAGCT
AATTCATACCTCATCAGGGAAGTTAACAGAAGATGACCTGATGGAGATGAGTGCCTGCGAACTAGTGTCA
GATGATGGGGAAGGAGACATAGAAGCAGCAGTGCCAGAAACAAATTGTTATTAGGCAATCTAGCAGAAGG
ATTCTGATAATTCAAGACTGTTTTTGGCTTCTTTTATAACAGGGACTCTTGTCTAATGTGGGCACTGAAA
CTAAAGCATGTGTTGGAAGAAGGATTAGTTCCATTTAGAAAAATTTTTAGAGAAATGACAAAACCACAAA
GTCAAATAGAAATTATGGCGTATTTATGAAATAGTTACTGAATGTACTTGCCTCTTTTGCCTTCCCTCTA
CCTCCTCCACCTCTTCCACCTCTTCTACCCTAGTGAAAGCAAGACCAGTGCCTCCCATTCCTTCTCCTCC
TCAGCCTACTCAATGTGAAGAGATGAGAAAGATCTTATGATGGTCCACTTCAACTTAATAGTAAATATGT
TTTATCTTCCCTGTGATTTTCTTTATAACATTTTTTCTCTAGCTTACTTTATATTAAGAATACTATATAT
AATACATATAACATACAAAACATGTGTTAATCAACTGTTTATGTTATTGGTAAGGATTCTGATCAACAGT
AGCTGGTATGATTTGGATCTGTGTTCCCGCCAAAGTCATGTAGAATTGTAATCCCCAATGACGGAGGTGG
GGCCTGGTGGGAGGTGATTGGGTGATAAAGGTAGTTTCTCATGAATAGTTTAACACCATCCCCCTTGATG
CTGATCTCATGATACTGAGTGAATTCTCATGAGATTTATTTGCTCAAAAGTGTGTAATACCTCCCCCCTC
TCTTCTTCCTGTAGAGACTGCAGAACTGCATAACTGAAACTTTATACCCATTGACTAACAACTCCCTGCT
TCCCCTTCCCCTTAATCACTGGCAATAACCATTCTACTCTTTGCTTCTGTGAGTGTTACTGTTTTATGTT
CCTCACATGAATGTAATCATGTAGTATATGTCCTTCTGTAACTGGTTCATTTGCCTAATGTCCTCAAAG
TTCATCCAAGTTATCACATATTGCAGAATATCCTTCTTTTTAAAGACTGAATAATATTCCATTGTATGTC
TATACAATATTTTCTTTATCCATTTATCCCTCAGCAGACATGAGGTTGTTTTTACAGCTAGCTATTATGA
ATAGTGCTGCAATGAACGTGCAAATGCAAATGGTCTCTTCAAGATAATGATTTCAATTCTTTTATATATG
TACCCAGAAGTGGGATTGCTGGGTCATATGAGAGTTCTGTATTTAATTTTTGAGGAATCTTTATAATACC
TTTTATACTGGCTGTACCTTTTTGTATTCTACCAGCAGTGTACCGTGTTCAAATATCTCCACATTCTTGC
AAACACTTTCTTTCTTAAATGATAGCCATTCTACAGGTGTAAGGTGTAGGAAAAGAGTGGAGTTGTGCTT
TTGATTTGCATTTCCCTGATATGCAATGTTGAAAATCTTTTTATTGACCTGTTGTTCATTTGTGTGTCTT
CTTTGGAGAAATTTCTATTCAGGTATGTAGCCTAATTGTTTTTTCAAATTAATTTTTTTTTTTGAGTCA
CTCTCACTCTGTCACCCAGGCTGGAGTGCAGTTGTGTGATCTCAGCTCACTGCAATCTCTGCCTGCCAGG
TTCCAGTGATTATCCAGCCTCAGCCTCCAGAGTATCTGGGATTACAGGTGCCTCCACCACACCTGGCTAA
TTTTTGTATTTTTAGTAGAGATGGGATTTCACCATGTTGGCCTGGCTGGTCTCAAACTCCTGACCTCAGG
TGATCCAATTTGTCTTGGCCTCCCAAAGTGCTGGGATTACAGGTTATCAGCCACTGACTGACATATATAA
```

FIG. 5 (continued)

```
AATTGTATTTTTATCATGTACACTCTAATGTTTTGAAATACATATATAAGTGGAATAGTTAAATTTAGCT
AATTAACAAATGCATTATCTTACATAGTTACTTTTGTAGTGGAAACACTTAACATCTACTCTCTCAGCAT
ATTTCAAAAATACAACATATTGTGGTTAAGAATAGTCACCCTGCTGCATAATAAATCTCTGCAATTTTTT
CCTCCTAATTGTAATTATGTATGCTTTGACCAGTATCTCCTCATGTGGGAGATCAGTCAGAGTGGTGGAA
GAAGCTATAGGGAAGGAAGCAGGCCTTTAGAAAGGTCAGAAGGCTCTGCAAAACTTCAGGGGAGACTAAG
CTGAAGATAGCTGTTCTCTTACCCTGAGGCAGAGCACAAGAAATAGGTATAAGGAAGTATAGGGGAATTT
ATCTAAATAGGCTTGTCTACCCATGTTGTCCAGAAACTGACCTTTGACCATCCGTACACGTGACTGTTCC
CAGTAAGGGGGAACAATAATGTTAATTACACACAGATTGTGTTGGCTCCAGCCTTTCGGCATTATGTCTG
TACTAAATAAAAGTGAGCAGCTCCAGCTTGTTGGGACTGCTACTCACTCTTTGGCAGTCCCCTAGCCACT
CTTTCACCACATACCTGTGTCTGAGTACTCCTTTCATCTGTTGGTAGGCCAGGGTCTACCAGGATGGACC
AGGCATCCTCAACTCCACTGTTCTCCCAACCACCTGGCTTCTGGTAGCCACCATTCTACTCACTAATAAC
TAATTAATTTTTATTTCAATAGCTTTGGGGTAGATGTTGTTTTTCGTTACATGGGTGAATTCTATAATG
ATAAATTTTGATATTTTACATACCTGAGTAATGTACATTGTACCCAATATGTAGTTTTTTTATCCCTCAG
TCCCCTTCCATCTTTCCCCTTCTGAGCCTCCTAAATCCACCACATCAATCTGTATGTCTTTGTATCTTCA
TGGCTTAGCTCCCAATGATAAGTGAGAACATACAGTATTTGGTTTTCCATTCCTGAGTTACTTCACTTAG
AATAATGTCCTCCAGTTCCATCCAAGTTCCTGCAAAATTTTTCATCGTTATTATTTTTTGCTATTGAGT
TGTAGGATTTCCCCGTGTGCTTTAGAAATTAACCCCTTTTCATATATAAATGATTTATAATATTTTATTT
TATTCTGCATATTTCTTTTTTACCCCATTTATTGTCTCTGTTCTGTTCCATTGGTCTATATTTCTGTCTT
TATGCTGGTACCATATTATATTAATTACTATAGCTTTAAAATACATTTTGTAATTAGGAAATATGAGGCA
GCTTTATTCTTTCTCAATGCTTTTTTGGCTATTTGATGTCCTTCTTGGTTCCATATGTATTTAGAATTG
TTTGTTATATTTTTGTAAAAATACTATTGGGCTTTTGATAGGTATTGTATTGAATCTTTACATATATTTG
GGTAGTATGGACATTTACTATTAATAAGTCCTTCAATTATTAACACAGAATGTCTTTCTAATTATTTATG
GCTTCTTTATTTCCTCAGTGTCTTGAAGTATTTCATGCACAAGTCTTTCACCTTCTTAAATTTATTTTTG
TGTTTTATTCTTTATGATTTTAGTGTAAATGGAATTGCTTTCCTAATGTCTTTTCAAATAGTACTTGGTT
AATTCATAGAAATATAAGTAATATCTTATAATTATTTTGTATCCTGCAACTTTACAGAATGTGTTTATTC
AATTCTAACAGGTGTGTGTGTGTGTGCATGTGTCATCTTTAGGGTTTTCTATATACAAAATCATGCCATC
TGCAAGTAGAGGCAATTTTACTTCTTTCTTTCAAGTTTGAATGTCTTTTATTTCTTTTTCTTGGTTAATT
GCTCTGGCATAAAATGGCAGGACTGTGTTGAATAGAAGTGATGAGAATGGCCATTCTTCCTTTGTTCCTG
AAAGCTTTCTGTTTTTCACTCTTGAATTTAATGCTAGCTGTGAGCTTTTTAAATATGCACTTCATTTTGT
TGAGGCAATTTTTATCTATTCCTAGCTTGTTGAAAGTTTTTATCACAAAACATTGTTGGATTTTATCAAA
TGCTGTTTAACATCTGCATATTTGATCATGTAGATTTGTCCTTTTTTGTTAATGTGTTACATTACGCT
TGGTGATATTTGTTAAACTTAGCATTTCAGGTATAAATCCCCCTTGAATATAGTGTAGTATCCTTTTTAT
ATGCTATTAAATTTGGTTTACTAGTATTGTTTGAGGATTTTCTCCTCTGTCTTCATCAGATATATTGGTT
TGTAGTTTTCTTCCTTTTGGTGTCTTTGTCTGGCTTTGGTATCAGAATAATGCTGGCCTTATAAAATTAG
TTTGAAGATGTTCTCTTCTCTTCAATTTTTGGCAAGAGATTGGAATGGATTGCCATTAATATTTTCTTTA
GCTATTTAGTAACACGCACCAGTAAAGCCATCGGTCCTAAGTTTTTTGTTGAGAAGTATTTGATTATTA
ATTCAATATTTTTACTGGTTGTAAATCTCTTTATATTTTCTATATTTTCTGTGTTTATGTCTCCAGGAA
TTTATTTTTTCTTTCTTATCTAATTTTTGATGTATAATTTCTCATAGTAATCTCTTATGATTGTTTATT
TTTCTAGCATCAATTAAATGTCTCTACTTTCAGCTCTTATTTTGTTTGTTTGAGTCTTTTCTCTTTTGCT
TAGTCTAGTTTAAAGTTTGTCAATTTTGCCTCTCTTTCAAAAAGATCAACACTTAGTTGTGTTGATATTT
TTTCTAATGTTTTTTTTTCCATATTCTTTATTGTATTTATTTCTTCTCTAATCTTTTTTTTCTCCTGCTAA
CTTTGGCCTTAGTTTGTTTTTCTTTTTATAATTTTGTGAGGTGTAAAATAGGTTGTTAGTTTAAGATAAT
TCTTTACTTTTTACTAGCATAATTATGTGATATTTATCAGTGTGTACTGAGAGCAAACAATGCCAGATGC
TACTAGTGACCATAAATTAGAGAAATAACCTATGTTTTTGGATATGGAAATGAAATTTACCCTACAAAT
GTAGATATTTTTTACTGAACACTTCCTCTTACTACTGTTCTTGCTGCATCTCACATTTTAGAATGTTTTG
TTTTTGATTCTCTTCGTATCTAAATATTTTCTAATTTCCCTTTTGATTTCTTTGACAATTTAATTATTGA
AAAGTTTGTTAGTATCCATATTTTTAAAATTTTCTACTTTTCTTTTTGATACTAATTTCCAGTTTTATTC
CATTGTAGTTAGAAAAGATAATTGGTATGATTTTAATTTAAATTTATCAAGACCTGTTGCATGATGTAA
CATGTGGTCTATCTTAGAAAATATTCCATTTCTATTTGAAAAGAATATACATTCTGTTTTTATTGAGTGA
AGTATTCTCTATGTGTCTGTTACGTTCAATTGGTCTATAATGTTGTTGAAGTCCTCTGTTTCCTCATTGA
TTTTCTCTCTAGTCATTCTATTTATAATTGAAAGTGAGATATTATGAAGTCAGCCTACTATGGAGGGCTA
ACTGTAATACACTATTTTATATAAGAGACTGGAGCATCCTTGGATTTTGGTATCCATAGGGAGTCCTAGA
ACCATTGTTCACAGATACCAAGAGATGATTTTATTGTATTTCTCTATATTTCTCTTTTCAGTTCTGTCCA
TGTTTGCTTTATAGCTTTTGGGTCTTTGAGATTGGGTGAATATATTGGGTTGTATATTCTTGGTGAATTA
ACTTAAAAAATCATTTTATAATGTCCTTTTTGCAACTTGAGACAGTTTTTACTTAAACTCTTTTTCTTT
CTTTGACAAATAGTTAGGTTGCAAATTTTCCAAACTTGTATGCTCTGCTTCCCCTTTAAATATAACTTTC
AACTTTAGGTCATTTCTTTGCTCTCATATCTGAGCATTGCATGTTAGAAGCAGCCAACCTATATCCTTAA
```

FIG. 5 (continued)

```
TGCTTTACTGCTTAGAAATTTCTTCCATCAGATGTTCTAAGTCATTGCTCTTTTTTTTATTTTGGAGAC
AGAGTCTCACTCTGTGGCCCAGGCTGGAGTGCAGTGGTGCGATCTCGGCTCACTACAAGCTCCACCTCCC
AGGTTCACACTATTCTCCTGTTTCTGCCTCCCAAGTAGCTGGGACTACAGGTGCCCACCACGATGCCTGG
CTAATTTTTTTGTATTTTTAGTAGAGATGGGGTTTCACCGTGTTAGCCAGGTTGGTCTCGATCTCCTGAC
CTTGTGATCCACCCACCTTGGCCTCCCAAAGTGCTGGGATTACAGGCGTGAGCCACCGTGCCCGGCCAAG
TCATCACCCTTTATTTCAGACTTCCACAGATCCCCTAGGGTATGAACAAAATGCAGCCAAGTACTTTGCC
CGACACCATGCCCGGCTTATTTTGTACTTTATTAGTGGAGACGGGGTTTCTCCATGTTGGTCAGGCTGGT
CTCAAACTCCCGACCTCAGATGATCCACCCGTCTCAGCCTCCCAAAGTGCTGGGATGACAGGCGTGAGCC
ACCGCGCCTGGCCTATTTTATTTTCTATAGCCTCATAACAGAGGTGAGACTAGTGATTTTAGAGCCACAC
TTCCTGGCTTCTGTTTTTATTATTTTAATTATTTTATTATTATTATTATTAATTTTGTTTTTTTGGGGGGG
TTGTTTTGTTTTGCTAAGGCATAACAAGAGTGACTTTTGCTCTAGCTCCCAATAACTGTCATTTCTATTT
GAGACCTTTTCAGCATGAACTTCATTGTCCATGTCACGATCTGCATTTTGGTCATAATCATTTATCAGTT
TCCAAGAAGTTTCAAACTTTCCTTCATTTTCTTATCTTCTTCTGAGTCCTCCAAGCTCTTGTAAGCTCTG
CTCATTACCTAGTTCCAAAGTCAAGTCCACATTTTCAGGTATCCTTATAGCAATGTCCCACTTCTTGGTA
ACAATTTTCTGTGTTAGGCCATTCTGGCATTCTTACACAAGAATGCATGAGACTGGCTAATTTATCAAGT
AAAGAGGTTTAATTGGCTTATGATTCTGCAAGCTGTACAGGCATGGCACTGGCATTATCTCAGATTCTGA
GGAGACCCCAAGGAGCTTTTACTCCTGGCAGAAGTTAAAGCAGGAGCAGGCACATCACATGTTGAGAGAA
AGAGCAAGGGGGAGGCAAGGTGCCACACACTTTTTAAGCAATCAGATCTTCTCCTGAGAACTCATACACT
ATTGCAAGGACAGCACCAAGCAATGAAGGATCAACCCCCATGACCCAAACACCTCCCACCAGGCCCTACC
TCCAACATTGGATATTCATTTCAGCAGGAGATTTGAACAAGACAAATACCCAAACCATATCAGCCTCCA
AGTCTTCATGGACTGGTATTGTATAGGAGAAAACTTTCTTCATTCAACCCCAGCAGAGCGTCTGTGGGCC
TCTCAAATTTTGATTCTTTTTTAAACTGCTATCTTTTTGTTAGGAACTTTCAGAATCTAGAGTATGTAGG
GTCTCATGAGCACTTTTAGACAGTGGACAGAGAAGCCCGTCACTTGGTCAACTCCCAGAAAATTTTGAAT
ATTTCACATGCTATCCAATTTTTTCCTTCCCAAGGAGAATTTGAAAACTGAGGTGTTTTCTTTGTTTTTT
GTTTGTTTGTTTGTTTTTCTTTTCTTTTTACCTCCTCACTCTGCATAGATCTGGGAGCAGGGAGGAGCT
GTAGCAAGTGCTCATGTGCTAATTTAAGCCACCATTTTTGTGCTCTTTGTAGCCCATTGGAAGCAAGCAT
ATGCCTAGCCCCAAGATAGGCAAGACAATGACCAGCTGCTGGAGTTGGACACAGAAAAGATGAAATGTTA
GGTTTGTGGTCGAAATATTTCCCTCCCCATAGAGAAGCTGGAGTTAAGTTTTTGTTTCTAATTTTTTTTA
ACTTGGTCATTCTGCCCTAAGCTATGGGCCAGGAGCTATGGGAATGCTTACATACTAGTTCAAGCTGCCT
TCTTTATTTTCCGTAGCCTCCAAAGGTCTGGTATATGCTGAGTCCTGTCAACACTTCAAGATAGGTGATA
TAGAAGACAGTCGCAAGGGTAGTACCTGAAAAGTTACAGTTTTGGATGTGCAGTCTCACTCTGTCTCTCC
ACAGGGATAAGCTGGAGATGCAGTTTTCTTACATTCAGTCTATGTTGAGCCAGGGAATAGAGCTATTGCA
AGTGTTCATAGGCACTTGCAAATTTCTAGTTCCTCTTGAATGCATGGTATTATAATGAGGAGAGGAACAG
CAAAGAGGTGTCTCCAATTTTCTTAAAAGTGTCAATGTAGCTAATATTGCACTTCCCTGGGGTACAATGG
CCTGTCAACTAGCTTCTGGATTTTCCACTAATGGAATTGATCGCTGTATAATTGTTGAATAAAAATATTGT
TGAAAGAAAAAAGGGTCCAGTCCTTCCTATTAGGCTATCTTGCTGATAACTCATATTGGCTTTTTTATT
ACTTAGATTGTTTATTTTATACCTGTTAAAAGAGTGCATTTACACTTGAGATATAGCATTTACATAATAC
TCTTATTCATGATTTAAAGAAAAATATGACTGAAATAAAATGGTTAAATTATCCTTAACTTTTAGAGTCT
AACTCTTCAGGGTTACTTTTAAACTCATATTTTCACTGTATTTTCTTATCCTCTGTGCTGTCAGGAGAGT
TGGAAATGCTTATTTCAGGCATGGTGGGAAGCCCCTTTATTGACTCAGTAGATTTCTTGCAAACTGCTAA
AATTTCATTGCTGACCCTTTCTTGATTTTATTAGCTTGTGCCAATAGACATTTTCAGACAACAATGAGAC
GTCATAGTTCTTCCACAGGTAGTAATTAAACAGTCTGCAAGCTTAAATGTCCAGTGATAGAAACTGTCCA
GTCATGTAATCAGAAAAGCCATCAAGTGCACACAAGCTCAGGCAATGACAACAATATCATGACTGATTCC
TAGACAGTATCTGTTGCATTATGTCATCAAATGTTAGACTGATCCTAGTCTCAGAGATGACAAAAAATTA
AAAGAAAAAAATCGTGTCTTGGAATTGAGGAAATGTAGTTTACTTTCTTCATACCATTATTTCCCTGAAC
CTATTGTATTTCAAAATGATTTTTGACTGGCTTCTATAATTATTTATTCTAGGCACTATCAGGATAACTC
CTACTGATTCTCGATGGGTTGGAGCTTGGTGGCTTAATTTCCTTGTGTCTGGACTATTCTCCATTATTTC
TTCCATACCATTCTTTTTCTTGCCCCAAACTCCAAATAAACCACAAAAAGAAAGAAAAGCTTCACTGTCT
TTGCATGTGCTGGAAACAAATGATGAAAAGGATCAAACAGCTAATTTGACCAATCAAGGAAAAAATATTA
CCAAAAATGTGACTGGTAAGTATTTAACATTCATTGTCAATTTGGAGTTGTTAATCTCAATGAAAAGGAA
GAATGAGTATTCCAAAATAATAAAGCATACCCAACTCATCTGGAGTTGGCTTTCTTTTGCACTAAATTTA
GATAAATTATTTTTCTAAAACTCCTATTAAAGTTAACATATATGTCTTGAGCACATAACAAGTGGAAGAG
AATTAGGTTTGTACTTTTTAGCAGGGAGAAACCAACAAAAGTTTACAAACATCCATTTTTTATGAGCCAA
ATAGTAAATATTAATTTTAGTATTATATGGTCTAAACTGGGAGAGTTCAAAGAATTATAATATTTCATTC
CTTCATTTATTCAACAAGTAGTACCAGGAACTGTACTATGCCCTGGTAATAAAACATTACCTCTATTTTT
CAAGAACCTAGTGGGTGATGCTGAGAAATATATAGACAATAGCAATATAGTGCCTTAAGTATTATGGTGA
AATTAAACTTAACTATTATCAGGTGTAGAGATGGATTAAGGAGAAGGAAGTCGGGAGAAGTTTCTCCCTA
```

FIG. 5 (continued)

```
TGTAATTAGAGTAATATTTATTTTGGTAATTATCTATCTATCTATCTTATCTAAATATTCAAAATAAAGT
GGAAGCAAAGGTGGTAGTTAAGATAATTAGACTAAGTAATGTAAATTAGGATGCATCAGCATTTGACAGT
GCCTCCTCTTTTGAATATAAACCCTGGGACTAATGGAGAACCATTGAGAGTCAATAAACAAAGAGAATGA
CTTGGCAGTAGCCAGAGCAAGATATGTGAATCAGTGAGGTGTTGACAGCAGTTTTCAGATTTGGGAGAAA
TGGTGAAATAGCCAAAGCAATGCAACACTTAAACCCTCAGCATCTTTTTCAAGTTTTCTTTAAAGTAAGA
TGACAAATTCTCCAGTGTAGCCTAGGTTCTTCCTTTCATCAGGTCTTTTACTTATTACTTTATTGCTATT
TTCTCCTTTCTATCACACTAACCCAAGAGCAGTGGTGTTCTGGTACTCTTTATATTGGCTCATAGCAGAG
GACTGTTAAGTTTCAGCTACATTGGTAGGTTGAAATTGTTCATGGCAAGAGAATTACCATGATTTATTAC
CATGGAAATTGGGATATACTACAAGTAGAAGTTTGTTTTCCTAAGAATCAGATGTTAAACATTTATGTTT
TTAAAATTTAACATTCACACTAAAAGTACTATACCAATAATTTTCATTTTGTATATGATGTTTCTACTGT
ACCAAATCAAATCTTTAAAAAATAGTAGATTGTCTAAACCTATAAGGAGCGGGGTTGACTGTGATCCAAA
CAGAACAGAGAGGATAATGAAGTTGTAAAAATAGGACAATTGTAGACATAATCTCTATTATGAACAGTTT
TTGTAGGTGTGACCCTAAGAAAGAGGATCTTAAGTATGTATCTATTAGGAATGGATAAAATAAGAATATA
TAGTCAGAAAAAATATTGAATTTATTCCATATGCTCTTGAATAGAACTAAAACTGATTAGAATGAAAAGA
TGATTTCAGTTCATTACAAAAACAGTGTGTAAACAATGAGAACTTTTCAAAAGTGGAGGAAATTGCTTCC
TAAGGTACTTAGTTTAATGCCACTTAAGTTGTTTATTGATCCACTTATTAATGATATATAGTAGATCATG
ACTATACAGAAGTTTACACTGGATGACATTGAATTTCTCATCCTCAAAAATGCAACGCTTGTGTGAATGT
ATATACTCCATTTCTGTTGAAGAAAGGCCACAACTCACTTATAATACTTACAAATCAGGGATGGTTTTTC
ATGACTGGGGAGACCTGTGGAGAGAAATGTGGCACTTTTGCCCAAGAATTTTAAATGTTGTTTATTCCCA
CTATACATTTTCTTATCTCTTCTTTTTTTCTTTTCTGTTTCTTTTCTCTAACTCCTTCTACTCCTTATTT
CAAGCAGATGCAACTGTTTCGTAGCTGACATTAAATGGATGTCTTAGTTCTGACCATATCTAATGAAAAT
CTTTAGAGATTTAAATAGAGAAAATATTTCAAAGTCCGTATCATCCAACTCTCAGTAACCATATCTTGG
CTCTGTCTTGATGAACTCTGATACTTCCTACTGTTTTTCTAAGTAGTTCCTTCTACTTTTAAGTCCTATT
ACAGCTAGTTGACCTGGTGATCACAGATCCAAATGACATAATTTCTACCATGAACAGAAGTTAGAAGTTT
GTTACCACAGCTGTTTGTAGGGATAGGTGGTTGTATTATTACTATTATAATACTACTTGGGACACAATAT
TATCCCCTGGCTGCTTTCCTTGTATCTTAAGACAGAGGGTTAATAATATTGCCAAATTTACTGAGAAAGT
ATGTTATGGTAGAAGAGCTGTATACTAGAGAAACAGGAGGTCTGAGTCCTCATACTAAATTAATCTTTAA
GAATTTTGAACCTCAATGGTCTTATTTCTGTGAGTTTTGAATTATGCTGTCTTTACATTTCCATTTAATA
GTTATATTTTAATATAATACTTATATCATTAAGTACTAATAAATAAGAAACATCATATGTCTTATTCAC
TTTTTGTTTGTTTTTGGGTTTTTTGTTTGTTTGTTTGTTTGTTTGTTTGAGATGGAGTCTTGTTG
CTCTATTGCCTAGGCTGGAGTGCAGTGTCACCATCTCAGCTCACTGCAACCTTCGCCTCCCTAATTCAAG
CAATTCTCCTGCCTCAGCCTCCCAAGTAGCTAAGATTACAGGTGTGTGCCATCGTGCTGGCCAATGTTTG
TATTTTTAGTAGAGTTGGGGTTTCACCATGTTGGCCAGGCTGGTCTCGAATTCCTGACCCCAGGTGATCC
ATCTGCCTCGGCCTCCCAAAGTGCTAGGATTACAGGAGTGAGCCACTGTGCCCGGCCTTCACTTTTGTTT
TTTGAACAATTAGCATATTGTCTGGTACCCAGTTGAAAACCTAACATTTGCTGAATGAATGAATAAGTGA
ATTAATATGTTTGCAATAGTATTGTAAAGTACCCAGGATAACCAAATATTAAGTGAAGAAAGCAAGTTAC
AAAACAGCACTTACGTATGACCCTATTTGAGGGTAAAATAAACTAAACTAATAAATATTAATATTCGTAT
GGAAAATATTGAAAGAATATATTTAAAAGCTGTGAACAGCCTGTGGTATTGCAGGCTATTCTCACTCTTT
GTGTTATGTGTTTATAGAATTTTAAATCTTACATGACTTACGTTCACAAATTTTAGATATAAATGTATAT
TTAAGTTGCATTCAAATATTTTCTTTATTTTTACAATTTTACAGGTTTTTTCCAGTCTTTTAAAAGCATC
CTTACTAATCCCCTGTATGTTATGTTTGTGCTTTTGACGTTGTTACAAGTAAGCAGCTATATTGGTGCTT
TTACTTATGTCTTCAAATACGTAGAGCAACAGTATGGTCAGCCTTCATCTAAGGCTAACATCTTATTGGG
TAAGACATATTTTTTACTTGTGTGCTTAATAAGTGAAATAATACTAAATACTGTATTCCAAGTGGTATTT
TATTGTGAAAGTGATTTTGTATTTTAGTAATACAGGATAAGTATAATTTTCTTGTATTCTTTCTCAAATG
TTATTAAACATATAAAACTTGTGATGTCACTATTGCTCTGCATTTGAAGTTGCATCTTATTTTAGATGAG
TTCCTGAAAAAAATGTTGCAAATAAATGGACAATTTAGAGGTAGTATCTGTATAATTGGATCTTATAATT
TAGTGCTAAGATCTGAGACAAACCCTTTTGTAATTATAATCATTATAATTCTATAATTTATGGACTTTGA
AATCAAGACTCAGTTACTTACAAAAATATGACACTAATAGTTCCAAAAAGAGTATCGATTTAAATACATC
AAAATATGCATAATTCAAAACAAATATATTTTACAGAGTATTTTTGCTACAATATCTATTTTCAATGGC
ACATTTAGATGTGCTTATTAAGGAAAGTTTCCTTGTATTATTCTTCCCACAACTCTAGTATTGTAGACAC
ATTATAGAAATTCAATATAAATATATGATGAATTAAACAACTTATCATGTGGTATGTAACTAGGTCATAA
GTAAACAAGAAAATGAACTGTACTGAAGCAGGAGACCAAGCTTCCAGATAATCTCTTTGTTGATCTTAAGA
TAAAAGTTTAAAATCGAAAAATAATGTTTTGACTCCCAGTAACCTAGCCTGAGCTTTTTCCTAGAGAAGA
CTTCATCTTTGTTAACTCTTATTAGACAAAGATATGGAAAAGTTATAGGAGGGATTAAACATTATTAATC
CTGTATGTAGAGCGATTTGTCAGTTCAGGTTCTGTATGTTTTTAATAAATGACAAAGATATATTAATTT
TTATGTTGTTAAGCTCTGGGCAGATTTAGTGTGAGTTACTGAGGGTTAGAACTCTATCTGAGAGAGGCAA
AAGGCTTTAGATGAAGTTCCATAGGCAGAAAGATGGTGTTTTGTTGTTGTTTATTTCCAGAAAAACAAAA
```

FIG. 5 (continued)

```
TTGCCTCATAGAAATTATCTGCTCCAACAAATATCCTCAGCCACACTGCCTTTTGCTATTGAGGAAACCA
AACTGTCATCATTGGCAGGAACAAATTACACAGATCCCCTACCACCATACTGCTATATCATTCTTCTTTT
TAAAAAGTAATAAGATTGGCATTCTACTATAAAGATACATGCACACATATGTTTATTGCAGCACTATTTG
CAATAGCAAAGACTTGGAACCAACCCAAATGACCACCAATCATAGACTGGATAAAGAAAATGTGGCACAT
GTGTACCATGGAATACTATGCAGCCATAAAAAAGAATGAGTTTATGTCCTTTGCAGGGACATGGATGAAG
CTGGAAACCATCATTCTCAGCAAACTAACACAGGAACAGAAAACCAAACACTGCATGTTCCCACTCATAA
GTGGGAGTTGAACAATGAGAACACATGGACACAGGGAGGGGAACATCACACACCGGGGACTGTTGAGGGG
TGGGAAGCAAGGGGAGGAAGAACATTAGGACAAATACCTAATGCATTCAGGGGTTAAAACCTAGATGACA
GTTTGATAGGTGCAGCAAACCACCATGGCACATGTATATGTATGTAACAAACATGCACATTCTGCACATG
TATCCCAGAACTTAAAGTAAAATTTTAAAAAGAAGCAATAATATTGAATAAATTTGATTGACATACATTG
TGTTTCATCTATAAAGACATATCAGAAAACTCATATATGATTACAACTTTTTTTCTTTTTTTTCTAGGAG
TCATAACCATACCTATTTTTGCAAGTGGAATGTTTTTAGGAGGATATATCATTAAAAAATTCAAACTGAA
CACCGTTGGAATTGCCAAATTCTCATGTTTTACTGCTGTGATGTCATTGTCCTTTTACCTATTATATTTT
TTCATACTCTGTGAAAACAAATCAGTTGCCGGACTAACCATGACCTATGATGGGTTTGTATATATCACTA
TATCAATTGCATAATATGTTAACCATCAAATTAAGAGTCTCTGTATAAGTAATATAAGGCAGAAAACAAT
TTTAACTAAACTTTCTTTAAGTTAAGAGAAATTTCAATTTTAAAATTTTTAAAATATCTGTTTCTTAAGA
CCTCAAACACATTCTTTTATTCCTCCACTAAAGAGAAGCAACATAGGTTGTAATAATAATAACTATTATT
TATGTGGTACTTACAATTAGTAGTGGGTACTTTTATCATTATTTTATGAATGGGAAAAGTAAGGCTTAGA
GAAATACATGGATTACACAGCTAGCATTATTAAGATTCTAACTCAAATTTGAGTTTTTTAAGTCCAAAAC
TCTTAGTCTTAACCACCACTGTAATCTTGGATGGATCATAAGAGTTACATAAATGGCATTAGCCAAAAGT
GACTAAACAACTTTTATCTACAGTTCATATCGATGTTCAACAACTATCTTAACAAAAGAACACTTTTAAT
GTTGTACTGAATTTTCTTTTTTGCAAGCTAATATTGTTTTTTTCTGATATTATCTACATTGGAAGTAGCA
TTAAGAAATATTCTATATATAATTGCATATTAGACATTGAAGAATCTTTACTTTTCCATGATTACCATGT
ATAGCAAAGTATTTTTAGTGCAACAGTCTCCACCTCAAATCAAGGGCAAGAATCCTATGCAGTTTTCTGA
TAATTTCCTGAATATAGCCAACAATTTAAGCTTAGGAAGGTTCACATTCAAGCAACAAGCAGAGATGCTC
AGATCACAATTCAGTAACCATGTTCTTTAGTGCTGCTTACTACTGGTGCTGAGCTTTCAAAGTCTGGATC
CCATGAGGTGTTGGTTTTAACTTGTCAAATATTCCCACATTTTCTTCTATAAACATTGTGCTATTCTTGG
AGGCTTGCCAAGGTTATCTGAAATTGTTTCCCTGCACACTGCTAATTCTGAACTGTTATTGGTATCTCCT
ATCCACCATCAACTACTGTAGTAAATTAAAATACATTGTCCTAGAATACTGAATTTTAGAGGTAAAAGAA
CCTTAGAGATGATGCAATCCAACCCTTGTATTATACTTTCCTTTATTATTGAAGAGTCAGAAAAAATGTA
ACATGTTGAAGTCACACAATGTCTTTAGACTCTAGACTGATCCTATGTCACACCCTTAGTTCAAAAGCCT
TCTTGGTTGTAAGGACAGGCCAGTTTCTTGACAACAAGGTTAGTCACTGTACAAAGTATACAAAAGATGG
CAGCAGAGTTAAACAGAATTTGTTTCATTTAATAAAATTTTATTAAGCCTTTCCTTAAAGGTAAATATTA
AGGATATTTGTAGGATACATCAGTTCCCTCATGGGACTCATAATCTAATGATAAATAATATAATTAATGG
ATTCAACATTCATAAAATCCTGCGACTGGGATAAGTTTTTTTTTAAGTATGAATTATTGCAGAGGTCTCG
GAATGTGTTCTGAATATCTCTAAGGATCCCTGAGACTTTATCAAGGGGTGCACAACTTCAAAACTATTTT
TATAATAATACTAAGACATTATTTGCCTTTTTATTCTCATGCTATCCTGACAGTATAGTGATATTTCTA
ATGCTCCAAGGTATGTTATTAATTCATTAATCTGACTGCTAAAATATGTGTGCTTATGTACTTTGTGTA
TTAAAATTTTCTTAGTATTACTTTCTAATATAGTACATGTCAAGAGGTACAACTTAATTTAACAAAATCC
CTTTGGAACAAGCCCTCAATCTTTTATAAGAGTGTGAAGGACTTCTGAGAACCAATTTTTTTTCCAAAAA
AAAAAAAAACCCTGTGAGGTTGGCATTATTATCTATGACTTACAAATGGCAAAACTGATTTTAGAAAGAA
GTGCCAGAATTAATATAAACACAGATGTGACTGATTGCAATATCTGGACTGGCATTGTCTTAGTCCAT
TCAGGCTGCAAAGTTCTAGGTAGCTTATTAATACACAGAAATTAATTTTTCAAGATTCTAAAGGCTGGAA
CATGTAAGACCAAGGTGATGGCACTTTTGGTGTCTAGGAAGGGCCCATTTCTTAATTTATAGACGGTACC
TTCTCATTGTGTCCAGGCATGGTGGATGGGGCAGGCAAAGGGTCAGTAATTCCATTCATGAGTACTCATC
CTCATGACCTTATCACTTTCTAGAGGCCTGACTTCATAAAGTCTTCATATACGAGATTAGTTTTCAATCT
ATGAATTTGGGGGCCACAAACATTCTGACTATAGTAGTCATAAACCATTCTACTTAACCACTCCAAGTAG
TATTTCCTCAAGCAGAATATGCTTTTAATAAAATTATTGATAATGTAGTTTCTGAAGTATGAATCTTAG
TTTTTCATTTAAATTATGTGCTCATTCAAAGATAACACATCAATCCTCAATTATTATCAAATTAAACATT
TGAAAGAAAATAATTTTTAAATGTTTAAGCAGAAATGAATTATACAAAAAATATATTTTATAATTTTAG
CTATGTTATAATCATATTTTATAATTTATAACCATTTCATAAAGGAAATCAGTATAAAGTATACTATAGT
TTTATTTCAAAAATATACTGAGCTTTTCTAGCCTTTTTCAACTCATTCTATTCTTGATTTTTCATTTTGT
AGAGGTTCTGCTTTAAGCATGTCTGTTTTTTTCTTACATATTAAAATAGAGATTTTTAAATTCAACCTAG
TTAAATAGCATTCGTAGACTCACAAGACTTTACAGTGAGCTGAAAGGAATGTCAGTCTAATGTCATCACC
TTACTGAAGAGAAACTCAGTCTCAGAAAAAAGATGTAACTTATCTAATGTGAAGTTTCTTCATAGAATTA
TAACAACTTCTTGTCTAAGTCCTACTTAACATCTTTGGTTTATTTTTACATTTTGCTTTTTCTAGGTCAC
AAGTCATGTATTGGCAAAGATGGAGAGCGTAAAATAAATAAGCATTAAAAAAAACTTTGCCATTTCGTCA
```

FIG. 5 (continued)

```
TCATCAAAGCAAATTTCTTCATATAAAGAAAAATTCTTTATCTACTTTTTTTCCCTCTTTCTCTGCTTTC
ACTTTACTTCTTCCTTCTCCTCCCCTTCTTTGTCTTTTTCTTCTCTCTCTCTCTTTTTGATATATGTCTA
TCATATATTTCCAGAAATAATCCAGTGACATCTCATAGAGATGTACCACTTTCTTATTGCAACTCAGACT
GCAATTGTGATGAAAGTCAATGGGAACCAGTCTGTGGAAACAATGGAATAACTTACATCTCACCCTGTCT
AGCAGGTTGCAAATCTTCAAGTGGCAATAAAAAGCCTATAGTGAGTATTAGTTTTTACTTTCCTCTCCTT
ATTCAAAAGCACAGATTAGATTGAACAATTTTTTACCAAATATTTCTGTAACTAAGGACTCCATTAAAAA
GATAAAAGAGAAAGTTTCCAGTATTATCTGTTGTGATGGGTGTGATGTATAAACAAAGTTTTATATA
AAAGTCTGCTTAGGGCACAATCAGGTTTTTCTGTTACTTGAATTCTAATTGGAGATCACCCCACTTTTTT
CCTTTGAGATTGTAAGACTATGACCTTTTAGAATTTGAATGCATTTAGAATATCTAAGAAGCACCTCATT
TGACTAAAGCCTATAATTTTCATTAAGTTGGAATTACTTTATCCCTCAGAATTCAGGAAAATGAGTTAAC
CCATTGTCAGCACTTCCTATCTTACTAAGACAACAGTCAATATGCAATGTTATATACAGATTCTGATCTG
TTTAGCTCTGGGATCACTACCCTTTTTACTTTTTAAGAAATTAATCAAGGCTTCATGCTCACTTGACTGC
CCTATTCTTGATTTTCTATTTTGATTTTTCCAAAGCTGGCACTTCTACCCAAGATAATGTAGTATCCTGC
TCACCTAATGTCAATATGTCCCATAGAAATGTCATTTATTCCGTCCTGCAAAACCTTTCTTTCCATGTGA
ACTACAGTTTTTCTCTAATCTCCTGGGTAGCTACCTGTCACTGGGAATGGGTTATGGTGTTTCCCATACC
TACAATCCACTCAACATCTCACAAAGTTGTGTAATGTTTTCCTAGGAACTTTTACTATTACCAACATTAC
TAAAACAGTCAACTATAATTATTGCTCTCTGCCACACCCTTCTGTGTTTGATTTTTAAACATTCTCCATC
TACTCTTGCCCATGGATCTACCTACCAATTATAATAAGGAATGGCATGTAGAATTTTAAAGAATAAAGCA
TCCTGGACTTTTTGAAGAAAGGCCACAACTTTAATAAACTTGCACAAATATGGCCCAAAGACTACTTAAA
AGCCCACATCTTAGTCATGGCAACAATGAATCTTTGTGCAGTTGTTTCCTTTTCCTTTGCTGTTTATTT
TTATTTTGCTGTTTTTTAAAAAAATAATTTAACTCTTATTTTAGGTAAAGGGGATACAAATGAATTTGTG
TTAGATGGGTATATTGTGATAAGCTAAAGTTTAGGGTACAATCATTCCCATCCCCCAGGTAGTGAGCATA
ATACCCAATAAGTGGCTTTTTAGTACTTGCTGTTTTTTATCTCTCCACTCTAGTAGTCTGTAATATGTAT
TTTTCCTGTCCTTATATTCGTGTGGACCCAGTGATTAGCTTCCACTTATAAGTGAGAACATGTGGCATCT
GGTTTTCTGTTCCTATGTTAATTCACTTAAGATAATGACCTCCAGCTGCATCCAGGTTGCTGCAAGGGAC
ATTATTTCATCCTTCTTTTGGCCATGTAGTATTCCATTGTCTATATGTACCACATTTCTTTATCTAATTC
ACTGTTGACGGGCACCCAGGTTGAGACCGTGTCTTTGCTATTGTGAATAGAGCTGTGATGACCATAGAAG
TATATAAGTAGATGTGTTTTGGTAGAAGAATTTATTTTCCTTTGGGTATATACCCGGTAGTGGGATTGC
TGAGTTGAATGGTAGTTCTGTTTAAGTTCTTTGGGAAATCTCGAAACTACTTTACACAGTGACTGAACTA
ATTTACATTCCTACCAACATAGGATAAGCATTCCCTTTCTTCTGCAGCCTTGCCAGCGTCTGTTTTTTTA
ATGTTTTGAACCAGTCAGCCCTTCTGACTGGTGTGAGATGGTATCTCCTTGGGATTTTGATTTGCATTTT
TTTGATGATTAGTGATGTTAAACATTTTTATGTGTTTGTTAGCTGCTTGTATGTCTTCTTTTGAGAAGTG
TCTGTTCATGTCCTTTGTCTACTTTTTAATATTGTTTTTGTTTTTTGCTTGTTGAATTGTTCAAGTTTCT
TATAGATTCTGGATATTAGTCCTGTGTTAGATGCATGGTTTGCAAAGGTTTTCTCCCATTCCATAGATTG
TCTTTTCACTCTGTTGATTATTTTTGTTGTGCAGAAGCTCATTAGTTTAATTATATCCCACTTGTCCATT
TTTTTTGTTGCAATTGCTTTTGAGAACTTAGTCACAAATTTTTTGCCAAGGCCAATATCCAGAATCTTTT
CTTGGTTTTCTTCAGTGGTTTTTATAGTTTTAGGTTTACATTTCAGTCTGTAATACATTTTGATTAAAT
TTTTTATATGAAAAGAAGGGGTCCAGTTTCATTTCTCTGCATAGTTAGCCAGTTATTCCAGCACCATTTA
CTGAATAATGAGTACTTTCCCCATTGCATTCTTTTGCTAACTTCATTGAAGATCAGATGGTTTTAGGTG
TGTGGCTTTGCTTCTGGGTTCTCTATTCTGTTCCTTTAGTCTAGGTGTCTGTTTTGAACCAGTACTATG
CTGTTTGGTTACTGTGGCCTTGCAGTATAGTTTGATATCAGGTAATGGGATGCCTCTCACTTTGTTCTTT
ATGCTTAGGATTGCTTTGACTATTCAGTCTCTTTTTCCTATGGAATTTTACAATAGTTTTATTCTAATT
CAGTGAAAAATCATGCCGGTTGTTTGATAAGAATACCATTGAATCTGTAGATTGCTTTGGGCAGTATAGA
CAGTTTAATGATAATTTTCTACCAATCCATGAGAGTAGAATGTTTTTCCACTTGTTTGTGTCACCTATA
ATTTCTTTCATCAGGGTTTGTATTTATCCTAGTAGAGATCTTTCACTTCCTTGGTTTAAATGTATTCCTA
GGTATTTAATTTATTGTAGTTATTCTAAATGGAATTGCATTATTGATTGGGTATCAGTTTAACTGTTAT
CGGTGTATAGAAATGCTACTAATTTTTTTCCATTGATTTGTATTCTGAAACTTTATTAGAGTATGTTGT
CAGTTCTAGGAGGCTTTTGGCAGAGTATTTAGGGTTTTTTTAATTAATTAATTTATTTATTTTTAATT
ATACTTTAAGTTTTAGGGTACATGTGCACATTGTGCAGGTTAGTTACATATGTATACATGTGCCATGCTG
GTGCACTGAACCCACTAACTCGTCATCTAGCATTAGGTATATCTCCCAATGCTATCCCTCCCCCCTCCTC
CCACCCCACAACAGTCCCCAGAGTGTGATATTCCCCTTCCTGTGTCCATGTGATCTCATTGTTCAATTCC
CACCTATGAGTGAGAATATGCGGTGTTTGGTTTTTTGTTCTTGCAACAGTTTACTGAGAATGATGTTTTC
CAGTTTCATCCATGTCCCTACAAAGGACATGAACTCATCATTTTTATGGCTGCATAGTATTCCATGGTG
TATATGTGCCACATTTTCTTAATCCAGTCTATCACTGTTGGACATTTGGGTGGGTTCCAAGTCTTTGCTA
TTGTGAATAATGCCACAATAAACATACGTGTGCATGTGTCTTTATAGCAGCATGATTTACAGTCATTTGG
GTATATACCCAGTAATGGGATGGCTGGGTCAAATGGTATTTCCAGTTCTAGATCTCTGAGGAATCGCCAC
ACTGACTTCCACAATGGTTAAACTAGTTTACAGTCCCACCAACAGTGTAAAAGTGTTCCTATTTCTCCAC
```

FIG. 5 (continued)

```
ATCCTCTCCAGCACCTGTTGTTTCCTGACTTTTTAATGATTGCCATTCTAACTGGTGTGAGATGGTATCT
CATTGTGGTTTTGATTTGCATTTCTCTGATGGCCAGTGATGATGAGCATTTTTTCATGTGTTTTTTGGCT
GCATAAGTGTCTTCTTTTGAGAAGTGTCTGTTCATGTCCTTCGCCCACTTTTTGATGGGGTTTTTTGTTT
TTTTCTTGTAAATCTGTTGGAGTTAATTGTAGATTCTGGATATTAGCCCTTTGTCAGATGAGTAGGTTGT
GAAAATTTTCTCCCATTTTGTAGGTTGCCTGTTCACTCTGATGGTAGTTTTTTTTGCTGTGCAGAAGCTC
TTTAGTTTAATTAGATCCCATTTGTCAATTTTGTCTTTTGTTGCCATTGCTTTTGGTGTTTTAGACATGA
ATTCCTTGCCCATGCCTATGTCCTGAATGGTAATGCCTAGGTTTTCTTCTAGGGTTTTTATGGTTTTAGG
TCTAACGTTTAAGTCTTTAATCCATCTTGAATTGATTTTTGTATAAGGTGTAAGGAAGGGATCCAGTTTC
AGCTTTCTACATATGGCTAGCCAGTTTTCCCAGCACCATTTATTAAATAGGGAATCCTTTCCCCATTGCT
TGTTTTTCTCAGGTTTGTCAAAGATCAGATAGTTGTAGATATGCGGCATTATTTCTGAGGGCTCTGTTCT
GTTCCATTGATCTATATCTCTGTTTTGGTACCAGTACCATGCTGTTTGGTTACTGTAGCCTTGTAGTAT
AGTTTGAAGTCAGGTAGTGTGATGATGCCTCCAGCTTTGTTCTTTTGGCTTAGGATTGACTTGGCGATGT
GGGCTCTTTTTTGGTTCCATATGAACTTTAAAGTATTTTCCAATTCTGTGAAGAAAGTCATTGGTAGCTT
GATGGGGATGACATTGAATCTGTAAATTACCTTGGGCAGTATGCCATTTTCACGATATTGATTCTTCCT
ACCCATGAGCATGGAATGTTCTTCCATTTGTTTGTATCCTCTTTTATTTCCTTGAGCAGTGGTTTGTAGT
TCTCCTTGAAGAGGTCCTTCACATCGCTTGTAAGTTGGATTCCTAGGTATTTTATTCTCTTTAAAGCAAT
TGTGAATGGGAGTTCACTCATGATTTGGCTCTCTGTTTGTCTGTTGTTGGTGTATAGGAATGCTTGTGAT
TTTTGTACATTGATTTTGTATCCTGAGACTTTGCTGAAGTTGCTTATCAGTTTAAGGAGATTTTGGGCTG
AGACAATGGGGTTTTCTAGATATACAATCATGTCATCTGCAAACAGGGACAATTTGACTTCCTCTTTTCC
TAATTGAATACCATTTATTTCCTTCTCCTGCCTAATTGCCCTGGCCAGAACTTCCAACACTCTGTTGAAT
AGGAGTGGTGAGAGAGGGCATCCCTGTTTTGTGCCAGTTTTCAAACGGAATGCTTCCAGTTTTTGCCCAT
TCAGTATGATATTGGCTGTGGGTTTGTCATAGATAGCTCTTATTATTTTGAAATACGTCCCATCAATACC
TAATTTATTGAGAGTTTTTAGCATGAAGTGTTGTTGCATTTTGTCAAAGGCTTTTTCTGCATCTATTGAG
ATAATCATGTGGTTTTTGTCTTTGGCTCTGTTTATATGCTGGATTACATTTATTGATTTGTGTATATTGA
ACCAGCCTTGCATCCCAGGGATGAAGCCCACTTGATCATGGTGGATAAGCTTTTGGATGTGCTGCTGGAT
TCATTTTGCCAGTATTTTATTGAGGATTTTTGCATCAATGTTCATCAAGGATATTGGTCTAAGATTCTCT
TTTTTTGTTGTGTCTCTGCCTGGCTTTGGTATCAGAATGATGCTGGCCTCATAAAATGAGTTAGGGAGGA
TTCCCTCTTTTTCTATTGACTGGAATAGTTTCAGAAGGAATGGTACCAGTTCCTCCTTGTACCTCTGGTA
GAATTCAGCTGTGAATCCATCTGGTCCTGGACTCTTTTTGGTTGGTAAGCTACTGATTATTGCCACAATT
TCAGATCCTGTTATTGGTCTATTCAGAGATTCAACATCTTCCTGATTTAGTCTTCGGAGAGTGTATATGT
CAAGGAATTTATCCATTTCTTCTAGATTTTCTTAGTTTATTTGCGTAGAGGTGTTTGTAGTATTCTCTGAT
GGTAGTTTGTATTTCTGTGGGATCGGTGGTGATATCCCCTTTATCGTTTTTTATTGTGTCTATTAGATTC
TTCTCTCTTTTTTTCTTTATTAGTCTTGCTAGCGGTCTATCAATTTTGTTGATCCTTTCAAAAAACCAGC
TCCTGGATTCACTAATTTTTTGAAGGTTTTTTTTTGTGTCTCTATTTCCTTCAGTTCTGCTCTGATTTTA
GTTATTTCTTGCCTTCTGCTAGCTTTTGAATGTGTTTGCTCTTGCTTTTCTAGTTCTTTTAATTGTGATG
TTAGGGTGTCAATTTTGGATCTTTCCTGCTTTCTCTTGTGGGCATTTAGTGCTATAAATTTCCCTCTACA
CACTGCTTTGAATGCGTCCCAGAGATTCTGGTATGTCGTGTCTTTGTTCTCGTTGGTTTCAAAGAACATC
TTTATTTCTGCCTTCATTTCGTTATGTACCCAGTAGTCATTCAGGAGCAGGTTGTTCAGTTTCCATGTAG
TTGAGCGGTTTTGAGTGAGATTCTTAATCCTGAGTTCTAGTTTGATTGCACTGTGGTCTGAGAGATAGTT
TGTTATAATTTCTGTTCTTTTCCATTTGCTGAGGAGAGCTTTACTTCCCAGTATGTGGTCAGTTTTGGAA
TAGGTGTGGTGTGGTGCTGAAAAAAAATGTATATTCTGTTGATTTGGGGTGGAGAGTTCTGTAGATGTCTA
TTAGGTCCGCTTGGTGCAGAGCTGAGTTCAATTCCTGGGTATCCTTGTTGACTTTCTGTCTCATTGATCT
GTCTAATGTTGACAGTGGGGTGTTAAAGTCTCCCATTATTAATGTGTGGGAGTCTAAGTCTCTTTGTAGG
TCACTCAGGACTTGCTTTATGAATCTTGGTGCTCCTGTATTGGGTGCATATATATTTAGGATAGTTAGCT
CTTCTTGTTGAATTGATCCCTTTACCATTATGTAATGGCCTTCTTTGTCTCTTTTGATCTTTGTTGTTTT
AAAGTCTGTTTTATCAGAGACTAGGATTGCAACCCCTAACTTTTTTTGTTTTCCATTTGCTTGGTAGATC
TTCCTCCATCCTTTTATTTTGAGCCTATGTGTGTCTCTGCACGTGAGATGGGTCTCCTGAATACAGCACA
CTGATGGGTCTTGACTCTTTATCCAATTTGCCAGTCTGTGTCTTTTAATTGGAGCATTTAGTCCATTTAC
ATTTAAAGTTAATATTGTTTATGTGTGAATTTGATCCTGTCTTTATGATGTTAGCTGGTTATTTTGCTCTT
TAGTTGACGCAGTTTCTTCCTAGTCTTGATGGTCTTTACATTTTGCCATGATTTTGCAGTGGCTGGTACC
AGTTGTTCCTTTCCATGTTTAGCGCTTCCTTCAGGAGCTCTTGTAGGGCAGGCCTGGTGGTGACAGAATC
TCTCAGCATTTGCTTGTCTGTAAAGTATTTTATTTCTCCTTCGCTTATGAAGCTTAGTTTGGCTGGATAT
GAAATTCTGGGTTGAAAATTCTTGTCTTTAAGAATGTTGAATATTGGCCCCCACTCTCTTCTGGCTTATA
GGGTTTCTGCCGAGAGATCCGCTGTTAGTCTGATGGCTTCCCTTTGAGGGTAACCCGACCTTTCTCTCT
GGCTGCCCTTAACATTTTTCCTTCATTTCAACTTTGGTGAATCTGACAATTATGTGTCTTGGAGTTGCT
CTTCTCAAGGAGTATCTTTGTGGCATTCTCTGTATTTCCTGAATCTGAACGTTGGCCTGCCTTGCTAGAT
TGGGGAAGTTCTCCTGGATAATATCCTGCAGAGTGTTTTCCAACTTGGTTCCATTCTCCCCATCACTTTC
```

FIG. 5 (continued)

```
AGGTACACCAATCAGACGTAGATTTGGTCTTTTCACATAGTCCCATATTTCTTGGAGGCTTTGCTCGTTT
CTTTTTATTCTTTTTTCTCTAAACTTCCCTTCTCACTTCATTTCATTCATTTCATCTTCCATTGCTGATA
CCCTTTCTTCCAGTTGATCGCATCGGCTCCTGAGGCTTCTGCATTCTCCACGTAGTTCTCGAGCCTTGGT
TTTCAGCTCCATCAGCTCCTTTAAGCACTTCTCTGTATTGGTTATTCTAGTTATACATTCTTCTAAATTT
TTTTCAAAGTTTTCAACTTCTTTGCCTTTGGTTTGAATGTCCTCCTGTAGCTCAGAGTAATTTGATCGTC
TGAAGCCTTCTCTCAGCTCGTCAAAGTCATTCTCCATCCAGCTTTGTTCCATTGCTGGTGAGGAACTGCA
TTCCTTTGGAGGAGGAGAGGTGCTCTGCTTTCTATAGTTTCCAGTTTTTCTGTTCTGTTTTTTCCCCATC
TTTGTGGTTTTATGTACTTTTGGTCTTTGATGATGGTGATGTACAGATGGGTTTTCGGTGTGGATGTCGT
TTCTGTTTGTTAGTTTTCCTTCTAACAGACAGGACCCTCAGCTGCAGGTCTGTTGGAATACCCTGCCGTG
TGAGGTGTCAGTGTGCCCCTGCTGGGGCGTGCCTCCCAGTTAGGCTGCTCAGGGGTCAGGGGTCAGGGAC
CCACTTGAGGAGGCAGTGTGCCCGTTCTCAGATCTCCAGCTGCGTGCCGGGAGAACCACTGCTCTCTTCA
AAGCTGTCAGACAGGGACATTTAAGTCTGCAGAGGTTACTGCTGTCTTTTTGTTTGTCTGTGCCCTGCCC
CCAGAGGTGGAGCCTACAGAGGCAGGCAGGCCTCCTTGAGCTGTGGTGGGCTCCGCCCACTTCGAGCTTC
CAGGCCGCTTTGTTTTTCCTAATCAAGCCTGGGCAATGGCGGGCGCCCCTCCCCCAGCCTCGCTGCCGCC
TTGCAGTTTGATCTCAGACTGCTGTGCTAGCAATCAGCGAGACTCCATGGGCGTAGGACCCTCCAAGACA
GGTGCGGGATGTAATCTCGTGGTGCGCCGTTTTTTAAGCCCCTCGGAAAAGCGCAGTATTCGGTGGGAG
TGACCCGATTTTCCAGGTGCTGTCCGTCACCCCTTTCTTTGACTGGGAAAGGGAACTCCCTGACCCCTTG
CGCTTCCCAAGCCAGGCAATGCCTCGCCCTGCTTCGGCTCACGCACGGTGCGCGCACCCACTGACCTGCG
CCCACTGTCTGGCACTCCCTAGTGAGATGAACCCGGTACCTCAGATGGAAATGCAGAAATCACCCGTCTT
CTGCGTCCGCTCACGCTGGGAGCTGTAGACCGGAGCTGTTCCTATTCGGCCATCTTGGCTCCTCCAACCAG
GGTTTTTGAGATATAGAATCATATCATAGTGCAGAGAGATAATGTGAGTTCATTTCCTATTTGTCAGTGT
TTTATTTCTGTCTCTTTCCTGATTGATCTGTCTAGGATTTCCAGTACTATGTTGAATAGGAGTGGTGAGA
GTGGGCATTCATGCTTTGCTCCTGTTCTTAAGAAGAATGCTTCCAGCTTTTGCACATTATATATGAAGTT
GGCTGTGGTTTTATCATAGATGGCTCTTATTATTTTGAGCTATGTTCCTTCAATGCCCAGTTTGTTGAAG
AACTTTATCATAAAAGGATGGTGGATTTTATTGAAAGCTTTTTCTGCATCTGGTGAAATGCTCATATACT
GTTTATCCTAAATTCCATTTATGTAGTGAATCACATTTATTGATTGTGTATACTGGACCATCCTTACATC
TCAAAAATAAAGCCTACTTGGTCATGATGAATTCACTTTTTGATGTGCTGCTGGATTCAGTTTGCTAGTG
TTTTGTTGAGGAATTTTGCACCTATATGCATCTATATTCATCTATATTCACCAGGGATATTGGCCTGTTG
GTTTGTTTTTGATGTTGTTGTTGTTTTTGTGTCTTGCTATATTTTGGTACCAGGATGATTCTGGCTTCAA
AAAAATCAGTTAAGAAAGAGTCCTTCTTTCTCAATTTTTCAGAATAATTTAGTACAGTGGGTACTCACTC
TTTTTTGTATTTCCAGTAGAATTTGGCTATGAATGCATTTGGTCTAGGGCTTTTATTGATAGGCAGGTTT
TTTCAGTACTGATTCAAATTTGGAACTCTATATTAGTGTTCAGGGTTTCAATTACTCTTTGTTCGTCTTG
GATGGTTGTTGGATGGTTCATTTTGGATGGTTGGATAAGAATGACCCAGTTAATACATGCTCCCTCTTTG
CACACTAGCGAAGGCCTGAAAGTGATAGAATATTAGAACCCTAAAAAGAATTGTGTCTACCACAAGACAT
AATCTTCATTATACTGGCAATGACTATGCCATTTGGGGACTATTGCAAAGTTTTTATTATTTATTTATTT
GTGTATTTATTTATTTATTACTAAATCCTCAATAATGAACCATCACTTCTTAAAATAGTGTTCTTTGTAC
CAAAGCTTAGTTTTATTGACCAATACACTTGTTCCATAAAAAATTCCTCTATATTATTCCTAGTGAAAAA
AAATAGTAAGAACTGTAAGTTTGGCAGAACTGTAGATGTATAGATTTAAATTCTTCTACAATTCTTCCTT
CAATAATTGATCTTTAGCATTAATAGATTCAACGTGAGGTTCCCTTAAACTTTAGCCTAGATTTAGAACA
GAATTTATTAAAGCCACCTGTCTATATAAACTGTTCAACTGATTAAAAATCTGAAATCACTTGTTTCTAC
ATTTTCCACTTCTGTGCTCTAAACACTAGTGGGGCATTCTGTTGTGTTTAACCTCTCTGGTAATAATATC
ATCTGTCATTGTATCCTTGGATTTTGTTTATGCCTGCTAAATTAAAAATTTTAGCATCTCTACCTGTCTCT
ATTTTTCCTGGACTCAGTGCCATTTTCATGGGTGACTCCAGTTAAATTTTGATTACTCCCAAACTGCTAA
ATTATCTGAATTCTTTGGATAATTCCTCCTCAGGGCATGTCTCTGAAACTTAGAGATTGTCCAAAAGAGT
ATGTGCTCTGCAGAGGGTAAAAGGGAATGGAAAATAATTATTAAAGAGAATCTATAGTGATGAGAAAATT
GTATACAGAGTTCTAGGCACTAATTTCTTTGTTTCTTAGTTTTAAAATTAAGAATGAACTAAATGTCAAT
CATGAATTACATTGTCTTATATAGAAAGAAATCCACAAAACTATTTTACCTTTTATCTCTTAAGCAACTG
TATTTTTAGAATCTTCTTAAACTGTAAATATATTAGTTTGAACAAGTGAGACTTCACTAAATATAATGCA
ATGTATTTGCAGCACTGTTAGGTCTTGCAAATTTCTTATGTCATATTTTATACACAACGCTTAAGGTGTT
TTACAACTGCAGTTGTTTGGAAGTAACTGGTCTCCAGAACAGAAATTACTCAGCCCATTTGGGTGAATGC
CCAAGAGATGATGCTTGTACAAGGAAATTTTACTTTTTTGTTGCAATACAAGTCTTGAATTTATTTTTCT
CTGCACTTGGAGGCACCTCACATGTCATGCTGATTGTTAAGTAAGTATGACTTTTAAAAACATTTTCATA
TGCATGAGACTATAAACACACCTAATGATATGCATATTTTTACATAATATACTGGGAATTCAAATTCATA
TTTCATCAAATTTTAATTTTCTGAGAATTCATTTTATTAAAATTACTATGAACTCTCAAGGCTGTAATTA
ATAATTTTGCCTCTAATTCTTCCATTAAAAGTCCAGATTCCATACGTTTCTTCTCTTACTAAGAATCTGA
AGACACAGACTGACAATTCTCTCAGTTGTAAAAGAATCGCCCTAGGATCCTAAAAGAACTTGTTGAATTT
TGAGTTGCCTTACATCCTAATGAGAGATGCCTTGCATCTCTCAGGGTAAATCTATTGATTTCACTAAAAT
```

FIG. 5 (continued)

```
AAAGCATTTGAAAACTAGATATAAAATATGCTCCATTTGATAACATTCCAAAACTTTTAATCGACTCACA
GCATGACTTTTATAATACCCTTGTAGAAAAATAAAAAAATACACAGGAAGAATTAGTTCCTTTCTTGGCT
CATTAGAAAAGATACAATGCTTGGTGAATATTACATGGTAAATGAAACCAATAAGATACTTGTTGTCATA
CAGCTTTCAAAATTACAGGAAAGACTGGTGTGAGATAAATAATCTTAAAATCAAAGCACATATTTATAAA
TTGTTCTGAGTCCTCATCAGGAAAAAGATTTCCCTAAAAAGAAAGATTCAAAAGGAAAGTTAATTTAGGA
TTGAGGTGGGGGGCTGTGAAGAAGAGGATTCAGAGTACATCTCAAAATAAGTAACATTTATTCTAAAGGT
CTAAAGAAAAAGCCAAATGAAAGGGTTTCCAGGAGAGGGTCTTGGTGCTGACGCCTTAATACAGGAAAGA
GCTGGTGTGTTTGAGAAATGAAAAGAAGCTGGCAGATTGAAACATACTGAATGAGAGGTTGTGACACATG
ATAAGATTGGAGAGTTAGGAAGGGTGCAGGTAATGCATGCCCTACTGGCCAAGTTGATTCAATCACCTAA
AACTTGTAACATGTAAATAATTGCTTTTAGATCTTAAAAATATACATGTGTAAGTATAGTGACCTGGGTT
AACATTCAATTGTACTTTTAAAACTTACATTGTTGATCATAAGTTCACTGTCAGCCAACAGCATGACATG
GTAGAGATGAAAAAAAAAAGCATTTTTAACATTTGTTAACATTAGTATCAACCTGTAAATTGAATTTACA
GTTGTTTAATTTTGACCCTGACTGCAAATCTTATCAAATTATTTATACTAAATATGCCACAGATATAGCT
CCATCTTAATATAAATGTTGTCTACTCAAAAGGAGAAGTCTTTCATATTTGCCAAATTAAATTCATTAA
CATATTAAAAATAACCTTAAAATTAAATAATAGTCTGCATATCAACAGGTTTTAGCTTTTTATTTTAAAC
TCATGAGTTTGAAAAAACACTGTTCCATCATCGATGATAACAATATCATATCTGTTTCAGAAATTGATTA
AATCAGCATTACAACTTGTCAAAAATATTTAACTCTTGCTAGCCTTTGATTTTATTGAAATAAGCATTTT
GTGAATATGACTACAGAATAAAAATATAAATTTCAGTTTGTTAATAGTTTTCTAATGCTTAACACTATGA
AGCTATTTTTTAAACTTGATTAAGTAGGCAGAAGGACATCCATTTATTCAATATGTATTCATTTTTTATG
TCAGGCATAGTTGTATGCACTGAGGATGCAACTGTGAACAAAAGTGATAGAACTTTATAAGCTTTTAGTA
TGGGTGGGGAATGAAGGAATGAATGTGTGTAGCAGAAAACACAGTAAACAAATAAGTGAGTAAACATCTA
AAATAGAGTAAGTGTGAAGCACTAGAAAGATAAATAAATCACAGTTAAGAAAATAGAAAAAAATGAGAAA
ATAGGCAAGAGATACTAGTTCAGATATGGTGCTTTGGAAGTCCTTTGAGTAAAGACCTGAATGAAGAGAT
AGAAAATAAAGGTACAAGCCATGCTAAATGGAGACATAGGAGGAACAATCCAGGCAAGGTAGAAGAAAGG
TCAGCGTCCTGGTGTGAAGTATAGTTGACATGTACAAGGTCCAAAAACGTGTGTAAGGAGGAGAGAGGTG
ACAAGTGCAGCAAGAGAGCTAGCCTAGTTCAGATCCTATGGGTCACAGGAAAGACTTTGAAATATATTCT
AAATGTGTTGAAAGCCCAAGGGGATTTAAGCATTAGTATTTGCAAAGATGCCTTACATAACTAGAAGATC
ACTCTGGCTGTGGGTAGAAAGTGTGTTTTGTGAAAACAATAGTGAAGTCAGGGAAAACAGAAGGCTTGAA
TTGTTCTTCTCAAGATGGAAGCTTGATTGAGAATGCTGATAATAGGAAAATATGAAGTAAATGAAATGAG
TAAATGAAACAAATATGAGTCTCAGTTGTTTTGCTTTATTTTATTATATTTATTTATTTTGAGAG
ACAGTCTTGCTCTGTCACCCAGGCTGGAGTGCAGTAGCACAACCTTGGATTGCTGCAACCCTCCGCCTCC
CAGGTTCAAACGATGCTCCTGCCTCAACCTCCTAAGTAGCTGGAATTACAGGTGCACGCCACCGTGCCTG
ACTAATTTTTGTATTTTTAGTAGGACCTGGTTTTACCACGTTGGCCAGGCTGGTCTCAAACTCCTGACCT
CAAGTGATCTGCTAGCCTCTGCCTCTCAAAGTGCTGGGATTACAGGCCTGAGCCACAGCCACCTGGCCTTT
GTTTTATTTTTTAATGCAAAGCCAGTAGGGTTTGCTGAGACATTGAATGTGGCATGTGAGAAAGATAATT
TAAGGATAATCCCAAAGTTCTGGCTTGAGTTCTGGAAGGATGGTGGTACTATTGAACAAAATGGGAAAGA
CTAAGAAAGGGTAGATTGGGAAAGTGAAAAAGCAAGAATTTGTTCTATCTCTATAAAGCTGAGCAGCCTG
TTCAATATCTAGCAATGTCATATATGCAATCCAACAGGAGAAACCTTGATGCCAGAGCCATAAATTTTAG
AGTCAGCAACGTACAGATGGTATTTATTTTTATTTTTACTTATTTATTTATTTAGAGACAAGGTCTCATT
TTGTTGTCCAGGCTGAAGTATAATGGCATGATTATAGCTCACTGTAACCTTGAATGCCTGTATTCAAGCA
ATCCCCCAAGGCGGTATTAAAATCCATGGAACTAATGAGATCTTCTAGGGACTGAGTACAGATAGAAACA
AGATCCTAGGATCAGTTCTCAATCACTCTAATTTAAAGATCACTAATAGGAGAAACCAATAAAGAAAACT
GAGGAGGTTTCATGAGAAAAACTAGGAAAGAGCGTTGTCCTCAAACTAATAAAGCATATGTCAAAAAGAG
CATAAGTAACTGTGTCAAGGGCTGCTGAGAGTTCACAGGAGTTGAACCTGGGAGGCGGAGGCTGCAGTGA
GCCAAGATCGCTCCACTGCACTCCAGCCTGGGAGACAGAGCAAGACTGGTCTAAAAAAAAAAAAAAGAA
AAGAAAACCACAAACCAATATCCCTGATGAACATATGAAAAAATTATCAATAAAACACTAGCAAATCAAA
TCCGATGGCACATAAGAAAAATTTTATAACATGATCAAGTTGTTTTATTCTAGGGATGAAGGGTTGGTT
CAACATATATAAATCAATAAATGTGATTTGCCACATAGAATAAACTAAAAACCAAAACCATTTGATAAGA
CAAAATTAAAAACAAAAACCATATGATCATCTCAATAGATGCAGAAAAATTATTTGATAAAATTTAACAT
CTTTCATGACAAAAATCCTCAACAATCTGGGCATCAAAGGAACATACCTCAAAATAATAAAAGCTATGTA
TGACAAACCCACTGCCAACTTCATACTGAAAGGAAAAAGTTGAAAGCATTCTCCTGAGACCTGAAACAA
GACAAGTGTGTCTATTTTCACTACTCTTACTGCACATAGTATGGGAAGTCCTAGCTAGAGCAATCAGGCA
ATAGAAAGAAAGAAAAGGTATCCAAATTAGAAAAGAGGAACTCAAATAAACTCTGTTCACTGATGATATG
CAACAATAACAACAAAAATAGACTAATGGGACTTAAACTAAAAATTTCCTGCACAGCAATGGAAATAATC
AACAGAGTAAACAGACAACCTACAGGAAGGGAAAAATATTTACAAACAATACATCTGACAAAGGGCTAA
TATCCTTAATCTATAAGAAATACAAAAAACTCATCAAGAAAAATTATTAAAAATAGGGTAAATGATA
CGACCAGCATGTTTCAAAAGACAAACAGTCAACAAACAACAAACATATGACAAAATGCTCAATATCACTA
```

FIG. 5 (continued)

ATCATCAGAGAAATGAAAATTAAAGCTACAGTGAGATTCCATTTTATACCAGTCAGAACGGCCATTACTA
AAAAGTCAAAAAGCAAGATACTGGTAAGAATGTTGAGGAAAAGGAATGCTTATATACTGTTGAGAATATA
AATTAGTACAACCTTTATGAAAAACAATGTGGAGATTTTTCAAGTATCTGAAAATAGAAGTACCATTTGA
CCCAGCAATCCAACTATTGGATATCTACCAAAAGGAAAGTAAATCATTTTATGAAAAAGACTCATGCTCT
TTCACACTTATTATAACACTGACTAGACCACAAAAAATCAGTATCTTCAGAGGCATAATAAAGTCTGTTC
TAACCACTTCCTCATAGGATTTTCATAAGTACCATATGAGAAAATATTTTAAGCCATCTTGAAATCATGA
TGCATTGAATAAATAAGGGAATAATTATTATTATTGCTCAAGTGTTTGCCTTTTAAAACAATTAAAATAT
AATTTTATATAATGGGGCCATTCAACTGTGAGCTTAATTCTATCATGGAGAAAAACAACACAGGAGAAGG
TTTAATGTTGTTTCGTTTTGATATTTTAATGATATTTAATGTTTCTTTGCCTTTGTCTTGTTTCAGAATT
GTTCAACCTGAATTGAAATCACTTGCACTGGGTTTCCACTCAATGGTTATACGAGCACTAGGTATGATGA
AAAAAAAAAAAAAAAAAAAAAAAAATATATATATATATATATATATATATATATACACACACACATACAT
ATATTAAATTTAAGTTATAAATATTAATGTCAAGGATTAAAGACTGTAATGAATCTTTAATTATGATAGT
AAATAAAATTAGTATCCTTTCTATTTCTGTGATAAATAAAAACAATAAGAGACAGAGTAAAATTGAGTGA
TGGACCTAAAGGAGAATTCGATTGTTAATTATACATAAAGTCAATCTGTTAAGACTAAGGAATTATTGTA
TTTGTATTACACTCTTTCAAACACAAAGATAGATGGTCCTCCAAATTTTTCTTTTTTTTCAGAAAAATAA
GAATATTTCCTCCCAGTAGGCAGAGTGAAGGGCCTAACTTCTAAACTGTGGCATGATTTAGGCAAGGCCT
AAAGCTAGCTTGGGAAGCGTGGGAATCTGGTCAGAGAATCTGGCCAGGCTATGGCCAAATTACAATGAAG
AAATTGTCTAAGAAGCGTATTTGATGATAAAGTCACAAATCCTCAAAGTTAAAAAAGAAGAAATATAAAG
GGAATAGAAGAGAGGAAATGAGATGCTATAGTATTCTGTTGGTTTTCTTCCCTCCGTTCCGTTTTGTGTG
TCTCTAATCTCCCAGACTCTGTACATTCTGGCAGGTTTCTACCTTCAGTTTCAATGGAGATACCTCTCTG
CTAGAACCTGGGTGACAAAAGCTTAAAGTAACATCTGGGTTGTTAGTACTCCTTCTCATATGTAGAAATG
AGACTATGAGAATGGAGTAAAATTTTTTTAGCAATAGAAAATAGGAAAAAAAATGAGTTTCACCATTCT
AATTCTGAGTATCCTATTTCGATGTATCCAATCTGTGGCACGATGGAACCTAAATGCACCTATGGAAAAA
ATACACATTTAGTACAAAACTTTCAATTCATAAACAATTGTCTTGAATACAATAAACGTGTAAATTGTGG
AAGGCCTATATATTTACCTGAAAAAGTCATTTAGAAAATAGGTTATGAGTTTTAAAATTGTAGTGATTAG
GACAAAGTTTATTACTTAAAACAATCCATTACGTTTGTTCAAATCAGTGGCATTATGTGGGGAAAATAAA
CTGTTAGCATATATTTTTCATTTTTCAAAGGGTGGCTGTGATTTTTGAAACCTGAAAATTTCTCACTCAT
TTCCTCAGTACCGGGTTTTCTCAGATACATTGGCCTCAGTCCCTTGTCATTTTAATATTTCTCACTCTCA
AAAAATTGAGACTGAGGAAAACTAAATGGAATTAGTAAAATTGTGATATATCAATCACTATCATTTTATC
CATGGCAAAATAAATTCTGAAAATTATTCACCACAATACAAAAAAAAACAAAGTAAAGTTATGAACACTT
TAGTTGCACCATCTTAAGGACAGTTCTCTACTGGCGTGTCCCTAAAATTCTTCATCAAATTACCTTTGCC
TAGAACCAGGAGTGAATCTCAGAGTTCATTAAAACAGCAGTGGAAGCAGATGGACACTTATTATATAAAC
AACATATCTGTCTGTGAAAAGCCTTGCATTCTGCTAAATCATGAGCTACAAATAAAAATTAACTAAGAAA
AAGACCACTGAAAACTTATCATTGTGATCAGAACACTAACACAAACAAAATTCAGTACCACAAGCCCTAA
CTTAGCCTAAGCTGCTTCAGGAGGTATTTACAAATGCACAAAATCAATTGTAGAAAATCACTGGACTGTG
AGCTCTAATGACATCAATAAGTGGGAAGTAGATGTCTGAGCCCAGAAAAAGTACAACCTGCCAAAAGCT
AAGCACTCTCTGAAGCTCAGCCTATACTTATCTGGGGAGGGAGTTCTGATGAAGCACTCACTTTTAAATT
CTCTTAAAATAATGTTAAAAAAAAAAAAAGTCTGCTTTTACAGCAATTGAGCCAAGATCTTTTCCTTTC
CCCATAAAATTGTAATTCTACTCCATTTCAGGTTTCTTTGCCTAAGAAAAATCCCATATTAACCAACATA
ACTTCCAAGTTTTACTAACAACATTCTCCTTTTTACCATTCAGGCTTAAGTTAATTGTTATCATAAGAAG
AACAGAGTATATATGCATGTATGTAGGGAGGGTACGAGTAGGTAAAAGGTGTCAATGACATTACTACATG
ATTTGGGTCTTTGAGATTTCTAATAATCTTTATTATTGGGTAGATGCAGAACAAAATAATAAACGAATCC
TCCAAATTTTTGAACTTTTATTTAATCAAAATATATCAATGTGGAATATCATGCAGTTACATTTAAAATA
TGTTCCCTAAACTGACATCTTCTCTTCTCCTATTACAGGAGGAATTCTAGCTCCAATATATTTTGGGGCT
CTGATTGATACAACGTGTATAAAGTGGTCCACCAACAACTGTGGCACACGTGGGTCATGTAGGACATATA
ATTCCACATCATTTCGTAAGTTGTCATAAATATATTTCATTATTTTTCTTTGACTATATTAATTCCTA
AAAAATATCATTTTCATTATATAATAATATTAATAATGATAGCCACCATTTAATGAAAACTGACTTTGCA
TGCAGTATGGTATCAAGCAATCTCGTATCTCATTTAGTACTCATAGAAACTATAGGAAATGGATATTTT
CTTCTATTCTGTTATATACGAAGAAACTGTGATTCAAGGATAATAACCAACTTGTCAAAAATCAGAGATA
ATAGAAAATGGCTAGGATTTGTATGTGAATCTTTTTTGTTTCCAAAACTCTCCTCATGTCAGTATATATA
AGGATAAATATACACATGTAAATATAGACACAGACATATATATATGCATGTGTGTATTCGATTGCCTC
TGACTTCTCTAGAAAGAAACAGAATGACTAGCTGGGGCTCTGGTCATATGTCAATTAAGAAAAACGGGA
AAATATGTTTCTATATTACTCTATTCGTGGGGAGAGATATTCCGTAAGTGACATGAAGATAACTGCATGG
GCATCTGGAAAAACAAAAAGCTACAATTATACTTTACCTCTTTAAAAAAAAACTAATTTCAAATTCATAT
ATTGACAAATTATACACTTTGAAATGTGAAACTACATGTATTAAAACTCATAGTATAATTTCTTTCAATT
ATCTACGAAGCAGAAACTAAGTATGACCCAAATGCCCAAAACCATAATAGAAAAAAAGACAAAATATTTA
TAAAATCTGCATCATTAAACTTTGAAAAGGAAATTTCAAAGTGAAAGTATAAATTAGGAGAATAATTTGC

FIG. 5 (continued)

```
AACTTGTAACACAGACACAGGCAAATATCCCGAATATATACGGAACTCTTAAACATCAGCAAAAAAACCA
TCCAATGCTGGCAAGGATGCAAAACAACAGGAATTTCCTTTAATTTTTCTTTCATTGCTGGTGGATATGT
AAAAAATAGTACAGCCATGGTAGAAGACAGTCTGGAAGTTTCTTACAAAGAAAAACACAGGCTTATGATA
CTGTTAAGTAATCATGCACCTAGGTATTTACCTAAGTTAGATGAAAACATGACCCCACAAAAACCTGCAC
TTGCATATGAAAAAATGGAAGCAAACAAGATGTCTTTCAATAGGTGAATGGATAGCCAAACTGGGGTATA
TTCATACAATAGAAAATTATTCAGCAATAAAAAGAAGTGACCTATCAACTCACAAAAAGACAAGAAAGAA
ATTAAATGCATGTAGCTAAGTGAAAGAAGGCAGTCTAAAGAAGCTTCTGGGCCTGGTGCAGTGGCCCATG
CCTGTAATCTAGGCACTTTGGGAGGCCAAGGTGGGAGGATTCATGAGGCCAGGATTTCAAGACCAGCCTG
GACAACATGACAAAACCCTGTCTCTACTAAAAATACAAAAATTAGCCAGTCACGGTGGTGCACATCTGTA
ATTTCAGCTACTTGGGAGGCTAAAGCACAAGAATCCCTTGAACCCAGGAGGCGGAGGTTGCAGTAAGCCA
AGCTCATGGCACTGCTCTCCGGCCTGGCTGACAGAGCGAGACTCTGTCTCAAAAAAAGAAAAAAAAAGAA
CATTAAAAAAAATTAAAGAAGCTTCTGACTGTATTATTCTAACTGTATGACCTTTTGTAAAAGGGCCAAA
CTATGAAGACAATGAAACATCAGTGGTTGCTAGGAGCTCAGTGGGGAGAAGATAAGGATGAGTAGGTGGA
GCACAGGGCATTTTAAGGGTGGTGAAATGATTTTATATGATATTATCATGTTGGATACATGATGTTATGT
ATTTGTCAAACCTATGGACCCATACCCATACAACATACAAACCACATAAAAAGCAAACTCTAATCTAAAA
TATGAATTTAATAATAATGCATTCATATTGGTTCATCAATTGTAACAAAGTTACACACTAATACAAACTG
TTAATGATAGGGGAAACTGTATGTGTGGGGCGGGGAGTATATGGGACTTCATACTTTCTGTACAGTTTTT
CTGTAAATCTAAAATTTCTGTAAAAAGTATGTTCTATTAAAAAAAAATCAAGTATCTCCCAAAGAAAAAT
CACGAATGGCTATTAAATATATAAAAAGATGCTCAAATTAATTGATAATGACAGGATTGCAATTAAAACT
CACCCAAATTGTCAACCATCAAAAATGTTAAGTAGACATTGTCTTGGCAAAAGTACAGAACTTTGAGCCA
GCAGCAAACTTCTAGAAATTTATCCTACAGATAACTATACTCCCAAATAGATAAAATGGCACATATATAA
GATTACATACATGTGTATGGCAACATTGTTTATGATGGCAAAATATTGGAAGCAACTTAAATATCTCTTG
ATAAGGGAGTAATTAGATAAATAGTTCTACCTGCAGGAAAATGAATAGTCTGATGTCTTGAAAAAGAAG
AAAAAATTATTTGTTTACTAATATGGAACCTTCTTCAAGACATATTTTTATATGAAAAAAAAGAACCATG
AAGAATGTGTATGGAGCATGCTATCATTTATATGAAAGTGGAGGTTTATTAGTTCAGGATACATCTCTGG
AGTAAAGACCTAGGATCAAATTTACCAAACAGACTCTCTTCCATTTAATGTGTAAATTCACTATCTAAAA
TCCCCAGCAGATAAAATGATCCAACTTTTTCCAGAATTGTACCCCACAGACATTCTCACAAATTTATTTA
AATATTAATGACAGAAAATGTCTCACAAAATGGGAGAAAGAAATGAAAAGAAATTACAAATGAAAACTTC
ATAAATTTATCTTAATGACTTTATTTAAGAATGTGTTCATTTTTTATTGAAATCATCATGTATTTCCAGG
ACACCTGGCAAGATGCTCCTCAGAATTTCCCCAAAGCAATGACCACAACTTCAAGTATTAATGTAACATT
TTGAGATGGCTTTATAATGGTTTGAGTATAAAAAGACCCTAAAACTATTTTTAAGCCATACTAGTTCCT
TTTTGTTCAGTGAAGGTTTAGTTAGAACTAAAATGGAATTTAAAAATATTTTATGTTAATTGATTTATTA
ATGCATTCTTCTTGTTGAACAACTGGTATAGTATCCAAATTTTTAATATACTGCAAAGACCATTGTGATA
ACATTATATAGTGTATATGTGTACTATATATATTTAATATGCATATATATGCATATATAAGACAGACATA
TTATATATATGTTATTCTTGTGTACTTTAATTTATGCTCATCCCAAGACTTTAAGATTTAAAGGGTCGGT
CTTTGTACATCCCCACATATTTATCATTTTCTTTTCTCTGATTTCTTCTTGCATGTCAGATTCTATCTAG
GGTCATTTTCCTTCTGATTAAAGTCGATTTTTAAAAATGTCTTTCAGTGAGCTCTTTAGTGGCAAATTGC
CAATTTAAATTTCTCTGGAAGGAACTTTAGTTCAACTGTATACTTAAAAGAAATGTACAAGGTATAGAAT
TCTAAATTGACAACTATTTTCTCTTGTCAGATTGAAGATATTACTCTATTGTCTTCTAAGTTCCATTTTA
CTCTTGATAAGTAAGCTGTTGTCTGTTTCTTGTTCCTTTAAGGTAACCTCACTCCTCTGTGGATTCTTT
AAATATCTTGTCTTAATCCCTGGAATCTGTAATTACACTATGTTCAGGTTGCAGATGGAATAAGTTTGCT
AATTAGCTGAACTCAAGATAAGAAAATTATTTGGTTGGGCCCAATATAACCACAAATATCCTAAAAAATA
AAAAGAGGAGGTCAGAAGGATGTGATGTGAGAAAGACTCAGTCTATTGTTGCTGGGTTTGAAGATGGAAG
AAAGGGGCCAGGAGCCGAGGAATGTAGGTGGCCTCTAGAAGTGAGAAAAAGCGAAGGAACAGCTTATTTC
CTGGAGGTCCCAGAAAGGAATACAGCCCTGCTGATACCTTGATTTTAGCCAACTAAGACAAGTATTAGGC
TTCTAACTGCCAGGAAATGCTCCGGGCTTAGCTCACACACCCTTTTCTTTCATAAAGTTCACACCATTCC
AACCAGCTGGAAATGACCAACCCTCTTTGGGACTTACCACATTGTAGCTAACTCATGGCCCTTATCACTT
TCCTTTTGGTCACTTGTGTTCTTTGCTTGATTGTGTAAAGTGGAATTTAAAAAAAAAAAAAGAGCAGTGC
ATTTACCAATGCAATACATAAAAAGTTAAATTGTTACCTTAAGAATTTTTTAAATAAACTCAATTTTAGAG
AGTTTTAGGATCACAGTAAAATTGAGGAGAAATTACAGAGATTTCCCACATACCACCTGCCCCACACATG
CATAGCCTATCCTACCATCAATGTCTCCCAACAAAGGGTGATACAGTTGTTACAAATGATGAAACAACAT
TAACACATCTTTATCTCCAGAGTCCACAGTTTACATTAGGTTTCACTCTTGACATTGTACTTTTATGGG
TTTGGACAAATGCATAATGACATATATCCACCATTACAGTATTATACAAAGTAGTTTCTCTACCCTAAAA
ATCCTCTGCTCTGCCTATTCATTCCTTCCTCCTCTAAAACCCTGGAGACCACTGTGCTTTTTACTGTTT
TCATAGTTTTGCGTTTTCCAGAATCATACAGTATGTAGCATTTTTAGACTAGCTTATTTAACTTAATCAC
ATGCATTTAAATTTCCTCCAGGTGTTTCAATTGCTTGATAGCTCATTTCTTTTTATTGCTGAATAATATT
CCATTGTCTAGATGTATAACAGATTATTTATATATTCACCTACTGAGGGCATCTTGATGGCTTCCAAGTT
```

FIG. 5 (continued)

```
TCATGTTTCTTTGATGATATATATGAAGATGTTTGATTCTGTTATATTAACCCTGGATCCTGTGTCCTGA
AACCTTGCAATAATTGCTTATTAGTTCCAAGTGTGTTTTTGTCTGTTATTTTAAACTTTCTACTTAGACA
ATTATGTCATATTGCAAACAAAGACAATTTCTTTCTTTTCAATCTATATACATTTCATTTTCTTTTCTTT
TTAAAAATTACATTAATTACGACTCCCAGTACCATGTTGAAAAACAGTGGTGAGAGGGGACGTTTTTGAC
TTGTTCCTGACCTTAGTGGGAAGACTTTGAGTTTCTCACTATTAAGTATGAAGTTAGATGTAGGGTTTTG
GCAGATATTTTTGATCAAGTTGAGGAGGTTCTCCCCTATTCCAAGTTTAATGGGAGTTTTTATTATAAAT
GAGTGTTTGATTTTGCAAATTCACTTTTCTAGATCTATTGATGTGATCATGTCATTTTATTATTCTTCTT
TAGCCTGTTAATGTAATGAACTGTAAGAATTCATTTTGAATGTTGAACCAGTCTTGGAAACCTGAGGGAA
ATCCCACTTAGTCATGATGTATACTATATTTATACATTGTTGGATTCAATCTGATATTTTTTGAGAATTT
TTGCGTCTATGTTCATGAGAGAAGTTGCTCTGTAGTATTCTTTTTTTTTTTTTTTTTTTTGGAGACA
TAGTTTTGCTCTTGTTACCCAGGCTGGAGGGCAATGGTGCGATCATGGCTCACCGCAACCTCCGCTTCCC
AGGTTCAAGCGATTCTCCTGCCTCAGCCTCCCGAGTAGCTGGGATTACAGGCATGCACCACCATACCCGG
CTAATTTTGTACTTTTAGTAGAGACAAGGTTTCTCCACGTTGGTCAGGCTGGTCTCGAACTCCTGACCTC
AGGTGATCCGCCCACCTCGGCCTCTCAAAGTGCTGGCATTGCAGGTGTGAGTCACCATGCCCAGCCCTCT
GTAGTATTCTTTTCTTTGTAATGTCTTTGTCTGATTTTGTTATTAGGATAATGCTAGCCTCACAGAATGAA
ATAGGAAGTACTTCTGCTGCTGCTATCATCTGAAGAAGATTGTAATGATTTGGTATAATTTCTTACTTAA
GTGTTTGATAGAATTCACCAATGAACCTATCTTAATTTGATGCTTTCTTTTTTATTATTATTATTATACT
TTAAGTTCTAGGGTACATGTGCACAATGTGCTGGTTTGTTACATAGGTATACATGTGCCATGTTGGTGTA
CTGCACCCATTAACTACTCATTTACATTAGGTATATCTCTCAGTGCTATCCCTCCCCCCTCCCCCCACCC
CACGACAGGCCCCAGTGTGTGATGTTCCCCTTCCTGTGTCCAAGTGTTCTCACTGTTCAATTCCCACCTA
TGAGTGAAAACATGTGGCATTTGGTTTTTTTGTCCTTGTGATAGTTTGCTGAGAATGATGGTTTCCAGCT
TCATCCATGTCCCTACAAAGGACATGAACTCATCCTTTTTATGGCTGCATAGTATTCCATGGTTTATAT
GTGCTACATTTTCTTAATCCAGTCTATCACTGATGGACATTTGGGTTGGTTCCAAGTCTTTGCTATTGTG
AATAGTGCAGCAATAAACAAACTTGGCTTTTTGGCTAATATCAAGTATAGTAATCTCGTTCTTTTCAGTTTA
GTTTGATGCTTTCTGTTTTAGAAGGTTATTAAATATGGATTCATTTTTAGAGAGTTCTATCCTCCTTCAA
TGCCTGGGGTTCCATGAGGAAATCAGAGCTTTTTCCCAAAAATGGTACCTCCTATTTTTCCCAAGGACTC
CTCGTCTGTTAGAAATGAACTTAGTTCCTTTCATGTGGTCATCAAGAGGGCAAAAAGACAGACTGAGGA
AATAATTCACTCAAGTGAGAAAAATAAATAAATAAAAACTTCTCAAAAAAAACAAGATCCAAGAAGAGAAA
AAGCACAAAGGTCTTGTATATAGATATATACACACACAGACACACACATATATATACATATATGTATA
TATGTGTGTATATATGTATATGCTATATATACATGTATATATGTGTATGTATATATACACACAAACGTAT
ATGTGTGTCTGTAAAGAGAGAGGGAGAGCGAGAGAGAGTATGGGAGAGCACTTGGATATCCATTTTTAAT
TAAGCTGACTTTTAGCTATAGTGCCCTTTAAAAAAAATCCTTTATATCTCTTATTATCTGACTTTAGCAA
GGCCAAACAGCCAGTATTTCTGGCTTTTGAACTTCTTTAGAAATAGTAATCTCCTAGGTGAAATAAATAA
GCCTTAACTGAGGTTGTAACTTAACCATGAGTGTATGAGGTATTTTCAAATAGGTGGTAAGCAGTTTTTA
CAAGATCTAGAATCTTCAAAGGTAACTCACAGAAACGAAAATTCAAGAAGGGAAGCCAGAAGTTGGTCAT
GGAGGAGCAGAGAATCAACAAATGGAAAAGCCACAAGAATATCAAATCAGAAAGCATTCATTCCCTGGG
CCAAGAATTGAGTCCCAGGCCACCATTGTGAAAAGACAAACTCTTAGCTTCTGAGCTATAGCATTGGATA
GTCTTCATTACCTTTCCCAGAAGGATTCCAGTGCAACCGATTTCAAGCTTGCAAAGGCTTTTAACTGCTC
GAGATAATTTTTAGAGCTAACTATGACATTAACTACAAAATTCCTGTCCTCTAGATGGCAGAGACCAAGA
GTAAGTACTGCCACATAGTTACAAGATCAAGCTCCCACGGACATAAAACAAGATGAGAGGGAAACCTCAT
CCAGTATAGGTTTCAGGAACACACAGCAAAGTTTGTAACCGACCAGCCCAAGAGGCTGGCTTAAAAAGTA
GGCTTATAGGAATCCTAAGCCTACTTTCTACATTCTTTCCTATGCACCCCTCTCCATTACAGAACAACA
CTAAAAGACAAATTCTTAGCACAAAGTACACCAGATTTGCTAAAGCCTAAGACTAGTCTCAAAAATTCAT
TTTTCTATTAATCAGACCACACACACACAGAGAGAGAGAGAGAGACAGAAAGACAGAGAGACAGAGAG
ACAGAGAAAGACAGAGACAGAGACAGAGAGACAGAGACCAGAAGCTTGGCTGGTAACAAATTCTTACCCC
TTTTGCCAGCATACCACGTTTCTGGGTTCCCTTTCTCTGCAGCTTCCAGAAGAATGAAGTGGCTTTTGAT
GACCCTGCTCATTGCACCATAGCTTTGGGGGCCAAGCCACTTTACAAAAGAAAATTATCCTTTTCTGTTT
TATAAAACTATAGGCAAAAGCTTCTCATTTTTGCAAGATGCTGCCCAATGGGCTGCATGAGGAACCAAAT
TAACATTTTCCACCCCAGCCTAGCAAAATACACATAACAAAACAGACATTTGTCACCTCATTCAGCACCC
AATATTGACCTGGCGAGGCTCAAACTTTCTTTCATTGGTCCCTATCATCTCTGATCCACTCAAGATGTGG
AGGGCTAAACTCCAACTGAGAATTCAGGTCTCTGGGCAAGATGAAGAAGTGGACAGTCACCCCGACTCAG
GCCTTTTTGAGCTTCCTTCAGGACTCACTGAATGTGACCAGACAAATAATGAGGGTTTTCTGAGTTAGGT
GTCCTAGACTTCCATCAGTAGTTCCTTTAGAGGTCTCCTCCACATATACAAATACACACAACAAAGACAA
GACAGACAGAAGGCCTTCCAAACCACGACTTCTAACCAAGAATTCCGAGTCTTCCTCCCAAACGAACCTT
CTATTCTCCACCTGAGAATTCTCCCTAAAATCTTCTTGATTGAAGAGAAATCTCCTGAACCAAGACTTCC
TACTAATTAGAGCTAACCAACACCTCCAAAGGAGCTGAACTGAGACCTCAAAAAAAAAAACAAACAAACAA
AAAAAAAAAACAAGAGCCCCAAAGGAGCCAAACCAAGGCCCCTAAAGAAGCCAAATCATGATCCCCAAA
```

FIG. 5 (continued)

```
GGAGCCAAACCAACTGGGAGAAGAAAGGAGGAGTTGGCAGTGCCTAGAATACTCACCAAATTAGTTTGGA
GACAGACATCATTTCCAGGAACTATTTCTCCATTGCAATTAAATCCATGCACATTGGGTCAGCAGCACCC
TGCCAGTAGAGACAGTGCCAGAGTCAGCCCACAGTCCAAGAGAACTAGGCAGCCACTTGGGCTGGCCTCT
GGATCCATCACCAGAGCAGGGCTACTGAACCATGGGCAGGTAGGCACAAAGGCAATCCCAGATGAGACCC
CTAGTGTGTAACCACCTAACGGGTTCACCTTGCCCACTGCCTAGACAGAGCTTATTTATCAAGAAAGATC
TTACTTATCAAAACAGAGAAATTGCAATAAAGAGTAATTCATGCAGAGCCAGCTGTGCAGTACACCAGAG
TTTTGTTATTATTCAAATCAGTCTCTCTGAGAATTTGAGGACTGGAGTTTTTAAAGATAATTTGGTGGGT
AGGGGGGCCAGTGAGTCAAGAGTTCTGATTGGTCAGGTGAGAGATGAAATCATAGGGAGTTGATACTGTC
CTCTCGTGCTGAGTCACTTCCTGGGAGGGGGCCACAGGATGAGATAGGCCAGTTTATCAATCTGGGTGGT
GTGAGCTCATCTGTGAAGTTCAGGATCTGCAAAATATATCAAGTATTGATCTTAGGTTTTACAATAGTGC
TGTTATCCTCAGGAGCAATTTGGTTAGAGTCAGAATCTTGTAGCCTCCAGATGCATTACTCCTAAATCAT
AATTTCTAATCTTTTGGCTAATTCGTTAGTCCTACAAAGGTAGTCTGTTTCCCAGGCAAGAAGCTGGTTT
GTTTTGGGAAAGGACTGTTACTGTCTTGGTTTTAAACTCGAAGCTATAAACTAAATTTCTCCCAGAATTA
GTTCGGCTTACACCCAGAAATCAACAAGAACAGCTTGGAGGATAGAAGCAAGATGGAGTTGGTTAGGTCA
GCTCTCTTTCAGTCTCGGTTATAGTTTTGCAGTGAAAATTTCATAAGCATTTAGTGCAATAAACTTTCCA
CTTTATGCTGTTGAAGCTATATCCTAGAGGTTTTAAAATACTTTGTCTCGATTTTCATTTGTTTAAAACA
AAAAAATTGTGTTCTGCTCTAATTTTGTTATTTACCCAAAAGTAATTCAGGACCAAGTTATACAGATTTC
TTGTAATTGTGTAGTTTCAAGAGTTGCTCTTGATACTGATTTCTATTTTTATTCTGCTGTGGTTCATGAA
GATGTTTGTTATAACTCTGATTTTTTAAAAAATTTATTGTGACTTATGACTTAGAATGTGGTTAGTTTTA
GAGAATGTTTTATGAACAGATAAAAAAATGCATTTTCTCTGATTTTTGGGTGAAGTATTCTCTAGATATCT
ATTAGATCCACTTGGTAAAGAGTCTACTTCAAGTCGAATTTTTTTTTTTTTTTTAGCTTTTGGCCTTG
ATGATGTGCCTGCCTAGTGCTGTCAGTCGGTGTCGAAGCTTATTACTCATTGTATTACTTTCTATCTCT
TTGCTTAGGTCTGGTAGTATTTATTTTATAAATATGATTGCTTCAGTATTGAGTGTGTATATATTTAGAT
TAGTTAAATCTTGTTGAATTAAATGCTTTATCATTATGTAATGCACTTACTTGGTTTTTTTAAACTGTT
GTTTGTTTAAGGTCTGTTTTATTTGATACAAAGAGAGGAATTTCAGCTTATTTTTGCTTTCCATTTGAAA
GATAGATCTTTCTTCATTCTTTTACTTTAAGTCTATGGGTGTCCTTACATACGAGATGGATTCCTTAAGG
GCAGCAGAAGGTTGCCTTTTTTTTTTAATCCACTTTGCTACTCTATGTCTTTTATATGAAGCATTTAGG
CAATTTACATTCAAAGTTAATATTGATATGTGAGATTTTGTACCTCTCATACTGTTGTTAGCTAGTTGCT
TTATAGTTGCAATTGTGTAGTTACTTAATAGGATCTGTAGGCTTTGTAATTATGGGTGCTTTTATAGTAG
CAAGTATTGGTCTGTTTTTCCTGTTTTGAACTCCTTTGAGCATTTTTTCTAAAACTGATCTGGTGGTGA
CATATTTCCTTAGTGTTTACTGGTCTGGGAAATATTTTATTTCTACTTTATTCACAAATCTTCATTTGGG
AAGTTATGAAGTTCTTGGCTGTCATTATTATTTTTCTTTTGTAAGTCTAACAATAGGCCCCCAGTCTCTT
CTAGCTTGTAATGTATCTGCTGGGAAGTTCACCTTTAGTCTAATGGTATTTCCTTCATAAATAATTTGGC
CCTTTTCTCTAGCTGCCGTTAGGATTTGTTTTTTCATGTTGAACTTAGGCAATCTGATGACTATATTCAT
ATAGTATCTGAATGGTTGTTTGTATAGTATCTCATACTATAGTATGTTTTGTATAGTATCTCATACACT
GTTGCACCCACAACAGTGTACAGTGGAGAGAGTGGGAAATTACCCTCTATCCAGATTCATTCCTGAGTGT
TGGTACTGCCTCCTTCAGTAATTGGTGCTGTGCCCATGTTCTCTTTGTCCCAGGGGAAGCTATAGTGGGC
TACAGTCCCCACTCTTTTAGGGGAAGAACACATTGAGGGTTAGATCTCCAGAGGTCCTGCTGTCTCCCCA
AAGTCCACTGACCCCTGTGCCTACCAAAGTCAGAGCAGTTTGTTGGACATGTTTGCCAGGAATTGGGTGG
CATGGTGACTCAAAGATGGAGAATCCTCAGGCAGGGCGGTGGCATACCATAGATGCACCAACAGTATGGC
ACATCTTTCCTTTAGATAGAAAGGTGGTGCAGCTGTACCTGTGCAGGCTGGCCACCTAGTTGTCTATCCC
TGGGGAGTTCCCAAATTGCCACCAATAGCATTACCCTGCATCAAGAGGGCAGAGGAAATTCCTAACAATT
TGGTGGTCAGCAGATTATCAGAGATGTGAGGGGAGCAGAGAAGCACTTTCAGCTAAATTTTCACAGGGTT
CTCTGGGGGTTGATTATTACCAGGCTTTTACCGCTTTCTTTACTACACCACAGCTGCTTCTTATGGGCA
CTATAACAGTTCCTGGCTCTCTTTCTCAGTTTTTTATTTGGTACTTCTTTATTCACCAGTAACTTTGATC
TTCTTTCTGAGGAGAACTGTAATTTGATGTCCCTGGTCAGCCATCTTGAAAAGAACTTGACTTATTTTTT
TATCAGTGGCAGCATGATATATCTTCCTCCATCTAATTACTTTTAATCTATACATCTATAAGTAGATCTC
TTAGAGACTACATATAGTTTGTTTCTTCTTTTTAATCCTTTAACAAACTCAGTCTTTTAATTGGTGGATT
TAGATCATTGACATTAAAAGTGACTACTGATGTTGTGAGACCAATGTTGATTATAATTTTACTATTGTCT
ATTTGTTATACTTGTTCTTTGATCCTATTTTTGTCTTCTATTCTTTTTCTTCTGTTGTGTTCTTAACTA
AATAGTCTATATGACTCTGATTTTATATGACTATATAATCATAACTTTTATGTTACCTTTCTTTATGTA
TATCAAGTTTCTGACCTATATGAGTCTCTCTAAAAAGCTTCTCTTAACATTTCTTACAAGGAAGATGTAC
TGGAAAAACATTTCTTCAATTGTTGTTTGTCTGAGAATGTGTTTATTTCTACTTTACTTTTAAAAGAATT
TCACAGAGTACAGAATTTTAAGTTGGTGATTTTTTTCTCTTAAGACTTTAAATATTTCACTCCACTCTCT
TCTTGCTTGCATGGTTTCTGAAGAGAAGTCTATTTTCTCCCCTATAGATAAAATTTGTTTTTCCTTCTGG
TTAGTTTCAGGATAAAGTTTTCTTTATCTTTGACTTTCTGTAATTTGAAAATAACACACCTACACGTAGT
TTTTCTGGTCAATAATAACTTATTTGTATATTTAAAAATAACTTAGGAAGTGTAGTTGAATTGTTTGTAA
```

FIG. 5 (continued)

```
CTCAAAGGACAAATCCTTAGCATTTTCTGAGTTTCCTGAATCTGTGATATAGTGTCTGACATTAATTTAA
GAGAAATTCTTAGTAATTTTTTTTTTTTTGAGATGGAGTCTCACTCTGTTGCCCAGGCTGGAGTGCAATG
GCATGATCTTGGCTCACTGCAACCCCCGCCTCCCGAGTTCAAGTGATTCTCCTGCCTCAGCCTCCTGAGT
AGCTGGGATAACAGGCACCCGCCACCACGCCCAGCTAGTTTTTGTATTTTTGGTATAGACGGGGTTTCAC
CATGTTGGTCAGGCTGGTCTCTAACTCCTGACCTCGTGATCTGCCTGCCTCAGTCTCCCAAAGTGCTGGG
ATTACAGGCATGATCCACTGCACCTGGCCAGTAATTATTTTTTAAAAATGTTTCTTTTGCTCCTTTTCTC
TTTGTTTTCCTTCTAACCTTTCCATTACACCCACTTATATAATTGTCTCAAAATTTTTATATGATTTCAA
TTGATTTACTTTTTAGTCTTGTTTCTCTTTGCTTTTCAGTTTTGGAGGTTTTCATTGATATATCCTCAAA
TTAGAGAGTCTTCATCAGTTGTGTTCTATCTACTAATAAGCCCATCAAAGGCATTCTTTATTTCTGCTAC
AGAATTTTTTATTTTTAGCATTTTCTTGGGTTCTTAAAATTTTTATTTTTATACTTACATTGTCCATCTG
TTATTGAATGCTGTCTACCTTATTGATTAGAACACTTAACATATTAATCATAGTTGTTTTAAATTCCATT
TTGAAAATTTCCACGTCCCGGACATATCTAGGTCTGGTTTAAAGCTTACTTATTCCTTTCAATCTATGTT
TTTTTTTTCACTTTTGGTATGACTGGCAATTTTTTTCATTACAGTTAAGCATAATGCATTAGGTAAAAGG
AACTGCTTTGATAAGCCTTTATTAATATGGTGTAAGGTGCTGGAGAAGGGGTAGCATTCTACAGGCCTAC
ATTTAGGTTTTATTATTTTAGTTATAATCCAGTAACCTCTGGATTATAAATTTCAAACATACTTCTCAGT
TTCTCCTCCCAGCTGTAGGTGGGGCAGGATGGCTTAACAGGGCTTGAGTTGTATATTTTTCTCGTTTTAT
GAAGAAGGCCAGAGGCAACTAGAGTATAGTTTCTATGGCTTCATAACCCTATTACAATAATAAAATATCT
ATCGTTATGCCCCAATAAAAGAATTATTAGAATTATTGTCTTAATATTTTATTTATAATTTTTTTTCTT
TAGGATCTGGATACTGGAGAAAATGTTTTAAGTTATTACACACAATTTAAACTGATTTATTGTTTTATTT
TCTCTATTTCTACAGAAGGGTCTACTTGGGCTTGTCTTCAATGTTAAGAGTCTCATCACTTGTTTTATAT
ATTATATTAATTTATGCCATGAAGAAAAAATATCAAGAGAAAGATATCAATGCATCAGAAAATGGAAGTG
TCATGGATGAAGCAAACTTAGAATCCTTAAATAAAAATAAACATTTTGTCCCTTCTGCTGGGCAGATAG
TGAAACACATTGTTAAGGGGAGAAAAAAAGCCACTTCTGCTTCTGTGTTTCCAAACAGCATTGCATTGAT
TCAGTAAGATGTTATTTTTGAGGAGTTCCTGGTCCTTTCACTAAGAATTTCCACATCTTTTATGGTGGAA
GTATAAATAAGCCTATGAACTTATAATAAAACAAACTGTAGGTAGAAAAAATGAGAGTACTCATTGTTAC
ATTATAGCTACATATTTGTGGTTAAGGTTAGACTATATGATCCATACAAATTAAAGTGAGAGACATGGTT
ACTGTGTAATAAAAGAAAAAATACTTGTTCAGGTAATTCTAATTCTTAATAAAACAAATGAGTATCATAC
AGGTAGAGGTTAAAAAGGAGGAGCTAGATTCATATCCTAAGTAAAGAGAAATGCCTAGTGTCTATTTTAT
TAAACAAACAAACACAGAGTTTGAACTATAATACTAAGGCCTGAAGTCTAGCTTGGATATATGCTACAAT
AATATCTGTTACTCACATAAAATTATATATTTCACAGACTTTATCAATGTATAATTAACAATTATCTTGT
TTAAGTAAATTTAGAATACATTTAAGTATTGTGGAAGAAATAAAGACATTCCAATATTTGCAAGCTGTGA
TTGTCAAACAACATATTACATTATGTGTTAAGTTTCCAGTGGGCCCACGGTAATGTATTAGGAAAAATTG
ACTTTGACTAATGTAGCCACTCTCATACTTATCTTAGCTAGATTTCCTAGATCATTTGCCGCACCTTCTA
CGTCAGCACTTGCTTCTTCACTTTGTACTTAGATAATGAAACCAGCTTCTTTTTTTAAACCCCGTGAAAC
AAATTCTACAGCTTTTTTTCTTTTGCAGCTTTCCCACGTCTCTTAGTCATCATAGAATGACAGAGAGTTA
TGTCCTTGCTCTAGATTAGATTTGGCCTAAGGGAACATTGTGGCTGCTTTGTTCTTCAATCCAGGCTACT
GAAGTTTTCTCCATGTTAGCCATAAGTCTGTTTCACTTTGTTATTATTTGTGTGTTCACTGAAGTAGGAC
TCTTAATTATCTTCAAGTACTTTATTTTTGCATTCACAACTTGGCTAACTGCTGAATGCAAGATGCTTAG
TTTTGACTTACCTTGGCTCTTGATATGCCTTCCTCACTAAACTTAATCATTTCTAAAATTTGACTTAAAA
TGAGAGATATGTGACTCTTTCTTTCACTCAAACACCTAGAGGTCATTGTAAGGTTATTATTTGGCTTAAT
TTCTATGTTGTTCTGTCTCAGGACATAGGAAGGCCCAAGGGGATGGAGAGAGATGTAGCAATAGCTGGTT
GGTGGAGCATTCAGAACACACACAACTTTATTGATTAAGTTCCACGTATTATATGGGTATGGATAGTGGC
AAGTCAAATCAATTACAATAGTAACATCAAAGATCACTAACCACAGGTCACTATCACAGATACAATAACA
ATGAATAAGTCTGAAATATTGTGAGAATTAGTAAAATGTGACACAGAGACATAAAGTGAGCACATATTTT
TGAAAAAATGATGTCAATAGACTTGTTTGATGCAGGATTGCCACAAACTTCCAATTTGAAAACAAAAAAC
AAACAAAAAAAACACCAAAATATGTGAAGTGCAATAAAGTGAAGTTCAATAAAATGAAGTATGCCAGGAA
TAAAAACTAGCAGGATCACAGGATCAACCTCTACTTAAAAGTATTAGAAATATGGAGGTAAATAGAAGAA
ATAGCTAAAAGAGTTGTAAATGCTTGCCTCTGGAAAGCAGTAATAATAAGCAGAGAAAAACTCATTTTC
AATATGAGATTTTTGATATAATCTTATTTTTACAACTTTGTGCATAAATGGCTTTGGTAAAAATTAAAAA
TCAATCATCAGACTGGTATGTCTCTTATTAATCAACAATAAACAATAATATTGATACCCAGGTACTACAC
TGAGAGCCTTGGGTGAGCCTCCAAGTCTTGCTGGCTTCAGATACCAGAAAGATCACAGGGGTTAATGCAC
TAAGCAGACTCTTGAGGTCCCTGATTCCAGGACTTGACTCTGGGATAGCATTTCTGAACCTGCCCTCGGC
CAGAGGGGAGCCCATTGTTCTGAAGTTTGAATCCCACCTCAGGCAGAATTCAATAGAAGCTGATTAAAGT
GCCCTTGGGCCTTAAGGAAACATTGGCAGTAGTCTAGCAGTACTCCCTGTGGGCCTGAAGTGTTGTGGCT
ATGGGTTGAGGCTCCTTTGTATTTGGAAATGCGAGGGAAGAGTGGGAAAGACGGTCTTGTGGTTTGCGTG
CCACCCTCAGCCACAATATGATAGAACACCAGGTAGACTTTACGAGTTTTGGCTCTAGTCTCTGACTCCTG
GATGGCATCTCTGGACCCACATGGGACCTGGGGGACCTCGCCACCCTGAAAGGAAGGACACAGGCCTTGC
```

FIG. 5 (continued)

```
TGGCTTTTCTGCCTGCTGATTGTAGAGCCCCATGGCCTTGAGCAAACATTGGCAGTAGTCAGGGAGTAAT
TACAGCAGACCTTGGGCAAGACTCATAAATGTGCTGGCTTCAGGTGTAACCCAATGTAGTCATAGTTCTG
GATGCCACAGAGGTGCTTACGCCACTCCAAACC
```

FIG. 6 Wildtype SLCO1B1 polypeptide sequence (NCBI Accession No. NP_006437.3) (SEQ ID No. 73)

```
MDQNQHLNKTAEAQPSENKKTRYCNGLKMPLAALSLSFIAKTLGAIIMKSSIIHIERRFEISSSLVGFID
GSFEIGNLLVIVPVSYFGSKLHRPKLIGIGCFIMGIGGVLTALPHFFMGYYRYSKETNINSSENSTSTLS
TCLINQILSLNRASPEIVGKGCLKESGSYMWIYVFMGNMLRGIGETPIVPLGLSYIDDFAKEGHSSLYLG
ILNAIAMIGPIIGFTLGSLFSKMYVDIGYVDLSTIRITPTDSRWVGAWWLNFLVSGLFSIISSIPFFFLP
QTPNKPQKERKASLSLHVLETNDEKDQTANLTNQGKNITKNVTGFFQSFKSILTNPLYVMFVLLTLLQVS
SYIGAFTYVFKYVEQQYGQPSSKANILLGVITIPIFASGMFLGGYIIKKFKLNTVGIAKFSCFTAVMSLS
FYLLYFFILCENKSVAGLTMTYDGNNPVTSHRDVPLSYCNSDCNCDESQWEPVCGNNGITYISPCLAGCK
SSSGNKKPIVFYNCSCLEVTGLQNRNYSAHLGECPRDDACTRKFYFFVAIQVLNLFFSALGGTSHVMLIV
KIVQPELKSLALGFHSMVIRALGGILAPIYFGALIDTTCIKWSTNNCGTRGSCRTYNSTSFSRVYLGLSS
MLRVSSLVLYIILIYAMKKKYQEKDINASENGSVMDEANLESLNKNKHFVPSAGADSETHC
``` us 9,198,890 B2

COMPOSITIONS AND METHODS FOR TREATING AND PREVENTING CORONARY HEART DISEASE

RELATED APPLICATION

The present application is a continuation of U.S. nonprovisional patent application Ser. No. 13/650,948, filed Oct. 12, 2012, which claims the benefit of and priority to U.S. provisional patent application Ser. No. 61/546,802, filed Oct. 13, 2011. Each of which is incorporated by reference in its entirety.

STATEMENT OF RIGHTS TO INVENTIONS MADE UNDER FEDERALLY SPONSORED RESEARCH

This work was supported by the following grant from the National Institutes of Health, Grant Number HL74753. The government has certain rights in the invention.

TECHNICAL FIELD

The present invention relates generally to compositions and methods for assessing the treatment of coronary heart disease (CHD) in individuals based on their individual genetic makeup. Specifically, the present invention pertains to methods for identifying genetic polymorphisms that affect uptake and metabolism of CHD specific therapeutics and assessing treatment/prophylactic protocols to maximize efficiency of CHD treatment.

BACKGROUND OF THE INVENTION

Coronary heart disease (CHD), the leading cause of morbidity and mortality worldwide, is caused by atherosclerotic plaque deposition in the coronary arteries (i.e. atherosclerosis). CHD is a multi-factorial disease, and independent risk factors include: age, gender, hypertension, smoking, diabetes, family history of premature CHD, elevated levels of low density lipoprotein cholesterol (LDL-C) (>160 mg/dl), and decreased levels of high density lipoprotein cholesterol (HDL-C) (<40 mg/dl for males and <50 mg/dl for females). However, these established CHD-risk factors account for only about half of the variability in CHD events in the U.S. population. Accumulating data indicate that emerging risk factors, including lipoprotein sub-fractions, are better markers of CHD than many of the established CHD risk factors. Additionally, other factors such as the genetic background of an individual may influence how much the major risk factors affect absolute risk.

A simple paradigm of atherosclerosis is that there is an antagonistic relationship between apolipoprotein-B (apo-B)-containing particles, such as low density lipoprotein (LDL) particles, and apoA-I-containing particles, such as high density lipoprotein (HDL) particles. For example, apo-B-containing particles promote atherosclerosis (i.e. they are atherogenic) because they are deposited on the arterial wall; however, apoA-I-containing particles counteract this effect (i.e. they are atheroprotective) because they remove excess cholesterol from the arterial wall.

The various HDL subpopulations differ in size and composition, which impart each of the varying HDL subpopulations with different functions and pathophysiological relevance. The many different functions of HDL are not distributed evenly among the various HDL subpopulations. The best illustration of this is the fact that cells have several different ways by which to remove excess cholesterol. Different HDL particles interact with the different pathways specifically depending on the cell type, the expressed receptor protein type on the surface of the cell, and the cellular cholesterol content. Moreover, the different HDL subpopulations participate differently in the anti-oxidation, anti-inflammation, and cell-signaling processes based on the particles' lipid and protein composition.

Most importantly, the HDL subpopulation profile can differentiate subjects with increased risk for CVD from subjects without such risk independently of HDL-C level. This is very important, as some subjects (or even an entire ethnic group) may have low HDL-C levels but present no history of elevated CVD risk. This is due to the fact that these subjects may have not only hyperactive HDL catabolism, but also hyperactive HDL function. However, some subjects with high HDL-C may experience a CVD event due to low HDL metabolism/catabolism or dysfunctional HDL.

Statins have emerged as an important class of therapeutic compounds for the treatment of CHD. Statins are drugs that inhibit HMG CoA reductase, the rate limiting enzyme in cholesterol biosynthesis, and thereby lower LDL cholesterol. By lowering cellular cholesterol synthesis, statins up-regulate the LDL receptor on the liver cell surface, resulting in enhanced LDL apolipoprotein B clearance. Lowering LDL cholesterol with statin therapy reduces the risk of CHD morbidity and mortality. It has been documented that the absolute reduction in statin induced LDL cholesterol lowering clearly predicts reduction in CHD events. Moreover the absolute reduction in LDL cholesterol levels is greatest in subjects with elevated LDL cholesterol levels at baseline. Additionally, lathosterol is a direct precursor of cholesterol in the bloodstream, and serves as an excellent marker of cholesterol biosynthesis. Individuals with elevated plasma lathosterol/cholesterol ratios generally have significantly greater LDL cholesterol lowering in response to statin therapy than individuals with low plasma lathosterol/cholesterol ratios.

The SLCO1B1 gene encodes a liver-specific polypeptide member of the organic anion transporter family. The SLCO1B1 transporter is primarily responsible for the ability of statins to inhibit cholesterol synthesis. About 20% of the population is heterozygous for the rs4149056 allele, while about 3% is homozygous for the rs4149056 allele. The rs4149056 allele (625T>C)) results in an amino acid substitution (V174A) in the SLCO1B1 protein that decreases the function of this transporter, thereby decreasing the efficacy of statin treatment in terms of LDL cholesterol lowering (Niemi M et al. (2006) "SLCO1B 1 polymorphism and sex effect the pharmacokinetics of pravastatin but not fluvastatin." Clin Pharmacol Ther 80:356-66).

Niemi et al. (2006) reported that following a single oral dose of 40 mg of pravastatin in 32 subjects the areas under the curve of pravastatin blood levels were significantly greater for those subjects carrying the uncommon CC phenotype versus the wildtype TT SLCO1B1 genotype. In a study of 28 subjects, the SLCO1B1 haplotype significantly affected the degree of lathosterol (a marker of cholesterol synthesis) lowering induced by pravastatin (Gerloff T et al. (2006) "Influence of the SLCO1B1*1b and *5 haplotypes on pravastatin's cholesterol lowering capabilities and basal sterol serum levels." Naunyn Smiedebergs Arch Pharmacol 373:45-50). In another study of 16 healthy volunteers, Igel and colleagues reported that SLCO1B1 haplotype was associated with a doubling of plasma pravastatin levels as compared to other haplotypes (Igel M et al. (2006) "Impact of the SLCO1B1 polymorphism on the pharmacokinetics and lipid-lowering efficacy of multiple-dose pravastatin." Clin Pharmacol Ther 79:419-26). In addition, it was also found that the SLCO1B1 genotype affected pravastatin metabolism and LDL-C lowering response in 20 children with familial hypercholesterolemia and 12 cardiac transplant recipients (Hedman M et al. (2006) "Pharmacokinetics and response to pravastatin in pediatric patients with familial hypercholesterolemia and in pediatric cardiac transplant recipients in relation to polymorphisms of the SLCO1B1 and ABCB1 genes". Br J Clin Pharmacol 61:706-15).

The Apolipoprotein E (ApoE) genotype predicts LDL cholesterol lowering response to statins, including atorvastatin and pravastatin. The ApoE gene makes a protein that becomes a lipoprotein when combined with fat. The lipoprotein ApoE is a very low-density lipoprotein, which is responsible in part for removing cholesterol from the bloodstream. Genetic variations in ApoE affect cholesterol metabolism, and may alter an individual's chances of having heart disease, and in particular a heart attack or a stroke.

There are three relatively common variants of ApoE, known as ApoE2, ApoE3, and ApoE4. About 15% of the population carry the ApoE2 allele and are more responsive to statins in terms of LDL cholesterol lowering, while about 20% of the population carry the ApoE4 allele and are less responsive in terms of statin induced LDL cholesterol lowering.

Combinatorial analysis of an individual's genotype at multiple loci and their blood chemistry profile can be used to assess treatment and/or prophylaxis of the individual with respect to coronary heart disease (CHD).

SUMMARY OF THE INVENTION

The present invention provides compositions and methods for assessing and treating coronary heart disease; and in particular for managing elevated cholesterol. According to the invention, baseline cholesterol, and especially LDL cholesterol, in combination with certain genetic factors (as provided herein) are useful in combination for determining the amount and type of cholesterol-lowering treatment for patients on an individualized basis. For example, the identification of particular genetic polymorphisms in combination with baseline cholesterol determines whether a statin is indicated and, if so, at what dose. The invention recognizes the synergistic combination of baseline cholesterol levels and genetic polymorphisms in the diagnosis and treatment of coronary heart disease on a personalized basis.

In a particular application, the SLCO1B1 locus and the apolipoprotein E (ApoE) locus are analyzed to determine which polymorphisms are present. That information is then used in combination with baseline LDL cholesterol in order to determine whether a cholesterol synthesis inhibitor (e.g., a statin) is indicated and at what dose; or whether a statin is contraindicated and, instead, a cholesterol absorption inhibitor (e.g., ezetimibe) should be prescribed. In certain embodiments, the inventive diagnostic algorithm indicates that both a statin and ezetimibe should be prescribed.

The invention is implemented in any manner consistent with the teachings herein. Provided below are algorithms to guide the analysis of the synergistic effects described herein and their relation to treatment and dosage. In a preferred embodiment, an algorithm according to the invention weights cholesterol baseline and genetic polymorphisms in order to determine treatment and/or dose. An example of weighted approach is provided below. The baseline cholesterol component of the diagnostic algorithm can be total cholesterol, LDL cholesterol, HDL cholesterol, or some combination thereof. In addition cholesterol baseline can be expressed as a balance of different types of sterols; for example a ratio of plasma lathosterol to cholesterol in umol/mmol.

The invention utilizes biomarkers that correlate with the efficacy of a cholesterol-reducing drug in view of baseline cholesterol in order to provide a proper treatment regimen and proper dose. Methods of the invention allow one to characterize the likelihood that a patient will respond to a drug treatment based on the patient's cholesterol levels and an array of polymorphisms associated with response to cholesterol-lowering drugs. The invention allows a patient to be characterized as hypo-responsive, hyper-responsive, or normally-responsive to statin treatment, which then allows proper prescribing and dosing.

In one aspect, the invention generally provides a method of determining a statin dosage for an individual in need of treatment with a statin. The method involves determining the genotype of the individual at the SLCO1B1 locus and the ApoE locus, and determining the presence or absence of the rs4149056 polymorphism at the SLCO1B1 locus, and the presence or absence of the ApoE2, ApoE3, and/or ApoE4 polymorphisms at the ApoE locus. According to the method, identifying the presence of the SLCO1B1 rs4149056 C polymorphism and the ApoE genotype or phenotype corresponding to either the ApoE3/ApoE4 or ApoE4/ApoE4 genotypes determines the statin dosage. In one embodiment, the method further involves identifying the plasma LDL cholesterol concentration (mg/dl) and/or the plasma lathosterol/cholesterol (LSC) ratio (umol/mmol) for the individual, where a LDL concentration below about 100 mg/dl and a LSC ratio less than about 70 umol/mmol in men and less than about 85 umol/mmol in women indicates that statin treatment is contraindicated, or at least will not be effective, in lowering LDL-C unless the individual has an ApoE genotype or phenotype corresponding to ApoE2/ApoE2 or ApoE2/ApoE3. Alternatively, LDL concentration below about 100 mg/dl and a LSC ratio less than about 90 irrespective of gender indicates that statin treatment will not be effective in lowering LDL-C unless the individual has an ApoE genotype or phenotype corresponding to ApoE2/ApoE2 or ApoE2/ApoE3.

In another aspect, the invention provides a method of assessing statin dosage for an individual in need of treatment with a statin, the method involves determining the genotype of the individual at the SLCO1B1 locus and the ApoE locus, and determining the presence or absence of the rs4149056 polymorphism at the SLCO1B1 locus, and the presence or absence of the ApoE3 and/or ApoE4 polymorphisms at the ApoE locus. According to the method, determining that the SLCO1B1 genotype is homozygous rs4149056 C/C polymorphism and the ApoE genotype or phenotype is ApoE3/ApoE4 or ApoE4/ApoE4, indicates that the statin dosage needs to be is in the range of about 40 mg to about 80 mg/day or the patient should receive ezetimibe therapy.

In another aspect, the invention provides a method of assessing statin dosage for an individual in need of treatment with a statin, the method involves determining the genotype of the individual at the SLCO1B1 locus and the ApoE locus, and determining the presence or absence of the rs4149056 polymorphism at the SLCO1B1 locus, and the presence or absence of the ApoE2, ApoE3, and/or ApoE4 polymorphisms at the ApoE locus. According to the method, determining that the SLCO1B1 genotype is heterozygous rs4149056 C/T or homozygous rs4149056 T/T and the ApoE genotype or phenotype is ApoE2/ApoE2, ApoE2/ApoE3, or ApoE3/ApoE3, indicates a statin dosage in the range of about t 20 mg to about 40 mg/day. In one embodiment, the method further involves identifying a plasma LDL cholesterol concentration (mg/dl) and a plasma lathosterol/cholesterol (LSC) ratio (umol/ mmol) for the individual, where an LDL cholesterol concentration of about 100 mg/dL or greater and a LSC ratio about 90 umol/mmol or greater in both men and women indicates that statin treatment is indicated unless the individual has a SLCO1B1 rs4149056 genotype of C/C and an ApoE genotype or phenotype comprising ApoE4/ApoE4. When the latter variants are present the combination of low dose statin and ezetimibe should be used.

In another aspect, the invention involves a method of treating a patient to reduce serum LDL cholesterol by assessing the patient's ability to respond to statin treatment by obtaining a plasma LDL cholesterol level and a plasma lathosterol/cholesterol ratio, determining a SLCO1B1 genotype from a nucleic acid sample of the patient by identifying the presence or absence of a SLCO1B1 rs4149056 polymorphism, and determining the patient's ApoE phenotype or genotype as either ApoE3/ApoE3 or ApoE4/ApoE4, where the combined characteristics of SCLO1B1 rs4149056 T/C or C/C genotype, ApoE3/ApoE4 or ApoE4/ApoE4, a plasma LDL cholesterol concentration of about 100 mg/dl and a LSC ratio of less than about 90 umol/mmol contraindicates statin treatment in the patient; and instead indicates treating the patient with ezetimibe and/or dietary modification to reduce the patient's cholesterol. In one embodiment, the combined characteristics include a plasma LDL cholesterol below about 160 mg/dl and a LSC ratio between about 90-160 umol/mmol in irrespective of gender indicate statin treatment in the patient. In another embodiment, the ApoE3/ApoE3 or ApoE4/ApoE4 status is determined by analyzing the nucleic acid of the patient. In another embodiment, the ApoE3/ApoE3 or ApoE4/ApoE4 status is determined by analyzing the protein of the patient.

In another aspect, the invention involves a method of treating a patient to reduce serum LDL cholesterol by assessing the patient's responsiveness to statin treatment by obtaining a plasma LDL cholesterol level and a plasma lathosterol/cholesterol ratio (LCR) and assigning weighted values (A) and (B), respectively, determining the patient's ApoE phenotype or genotype as one of ApoE3/ApoE3 or ApoE4/ApoE4 and assigning weighted value (C), and determining a SLCO1B1 genotype from a nucleic acid sample of the patient by identifying the presence or absence of a SLCO1B1 rs4149056 polymorphism and assigning weighted value (D). The weighted value is assigned to the plasma LDL cholesterol level (A) as follows: an LDL cholesterol concentration greater than about 160 mg/dl is assigned a weighted value of +2, an LDL cholesterol concentration between and including about 100 to about 160 mg/dl is assigned a weighted value of +1, and an LDL cholesterol concentration less than about 100 is assigned a weighted value of 0. The weighted value is assigned to the plasma LCR ratio (B) as follows: a plasma lathosterol/cholesterol ratio greater than about 160 umol/mmol in both men and women is assigned a weighted value of +4, a plasma lathosterol/cholesterol ratio between 90-160 umol/mmol in men and women is assigned a weighted value of 0, and a plasma lathosterol/cholesterol ratio <90 umol/mmol in both men and women is assigned a weighted value of −4. The weighted value is assigned for ApoE type (C) as follows: an ApoE type of ApoE2/ApoE2 is assigned a weighted value of +2, an ApoE type of ApoE2/ApoE3 is assigned a weighted value of +1, an ApoE type of ApoE3/ApoE3 or ApoE2/ApoE4 is assigned a weighted value of 0, an ApoE type of ApoE3/ApoE4 is assigned a weighted value of −1, or an ApoE type of ApoE4/ApoE4 is assigned a weighted value of −2. The weighted value is assigned to the SLCO1B1 genotype (D) as follows: an SLCO1B1 genotype of T/T is assigned a weighted value of 0, an SLCO1B1 genotype of T/C is assigned a weighted value of −1, or an SLCO1B1 genotype of rs4149056/rs4149056 is assigned a weighted value of −2. The weighted values (A), (B), (C), (D) are combined. When the combined weighted value is in the range of +4 to +8, the patient may be characterized as hyper-responsive to statin treatment and requires a statin dosage in the range of about 10-20 mg/day. When the combined weighted value is in the range −3 to +3, the patient may be characterized as a normal responder and requires a statin dosage in the range of about 40 mg/day. When the combined weighted value is in the range −8 to −4, the patient may be characterized as hypo-responsive to statin treatment and requires treatment with maximal doses of statins at 40-80 mg/day and/or ezetimibe treatment. Once the patient is characterized as a particular type of responder, the method involves administering the required statin dosage to the patient, thereby treating the patient so as to reduce serum LDL cholesterol. In one embodiment, the hypo-responsive patient is treated with a non-statin drug. In another embodiment, the non-statin drug is ezetimibe.

In another aspect, the invention includes an in-vitro diagnostic kit for identifying an appropriate therapeutic regiment to enable an individual in need of treatment to obtain a target cholesterol level. The kit includes a first reagent for detecting the presence or absence of a polymorphism in the SLCO1B1 gene, and a second reagent for detecting ApoE3/ApoE3 or ApoE4/ApoE4 in a biological sample from the individual, where the first reagent includes an rs4149056 specific primer set, and the second reagent includes an rs7412 specific primer set and an rs429358 specific primer set, or an anti-ApoE antibody, and packaging therefore.

The present invention pertains to compositions and methods for assessing the treatment of CHD in individuals based on their genetic makeup (i.e. personal genome sequence) by identifying genetic polymorphisms at genetic loci that affect uptake and/or metabolism of CHD specific therapeutics, and assessing treatment/prophylactic protocols to maximize efficacy of CHD treatment. In a preferred embodiment, the invention provides compositions and methods for assessing the treatment of CHD in an individual based on their genotype at both the SLCO1B1 and ApoE loci.

Other and further aspects and features of the invention will be evident from the following detailed description and the accompanying drawings, which are intended to exemplify, not limit, the invention.

BRIEF DESCRIPTION OF THE DRAWINGS

FIG. 1 shows the wildtype ApoE nucleic acid molecule (NCBI Accession No. NM_000041.2) (SEQ ID No. 68).

FIG. 2 shows another exemplary wildtype ApoE nucleic acid molecule (NCBI Accession No. NG_007084.2) (SEQ ID No. 69)

FIG. 3 shows an exemplary ApoE polypeptide wildtype sequence (NCBI Accession No. NP_000032.1) (SEQ ID No. 70).

FIG. 4 shows an exemplary SLCO1B1 nucleic acid molecule (NCBI Accession No. NM_006446.4) (SEQ ID No. 71).

FIG. 5 shows an exemplary wildtype SLCO1B1 nucleic acid molecule (NCBI Accession No. NG_011745.1) (SEQ ID No. 72).

FIG. 6 shows an exemplary wildtype SLCO1B1 polypeptide sequence (NCBI Accession No. NP_006437.3) (SEQ ID No. 73).

DETAILED DESCRIPTION OF THE INVENTION

The invention features compositions and methods that are useful for assessing the treatment and/or prophylaxis of coronary heart disease (CHD) in individuals based on their individual genetic makeup.

The present invention provides methods of assessing the treatment and/or prophylaxis of coronary heart disease (CHD) by determining a subject's genotype and/or plasma LDL cholesterol level and/or plasma lathosterol/cholesterol ratio, and administering a therapeutically effective amount of a compound, such as, for example, a statin, to a subject (e.g., a mammal such as a human). The present invention is based, at least in part, on the inventors' discovery that polymorphisms within genes that encode proteins involved in the uptake and metabolism/catabolism of therapeutic agents used to treat CHD modulate the efficacy of the therapeutic agent, and that this modulation is combinatorial (i.e. polymorphisms at different loci may interact with one another in either antagonistic or synergistic ways). A polymorphism or variant is a polynucleotide or polypeptide sequence that differs from a wild-type or reference sequence by one or more nucleotides or one or more amino acids. A polymorphism may include single or multiple nucleotide insertions, deletions, and/or alterations of the genomic sequence of a specified locus.

Thus, one embodiment is a method of assessing treatment of a subject suffering from or susceptible to CHD, or a symptom thereof that is based, at least in part, on a knowledge of the combination of an individual's genotype at the solute carrier organic anion transporter family member 1B1 (SLCO1B1) locus and the apolipoprotein E (ApoE) locus. The method includes the steps of determining the subject's genotype at least at SLCO1B1 and ApoE, and administering to the subject an assessed therapeutic amount of a statin dosage, or other suitable therapeutic compounds to treat CHD, or symptoms thereof, under conditions such that the disease is treated in a manner that has been assessed for the subject's own genomic sequence at the SLCO1B1 and ApoE loci. In one embodiment, knowledge of a subject's SLCO1B1 and ApoE genotype may be combined with knowledge of the subject's plasma LDL cholesterol level and plasma lathosterol/cholesterol ratio, thereby further assessing treatment.

The therapeutic methods of the invention (which include prophylactic treatment) in general comprise administration of a therapeutically effective amount of the compounds herein, such as a statin to a subject (e.g., animal, human) in need thereof, including a mammal, particularly a human. Such treatment will be suitably administered to subjects, particularly humans, suffering from, having, susceptible to, or at risk for heart disease, disorder, or symptom thereof, for example, CHD. Determination of those subjects "at risk" can be made by any objective or subjective determination by a diagnostic test or opinion of a subject or health care provider (e.g., genetic test, enzyme or protein marker, marker (as defined herein), family history, as well as other medically accepted indicators).

In one embodiment, the invention provides a method of monitoring treatment progress. The method includes the step of determining a level of diagnostic marker (marker) (e.g., any SLCO1B1 and/or ApoE polymorphism delineated herein) or diagnostic measurement (e.g., screen, assay) in a subject suffering from or susceptible to a disorder or symptoms thereof associated with CHD, in which the subject has been administered a therapeutic amount of a compound herein sufficient to treat the disease or symptoms thereof. The level of marker determined in the method can be compared to known levels of marker in either healthy normal controls or in other afflicted patients to establish the subject's disease status. The controls or reference level can be established by determining the levels of markers in a subject that has not been diagnosed with a disease according to the invention, for example heart disease or CHD, and/or does not exhibit any detectable symptoms associated with this disease. In addition, controls or reference levels can be determined by levels of markers in a subject positively diagnosed with a disease according to the invention. In preferred embodiments, a second level of marker in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to this invention; this pre-treatment level of marker can then be compared to the level of marker in the subject after the treatment commences, to determine the efficacy of the treatment.

Methods of the invention are used to assess treatment of heart disease. Heart disease includes but is not limited to coronary heart disease (CHD), cardiomyopathy, cardiovascular disease (CVD), ischemic heart disease, heart failure, hypertensive heart disease, inflammatory heart disease, and valvular heart disease. Heart disease is a systemic disease that can affect the heart, brain, most major organs, and the extremities. Coronary heart disease that causes the failure of coronary circulation to supply adequate circulation to the cardiac muscles and surrounding tissues. Cardiovascular disease is meant any of a number of specific diseases that affect the heart itself and/or the blood vessel system, especially the myocardial tissue, as well as veins and arteries leading to and from the heart. For example, CVD may include, but is not limited to, acute coronary syndromes, arrhythmia, atherosclerosis, heart failure, myocardial infarction, neointimal hyperplasia, pulmonary hypertension, stroke, and/or valvular disease. CVD may be diagnosed by any of a variety of methods known in the art. For example, such methods may include assessing a subject for dyspnea, orthopnea, paroxysmal nocturnal dyspnea, claudication, angina, chest pain, which may present as any of a number of symptoms known in the art, such as exercise intolerance, edema, palpitations, faintness, loss of consciousness, and/or cough.

Atherosclerosis is a heart disease in which an artery wall thickens as the result of a build-up of fatty materials such as cholesterol. It is a syndrome affecting arterial blood vessels, a chronic inflammatory response in the walls of arteries, in large part due to the accumulation of macrophage white blood cells and promoted by low-density lipoproteins (plasma proteins that carry cholesterol and triglycerides) without adequate removal of fats and cholesterol from the macrophages by functional high density lipoproteins (HDL). It is commonly referred to as a hardening or furring of the arteries. It is caused by the formation of multiple plaques within the arteries.

In certain embodiments, methods of the invention are used to determine an appropriate treatment to lower low density lipoprotein (LDL) cholesterol (LDL-C), which is associated with increased heart risk. Typically, a low HDL-C blood concentration value is below 40 mg/dl in men and is below 50 mg/dl in women. In contrast to LDL, high density lipoprotein (HDL) cholesterol (HDL-C)," is the cholesterol level of "good particles" measured in plasma, after the removal of apo-B containing lipoproteins (very low density lipoprotein cholesterol and low density lipoprotein particles). High blood concentration values of HDL-C are above 60 mg/dl and protect against heart disease. A HDL-C blood concentration value between 40 and 60 mg/dl is considered borderline.

Methods of the invention can be used to determine a patient's responsiveness to statin treatment to reduce LDL cholesterol and to determine a proper statin dosage for the patient. By Statin is class of drugs used to lower cholesterol levels by inhibiting the enzyme HMG-CoA reductase, which plays a central role in the production of cholesterol in the liver. Statins may include but are not limited to Advicor® (niacin extended-release/lovastatin), Altoprev® (lovastatin extended-release), Caduet® (amlodipine and atorvastatin), Crestor® (rosuvastatin), Lescol® (fluvastatin), Lescol XL (fluvastatin extended-release), Lipitor® (atorvastatin), Livalo® (pitavastatin), Mevacor® (lovastatin), Pravachol® (pravastatin), Simcor® (niacin extended-release/simvastatin), Vytorin® (ezetimibe/simvastatin), Zocor® (simvastatin), or generic atorvastatin, lovastatin, pravastatin, or simvastatin. In certain embodiments, the proper statin dosage is the amount of a statin required to reduce LDL-C to target levels, relative to an untreated patient. The effective amount of statin(s) used to practice the present invention for therapeutic treatment of a disease varies depending upon the manner of administration, the age, body weight, and general health of the subject. Additionally, statin dosage may vary depending upon which statin is being administered. For example, a typical statin dosage range for atorvastatin, pravastatin, lovastatin, and simvastatin is from about 10 mg to about 80 mg. For these three statins, a "normal" statin dosage may range from about 10 mg to about 40 mg, while a "high" statin dosage may range from about 40 mg to about 80 mg.

Diagnostic Methods

The present invention provides a number of diagnostic assays that are useful for characterizing the genotype of a subject. The present invention can be employed to genotype a gene of interest in a subject, where the gene of interest has similar or variant isoform(s). In certain embodiments, genotyping is the characterization of two alleles in one or more genes of interest. Desirably, the methods of the invention discriminate between the genotype of a gene of interest and the genotype of the similar isoform(s). Preferably, both or all alleles corresponding to a gene of interest are identified. Accordingly, the invention provides for genotyping useful in virtually any clinical setting where conventional methods of analysis are used.

The genotype of an individual may be determined as heterozygous or homozygous for one or more variant alleles of interest. Heterozygous generally means that a chromosomal locus has two different alleles. In one embodiment of the invention, heterozygous refers to a genotype in which one allele has a wild-type SLCO1B1 sequence (e.g., encoding a SLCO1B1 protein that has normal transporter activity) and the other allele has a sequence encoding a SLCO1B1 variant such as, for example, rs4149056 that does not have normal transporter activity (e.g., an alteration of Valine 174 to Alanine). Homozygous generally means a chromosomal locus has two identical alleles. In one embodiment, homozygous refers to a genotype in which both alleles have a wild-type SLCO1B1 sequence (e.g., encoding a SLCO1B1 protein that has normal transporter activity). In some embodiments, homozygous can refer to a genotype in which both alleles have a sequence encoding a SLCO1B1 variant that does not have normal transporter activity such as, for example, rs4149056 that does not have normal transporter activity (e.g., an alteration of Valine 174 to Alanine). In particular embodiments, the SLCO1B1 variant alleles with reduced or eliminated transporter activity are identical at one or more SNPs.

In various aspects, the methods of the invention determine or detect the presence of both of SLCO1B1 and APOE genetic variants, whether at the nucleic acid or protein level. The present methods provide a genetic means for the analysis of biomarkers in SLCO1B1 and APOE associated with drug metabolism, for example, statin metabolism. Results obtained from SLCO1B1 and APOE genotyping assays may be used to select an appropriate therapy for a subject, monitor drug therapy in a subject, identify a subject as responsive to drug therapy, or identify a subject as sensitive to a drug. This level of genotyping will better enable individualized pharmacogenetic-based therapy.

An apolipoprotein E (ApoE) nucleic acid molecule is a polynucleotide encoding an ApoE protein that, when combined with fat, becomes a lipoprotein. An exemplary wildtype ApoE nucleic acid molecule is provided at NCBI Accession No. NM_000041.2 (SEQ ID. No. 68) (see FIG. 1). Another exemplary wildtype ApoE nucleic acid molecule is provided at NCBI Accession No. NG_007084.2 (SEQ ID No. 69) (see FIG. 2). In certain embodiments, a ApoE polypeptide is a polypeptide or fragment thereof having at least about 85% amino acid identity to the exemplary wildtype sequence of NCBI Accession No. NP_000032.1 (SEQ ID No. 70) (see FIG. 3). In certain embodiments, an ApoE2 is an ApoE allele that encodes an ApoE protein that has a cysteine residue at amino acid positions 130 and 176 (sometimes listed as amino acid positions 112 and 158 in the early ApoE literature) in the receptor-binding region of ApoE. At the genotypic level, ApoE2 is defined by two SNPs: rs429358 (position 471 of the ApoE cDNA, position 7903 of the ApoE genomic DNA, and position 17680159 of the chromosome) and rs7412 (position 609 of the ApoE cDNA, position 8041 of the ApoE genomic DNA, and position 17680297 chromosome). The ApoE2 genotype is rs429358 (T) and rs7412 (T). In certain embodiments, ApoE3 is meant an ApoE allele that encodes an ApoE protein that has a cysteine at position 130 and an arginine at position 176. At the genotypic level, ApoE3 is defined by two SNPs-rs429358 and rs7412 (see above for nucleotide positions of these two SNPs). The ApoE3 genotype is rs429358 (T) and rs7412 (C). In certain embodiments, ApoE4 is meant an ApoE allele that encodes an ApoE protein that has an arginine at both positions 130 and 176. At the genotypic level, ApoE4 is defined by two SNPs-rs429358 and rs7412 (see above for nucleotide positions of these two SNPs). The ApoE4 genotype is rs429358 (C) and rs7412 (C).

Exemplary ApoE polymorphisms include rs7412, rs429358, rs769452, rs769455, rs11542029, rs11542031, rs11542038, rs28931576, rs28931578, rs28931579, rs111833428, rs121918392, rs121918393, rs121918394, rs121918395, rs121918396, rs121918397, rs121918398, and rs121918399. The most common ApoE polymorphism are commonly referred to as ApoE2, ApoE3, and ApoE4, respectively. These polymorphic forms differ from each other only by amino acid substitutions at positions 130 and 176 of the ApoE protein. These amino acid changes are caused by SNPs at nucleotide positions 471 (rs429358) and 609 (rs7412) of the ApoE cDNA, respectively. The ApoE2 allele has a cysteine at amino acid positions 130 and 176 in the receptor-binding region of ApoE. The ApoE3 allele has a cysteine at amino acid position 130 and an arginine at amino acid position 176. The ApoE E4 allele has an arginine at both amino acid positions 130 and 130.

SLCO1B1 is the name for a solute carrier organic anion transporter family, member B1 nucleic acid molecule. In certain embodiments a SLCO1B1 is a polynucleotide encoding an SLCO1B1 polypeptide. SLCO1B1 is a gene that encodes a liver-specific member of the organic anion transporter family. The SLCO1B1 protein is a transmembrane receptor that mediates the sodium-independent uptake of numerous endogenous compounds including bilirubin, 17-beta-glucuronosyl estradiol and leukotriene C4. This protein is also involved in the removal of drug compounds such as statins, bromosulfophthalein and rifampin from the blood into the hepatocytes. An exemplary SLCO1B1 nucleic acid molecule is provided at NCBI Accession No. NM_006446.4

(SEQ ID No. 71) (FIG. 4). Another exemplary wildtype SLCO1B1 nucleic acid molecule is provided at NCBI Accession No. NG_011745.1 (SEQ ID No. 72) (FIG. 5). In certain embodiments, a SLCO1B1 polypeptide is a polypeptide or fragment thereof having transporter activity and at least about 85% amino acid identity to the exemplary wildtype sequence of NCBI Accession No. NP_006437.3 (SEQ ID No. 73) (FIG. 6). In certain embodiments, a SLCO1B1-056 polymorphism is the rs4149056 polymorphism, which results in a T to C nucleotide change at position 625 within the gene (sometimes referred to as position 521 in the early literature) that causes a missense mutation at position 174 in the SLCO1B1 protein from valine to alanine (V174A).

Exemplary SLCO1B1 polymorphisms include rs4149056, rs61176925, rs61760183, rs61760245, rs71581941, rs71581978, rs71581987, rs71581988, rs72559742, rs72559745, rs72559746, rs72559747, rs72559748, rs72661137, rs74064211, rs74064213, rs74700754, rs77468276, rs77871475, rs79109623, rs79135870, rs112560299, rs112909948, rs113495867, and rs113635866.

In particular embodiments, the invention provides for the detection of SLCO1B1 and APOE allelic variants and SNPs listed in Table 1 and Table 2, respectively. In preferred embodiments, the invention provides for the detection of the rs4149056 (corresponding to a T to C change at nucleotide position 625 of the SLCO1B1 cDNA, and a valine to alanine change at position 174 of the SLCO1B1 protein) polymorphism in the SLCO1B1 gene, and the rs429358 (corresponding to a T to C change at nucleotide position 471 of the ApoE cDNA, and an arginine to cysteine change at position 130 of the ApoE protein) and rs7412 (corresponding to a C to T change at position 609 of the ApoE cDNA, and an arginine to cysteine change at position 176 of the ApoE protein) polymorphisms in the ApoE gene. Advantageously, the methods of the invention distinguish between homozygous and heterozygous alleles of SLCO1B1 and/or ApoE.

TABLE 1

SLCO1B1 Polymorphisms That Alter Amino Acid Identity

| Polymorphism ID | Position on Chromosome 19 | SEQ ID NO. | Sequence | Polymorphism: N in Sequence | Amino Acid Change |
| --- | --- | --- | --- | --- | --- |
| rs2291075 | 21331625(+) | 1 | GATTTNGCTAA | C/T | F |
| rs2306282 | 21329802(−) | 2 | CTCTANTGAGT | T/C | N/S |
| rs2306283 | 21329738(−) | 3 | TGAATNGATAT4N | C/T | D |
| rs4149056 | 21331549(+) | 4 | ATATGNGTTCA | T/C | V to A |
| rs4149057 | 21331599(+) | 5 | TACCANTGGGG | T/C | L |
| rs4603354 | 21331636(+) | 6 | AGAAGNACATT | A/G | E, G |
| rs11045818 | 21329761(+) | 7 | ACATCNACCTT | G/A | S |
| rs11045819 | 21329813(+) | 8 | CATCANCTGAG | C/A | T, P |
| rs11045852 | 21349885(+) | 9 | GCACTNTCAGG | A/G | I, V |
| rs11045853 | 21349910(+) | 10 | TTCTCNATGGG | G/A | Q, R |
| rs11045854 | 21350034(+) | 11 | TCACTNTCTTT | G/A | L |
| rs11045859 | 21355537(+) | 12 | GCTGTNATGTC | G/A | V |
| rs11557087 | 21294536(+) | 13 | ATAAANCAGCA | A/G | T, A |
| rs34671512 | 21391976(+) | 14 | ATATTNATTTA | A/C | L, F |
| rs55737008 | 21392047(+) | 15 | GGATGNAGCAA | A/G | E, G |
| rs55901008 | 21353529(+) | 16 | CTATANTGGTG | C/T | T, I |
| rs56061388 | 21327529(+) | 17 | GATTGNATTTG | C/T | A, V |
| rs56101265 | 21325716(+) | 18 | GAAGCNTTGAA | C/T | L, F |
| rs56199088 | 21392011(+) | 19 | GAAAGNTATCA | A/T | D, V |
| rs56387224 | 21355583(+) | 20 | GTGAANACAAA | A/T | N, Y |
| rs57040246 | 21353557(+) | 21 | AAATANGTAGA | C/T | Y |
| rs59113707 | 21355489(+) | 22 | AAATTNAAACT | C/G | F, L |
| rs59502379 | 21358933(+) | 23 | AGCAGNTTGCA | G/C | A/G |
| rs61176925 | 21355561(+) | 24 | CTATTNTATTT | A/C | L, F |
| rs61760183 | 21325669(+) | 25 | CTGGGNTAAAT | A/G | Q, R |
| rs61760245 | 21353483(+) | 26 | AGGGANGGGAA | A/G | I, V, Y |

TABLE 1-continued

SLCO1B1 Polymorphisms That Alter Amino Acid Identity

| Polymorphism ID | Position on Chromosome 19 | SEQ ID NO. | Sequence | Polymorphism: N in Sequence | Amino Acid Change |
|---|---|---|---|---|---|
| rs71581941 | 21375289(+) | 27 | TTATANGAGCA | C/T | RX |
| rs71581978 | 21327539(+) | 28 | GTGAGNTACTT | C/T | S |
| rs71581987 | 21370128(+) | 29 | AATGCNCAAGA | C/T | P, S |
| rs71581988 | 21370177(+) | 30 | AATACNAGTCT | A/T | Q, L |
| rs72559742 | 21349993(+) | 31 | TGCCGNAAAAT | -/A | K, Q |
| rs72559745 | 21329817(+) | 32 | ACCTGNGATAG | A/G | E, G |
| rs72559746 | 21331606(+) | 33 | GGGGCNTTCTT | G/T | R, L |
| rs72559747 | 21353478(+) | 34 | TAATCNCCTGT | C/G | P, R |
| rs72559748 | 21358855(+) | 35 | CTCAGNCTGCA | A/G | D, G |
| rs72661137 | 21370183(+) | 36 | AGTCTNGAATT | G/T | W, L |
| rs74064211 | 21358922(+) | 37 | TCACCNTGTCT | C/T | P |
| rs74064213 | 21358965(+) | 38 | AGCCTNTAGTG | A/G | I, V |
| rs74700754 | 21375275(+) | 39 | TTTCCNCTCAA | A/T | H, L |
| rs77468276 | 21355535(+) | 40 | CTGCTNTGATG | G/C | L, V |
| rs77871475 | 21353471(+) | 41 | TCCTTNCTAAT | A/T | T, S |
| rs79109623 | 21353505(+) | 42 | TTTGANGTTGT | C/T | T, M |
| rs79135870 | 21331891(+) | 43 | CAATCNTTGGC | A/G | I, V |
| rs112560299 | 21391957(+) | 44 | ATCACNTGTTT | A/T | H, L |
| rs112909948 | 21370119(+) | 45 | ATTTGNGTGAA | A/G | S, G |
| rs113495867 | 21353483(+) | 46 | CCTGTNTATGTT | -/G | Y, V |
| rs113635866 | 21294538(+) | 47 | AAAACNGCAGA | A/G | T |

TABLE 2

Polymorphisms That Alter Amino Acid Identity

| SNP ID | CHROMOSOME 19 POSITION | SEQ ID NO. | SEQUENCE | Polymorphism: N in Sequence | Amino Acid Change |
|---|---|---|---|---|---|
| rs7412 (E2) | 45412079(+) | 48 | AGAAGNGCCTG | C/T | R to C |
| rs429358 (E4) | 45411941(+) | 49 | ACGTGNGCGGC | T/C | R to C |
| rs769452 | 45411110(+) | 50 | GGAACNGGCAC | T/C | P to L |
| rs769455 | 45412040(+) | 51 | AGCTGNGTAAG | C/T | R to C |
| rs11542029 | 45411121(+) | 52 | TGGGTNGCTTT | C/T | R to C |
| rs11542031 | 45411123(+) | 53 | GGTCGNTTTTG | C/T | R |
| rs11542038 | 45411153(+) | 54 | CAGACNCTGTC | A/G | T |
| rs28931576 | 45411151(+) | 55 | TGCAGNCACTG | A/G | T to A |
| rs28931578 | 45412008(+) | 56 | GCTGCNGGTGC | A/G | Q to R |
| rs28931579 | 45412493(+) | 57 | TGCCCNGCGAC | A/C | S to R |

TABLE 2-continued

Polymorphisms That Alter Amino Acid Identity

| SNP ID | CHROMOSOME 19 POSITION | SEQ ID NO. | SEQUENCE | Polymorphism: N in Sequence | Amino Acid Change |
|---|---|---|---|---|---|
| rs111833428 | 45411042(+) | 58 | CAAGCNGTGGA | A/G | A |
| rs121918392 | 45411034(+) | 59 | AGGTGNAGCAA | A/G | K to E |
| rs121918393 | 45412013(+) | 60 | GGGTGNGCCTC | A/C | S to R |
| rs121918394 | 45412043(+) | 61 | TGCGTNAGCGG | A/C/G | K to Q |
| rs121918395 | 45412289(+) | 62 | GCGACNGCCTG | C/T | R to C |
| rs121918396 | 45412236(+) | 63 | GGCCTNGGGCG | A/G | X to W |
| rs121918397 | 45412041(+) | 64 | GCTGCNTAAGC | A/C/G | H to R |
| rs121918398 | 45412428(+) | 65 | GCAGCNCCAGT | A/G | H to R |
| rs121918399 | 45411100(+) | 66 | GCCAGNGCTGG | C/T | H to R |
| rs7412 | 45412079(+) | 67 | AGAAGNGCCTG | C/T | R to C |

Types of Biological Samples

The genotyping methods of the invention involve detecting or determining a genetic variant or biomarker of interest in a biological sample. In one embodiment, the biologic sample contains a cell having diploid DNA content. Human cells containing 46 chromosomes (e.g., human somatic cells) are diploid. In one embodiment, the biologic sample is a tissue sample that includes diploid cells of a tissue (epithelial cells) or organ (e.g., skin cells). Such tissue is obtained, for example, from a cheek swab or biopsy of a tissue or organ. In another embodiment, the biologic sample is a biologic fluid sample. Biological fluid samples containing diploid cells include saliva, blood, blood serum, plasma, urine, hair follicle, or any other biological fluid useful in the methods of the invention.

Genotyping of SLCO1B1 and APOE Polymorphisms

A SLCO1B1 and/or ApoE isoform is amplified by long range PCR to determine the genotype of the polymorphism, e.g., the rs4149056 (corresponding to a T to C change at nucleotide position 625 of the SLCO1B1 cDNA, and a valine to alanine change at position 174 of the SLCO1B1 protein) polymorphism in the SLCO1B1 gene, and the rs429358 (corresponding to a T to C change at nucleotide position 471 of the ApoE cDNA, and an arginine to cysteine change at position 130 of the ApoE protein) and rs7412 (corresponding to a C to T change at position 609 of the ApoE cDNA, and an arginine to cysteine change at position 176 of the ApoE protein) polymorphisms in the ApoE gene. The amplified nucleic acid corresponding to the SLCO1B1 and/or ApoE polymorphism may be analyzed using a variety of methods for detecting variant alleles to determine the genotype. For example, the presence or absence of one or more of the rs4149056 (corresponding to a T to C change at nucleotide position 625 of the SLCO1B1 cDNA, and a valine to alanine change at position 174 of the SLCO1B1 protein) polymorphism in the SLCO1B1 gene, and the rs429358 (corresponding to a T to C change at nucleotide position 471 of the ApoE cDNA, and an arginine to cysteine change at position 130 of the ApoE protein) and rs7412 (corresponding to a C to T change at position 609 of the ApoE cDNA, and an arginine to cysteine change at position 176 of the ApoE protein) polymorphisms in the ApoE gene may be evaluated using various techniques. For example, the SLCO1B1 gene is amplified by long range PCR and sequenced to determine the presence or absence of a single nucleotide polymorphism (SNP). In certain embodiments, real-time PCR may be used to detect a single nucleotide polymorphism of the amplified products. In other embodiments, a polymorphism in the amplified products may be detected using a technique including hybridization with a probe specific for a single nucleotide polymorphism, restriction endonuclease digestion, primer extension, microarray or gene chip analysis, mass spectrometry, or a DNAse protection assay.

Long range Polymerase Chain Reaction (PCR)

Polymerase chain reaction (PCR) is widely known in the art. For example, U.S. Pat. Nos. 4,683,195, 4,683,202, and 4,800,159; K. Mullis, Cold Spring Harbor Symp. Quant. Biol., 51:263-273 (1986); and C. R. Newton & A. Graham, Introduction to Biotechniques: PCR, 2.sup.nd Ed., Springer-Verlag (New York: 1997), the disclosures of which are incorporated herein by reference, describe processes to amplify a nucleic acid sample target using PCR amplification extension primers which hybridize with the sample target. As the PCR amplification primers are extended, using a DNA polymerase (preferably thermostable), more sample target is made so that more primers can be used to repeat the process, thus amplifying the sample target sequence. Typically, the reaction conditions are cycled between those conducive to hybridization and nucleic acid polymerization, and those that result in the denaturation of duplex molecules.

Exemplary methods for performing long range PCR are disclosed, for example, in U.S. Pat. No. 5,436,149; Barnes, Proc. Natl. Acad. Sci. USA 91:2216-2220 (1994); Tellier et al., Methods in Molecular Biology, Vol. 226, PCR Protocols, 2nd Edition, pp. 173-177; and, Cheng et al., Proc. Natl. Acad. Sci. 91:5695-5699 (1994); the contents of which are incorporated herein by reference. In various embodiments, long range PCR involves one DNA polymerase. In some embodiments, long range PCR may involve more than one DNA polymerase. When using a combination of polymerases in long range PCR, it is preferable to include one polymerase having 3'→5' exonuclease activity, which assures high fidelity generation of the PCR product from the DNA template. Typically, a non-proofreading polymerase, which is the main polymerase is also used in conjunction with the proofreading polymerase in long range PCR reactions. Long range PCR can also be performed using commercially available kits, such as LA PCR kit available from Takara Bio Inc. Polymerase enzymes having 3'→5' exonuclease proofreading activity are known to those in the art. Examples of suitable proofreading enzymes include TaKaRa LA Taq (Takara Shuzo Co., Ltd.) and Pfu (Stratagene), Vent, Deep Vent (New England Biolabs).

Sequencing

DNA sequencing may be used to evaluate a polymorphism of the present invention. One DNA sequencing method is the Sanger method, which is also referred to as dideoxy sequencing or chain termination. The Sanger method is based on the use of dideoxynucleotides (ddNTP's) in addition to the normal nucleotides (NTP's) found in DNA.

Pyrosequencing is another method of DNA sequencing that may be used to evaluate a polymorphism of the present invention, for example as described in U.S. Pat. Publ. No. 2006008824; herein incorporated by reference). Pyrosequencing, which is also referred to as sequencing by synthesis, involves taking a single strand of the DNA to be sequenced, synthesizing its complementary strand enzymatically one base pair at a time, and detecting by chemiluminescence the base that is added.

Pyrosequencing, optionally coupled with amplification of the nucleic acid target, can sequence large numbers of target molecules, usually employing automated sequencing apparati, including long sequences (e.g., 400 million bp/10 hr in a single run). Sequencing methods are well known to those of skill in the art.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

Real-Time PCR (rtPCR)

The presence or absence of polymorphisms in SLCO1B1 and/or ApoE isoforms may be detected using real-time PCR. Real-time PCR typically utilizes fluorescent probes for the selective detection of the polymorphisms. Various real-time PCR testing platforms that may be used with the present invention include: 5' nuclease (TaqMan® probes), molecular beacons, and FRET hybridization probes. These detection methods rely on the transfer of light energy between two adjacent dye molecules, a process referred to as fluorescence resonance energy transfer (see, e.g., Espy et al (2006) Clin Microbiol Rev. 2006 January; 19(1): 165-256 for a review of various rtPCR approaches that may be used with the present invention).

5' Nuclease Probes

In certain embodiments, a 5' nuclease probe may be used to detect a polymorphism of the present invention. 5' nuclease probes are often referred to by the proprietary name, TaqMan® probes. A TaqMan® probe is a short oligonucleotide (DNA) that contains a 5' fluorescent dye and 3' quenching dye. Molecular beacons and FRET hybridization probes typically involve the measurement of fluorescence during the hybridization step.

Genotyping for the 12754T>del ("Asp260fs") or Gly143Glu (428G>A, "Gly143Glu") in the carboxylesterase-1 gene may be evaluated using the following (5' endonuclease probe) real-time PCR technique. Genotyping assays can be performed in duplicate and analyzed on a Bio-Rad iCycler Iq® Multicolor Real-time detection system (Bio-Rad Laboratories, Hercules, Calif.). Real-time polymerase chain reaction (PCR) allelic discrimination assays to detect the presence or absence of specific single nucleotide polymorphisms in the SLCO1B1 and/or ApoE gene, may utilize fluorogenic TaqMan® Probes.

Real-time PCR amplifications may be carried out in a 10 µl reaction mix containing 5 ng genomic DNA, 900 Nm of each primer, 200 Nm of each probe and 5 µl of 2×TaqMan® Universal PCR Master Mix (contains PCR buffer, passive reference dye ROX, deoxynucleotides, uridine, uracil-N-glycosylase and AmpliTaq Gold DNA polymerase; Perkin-Elmer, Applied Biosystems, Foster City, Calif.). Cycle parameters may be: 95° C. for 10 min, followed by 50 cycles of 92° C. for 15 sec and 60° C. for 1 min. Real-time fluorescence detection can be performed during the 60° C. annealing/extension step of each cycle. The IQ software may be used to plot and automatically call genotypes based on a two parameter plot using fluorescence intensities of FAM and VIC at 49 cycles.

FRET Hybridization Probes

FRET hybridization probes, also referred to as LightCycler® probes, may also be used to detect a polymorphism of the present invention. FRET hybridization probe technology permits melting curve analysis of the amplification product. Like molecular beacons, FRET hybridization probes have the advantage of being recycled or conserved during PCR temperature cycling, and a fluorescent signal does not accumulate as PCR product accumulates after each PCR cycle.

Primer Extension

Primer extension is another technique which may be used according to the present invention. A primer and no more than three NTPs may be combined with a polymerase and the target sequence, which serves as a template for amplification. By using less than all four NTPs, it is possible to omit one or more of the polymorphic nucleotides needed for incorporation at the polymorphic site. It is important for the practice of the present invention that the amplification be designed such that the omitted nucleotide(s) is(are) not required between the 3' end of the primer and the target polymorphism. The primer is then extended by a nucleic acid polymerase, in a preferred embodiment by Taq polymerase. If the omitted NTP is required at the polymorphic site, the primer is extended up to the polymorphic site, at which point the polymerization ceases. However, if the omitted NTP is not required at the polymorphic site, the primer will be extended beyond the polymorphic site, creating a longer product. Detection of the extension products is based on, for example, separation by size/length which will thereby reveal which polymorphism is present. For example, U.S. Ser. No. 10/407,846, which is which is hereby incorporated by reference, describes a form of primer extension.

RFLP

Restriction Fragment Length Polymorphism (RFLP) is a technique in which different DNA sequences may be differentiated by analysis of patterns derived from cleavage of that DNA. If two sequences differ in the distance between sites of cleavage of a particular restriction endonuclease, the length of the fragments produced will differ when the DNA is digested with a restriction enzyme. The similarity of the patterns generated can be used to differentiate species (and even strains) from one another.

Restriction endonucleases in turn are the enzymes that cleave DNA molecules at specific nucleotide sequences depending on the particular enzyme used. Enzyme recognition sites are usually 4 to 6 base pairs in length. Generally, the shorter the recognition sequence, the greater the number of fragments generated. If molecules differ in nucleotide sequence, fragments of different sizes may be generated. The fragments can be separated by gel electrophoresis. Restriction enzymes are isolated from a wide variety of bacterial genera and are thought to be part of the cell's defenses against invading bacterial viruses. Use of RFLP and restriction endonucleases in SNP analysis requires that the SNP affect cleavage of at least one restriction enzyme site.

Mass Spectrometry

Mass spectrometry may also be used to detect a polymorphism of the present invention. By exploiting the intrinsic properties of mass and charge, mass spectrometry (MS) can resolved and confidently identified a wide variety of complex compounds. Traditional quantitative MS has used electrospray ionization (ESI) followed by tandem MS (MS/MS) (Chen et al., 2001; Zhong et al., 2001; Wu et al., 2000) while newer quantitative methods are being developed using matrix assisted laser desorption/ionization (MALDI) followed by time of flight (TOF) MS (Bucknall et al., 2002; Mirgorodskaya et al., 2000; Gobom et al., 2000). Methods of mass spectroscopy that may be used with the present invention include: ESI, ESI tandem mass spectroscopy (ESI/MS/MS), Secondary ion mass spectroscopy (SIMS), Laser desorption mass spectroscopy (LD-MS), Laser Desorption Laser Photoionization Mass Spectroscopy (LDLPMS), and MALDI-TOF-MS.

Hybridization

There are a variety of ways by which one can assess genetic profiles, and may of these rely on nucleic acid hybridization. Typically, a probe or primer of between 13 and 100 nucleotides, preferably between 17 and 100 nucleotides in length up to 1-2 kilobases or more in length will allow the formation of a duplex molecule that is both stable and selective. For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

Pharmacogenetics: Consequence for Drug Therapy

SLCO1B1 is important for the uptake and metabolism of many known compounds in humans and non-human animals such as, for example, bilirubin, 17-beta-glucuronosyl estradiol and leukotriene C4, statins, bromosulfophthalein and rifampin. Thus, the presence or absence of one or more polymorphisms of the present invention may be used to "individualize" or modify a therapy for a subject or patient based on the sensitivity of the subject to a therapeutic due to the presence or absence of a polymorphism of the present invention.

A number of SLCO1B1 genetic variants alter the coding sequence of the SLCO1B1 protein, including rs4149056, rs61176925, rs61760183, rs61760245, rs71581941, rs71581978, rs71581987, rs71581988, rs72559742, rs72559745, rs72559746, rs72559747, rs72559748, rs72661137, rs74064211, rs74064213, rs74700754, rs77468276, rs77871475, rs79109623, rs79135870, rs112560299, rs112909948, rs113495867, and rs113635866 (see, e.g., Table 1). The SLCO1B1 gene polymorphism rs4149056 (nt 625 T to C) results in Valine at position 174 being replace with Alanine) is termed the SLCO1B1-056 mutation. It is further contemplated within the scope of the invention that any genetic polymorphism that encodes a V174A mutation is equivalent to rs4149056. This genetic variant, especially in the homozygous state, markedly impairs the catabolism of statins, resulting in significantly higher statin blood level relative to statin blood level in an individual after administration an oral dose of statin. High statin blood levels also result in reduced efficacy in suppressing endogenous cholesterol synthesis and LDL-C lowering, and an estimated 50% chance of developing significant adverse effects especially myopathy on statin therapy in homozygotes. The 625T>C SNP due to the rs4149056 allele at SLCO1B1 resulting in the replacement of valine by alanine at residue 174 in the amino acid sequence of the SLCO1B1 protein results in significantly less Pravastatin induced LDL-C lowering in a large elderly population with either established vascular risk or at risk of vascular disease.

In certain embodiments, evaluating the presence or absence of a polymorphism of the present invention may be used to individualize a therapy and/or determine the sensitivity of a subject to a compound. The compound may be a prodrug, an illicit drug, an opioid, a dopaminergic or noradrenergic drug, an ACE Inhibitor, or an HMG-CoA reductase inhibitor or "statin".

Kits

The invention also provides kits for genotyping any one or more of a SLCO1B1 and/or ApoE polymorphism. Such kits are useful for the diagnosis of a sequence alteration in SLCO1B1 and/or ApoE relative to wild-type SLCO1B1 and/or ApoE sequences in a biological sample obtained from a subject. Alternatively, the invention provides for selecting a drug treatment regimen for CHD, or adjusting a dosage of a CHD specific therapeutic, such as, for example, a statin. In various embodiments, the kit includes at least one primer pair that identifies a SLCO1B1 polymorphism and at least one primer pair that identifies a ApoE polymorphism (e.g., the rs4149056 (nt 625 T to C; aa 174 V to A) polymorphism in the SLCO1B1 gene, and the rs429358 (nt 130 T to C; aa 130 R to C) and rs7412 (nt 176 C to T; aa 176 R to C) polymorphisms in the ApoE gene), together with instructions for using the primers to genotype in a biological sample. In additional embodiments, the kit also includes instructions for selecting an appropriate therapy for a subject, monitoring drug therapy in a subject, identifying a subject as responsive to drug therapy, or identifying a subject as sensitive to a drug. Advantageously, such testing is carried out prior to drug administration or after an adverse event associated with drug administration. Preferably, the primers are provided in combination with a thermostable DNA polymerase capable of long-range PCR amplification (e.g., a high density array). In yet another embodiment, the kit further comprises a pair of primers capable of binding to and amplifying a reference sequence. The reference sequences serves as a basis for sequence comparison. By "single nucleotide polymorphism" or "SNP" is meant a DNA sequence variation occurring when a single nucleotide in the genome differs between members of a biological species or paired chromosomes in an individual. SNPs are used as genetic markers for variant alleles.

In various other embodiments, the kit includes reagents or components for genotyping SLCO1B1 and ApoE in combination with reagents or components for the detection of a single nucleotide polymorphism (SNP) or variant of a gene encoding an additional enzyme involved in drug. The kits which contain reagents and components for determining a SLCO1B1 and/or ApoE genotype and for detecting variants in additional enzyme and/or transporters involved in drug metabolism, are useful for guiding disease specific pharmacotherapies. For example, in the treatment of CHD, one or more drugs, including Angiotensin converting enzyme (ACE) inhibitors including Capoten® (captopril), Vasotec® (enalapril), Prinivil®, Zestril® (lisinopril), Lotensin® (benazepril), Monopril® (fosinopril), Altace® (ramipril), Accupril® (quinapril), Aceon® (perindopril), Mavik® (trandolapril), and Univasc® (moexipril)); Angiotensin II receptor blockers (ARBs) including Cozaar® (losartan), Diovan® (valsartan), Avapro® (irbesartan), Atacand® (candesartan), and Micardis® (telmisartan); Antiarrhythmia drugs including Tambocor® (flecainide), Procanbid® (procainamide), Cordarone® (amiodarone), and Betapace® (sotalol); Antiplatelet drugs; Beta Blockers including Sectral® (acebutolol), Zebeta® (bisoprolol), Brevibloc® (esmolol), Inderal® (propranolol), Tenormin® (atenolol), Normodyne®, Trandate® (labetalol), Coreg® (carvedilol), Lopressor®, and Toprol-XL® (metoprolol); and Calcium Channel Blockers including Norvasc® (amlodipine), Plendil® (felodipine), Cardizem®, Cardizem CD®, Cardizem SR®, Dilacor XR®, Diltia XT®, Tiazac® (diltiazem), Calan®, Calan SR®, Covera-HS®, Isoptin®, Isoptin SR®, Verelan®, Verelan PM® (verapamil), Adalat®, Adalat CC®, Procardia®, Procardia XL® (nifedipine), Cardene®, Cardene SR® (nicardipine), Sular® (nisoldipine), Vascor® (bepridil); aspirin; digoxin; diuretic drugs; Heart Failure Drugs including Dobutrex® (dobutamine) and Primacor® (milrinone); Vasodialators such as Dilatrate-SR®, Iso-Bid®, Isonate®, Isorbid®, Isordil®, Isotrate®, Sorbitrate® (isosorbide dinitrate), IMDUR® (isorbide mononitrate), Apresoline® (hydralazine), and BiDil® (hydralazine with isosorbide dinitrate); warfarin; and surgery. In one preferred embodiment, an agent of the invention is administered in combination with a statin, such as Advicor® (niacin extended-release/lovastatin), Altoprev® (lovastatin extended-release), Caduet® (amlodipine and atorvastatin), Crestor® (rosuvastatin), Lescol® (fluvastatin), Lescol XL (fluvastatin extended-release), Lipitor® (atorvastatin), Livalo® (pitavastatin), Mevacor® (lovastatin), Pravachol® (pravastatin), Simcor® (niacin extended-release/simvastatin), Vytorin® (ezetimibe/simvastatin), and Zocor® (simvastatin) may be prescribed depending on their predicted efficacy in a patient. The patient is evaluated for SLCO1B1 and ApoE genotype and/or expression or catalytic activity to predict the responsiveness of the patient to an CHD-specific therapeutic whose metabolism is affected by SLCO1B1 and ApoE genotype. Such kits may contain one or more genomic tests of enzymes or drug transporters documented to have important SNPs. SNPs may be evaluated using a disease targeted panel of tests (e.g., a microarray). Such panels include commercially available microarrays for detecting one or more SNPs (e.g., AmpliChip® CYP450 Test; Roche). In other embodiments, the kit includes instructions for selecting one or more treatments based on the results of genotyping SLCO1B1 and ApoE and detecting one or more genetic variants in an enzyme involved in drug metabolism or drug transporter.

Thus, testing performed on a patient using the kits of the invention may guide treatment selection specifically tailored to the individual.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Determination of Sample Population Baselines for Key Risk Factors

As summarized in Table 3, the participating subjects were elderly, with a median age of 75±3 years at baseline. Mean LDL-C levels were in the moderate-risk category (130-160 mg/dl), as defined by the United States National Cholesterol Education Program (Expert Panel. Executive Summary of The Third Report of The National Cholesterol Education Program (NCEP) Expert Panel on Detection, Evaluation, And Treatment of High Blood Cholesterol In Adults (Adult Treatment Panel III). JAMA 2001; 285:2486-97). Also, approximately 50% of the men and about one third of the women reported a history of all types of vascular disease. Data on ApoE phenotype distribution in this population are also shown in Table 3. Genotype frequencies for all SNPs examined conformed to Hardy-Weinberg equilibrium (p>0.05, data not shown).

TABLE 3

Study Subjects (n = 5,418)

| Study Characteristics<br>Mean (SD)a | Men<br>(n = 2,621) | Women<br>(n = 2,797) |
|---|---|---|
| Age (years) | 74.99 (3.3) | 75.64 (3.4)b |
| BMI (kg/m2) | 26.56 (3.6) | 27.12 (4.7)b |
| History diabetes mellitus, n (%) | 324 (12.4) | 251 (9.0)b |
| History hypertension, n (%) | 1333 (50.9) | 2026 (72.5)b |
| History vascular disease, n (%) | 1371 (52.3) | 1033 (37.0)b |
| History of MI, n (%) | 508 (19.4) | 222 (7.9)b |
| Current smoking, n (%) | 847 (32.3) | 586 (21.0)b |
| Alcohol consumption, n (%) | 1851 (70.6) | 1165 (41.7)b |
| Total cholesterol (mg/dl) | 207.0 (30.7) | 231.9 (34.5)b |
| LDL-cholesterol (mg/dl) | 138.5 (27.8) | 154.9 (35.3)b |
| HDL-cholesterol (mg/dl) | 45.6 (12.2) | 53.0 (13.4)b |
| Triglyceride (mg/dl) | 132.4 (64.3) | 140.6 (59.4)b |
| apoA-I (mg/dl) | 124.4 (22.2) | 139.9 (24.1)b |
| apoB (mg/dl) | 110.6 (21.3) | 119.1 (22.6)b |
| apoE 2/2 + 2/3 (%) | 13.1 | 11.3 |
| apoE 3/3 (%) | 63.1 | 65.7 |
| apoE 3/4 + 4/4 (%) | 23.8 | 23.0 |
| SLCO1B1__625T > C-rs4149056 | MAF C:0.16 | |
| SLCO1B1__388A > G-rs2306283 | MAF G:0.38 | |
| LXRA__-115G > A-rs12221497 | MAF A:0.14 | |

BMI: body mass index. MAF: minor allele frequency.
aMeans (S.D.) unless otherwise specified; differences between men and women were assessed using a t-test for continuous traits and $\chi2$ test for binary traits.
bp < 0.001, apoE 2/4 carriers were excluded (see Materials and Methods section)

a) Sample Population Baseline TC or LDL-C Levels Are Not Genotype Dependent

Genetic analysis of the sample population revealed no association of baseline TC or LDL-C levels with any SLCO1B1 or LXRA genotype as stratified by gender (see Table 4).

TABLE 4

Adjusted Baseline Lipid Levels (mean ± SD, mg/dl) by Gender and Genotype

| Gene | SNP | Genotype | n Men | n Women | TC Men | TC Women | p[a] | LDL-C Men | LDL-C Women | p[a] |
|---|---|---|---|---|---|---|---|---|---|---|
| SLCO1B1 | 625 T > C | TT | 1871 | 1997 | 207.2 ± 30.9 | 232.3 ± 34.8 | 0.880 | 138.6 ± 28.0 | 155.2 ± 31.8 | 0.850 |
|  |  | TC | 674 | 721 | 207.2 ± 30.3 | 231.7 ± 33.4 |  | 138.8 ± 27.6 | 154.6 ± 30.3 |  |
|  |  | CC | 73 | 75 | 207.1 ± 29.1 | 232.1 ± 37.6 |  | 139.7 ± 26.5 | 153.9 ± 30.7 |  |
| SLCO1B1 | 388 A > G | AA | 1010 | 1125 | 208.3 ± 29.5 | 232.7 ± 33.9 | 0.161 | 139.3 ± 27.9 | 155.1 ± 31.0 | 0.330 |
|  |  | AG | 674 | 1280 | 206.6 ± 30.9 | 231.3 ± 34.8 |  | 138.2 ± 27.9 | 154.6 ± 31.5 |  |
|  |  | GG | 395 | 388 | 206.4 ± 29.9 | 232.5 ± 35.6 |  | 138.3 ± 27.2 | 155.6 ± 32.6 |  |
| LXRA | 115 G > A | GG | 1924 | 2076 | 206.8 ± 30.6 | 232.6 ± 34.9 | 0.936 | 138.2 ± 27.9 | 155.3 ± 32.0 | 0.729 |
|  |  | GA | 647 | 661 | 208.5 ± 31.0 | 230.5 ± 33.8 |  | 140.1 ± 27.9 | 154.3 ± 30.2 |  |
|  |  | AA | 46 | 53 | 206.8 ± 28.3 | 231.6 ± 29.9 |  | 135.9 ± 24.7 | 155.3 ± 26.5 |  |

[a] p values using the three genotypes, men and women combined; adjusted for gender, body mass index, age, alcohol, smoking, diabetes, ApoE phenotype, and country.

b) SLCO1B1 SNP is Associated with Lowered LDL-C Response to Pravastatin

The effect of SNPs at nucleotide positions 388 (e.g. A>G) and 625 (e.g. T>C) of the SLCO1B1 gene and also at nucleotide position −115 (e.g. G>A) of the LXRA gene on responsiveness to Pravastatin in subjects of various genotypes was assessed by analyzing the correlation of different SNP genotypes with the 6 month and 12 month changes in TC and LDL-C levels in treated subjects, as shown below in Table 5. Neither the presence of the LXRA SNP at nucleotide position −115 nor the SLCO1B1 SNP at nucleotide position 388 were associated with lipid lowering. However, subjects carrying the SLCO1B1 SNP at nucleotide position 625 (e.g. T>C) had significantly less LDL-C lowering in response to Pravastatin. For example, subjects who were wildtype (T/T) for the SNP at position 625 represented about 71.5% of the sample population and displayed −37.0% LDL-C lowering, subjects who where heterozygous (T/C) for the SNP at position 625 represented about 25.8% of the sample population and showed −36.0% LDL-C lowering, and subjects who were homozygous (C/C) for the SNP at position 625 represented about 2.7% of the population and showed −31.8% LDL-C lowering (p=0.003 at 6 months, and p=0.022 at 12 months). The percentage reductions in LDL-C given are for the 6 month time point (Table 5).

TABLE 5

Percent LDL-C Response to Pravastatin by Genotype

| Gene | SNP | Genotype | n | 6 months | p[b] | n | 12 months | p[b] |
|---|---|---|---|---|---|---|---|---|
| SLCO1B1 | 625 T > C |  |  |  |  |  |  |  |
|  |  | TT | 1345 | −37.0 ± 10.8 |  | 1331 | −35.9 ± 11.8 |  |
|  |  | TC | 509 | −36.0 ± 10.4 | 0.003 | 504 | −34.6 ± 12.5 | 0.022 |
|  |  | CC | 47 | −31.8 ± 12.8 |  | 45 | −31.8 ± 11.7 |  |
| SLCO1B1 | 388 A > G |  |  |  |  |  |  |  |
|  |  | AA | 772 | −36.7 ± 10.5 |  | 758 | −35.9 ± 11.2 |  |
|  |  | AG | 859 | −36.6 ± 10.7 | 0.775 | 861 | −35.3 ± 12.3 | 0.157 |
|  |  | GG | 269 | −36.2 ± 11.6 |  | 260 | −34.3 ± 12.8 |  |
| LXRA | 115 G > A |  |  |  |  |  |  |  |
|  |  | GG | 1412 | −36.6 ± 10.7 |  | 1403 | −35.5 ± 12.1 |  |
|  |  | GA | 463 | −36.4 ± 10.7 | 0.822 | 150 | −35.1 ± 11.6 | 0.871 |
|  |  | AA | 27 | −37.4 ± 10.9 |  | 29 | −35.3 ± 11.2 |  |

[a] Values are provided as mean ± S.D,

[b] p values for data combining men and women, adjusted for gender, body mass index, age, alcohol, smoking, diabetes, ApoE phenotype, and country.

c) SLCO1B1/LXRA SNPs Are Not Associated with History and Incidence of CVD

Genetic analysis of the sample population revealed no association of any of the SLCO1B1 or LXRA SNPs with either vascular disease at baseline or fatal or non-fatal CHD events on trial in either the placebo or statin groups (see, e.g., Table 6).

4) solute carrier organic anion transporter (SLCO1B1 rs4149056) genotype.

According to the invention, a novel point system was developed to predict statin induced LDL cholesterol lowering response, as shown below. This model provides an excellent fit ($p<0.0001$) to actual data with regard to LDL cholesterol lowering generated on over 3,000 subjects studied at baseline

TABLE 6

Analysis of Incidence of Coronary Heart Disease (CHD) Death or Nonfatal Myocardial Infarction (MI) on Trial by SNP Carrier Status

| SNP | Genotype | Number of new case/Total subjects (%) | Adjusted[a] HR[c] | p | Number of new case/Total subjects (%) | Placebo[b] HR[c] | p | Number of new case/Total subjects (%) | Pravastatin[b] HR[c] | p |
|---|---|---|---|---|---|---|---|---|---|---|
| 625 T > C | TT | 427/3868 (11.0) | 1 | | 232/1956 (11.9) | 1 | | 195/1912 (10.2) | 1 | |
| | TC | 155/1395 (11.1) | 1.01 (0.84-1.21) | 0.996 | 83/693 (12.0) | 1.03 (0.80-1.33) | 0.738 | 72/702(10.3) | 0.99 (0.76-1.30) | 0.659 |
| | CC | 16/148 (10.6) | 0.99 (0.60-1.64) | | 12/81 (14.8) | 1.24 (0.69-2.22) | | 4/67(6.0) | 0.64 (0.24-1.73) | |
| 388 A > G | AA | 224/2135 (10.5) | 1 | | 122/1051 (11.6) | 1 | | 102/1084 (9.4) | 1 | |
| | AG | 279/2489 (11.2) | 1.08 (0.90-1.29) | 0.426 | 150/1275 (11.8) | 1.04 (0.82-1.32) | 0.577 | 129/1214 (10.6) | 1.13 (0.87-1.47) | 0.629 |
| | GG | 94/783 (12.0) | 1.17 (0.92-1.49) | | 54/404 (11.4) | 1.17 (0.85-1.61) | | 40/379 (10.6) | 1.12 (0.78-1.62) | |

[a] p values for men and women combined; adjusted for gender, body mass index, age, alcohol, smoking, diabetes, hypertension, ApoE phenotype, randomized treatment, and country. No significant differences were noted when men and women were separated.
[b] p values for men and women combined; adjusted for gender, body mass index, age, alcohol, smoking, diabetes, hypertension, ApoE phenotype, and country. No significant differences were noted when men and women were separated.
[c] Hazards ratio (95% confidence intervals).

The SNPs 625T>C and 388A>G are within SLCO1B1 d) SLCO1B1 SNP is not Associated with Myositis and/or Myalgia

In this randomized study with 5,804 subjects, 2,913 subjects received placebo and 2,891 received Pravastatin (three of whom refused medication). Of the 2,888 subjects started on Pravastatin, 724 discontinued their medication (5 withdrew consent, 219 died, 346 refused to participate or did not attend follow up examinations, and 107 had non-fatal adverse events). This adverse event rate was very similar to the placebo group where 116 subjects discontinued medication because of non-fatal adverse events. There were no reported cases of rhabdomyolysis in PROSPER, and there were 36 reported cases of myalgia in the Pravastatin group versus 32 cases of myalgia in the placebo group. At the 3 month visit there no subjects that had creatine kinase levels >10 the upper limits of normal. There was no association of the SLCO1B1 rs4149056 SNP with myalgia in the Pravastatin group.

Example 2

Assessing Statin Dosage Using Combined SLCO1B1 and ApoE Genotyping

Elevated levels of plasma or serum low density lipoprotein (LDL) cholesterol are a major risk factor for coronary heart heard disease, a leading cause of death and disability in our society (1,2). Lowering LDL cholesterol with statin drugs has clearly been shown to inhibit cholesterol biosynthesis, and decrease the risk of CHD. Moreover the degree of risk reduction is dependent on the amount of LDL cholesterol lowering. Four factors that are clearly and significantly related to LDL cholesterol lowering response to statins were identified:
1) the plasma level of LDL cholesterol,
2) the ratio of lathosterol/cholesterol in plasma,
3) apolipoprotein (apo) E genotype, and and then placed on pravastatin 40 mg/day for 6 months. Moreover this model predicts more than 75% of the marked variability in statin response that is observed. Those with +4 to +8 points are hyper-responders to statins, and are ideal candidate for statin treatment. Those with −4 to +4 points are normal responders and are candidates for statin therapy. Those with −8 to −4 points are hypo-responder to statins (emphasize dietary modification and consider use of ezetimibe and/or anion exchange resins).

| Prediction of LDL Cholesterol Lowering Point System |  |
|---|---|
| 1. Plasma LDL Cholesterol (mg/dl): | |
| >160: | +2 |
| 100-160: | +1 |
| <100: | 0 |
| LDL Cholesterol Points = | — |
| 2. Plasma Lathosterol/Cholesterol Ratio umol/mmol cholesterol: | |
| >160: | +4 |
| 90-160: | 0 |
| <90: | −4 |
| Lathosterol Points: | — |
| 3. ApoE Genotype: | |
| ApoE2/2: | +2 |
| ApoE2/3: | +1 |
| ApoE3/3: | 0 |
| ApoE3/4: | −1 |
| ApoE4/4: | −2 |
| ApoE Genotype Points: | — |
| 4. Statin Uptake Transporter (SLCO1B1) Genotype: | |
| T/T: | 0 |
| T/C: | −1 |

| Prediction of LDL Cholesterol Lowering Point System | |
|---|---|
| C/C: | −2 |
| Statin Uptake Genotype Points: | — |
| 5. Total Points: | |
| +4 to +8 Points = | Hyper-responder (ideal candidate for statins) |
| −3 to +3 Points = | Normal Responder (candidate for statin) |
| −8 to −4 Points = | Hypo-responder to statins (emphasize dietary modification and consider use of ezetimibe and/or anion exchange resins) |

According to one embodiment, the determination of whether an individual having high LDL cholesterol and in need of statin treatment to reduce the level of LDL cholesterol is a hyper-responder, a normal-responder, or a hypo-responder with respect to the ability of the individual to metabolize a statin can be made by solving the equation $X=A+B+C+D$, where A is the number of points associated with the individual's plasma LDL cholesterol level, B is the number of points associated with the individual's plasma lathosterol/cholesterol ratio, C is the number of points associated with the individual's ApoE genotype, and C is the number of points associated with the individual's SLCO1B1 genotype. The resulting value of X is then used to determine the class of responder to which the individual belongs.

Methods and Materials

Study Subjects: The results and the methodology used in the PROspective Study of Pravastatin in the Elderly at Risk (PROSPER) study have been previously described (see e.g., Shepherd J et al. PROspective Study of Pravastatin in the Elderly at Risk. Pravastatin in elderly individuals at risk of vascular disease (PROSPER): a randomized controlled trial. Lancet (2002) 360:1623-30 and Shepherd J et al. The design of a prospective study of Pravastatin in the Elderly at Risk (PROSPER). PROSPER Study Group. PROspective Study of Pravastatin in the Elderly at Risk. Am J Cardiol (1999) 84:1192-97).

In the present study 2,804 men and 3,000 women between the ages of 70 and 82 with pre-existing vascular disease (n=2,404) or at least one of three major vascular risk factors (diabetes n=575, smoking n=1,433, or hypertension n=3,360) were randomized to Pravastatin 40 mg/day (n=2,891) or placebo (n=2,913) and followed up on for 3.2 years, on average. Over this 3.2 year period of time, the mean LDL-C reduction in the active treatment group was 32%, and the risk of developing CHD was decreased by 19%, which was statistically significant (Shepherd J et al. (2002) Lancet 360:1623-30). This effect translates into an estimated 30% risk reduction in CHD events over 5 years, which is consistent with other statin trials. Additionally, analysis of the treatment group found that HDL-C was increased by 5% and triglycerides were decreased by 12% versus baseline in those subjects placed on Pravastatin. For subjects that were judged to have good compliance (i.e. taking medication more than 75% of the time), these alterations on the lipid levels were even greater: −34% (risk reduction for CHD), +5% (increased HDL-C), and −13% (decreased triglycerides), respectively. No significant lipid changes were noted in the placebo group. Lipid levels were similar at onset of the study in subjects randomized to Pravastatin or placebo.

Biochemical and DNA analysis: Total cholesterol (TC), HDL-C, and triglycerides were assessed in subjects after an overnight fast at 6 months, and at 12 months, and LDL-C was calculated by the Friedewald formula, as previously described (Shepherd J et al. (2002) Lancet 360:1623-30). Apolipoprotein B (apoB) was measured only at baseline as described. DNA was isolated from cells from this cohort, and DNA from 5,783 subjects participating in this study was also available. ApoE phenotype was determined on plasma samples by Western blotting, using the method of Havekes et al. in the central laboratory of the Royal Infirmary in Glasgow, Scotland (Havekes L M et al. A rapid micro method for apolipoprotein E phenotyping directly in serum. J Lipid Res (1987) 28:455-63). Subjects were classified according to the presence of apoE2, apoE3, or apoE4 bands on gel blotting (Havekes L M et al. (1987) J Lipid Res 28:455-63). This gel phenotyping method has been shown to have 99% concordance with genotyping (Lahoz C et al. Frequency of phenotype-genotype discrepancies at the apolipoprotein E locus in a large population study. Clin Chem (1996) 42:1817-23).

DNA analysis was conducted by genotyping two single nucleotide polymorphisms (SNPs) of the SLCO1B1 gene—388A>G (rs2306283) and 511T>C (rs4149056)—using standard methods (e.g. Taq Man® SNPs genotyping assays by Applied Biosystems, Foster City, Calif.). The custom assay identification numbers for these analyses were C__1901697__20 and C__30633906__10, respectively. Additionally, DNA analysis was also conducted by genotyping one SNP of the LXRA gene, rs12221497, and the custom assay identification number for this analysis was C__30887860__10. The end points were ascertained after PCR amplification was performed using standard methods (e.g. an Applied Biosystems 7900 HT Sequence Detection System). Genotypes with quality scores below the 95% threshold were repeated and 5% blinded replicates for genotype determinations were performed. In addition, a total of 119 subjects (~2.2% of the sample size) who had the apoE4/2 phenotype were excluded from these analyses, as well as 246 subjects who had missing apoE phenotype. These subjects were excluded because apoE phenotype or genotype can affect statin-induced LDL-C lowering response, as well as CHD risk, in an allele dependent manner. For example, subjects carrying the apoE4 allele having the greatest response in terms of LDL-C lowering and the highest CHD risk, however, apoE2 and apoE4 phenotype have opposite effects in this regard. The subject characteristics for these individuals representing the 5,418 subjects are shown in Table 3.

Statistical analysis: Observed genotype frequencies were compared with those expected under Hardy-Weinberg equilibrium using a $\chi^2$ test. For data analysis, multivariable analysis of covariance (ANCOVA) was performed to detect associations between the lipoprotein levels at baseline as well as changes in response to the treatment with Pravastatin at 6 months and with SLCO1B1 genotypes adjusted for gender, body mass index, age, alcohol, smoking, diabetes, apoE phenotype, and country of origin, since subjects participating in PROSPER were either from Scotland, Ireland, or the Netherlands. Prevalence at baseline of myocardial infarction (MI) and all types of vascular disease (history of angina, claudication, MI, stroke, transient ischemic attack, peripheral arterial disease surgery, or amputation for vascular disease more than 6 months before study entry) at baseline, as well as incidence of primary endpoints (CHD death or nonfatal MI or fatal non-fatal stroke), and all cardiovascular events (primary endpoints and coronary artery bypass grafting, coronary angioplasty, and peripheral artery surgery or angioplasty), were compared between carriers of different SLCO1B1 SNP genotypes using multivariable logistic regression analysis in all subjects and stratified by gender and treatment. All analyses were fully adjusted for age, gender, country, history of vascular disease, body mass index, history of diabetes, as well as history of hypertension, alcohol use, current smoking, and apoE phenotype. To evaluate the modifying effects of genotypes and gender on the response to treatment, gene-treatment and gene-gender interaction terms were added to the regression models. Lewontin's D value was calculated to assess the linkage disequilibrium (LD) between the two SNPs of interest (Lewontin R C. The interaction of selection and linkage. II. Optimum models. Genetics 1964; 50:757-82). There was no interaction between these SNPs and also no interaction between these SNPs and apoE genotype. All analyses were performed using SAS/STAT and SAS/Genetics [including proc haplotype procedure] (SAS Version 9.1, SAS Institute Inc., Cary, N.C.). A two-sided p<0.05 was considered statistically significant.

OTHER EMBODIMENTS

From the foregoing description, it will be apparent that variations and modifications may be made to the invention described herein to adopt it to various usages and conditions. Such embodiments are also within the scope of the following claims.

INCORPORATION BY REFERENCE

All citations to sequences, patents and publications in this specification are herein incorporated by reference to the same extent as if each independent patent and publication was specifically and individually indicated to be incorporated by reference.

We claim:

1. A method of characterizing a subject's response to a cholesterol lowering therapy, the method comprising:
   determining a level of cholesterol in a sample obtained from a patient;
   conducting an assay in the sample to identify a polymorphism associated with statin efficacy, wherein the polymorphism is selected from the group consisting of a SLCO1B1 polymorphism, an Apolipoprotein E (ApoE) polymorphism, and a combination of a SLCO1B1 polymorphism and an ApoE polymorphism;
   establishing weighted values based on the level of cholesterol and a genotype of the polymorphism; and
   characterizing said patient's likelihood of responding to a cholesterol lowering therapy based on said weighted values.

2. The method of claim 1, wherein the genotype of the SLCO1B1 polymorphism is selected from the group consisting of a C/T genotype, a C/C genotype, and a T/T genotype at the SLCO1B1 rs4149056 locus.

3. The method of claim 1, wherein the genotype of the ApoE polymorphism is selected from the group consisting of ApoE2/E2, ApoE2/E3, ApoE3/E3, ApoE3/E4, and ApoE4/E4.

4. The method of claim 1, further comprising categorizing said patient as a normal responder or a hypo-responder based on the weighted values.

5. The method of claim 4, further comprising the step of obtaining a plasma lathosterol/cholesterol ratio in the sample and assigned a weighted value to the ratio.

6. The method of claim 5, wherein said characterizing step further comprises the weighted value of the ratio.

7. The method of claim 6, wherein said weighted values contraindicate statin treatment.

8. A method of determining a cholesterol lowering therapy of a subject, the method comprising:
   determining a level of cholesterol in a sample obtained from a patient;
   conducting an assay in the sample to identify the presence or absence of a biomarker associated with statin efficacy, wherein the biomarker is one or more genes selected from the group consisting of SLCO1B1 and Apolipoprotein E (ApoE);
   establishing weighted values based on the level of cholesterol and the presence or absence of the biomarker;
   determining a dosage of a drug for reducing cholesterol based on the weighted value; and
   administering the dosage of the drug to the patient.

9. The method of claim 8, wherein the weighted value of the biomarker is assigned based on a genotype of the biomarker.

10. The method of claim 8, wherein said cholesterol is LDL-cholesterol.

11. The method of claim 8, wherein the biomarker is a SLCO1B1 rs4149056 polymorphism.

12. The method of claim 8, wherein the biomarker is an ApoE polymorphism selected from the group consisting of an ApoE2 polymorphism, an APoE3 polymorphism, and an ApoE4 polymorphism at an ApoE locus.

13. The method of claim 11, wherein said SLCO1B1 rs4149056 polymorphism has a C/T genotype, a T/T genotype, or a C/C genotype.

14. The method of claim 12, wherein the ApoE polymorphism is a genotype selected from the group consisting of ApoE2/E2, ApoE2/E3, and ApoE3/E3.

15. The method of claim 8, wherein the drug for reducing cholesterol is selected from the group consisting of statin, ezetimibe, and combination thereof.

16. The method of claim 15, wherein said dosage of statin is between about 20 and about 40 milligrams.

17. The method of claim 15, wherein said dosage of statin is between about 40 and about 80 milligrams.

* * * * *

SEQUENCE LISTING

```
<160> NUMBER OF SEQ ID NOS: 73

<210> SEQ ID NO 1
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 1
gatttngcta a                                                          11

<210> SEQ ID NO 2
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is t or c

<400> SEQUENCE: 2
ctctantgag t                                                          11

<210> SEQ ID NO 3
<211> LENGTH: 12
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t
<220> FEATURE:
<221> NAME/KEY: misc_feature
<222> LOCATION: (12)..(12)
<223> OTHER INFORMATION: n is c or t

<400> SEQUENCE: 3
tgaatngata tn                                                         12

<210> SEQ ID NO 4
<211> LENGTH: 11
```

```
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is t or c

<400> SEQUENCE: 4
atatgngttc a                                                          11

<210> SEQ ID NO 5
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is t or c

<400> SEQUENCE: 5
taccantggg g                                                          11

<210> SEQ ID NO 6
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 6
agaagnacat t                                                          11

<210> SEQ ID NO 7
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is g or a

<400> SEQUENCE: 7
acatcnacct t                                                          11

<210> SEQ ID NO 8
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or a

<400> SEQUENCE: 8
catcanctga g                                                          11

<210> SEQ ID NO 9
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 9
```
gcactntcag g							11

<210> SEQ ID NO 10
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is g or a

<400> SEQUENCE: 10
ttctcnatgg g							11

<210> SEQ ID NO 11
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is g or a

<400> SEQUENCE: 11
tcactntctt t							11

<210> SEQ ID NO 12
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is g or a

<400> SEQUENCE: 12
gctgtnatgt c							11

<210> SEQ ID NO 13
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 13
ataaancagc a							11

<210> SEQ ID NO 14
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or c

<400> SEQUENCE: 14
atattnattt a							11

<210> SEQ ID NO 15
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 15
ggatgnagca a                                                           11

<210> SEQ ID NO 16
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 16
ctatantggt g                                                           11

<210> SEQ ID NO 17
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 17
gattgnattt g                                                           11

<210> SEQ ID NO 18
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 18
gaagcnttga a                                                           11

<210> SEQ ID NO 19
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or t

<400> SEQUENCE: 19
gaaagntatc a                                                           11

<210> SEQ ID NO 20
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or t

<400> SEQUENCE: 20
gtgaanacaa a                                                           11

<210> SEQ ID NO 21

```
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 21
aaatangtag a                                                              11

<210> SEQ ID NO 22
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or g

<400> SEQUENCE: 22
aaattnaaac t                                                              11

<210> SEQ ID NO 23
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is g or c

<400> SEQUENCE: 23
agcagnttgc a                                                              11

<210> SEQ ID NO 24
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or c

<400> SEQUENCE: 24
ctattntatt t                                                              11

<210> SEQ ID NO 25
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 25
ctgggntaaa t                                                              11

<210> SEQ ID NO 26
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 26
```

-continued agggangggga a					11

<210> SEQ ID NO 27
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 27
ttatangagc a					11

<210> SEQ ID NO 28
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 28
gtgagntact t					11

<210> SEQ ID NO 29
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 29
aatgcncaag a					11

<210> SEQ ID NO 30
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or t

<400> SEQUENCE: 30
aatacnagtc t					11

<210> SEQ ID NO 31
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is - or a

<400> SEQUENCE: 31
tgccgnaaaa t					11

<210> SEQ ID NO 32
<211> LENGTH: 11
<212> TYPE: DNA
<213> ORGANISM: Homo sapiens
<220> FEATURE:

```
<221> NAME/KEY: misc_feature
<222> LOCATION: (6)..(6)
<223> OTHER INFORMATION: n is a or g

<400> SEQUENCE: 32
acctgngata g                                                            11

<210> SEQ ID NO 33
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is g or t

<400> SEQUENCE: 33
ggggcnttct t                                                            11

<210> SEQ ID NO 34
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or g

<400> SEQUENCE: 34
taatcncctg t                                                            11

<210> SEQ ID NO 35
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 35
ctcagnctgc a                                                            11

<210> SEQ ID NO 36
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is g or t

<400> SEQUENCE: 36
agtctngaat t                                                            11

<210> SEQ ID NO 37
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 37
tcaccntgtc t                                                            11
```

-continued

```
<210> SEQ ID NO 38
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 38
agcctntagt g                                                              11

<210> SEQ ID NO 39
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or t

<400> SEQUENCE: 39
tttccnctca a                                                              11

<210> SEQ ID NO 40
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is g or c

<400> SEQUENCE: 40
ctgctntgat g                                                              11

<210> SEQ ID NO 41
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or t

<400> SEQUENCE: 41
tccttnctaa t                                                              11

<210> SEQ ID NO 42
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 42
tttgangttg t                                                              11

<210> SEQ ID NO 43
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g
```

```
<400> SEQUENCE: 43
caatcnttgg c                                                              11

<210> SEQ ID NO 44
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or t

<400> SEQUENCE: 44
atcacntgtt t                                                              11

<210> SEQ ID NO 45
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 45
atttgngtga a                                                              11

<210> SEQ ID NO 46
<211> LENGTH: 12
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is - or G

<400> SEQUENCE: 46
cctgtntatg tt                                                             12

<210> SEQ ID NO 47
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 47
aaaacngcag a                                                              11

<210> SEQ ID NO 48
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 48
agaagngcct g                                                              11

<210> SEQ ID NO 49
<211> LENGTH: 11
<212> TYPE: DNA
<213> ORGANISM: Homo sapiens
```

```
<220> FEATURE:
<221> NAME/KEY: misc_feature
<222> LOCATION: (6)..(6)
<223> OTHER INFORMATION: n is t or c

<400> SEQUENCE: 49
acgtgngcgg c                                                                11

<210> SEQ ID NO 50
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is t or c

<400> SEQUENCE: 50
ggaacnggca c                                                                11

<210> SEQ ID NO 51
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 51
agctgngtaa g                                                                11

<210> SEQ ID NO 52
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 52
tgggtngctt t                                                                11

<210> SEQ ID NO 53
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 53
ggtcgntttt g                                                                11

<210> SEQ ID NO 54
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 54
cagacnctgt c                                                                11
```

```
<210> SEQ ID NO 55
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 55
tgcagncact g                                                            11

<210> SEQ ID NO 56
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 56
gctgcnggtg c                                                            11

<210> SEQ ID NO 57
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or c

<400> SEQUENCE: 57
tgcccngcga c                                                            11

<210> SEQ ID NO 58
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 58
caagcngtgg a                                                            11

<210> SEQ ID NO 59
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 59
aggtgnagca a                                                            11

<210> SEQ ID NO 60
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or c
```

```
<400> SEQUENCE: 60
gggtgngcct c                                                        11

<210> SEQ ID NO 61
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, or g

<400> SEQUENCE: 61
tgcgtnagcg g                                                        11

<210> SEQ ID NO 62
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 62
gcgacngcct c                                                        11

<210> SEQ ID NO 63
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 63
ggcctngggc g                                                        11

<210> SEQ ID NO 64
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, or g

<400> SEQUENCE: 64
gctgcntaag c                                                        11

<210> SEQ ID NO 65
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 65
gcagcnccag t                                                        11

<210> SEQ ID NO 66
<211> LENGTH: 11
<212> TYPE: DNA
```

```
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 66
gccagngctg g                                                           11

<210> SEQ ID NO 67
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 67
agaagngcct g                                                           11

<210> SEQ ID NO 68
<211> LENGTH: 1223
<212> TYPE: DNA
<213> ORGANISM: Homo sapiens

<400> SEQUENCE: 68
gggatccttg agtcctactc agccccagcg gaggtgaagg acgtccttcc ccaggagccg       60
actggccaat cacaggcagg aagatgaagg ttctgtgggc tgcgttgctg gtcacattcc      120
tggcaggatg ccaggccaag gtggagcaag cggtggagac agagccggag cccgagctgc      180
gccagcagac cgagtggcag agcggccagc gctgggaact ggcactgggt cgcttttggg      240
attacctgcg ctgggtgcag acactgtctg agcaggtgca ggaggagctg ctcagctccc      300
aggtcaccca ggaactgagg gcgctgatgg acgagaccat gaaggagttg aaggcctaca      360
aatcggaact ggaggaacaa ctgacccccgg tgcggaggga cacgcgggca cggctgtcca      420
aggagctgca ggcggcgcag gcccggctgg gcgcggacat ggaggacgtg tgcggccgcc      480
tggtgcagta ccgcggcgag gtgcaggcca tgctcggcca gagcaccgag gagctgcggg      540
tgcgcctcgc ctcccacctg cgcaagctgc gtaagcggct cctccgcgat gccgatgacc      600
tgcagaagcg cctggcagtg taccaggccg ggccccgcga gggcgccgag cgcggcctca      660
gcgccatccg cgagcgcctg gggcccctgg tggaacaggg ccgcgtgcgg gccgccactg      720
tgggctccct ggccggccag ccgctacagg agcgggccca ggcctggggc gagcggctgc      780
gcgcgcggat ggaggagatg ggcagccgga cccgcgaccg cctggacgag gtgaaggagc      840
aggtggcgga ggtgcgcgcc aagctggagg agcaggccca gcagatacgc ctgcaggccg      900
aggccttcca ggcccgcctc aagagctggt tcgagcccct ggtggaagac atgcagcgcc      960
agtgggccgg gctggtggag aaggtgcagg ctgccgtggg caccagcgcc gcccctgtgc     1020
ccagcgacaa tcactgaacg ccgaagcctg cagccatgcg accccacgcc accccgtgcc     1080
tcctgcctcc gcgcagcctg cagcgggaga ccctgtcccc gccccagccg tcctcctggg     1140
gtggacccta gtttaataaa gattcaccaa gtttcacgca aaaaaaaaaa aaaaaaaaa      1200 aaaaaaaaa aaaaaaaaaa aaa                                             1223

<210> SEQ ID NO 69
<211> LENGTH: 10612
<212> TYPE: DNA
<213> ORGANISM: Homo sapiens
```

<400> SEQUENCE: 69

```
tggagagctg gtctaccacc ggcggcctgg agaggagggc actgtcatgt ctctagctgg      60
gaaatacaca tgtgagcctg gcgcctgggt ccgagggtgg aggggctggg cccctggact     120
cctcctgggt ctgagggagg acgggctagg gccctggaca ctcaggtctg agggaggagg     180
cctgggttcc cagatgccca atccccttg gtaatgagac cccgcctcca ccccactctc      240
tgacagtgaa caactggttg gcaacggtaa cgttgggcca ggcgggcatg cacgcaacat     300
actaccacaa agccagtgac caggtgagtg ggtgcaggga ctagctggtg ctgccagggg     360
ctgctgggcc tggaagtcca ggtggggcca cttgctaatt tcatgtgtt gctccggccc      420
ctccagctgc aggtgggtgt ggagtttgag gccagcacaa ggatgcagga caccagcgtc     480
tccttcgggt accagctgga cctgcccaag gccaacctcc tcttcaaagg taaaggtctc     540
ggttccccta cgcgggaaac aggcaggagg tgactcaact ctgagtggat gtgtgggcca     600
ccacaggtgc tggaggacag tgtgctgcca ccctgtgggc ctccacatta ccagggaaca     660
cttgttaaaa ggtaggtggg gccgggtgcg gtggctcacg cctgtaatcc cagcactttg     720
ggaggccaag gcgggccgag gtaaggagat tgagaccatc ctggctaaca cggtgaaact     780
ccgtctctac taaaaataca aaaacaaaat tagccgggtg tggttgcggg tgcctatagt     840
cccaactact gaggctgagg cgggaaaatg gtatgaaccc aggaggcgga gcttgcggtg     900
agccgagatc gtgccaccgc actccagcct gggtgacaga gcaagactcc atctcaaaaa     960
aaaaaagta ggtggacaac cctctactat gtttatgct tggaaaaaaa aagtaggtag     1020
agcagccagg cgtggtgact cacgcctgta atcccagcat tttgggaggc caagccaggt    1080
agaatacttg aggccaggag ttggagacca gcctggccaa cgtggtgaaa tcccctctct    1140
actaaaagta caaaaattag ccaggtgtgg tagcgtgctg caactgtagt ccccgctact    1200
taggaggctg aggcacaaga atcacttgaa cctgggaggc ggaggttgca gggagttgag    1260
actgcaccac tgcactccag cctgggtgac agagtgagac tccatctcca aaaaaataa    1320
aatgaaataa ataaataaat gttaaaaaaa atctggtgga gcatctgatg ggtgtttggg    1380
ccaagctgga gctttgtcca tcccctctta ttttctgca cttgactctc ttattttct     1440
gagactggtc tccctctgtc gcccaggcta gagtgcagca gtgcaactgc ggctcactgc    1500
agcctccacc tcccgggctc aagcagcctt cccacctcag cctcctgagt agctaggacc    1560
acaggtgtat gccaccaggc ccagctaatt tttttgatag ttttgggaga catgggggtt    1620
tcaccatgtt gcccaggctg gtctcgaact cctggactca agccttggcc tcccaaagtg    1680
ctgggattat aggtgtgagc caccacaccc agccagggta aaggcactt tggaagcctc     1740
gagcctgccc cattcatctt acgttagtgg aaactgagc ttccagaggt ttcaaggtca     1800
caactaaatc cagaacctca tctcaggcac actggtcgta gtcccaatgt ccagtcttaa    1860
gtcttcttgg atatctgtgg ctcacagatt ttgggtgttt gagcctcctg ctgagcactg    1920
ctggggccac agcggtgacc agccctgtct tcacgggact cagtgagagg aacagattca    1980
tccgcagagt gggcaggact aggttggggg aacccagggg tctagagggc ttttcagagg    2040
gcagggtca ctgagcggag agcagaggag gagtgagcca tttgctccag cgtgaagttg     2100
ttggtgtgat ggggtttcag ggtggcagga gcagtgtggt taaaggtctg gaagctgtcg    2160
gcatgtggct ggtatccaag gtggccagga actctgcatg gatatggtgg aagctggca    2220
cgcctctcac ctcagctctt ccctgcaggc tctgtggata gcaactggat cgtgggtgcc    2280
```

```
acgctggaga agaagctccc acccctgccc ctgacactgg cccttggggc cttcctgaat    2340
caccgcaaga acaagtttca gtgtggcttt ggcctcacca tcggctgagc cctcctggcc    2400
cccgccttcc acgcccttcc gattccacct ccacctccac ctcccccttgc cacagagggg   2460 agacctgagc cccctccct tccctccccc cttgggggtc ggggggggaca ttggaaagga    2520 gggaccccgc caccccagca gctgaggagg ggattctgga actgaatggc gcttcgggat    2580
tctgagtagc aggggcagca tgcccagtgg gcctggggtc ccgggaggga ttccggaatt    2640
gaggggcacg caggattctg agcaccaggg gcagaggcgg ccagacaacc tcagggagga   2700
gtgtcctggc gtccccatcc tccaaagggc ctgggcccgc cccgaggggg cagcgagagg   2760
agcttcccca tccccggtca gtccaccctg ccccgtccac tttcccatct cctcggtata    2820
aatcatgttt ataagttatg gaagaaccgg gacattttac agaaaaaaaa caaaaaacaa    2880
caaaaaatat acgtgggaaa aaaaacgatg ggaggcctcc gttttctcaa gtgtgtctgg    2940
cctgttttga gcatttcatc cggagtctgg ccgccctgac cttcccccag ccgcctgcag    3000
ggggcgccag agggccggag cacgaaaagc agcggatcct tgatgctgcc ttaagtccgg    3060
ctcagagggg cgcagcgtgg cctggggtcg ctatcttccc atccggaaca tctgccctgc    3120
tgggggacac tacgggcctt cccttgcctg agggtagggt ctcaaggtca cttgccccca    3180
gcttgacctg gccggagtgg ctatagagga cttttgtccct gcagactgca gcagcagaga   3240
tgacactgtc tctgagtgca gagatggggg cagggagctg ggagagggtt caagctactg    3300
gaacagcttc agaacaacta gggtactagg aactgctgtg tcaggagaa ggggctcaag    3360 gactcgcagg cctggggaga ggggcctagg ccagccatgg gagttgggtc acctgtgtct    3420
gaggacttgg tgctgtctgg attttgccaa cctagggctg gggtcagctg atgcccacca    3480
cgactcccga gcctccagga actgaaaccc tgtctgcccc cagggtctgg ggaaggaggc    3540
tgctgagtag aaccaacccc aggttaccaa ccccacctca gccacccctt gccagccaaa    3600
gcaaacaggc ccgccccggc actggggggtt ccttctcgaa ccaggagttc agcctcccct    3660
gacccgcaga atcttctgat cccacccgct ccaggagcca ggaatgagtc ccagtctctc    3720
ccagttctca ctgtgtggtt ttgccattcg tcttgctgct gaaccacggg ttctcctct     3780 gaaacatctg ggatttataa cagggcttag gaaagtgaca gcgtctgagc gttcactgtg    3840
gcctgtccat tgctagccct aacataggac cgctgtgtgc cagggctgtc ctccatgctc    3900
aatacacgtt agcttgtcac caaacatacc cgtgccgctg ctttcccagt ctgatgagca    3960
aaggaacttg atgctcagag aggacaagtc atttgcccaa ggtcacacag ctggcaactg    4020
gcagagccag gattcacgcc ctggcaattt gactccagaa tcctaacctt aacccagaag    4080
cacggcttca gcccctgga aaccacaata cctgtggcag ccaggggggag gtgctggaat    4140 ctcatttcac atgtggggag ggggctcccc tgtgctcaag gtcacaacca agaggaagc    4200 tgtgattaaa acccaggtcc catttgcaaa gcctcgactt ttagcaggtg catcatactg    4260
ttcccacccc tccatcccca cttctgtcca gccgcctagc cccactttct ttttttcttt    4320
tttttgagac agtctcctct ttgctgaggc tggagtgcag tggcgagatc tcggctcact    4380
gtaacctccg cctcccgggt tcaagcgatt ccctgcctc agcctcccaa gtagctagga    4440
ttacaggcgc ccgccaccac gcctggctaa cttttgtatt tttagtagag atggggtttc    4500
accatgttgg ccaggctggt ctcaaactcc tgacctttaag tgattcgccc actgtggcct    4560
cccaaagtgc tgggattaca ggcgtgagct accgccccca gccctcccca tcccacttct    4620
gtccagcccc ctagccctac tttctttctg ggatccagga gtccagatcc ccagccccct    4680
```

```
ctccagatta cattcatcca ggcacaggaa aggacagggt caggaaagga ggactctggg   4740
cggcagcctc cacattcccc ttccacgctt ggccccagaa atggaggagg gtgtctgtat   4800
tactgggcga ggtgtcctcc cttcctgggg actgtggggg gtggtcaaaa gacctctatg   4860
ccccacctcc ttcctccctc tgccctgctg tgcctggggc aggggagaa cagcccacct    4920
cgtgactggg ggctggccca gcccgcccta tccctggggg aggggcggg acaggggag     4980
ccctataatt ggacaagtct gggatccttg agtcctactc agcccagcg gaggtgaagg    5040
acgtccttcc ccaggagccg gtgagaagcg cagtcggggg cacgggatg agctcagggg    5100
cctctagaaa gagctgggac cctgggaacc cctggcctcc aggtagtctc aggagagcta   5160
ctcggggtcg ggcttgggga gaggaggagc gggggtgagg caagcagcag gggactggac   5220
ctgggaaggg ctgggcagca gagacgaccc gacccgctag aaggtggggt ggggagagca   5280
gctggactgg gatgtaagcc atagcaggac tccacgagtt gtcactatca tttatcgagc   5340
acctactggg tgtccccagt gtcctcagat ctccataact ggggagccag gggcagcgac   5400
acggtagcta gccgtcgatt ggagaacttt aaaatgagga ctgaattagc tcataaatgg   5460
aacacggcgc ttaactgtga ggttggagct tagaatgtga agggagaatg aggaatgcga   5520
gactgggact gagatggaac cggcggtggg gaggggtgg ggggatggaa tttgaacccc    5580
gggagaggaa gatggaattt tctatggagg ccgacctggg gatggggaga taagagaaga   5640
ccaggaggga gttaaatagg gaatgggttg ggggcggctt ggtaaatgtg ctgggattag   5700
gctgttgcag ataatgcaac aaggcttgga aggctaacct ggggtgaggc cgggttgggg   5760
ccgggctggg ggtgggagga gtcctcactg gcggttgatt gacagtttct ccttccccag   5820
actggccaat cacaggcagg aagatgaagg ttctgtgggc tgcgttgctg gtcacattcc   5880
tggcaggtat ggggcgggg cttgctcggt tccccccgct cctcccctc tcatcctcac     5940
ctcaacctcc tggccccatt caggcagacc ctgggccccc tcttctgagg cttctgtgct   6000
gcttcctggc tctgaacagc gatttgacgc tctctgggcc tcggtttccc ccatccttga   6060
gataggagtt agaagttgtt ttgttgttgt tgtttgttgt tgttgttttg ttttttttgag   6120
atgaagtctc gctctgtcgc ccaggctgga gtgcagtggc gggatctcgg ctcactgcaa   6180
gctccgcctc ccaggtccac gccattctcc tgcctcagcc tcccaagtag ctgggactac   6240
aggcacatgc caccacaccc gactaacttt tttgtatttt cagtagagac ggggtttcac   6300
catgttggcc aggctggtct ggaactcctg acctcaggtg atctgcccgt ttcgatctcc   6360
caaagtgctg ggattacagg cgtgagccac cgcacctggc tgggagttag aggtttctaa   6420
tgcattgcag gcagatagtg aataccagac acggggcagc tgtgatcttt attctccatc   6480
acccccacac agccctgcct ggggcacaca aggacactca atacatgctt ttccgctggg   6540
cgcggtggct cacccctgta atcccagcac tttgggaggc caaggtggga ggatcacttg   6600
agcccaggag ttcaacacca gcctgggcaa catagtgaga ccctgtctct actaaaaata   6660
caaaaattag ccaggcatgg tgccacacac ctgtgctctc agctactcag gaggctgagg   6720
caggaggatc gcttgagccc agaaggtcaa ggttgcagtg aaccatgttc aggccgctgc   6780
actccagcct gggtgacaga gcaagaccct gtttataaat acataatgct ttccaagtga   6840
ttaaaccgac tcccccctca ccctgcccac catggctcca agaagcatt tgtggagcac    6900
cttctgtgtg ccctaggta ctagatgcct ggacggggtc agaaggaccc tgacccacct    6960
tgaacttgtt ccacacagga tgccaggcca aggtggagca agcggtggag acagagccgg   7020
```

```
agcccgagct gcgccagcag accgagtggc agagcggcca gcgctgggaa ctggcactgg      7080
gtcgcttttg ggattacctg cgctgggtgc agacactgtc tgagcaggtg caggaggagc      7140
tgctcagctc ccaggtcacc caggaactga ggtgagtgtc cccatcctgg cccttgaccc      7200
tcctggtggg cggctatacc tccccaggtc caggtttcat tctgcccctg tcgctaagtc      7260 ttgggggggcc tgggtctctg ctggttctag cttcctcttc ccatttctga ctcctggctt      7320
tagctctctg gaattctctc tctcagcttt gtctctctct cttcccttct gactcagtct      7380
ctcacactcg tcctggctct gtctctgtcc ttccctagct cttttatata gagacagaga      7440
gatggggtct cactgtgttg cccaggctgg tcttgaactt ctgggctcaa gcgatcctcc      7500
cgcctcggcc tcccaaagtg ctgggattag aggcatgagc caccttgccc ggcctcctag      7560
ctccttcttc gtctctgcct ctgccctctg catctgctct ctgcatctgt ctctgtctcc      7620
ttctctcggc ctctgccccg ttccttctct ccctcttggg tctctctggc tcatcccat       7680 ctcgcccgcc ccatcccagc ccttctcccc gcctcccact gtgcgacacc ctcccgccct      7740
ctcggccgca gggcgctgat ggacgagacc atgaaggagt tgaaggccta caatcggaa       7800 ctggaggaac aactgacccc ggtggcggag agacgcgggc acggctgtc caaggagctg       7860 caggcggcgc aggcccggct gggcgcggac atggaggacg tgtgcggccg cctggtgcag      7920
taccgcggcg aggtgcaggc catgctcggc cagagcaccg aggagctgcg ggtgcgcctc      7980
gcctcccacc tgcgcaagct gcgtaagcgg ctcctccgcg atgccgatga cctgcagaag      8040
cgcctggcag tgtaccaggc cggggcccgc gagggcgccg agcgcggcct cagcgccatc      8100
cgcgagcgcc tggggcccct ggtggaacag ggccgcgtgc gggccgccac tgtgggctcc      8160
ctggccggcc agccgctaca ggagcgggcc caggcctggg gcgagcggct gcgcgcgcgg      8220
atggaggaga tgggcagccg gacccgcgac cgcctggacg aggtgaagga gcaggtggcg      8280
gaggtgcgcg ccaagctgga ggagcaggcc cagcagatac gcctgcaggc cgaggccttc      8340
caggcccgcc tcaagagctg gttcgagccc ctggtggaag acatgcagcg ccagtgggcc      8400
gggctggtgg agaaggtgca ggctgccgtg ggcaccagcg ccgcccctgt gcccagcgac      8460
aatcactgaa cgccgaagcc tgcagccatg cgaccccacg ccaccccgtg cctcctgcct      8520
ccgcgcagcc tgcagcggga gaccctgtcc ccgcccagc cgtcctcctg ggtggaccc       8580 tagtttaata aagattcacc aagtttcacg catctgctgg cctcccctg tgatttcctc       8640 taagccccag cctcagtttc tctttctgcc cacatactgg ccacacaatt ctcagccccc      8700
tcctctccat ctgtgtctgt gtgtatcttt ctctctgccc ttttttttt ttttagacgg       8760 agtctggctc tgtcacccag gctagagtgc agtggcacga tcttggctca ctgcaacctc      8820
tgcctcttgg gttcaagcga ttctgctgcc tcagtagctg ggattacagg ctcacaccac      8880
cacacccggc taattttgt atttttagta gagacgagct ttcaccatgt tggccaggca      8940
ggtctcaaac tcctgaccaa gtgatccacc cgccggcctc ccaaagtgct gagattacag      9000
gcctgagcca ccatgcccgg cctctgcccc tctttctttt ttaggggca gggaaaggtc       9060 tcaccctgtc acccgccatc acagctcact gcagcctcca cctcctggac tcaagtgata      9120
agtgatcctc ccgcctcagc cttttccagta gctgagacta caggcgcata ccactaggat      9180
taatttgggg ggggggtgg tgtgtgtgga gatggggtct ggctttgttg gccaggctga       9240
tgtggaattc ctgggctcaa gcgatactcc caccttggcc tcctgagtag ctgagactac      9300
tggctagcac caccacaccc agcttttat tattatttgt agagacaagg tctcaatatg       9360
ttgcccaggc tagtctcaaa cccctgggct caagagatcc tccgccatcg gcctcccaaa      9420
```

```
gtgctgggat tccaggcatg gggctccgag cccggcctgc caacttaat  aatacttgtt     9480 cctcagagtt gcaactccaa atgacctgag attggtgcct ttattctaag ctatttcat      9540 tttttttctg ctgtcattat tctccccctt ctctcctcca gtcttatctg atatctgcct     9600
ccttcccacc caccctgcac cccatcccac ccctctgtct ctccctgttc tcctcaggag     9660
actctggctt cctgttttcc tccacttcta tcttttatct ctccctccta cggtttcttt     9720
tctttctccc cggcctgctt gtttctcccc caaccccctt catctggatt tcttcttctg     9780
ccattcagtt tggtttgagc tctctgcttc tccggttccc tctgagctag ctgtcccttc     9840
acccactgtg aactgggttt ccctgcccaa ccctcattct ctttctttct ttcttttttt     9900
tttttttttt tttttttttt ttttgagaca gagtcttgct ctgttgccca gcctggagtg     9960
cagtggtgca atcttggttc actgcaacct ccacttccca gattcaagca attctcctgc    10020
ctcagcctcc agagtagctg ggattacagg cgtgtcccac cacacccgac taattttgt     10080 attttggta gagacaaggc ttcggcattg ttggccaggc aggtctcgaa ctcctgacct     10140
caagtaatct gcctgcctca ccctcccaaa gtgctgggat tacaggcatg agccacctca    10200
cccggaccat ccctcattct ccatcctttc ctccagttgt gatgtctacc cctcatgttt    10260
cccaacaagc ctactgggtg ctgaatccag gctgggaaga aagggagcg gctcttctgt     10320 cggagtctgc accaggccca tgctgagacg agagctggcg ctcagagagg ggaagcttgg    10380
atggaagccc aggagccgcc ggcactctct tctcctccca ccccctcagt tctcagagac    10440
ggggaggagg gttcccacca acgggggaca ggctgagact tgagcttgta tctcctgggc    10500
cagctgcaac atctgcttgt ccctctgccc atcttggctc ctgcacaccc tgaacttggt    10560
gctttccctg gcactgctct gatcacccac gtggaggcag caccctccc  ct            10612
```

<210> SEQ ID NO 70
<211> LENGTH: 317
<212> TYPE: PRT
<213> ORGANISM: Homo sapiens

<400> SEQUENCE: 70

```
Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Cys Gly Arg Leu Val Gln Tyr Arg Gly Glu Val Gln Ala Met Leu
    130                 135                 140

Gly Gln Ser Thr Glu Glu Leu Arg Val Arg Leu Ala Ser His Leu Arg
145                 150                 155                 160
```

```
Lys Leu Arg Lys Arg Leu Leu Arg Asp Ala Asp Leu Gln Lys Arg
            165                 170                 175

Leu Ala Val Tyr Gln Ala Gly Arg Glu Gly Ala Glu Arg Gly Leu
        180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
        210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
                260                 265                 270

Glu Ala Phe Gln Ala Arg Leu Lys Ser Trp Phe Glu Pro Leu Val Glu
            275                 280                 285

Asp Met Gln Arg Gln Trp Ala Gly Leu Val Glu Lys Val Gln Ala Ala
        290                 295                 300

Val Gly Thr Ser Ala Ala Pro Val Pro Ser Asp Asn His
305                 310                 315

<210> SEQ ID NO 71
<211> LENGTH: 2800
<212> TYPE: DNA
<213> ORGANISM: Homo sapiens

<400> SEQUENCE: 71
aaagggtgga cttgttgcag ttgctgtagg attctaaatc caggtgattg tttcaaactg      60
agcatcaaca acaaaaacat ttgtatgata tctatatttc aatcatggac caaaatcaac     120
atttgaataa acagcagag gcacaacctt cagagaataa gaaacaaga tactgcaatg       180
gattgaagat gttcttggca gctctgtcac tcagctttat tgctaagaca ctaggtgcaa     240
ttattatgaa aagttccatc attcatatag aacggagatt tgagatatcc tcttctcttg    300
ttggttttat tgacggaagc tttgaaattg gaaatttgct tgtgattgta tttgtgagtt    360
actttggatc caaactacat agaccaaagt taattggaat cggttgtttc attatgggaa    420
ttggaggtgt tttgactgct ttgccacatt tcttcatggg atattacagg tattctaaag    480
aaactaatat caattcatca gaaaattcaa catcgacctt atccacttgt ttaattaatc    540
aaattttatc actcaataga gcatcacctg agatagtggg aaaaggttgt ttaaaggaat    600
ctgggtcata catgtggata tatgtgttca tgggtaatat gcttcgtgga atagggaga    660
ctcccatagt accattgggg ctttcttaca ttgatgattt cgctaaagaa ggacattctt    720
ctttgtattt aggtatattg aatgcaatag caatgattgg tccaatcatt ggctttaccc    780
tgggatctct gttttctaaa atgtacgtgg atattggata tgtagatcta agcactatca    840
ggataactcc tactgattct cgatgggttg agcttggtg gcttaatttc cttgtgtctg     900
gactattctc cattatttct tccataccat tctttttctt gccccaaact ccaaataaac    960
cacaaaaaga aagaaaagct tcactgtctt tgcatgtgct ggaaacaaat gatgaaaagg   1020
atcaaacagc taatttgacc aatcaaggaa aaatattac caaaaatgtg actggttttt    1080
tccagtcttt taaagcatc cttactaatc ccctgtatgt tatgtttgtg cttttgacgt    1140
tgttacaagt aagcagctat attggtgctt ttacttatgt cttcaaatac gtagagcaac   1200
agtatggtca gccttcatct caaggctaaca tcttattggg agtcataacc ataccctattt  1260
```

```
ttgcaagtgg aatgttttta ggaggatata tcattaaaaa attcaaactg aacaccgttg    1320
gaattgccaa attctcatgt tttactgctg tgatgtcatt gtccttttac ctattatatt    1380
ttttcatact ctgtgaaaac aaatcagttg ccggactaac catgacctat gatggaaata    1440
atccagtgac atctcataga gatgtaccac tttcttattg caactcagac tgcaattgtg    1500
atgaaagtca atgggaacca gtctgtggaa acaatggaat aacttacatc tcaccctgtc    1560
tagcaggttg caaatcttca gtggcaata aaaagcctat agtgttttac aactgcagtt    1620
gtttggaagt aactggtctc cagaacagaa attactcagc ccatttgggt gaatgcccaa    1680
gagatgatgc ttgtacaagg aaattttact tttttgttgc aatacaagtc ttgaatttat    1740
ttttctctgc acttggaggc acctcacatg tcatgctgat tgttaaaatt gttcaacctg    1800
aattgaaatc acttgcactg gtttccact caatggttat acgagcacta ggaggaattc    1860
tagctccaat atattttggg gctctgattg atacaacgtg tataaagtgg tccaccaaca    1920
actgtggcac acgtgggtca tgtaggacat ataattccac atcattttca agggtctact    1980
tgggcttgtc ttcaatgtta agagtctcat cacttgtttt atatattata ttaatttatg    2040
ccatgaagaa aaaatatcaa gagaaagata tcaatgcatc agaaaatgga agtgtcatgg    2100
atgaagcaaa cttagaatcc ttaaataaaa ataaacattt tgtcccttct gctggggcag    2160
atagtgaaac acattgttaa ggggagaaaa aaagccactt ctgcttctgt gtttccaaac    2220
agcattgcat tgattcagta agatgttatt tttgaggagt tcctggtcct ttcactaaga    2280
atttccacat cttttatggt ggaagtataa ataagcctat gaacttataa taaacaaac    2340 tgtaggtaga aaaatgaga gtactcattg ttacattata gctacatatt tgtggttaag    2400
gttagactat atgatccata caaattaaag tgagagacat ggttactgtg taataaaaga    2460
aaaaatactt gttcaggtaa ttctaattct taataaaaca aatgagtatc atacaggtag    2520
aggttaaaaa ggaggagcta gattcatatc ctaagtaaag agaaatgcct agtgtctatt    2580
ttattaaaca aacaaacaca gagtttgaac tataatacta aggcctgaag tctagcttgg    2640
atatatgcta caataatatc tgttactcac ataaaattat atatttcaca gactttatca    2700
atgtataatt aacaattatc ttgtttaagt aaatttagaa tacatttaag tattgtggaa    2760
gaaataaaga cattccaata tttgcaaaaa aaaaaaaaa                           2800
```

<210> SEQ ID NO 72
<211> LENGTH: 115603
<212> TYPE: DNA
<213> ORGANISM: Homo sapiens

<400> SEQUENCE: 72

```
gattcctctg cagtgtaact tcatggtttt tgaggcaaag gaaggctggc agtaaacaaa      60
atatgtgagt aaaatttata gtatgatggt gagagaataa aaattgagtg tcaaagggag     120
taatattaaa aaattgttag agaagacttc gctgggaaag tgtcatttgt ttgggtacta     180
gaatatggtg agggagtaag ttatgcagct atagggaaag aacattccag acagaaagaa     240
aaataggaac aaagattctc agtagaggat ctataactta taaggcctta aagctgttct     300
ttggattttt gagtgatatg tgaagccaat ggggatttg agcagagcta tgacatggta     360
tgaccctcac ttatatgtta agatttacac aggggaagga ggttgggaa gaggggctgt     420 gagtggtcag gaggaaagct gagatacaag tatgagggta ttgcaataat tcaggaccag     480
cctgaaagtt gtggaggagg taagaaatca tcagattctg ggtatatttg gaaattagag     540
```

-continued

```
cctaatgtga gtgtgagaaa tagagaagaa tgattctaat attgtatgtg gctgtgcatg      600
tgcacgcatg tgtgcaactg gaatgacaga attacaatgt atggggatta ttgtcttccc      660
tggacaataa tccctggaaa tggggattat tacaagagga gaggttgggg aaggaaagac      720
aaagatacca tgttagaaaa tattaagtgt aagatgccta ttagagatat ataggaagat      780
ggtgagaagt caatggataa atctagagtt catgagtaac ttggctagag aaaaaatttt      840
ggaattatca acgtatggat aagatttaaa gacatgagaa tagatgaggt cacaaacaca      900
cacagtaagg ttattgtctg acatgcttca atttagaaga caaagataaa gaatttagag      960
taaatgaagt gtaaataagt aagtcagtga gttagaaggc aaaccacaaa gggtagtgtc     1020
ctgcaaagtt ttgcttaggg agggaattct cagttctgaa aaatgctgct aatagttcaa     1080
gtcagatgag gactattaga tgtagcattt aggtaattta tgacttagga aaagtagttt     1140
cagtggaaat ttgggggcaa aagcctgata agagtgtgct caagagagaa tgtagagaga     1200
gagattgaaa gcaataatta gacaagctat ttctctgtaa aaatagcaca gaaatagggc     1260
aatattagga aaaaatggga tcaaaagaga gattttggga agatgaaaaa gtgacagcat     1320
tcttacatgc tgatggaaac atttaaaaag aggatagtgc tatccttaaa aacacaaggg     1380
gaggagtcaa tgtcatatgc aagtggagat tggccttagc ttaaacttgg gtagttcact     1440
aaggcagacc atgtggtggt actggggctt tacatagata aatgtggtca agggagcttt     1500
tgaagtttct tctttattta tttatttttt cagtaaaata attcatcagc tgaaggtggg     1560
gaagggatgt attagaattt caaaaaaaaa aaaaaagat gaaggcacaa aatgctcaga     1620
gtgcaaaatg gcgtgaatga tttcttggca aaatgaaagg tccatttggg cttcctaatc     1680
atacgtttaa agtcagcatg gttgagagat tttcctcagt tacatttagc ttcataaggg     1740
aaatgtgcag agttatttga gagttaaatt taatcaagat tgtggctttg acatgcaatt     1800
aaaataatgc aaaacagtca aaattatatg aagttatata aagagagtg attaccgtga     1860 ccattaaatt aacccagatg tatagataag gaacaccgaa atctctggca aaatcaaatt     1920
gtaggttata catcctggtc agtggaagca tgtggatcta gggtgttact gagtgtgagc     1980
taggagtgat aaagagtggt gctccaatct ttgatattat ggagagatta cagtggtgtg     2040
aaaagcatag gatatgccca tagcagtagg tagaagccaa gatcattgag gagaaggcta     2100
aaaaataaaa agaaaataaa aagaaaacag agaattaaaa agattctctt catggtcatt     2160
accatcatga ataattaaaa tagtagtagc attttgagag aatggctttg gatcgagagc     2220
taaaattgtc atgaaatgag tgggagtgac tgagcgttga tagatgattt caacaagagg     2280
aataagtgat agagtctttc aatatgagat ccaaaactat ggattatgag tgtaaagggt     2340
ggggaaatgt aaagaaacta gcaaagtgag gcacattgga aaccagccca tctggtttgc     2400
agcaatatgg gggataaggc aacccctatg tatcactgct gcaggagagg gagtgtctca     2460
gggaagacca atttttaagt tcaaggcaga agtgaagcag aataactcag agaagaggta     2520
aaggtaaggg gagtttcagt catgactagt gatgggttcc agaaaactca agagaagaat     2580
ttcagtccag gattgggaga agagagaag atgggggcaa acataggaat gtgcagagcc     2640
ctgtggggat tagagaagag gtgatgagtc atcagggaat ccctaccttc ttatggtggt     2700
cactaccata agagcgataa ttgccatggt aatattagtc ttgatgatgc cagagctttg     2760
atcattggtg ggtatagaaa catgtttgga gaataatatg tagaatagga gttctttcca     2820
ggagagtgta gctttctgga gctgtctctt aatcagcacc aacagaagtg aaatgttcgg     2880
gtaagggcgg atctgcttgg agcctgacgg ttccctcttg aggtgtgcct gtggtacaca     2940
```

```
cctgagaact ctggggctaa aacctattgg acataggttt tacagatcta caggatacag    3000
atctcagaga ttttatttgt attcatttaa tataaattaa ctgctctaaa atttataata    3060
tgcaaatatc atacaattaa tctaattagg tgttgaatct ataatgtgcc aggcattatg    3120
taaggcactt tacatacact aaatctttat tccaaatata gacttcttac tttatagatg    3180
agtgcactga tgctcagaaa tggtaaataa cctactgatg tttatactgc tggcaggtag    3240
cagagacata tcggcattta agtctttcag acttcaaagg ccatgatatt tcatcagagc    3300
tgtgatagcc gttcctgaaa aaatatcag ctgattcttt aaatcaattt ttgtcatcta    3360
actgatgcgt ggctgttagc ataatattga tcttgaaaga tgttttgcaa catctttccc    3420
ctggtgtact cttgttttc catgatccca caaatgagc agtctaatta tttacacaat    3480
taggaagaga aaaggggcac agagaatgct ctttgacctc tgaaaatatt ggagaatttt    3540
acaactggca cctttagctc aggattataa aggttgttag ttagtttgta ctgttttatc    3600
ttcattgtat ataatatata tattagtctc caaacatgtt gatgtgtttt caatgaaatg    3660
gatgtctgag gagaaaacca ttagcctgag aaaacccaaa ctgtattccc attgtgaata    3720
aaaggaagtc cataaaaatg atggaaaatg ttctgcattc ctgttatgat atcaaaatct    3780
ggcagtacat gaaaattttt caaagtgctt atttaacagg cataatcttt ggtctcctga    3840
gccagaatct gctgggtatg ggactggatt gctattttga caactcgcca gtagattctt    3900
actcagcaga gtatttggaa gccttactct aatattttgg ccttgggtct acatttctca    3960
gttctgcaca gtcattcttc ccctctacac tactctttag tttgtctcat gattccaata    4020
ctctcaataa ttaaccaaga atagaactaa tcaatcagat aactgtggca cagacatcaa    4080
atacattttg ctgcaaccat atcaacaaat gtcccatgaa tgataagggg taaccatatt    4140
ctcatatatg catcctcaca ttaccacata tatatatgtg catatgtgta tacaggtaaa    4200
agtgtgtata tatgtataca tgtatgtttg tgtgtatata catacatata tcttcacact    4260
tttctgaaat atatatattt atgtgagaga agggtctgta ctttatttca gaagagagct    4320
taatgtccaa ggtataattg agagtctaaa atgtttgagt tattgaatta attaaacttc    4380
atctctactc aagaaaactt ttaactgagt taagctcttc cttctccac aagtcaagtc    4440 aataaaagga aactgtgata ttaataattc tttcctgttt tgatgtaaag aatctatcgc    4500
ataaagcagt cttaattttc atcattcaga aaaatggtct tgcagttaat tgggactctc    4560
ttattccagg tggtatctcc agtctccata cataccacgt tagaaccata cttatgtacc    4620
aagcaaagag ggtatatttt aatttttaaa tgccaatgta acctgtaggc atattttta    4680 tttgtcttaa attatttcct atttggaagt tttaaatacc tggaataatt tattgtactc    4740 atattttaa agaaaaaat cttatgccac caacttaatt gaataaacaa gtaaagcca    4800 ttcccaaaag taaggtttac ttgttaagat taacaaaaaa taatgtgaga attctgagaa    4860
atataatctt taaatattgg caactggagt gaactcttaa aactaactag gttttatatg    4920
tttgactaga gcaatgacat aataaggtgg ttaatcatca ctggacttgt tttcaaaaag    4980
ccaactactt taagaggaat aaagggtgga cttgttgcag ttgctgtagg attctaaatc    5040
caggtaagaa ccattgagat tctctaattt ttacatatat tttatgtaag aaattttcac    5100
ggaagaagat tttgatggtc ttgaaaaata ttacgaattt tatgctctgt gtcttccaca    5160
cgcttacatt ctgagccctt aaaacatagt aaatattcct tctgggagta gaagagcctc    5220
aggtttatat actgttaaaa ataaagtaga gaaaataata cctttatata tttaaatata    5280
```

```
aagtttcaaa tcttggtctt attaatttcc aaacaaataa aaatcaagtc tcaaaaatga    5340
agctctagtt accttcttaa aatatgctac aggataatta ttttgtcaa ctacattgac     5400 tgatcacact agactcctta tttctttgat gtcttcttaa ctggatgaag gcagccaagg    5460
gtgggagtag agggaagagt taattggcaa acataaaaaa caggtgtctc aaagtcacat    5520
aaccacctca gtttccttgt ttcaactcaa gtttgataca gggtgaaggg aaatatattt    5580
tctagataat ttatctccaa ttaaataagc aaaaagtctt ctcagtacag tttttttctt    5640
tttttatttc attattatta tactttaagt tttagggtac atgtgcacaa catgcaggtt    5700
tgttacatat gtatacatgt gccatgttgg tgtgctgcac ccattaactc atcatttaac    5760
attgggcata tctcctaatg ctatccctcc cctctccccc accccacaac agtcccggt     5820 gtgtgatgtt cccttttcctg tgtccatgtg ttctcattgt tcagttccca cctatgagtg   5880
agaacatgcg gtgtttggtt ttttgtcctt gcgatagttt gttgagaatg atggtttcca    5940
gtttcatcca tgtccctaca aaggacataa actcatcatt tttatggctg catagtattc    6000
catggtgtat gtgtgccaca ttttcttaat ccactctatc gttgttggac atttaggttg    6060
gttccaagtc tttgctactg tgaatagtgc cgctataaac atacgtgtgc atgtgtcttt    6120
atagcagcat gatttataat cccttgggta tatatccact tatgggatgg ctgggtcaaa    6180
tggtatttcc agttctagat ccctgaggaa tcgccacact gtcttccaca atggttgaac    6240
tagtttacag tcccaccaac agtgtaaaag tgttcctatt tctccacatc ctctccagca    6300
cctgttgttt cctgactttt taatgatcgc tattctaact ggtgtgagat agtatctcat    6360
tgtggttttg atttgcattt ctctgatggc cagtgatgat gagcattttt tcacgtgttt    6420
tttggctgca taaatgtctt ctgttgagaa gtgtctgttc atgtccttca cccacttctt    6480 gatgggtcg tttgtctttt gtaaatttgt ttgagttcat tgtagatttt gggtattagc     6540
cttttgtcag atgagtaggt tgcaaaaatt ttctcccatt ctgtaggttg cctgttcact    6600
ctgatggtag tttcttttgc tgtgcagaag ctctttagtt taattatatc tcatttgtca    6660
tttttggctt ttgttgccat tgcttttggt gttttagaca tgaagtcctt gcccatgcct    6720
atgtcctgaa tggtattgcc taggttttct tctagggttt ttatggtttt aggtctaaca    6780
tttaagtctt taatccatct tgaattaatt tttgtgtaag gtgtaaggaa gggatccagt    6840
ttcagctttc tacatatggc ttgccagttt tcccagcatc atttattaaa tagggaatcc    6900 tttcccatt gcttgttttt ctcaggtttg tcaaagatca gatagttgta gatatgcggc     6960
actatttctg agggctctgt tctgttccat tggtctatat ctctgttttg gtaccagtac    7020
catgctgttt tggttactgt agccttgtag tatagtttga agtcaggtag ggtgatgcct    7080
ccagctttgt tcttttcgct taggattgac ttggtatgcg ggctcttttt tggttccata    7140
tgaactttaa agtagttttt tccaattctg tgaagaaagt cattggtagc ttgatgggga    7200
tggcattgaa tctataaaatt accttggaca gtatggccat tttcatgata ttgattcttc    7260
ctgcccatga gcatggaatg ttcttctatt tgttcgtatc ctcttttatt tcattgagca    7320
gtggtttgta gttctccttg aagaggtcct tcacatccct tgtaagttgg attcctaggt    7380
attttattct ctttgaagca attgtgaatg ggagttcact catgatttgg ctctctgttt    7440
gtctgttatt ggtgtataag aatgcttgtg atttttatac attgattttg tattctgaga    7500
ctttgctgaa gttgcttatc aacttgagga aattttgggc tgagatgatg gggttttcta    7560
gatatacaat catgtgatct gcaaacaggg acaatttgac ttcctctttt cctaattgaa    7620 tacccttat tttcttctcc tgcctgattg ccctggccag aacttccaac attatgttga     7680
```

```
ataggagcag tgagagaggg catccctgtc ttgtgcccgt tttcaaaggg aatgcttcca    7740
gtttttgccc attcagtatc atattggctg caggtttgtc atagatagct cttattattt    7800
tgagatacat cccatcaata cctaatttat tgagagtttt tagcatgaag ggttgttgaa    7860
ttttgtcaaa ggccttttct gcatctattg agatgatcat gtagttttg  tctttggttc    7920
tgtttatatg ctggattaca tttattgatt tgcgtatgtt gaaccagcct tgcatcccag    7980
ggatgaatcc cacttggtca tgttggataa gcttttgat  gtgctgttgg atttggtttg    8040
ccagtatttt attgaggatt tttgcatcaa tgttcatcaa ggatattggt ctaaaattct    8100
cttttttgt  tgtttctctg ccaggctttg gtatcaggat gatgctggcc tcataaaatg    8160
agttagggag gattccctct ttttctattg attggaatag tttcagaagt attggtacca    8220
gttcctcctt gtacctctgg tagaattcgg ctgtgaatcc atctggtcct ggactttttt    8280
ttgttggtaa gctattgagt attgcctcaa tttcagagcc tgttattggt ctattcagag    8340
atgcaacttc ttcctggttt agtcttggga ggatgtatgt gtcaaggaat ttatccattt    8400
ctgctagatt ttctagttta tttgcctaga ggtgtttata gtattctctg atggtagttt    8460
gtatttctgt gggatcggtg gttatatcct ctttatcatt ttttattgca tctatttgat    8520
tcttctctgt tttcttcttt attagtcttg ctagtggtct atcaattttg ttgatgcttt    8580
caaaaaacca gctcctggat tcattaattt tttgaagggt ttttgtgtc  tctatttcct    8640
tcagttctgc tctgatggta gttatttctt gccttctgct agcttttgaa tgtgtttgct    8700
cttgcttttc tagttctttt aattgtgatg ttggggtgtc aatttggat  ctttcctgct    8760
ttctcttgtg ggcatttagt gctataaatt tccctctaca cactgcttta aatgtgtccc    8820
agagattctc gtatgttgtg tgtttgttct cattggtttc aaagaacatc tttatttatg    8880
ccttcatttc attatgtacc cagtagtcat tcagtagcag attgttcagt ttccatgcag    8940
ttgagcagtt ttgagtgagt ttcttaatcc tgagttctag tttgattgcg ctgtggtctg    9000
agaaacagtt tgttataatt tctgttcttt tccatttgct gaggagagct ttacttccaa    9060
ctatgtggtc aatttcagag taggtgtggt gtggtgctga aaagaatgta tattctgttg    9120
atttggggtg gagagttctg tagatgtcta ttaggtccgc ttggtgcaga gctgagttca    9180
attcctgggt atccttgtta acttctgtc  tcattgatct gtctaatgtt gacagtgggg    9240
tgttaaagtc tcccattatt attgagtgga attctaagtc tctttgtagg tcactaagga    9300
cttgctttat gaatctgggt gctcctgtat tgggtgcata tatttagg  atagttagcg    9360
cttcttgttg aattgatccc tttaccatta ggtaatggcc ttctttgtct cttttgatct    9420
ttgttggtat aaagtctgtt ttatcagaga ctaggattgc aacccctgcc ttttttgtt    9480
ttccatttgc ttggtagatc ttcctccatc cctttatttt gagcctatgt gtgtctctgc    9540
atgtgagatg gatttcctga ctacagtgca ctgattggtc ttgactcttt atccaatttg    9600
ccagtctgtg tcttttaatt gcagcattta gcccatttac atttaaagtt aatattgtta    9660
tgtgtgaatt tgatcctgtc attgtgatgt tagctggtta ttttgctcat tagttgatgc    9720
agtttcttcc tagccttgat ggtctttaca atttggcatg tttttgcagt ggctggtacc    9780
agttgttcct ttccatgttt agtgcttcct tcaggagctc ttttagggca ggcctggtgg    9840
tgacaaaatc agcatttgct tgtctgtgaa ggattttgtt tctccttcac ttatgaagct    9900
tcgtttggct ggatatgaaa ttctggggttg aaaattcttt tctttaagaa tgttgaatat    9960
tggtccccac tctcttctgg cttgtagagt ttctgccgag agatcagctg ttagtctgat   10020
```

```
gggcttccct tgtgggtaa cccaacctttt ctctctggct gcccttaata ttttttcctt    10080
catttcaact ttggtgaatc tgacaattat gtgtcttgga gttgctcttc tcgaggagta    10140
tctttgtggc gtactctgta tttcctgaat ctgaacgttg gcctgccttg ctagattggg    10200
gaagttctcc tggataatat cctgcagagt gttttccaac ttggttccct tctccccatc    10260
actttcaggt acaccaatca gacgtagatt tggtcttttc acatagtccc atatttcttg    10320
gaggctttgt tcgtttcttt ttattctttt ttctctaaac ttctcttctc acttcatttc    10380
attcatttcg tcttccatca ctgataacct ttcttccagt tgatcctatc agctactgag    10440
gcttctgcat ttgtcatgtg gctctcttgc cttggttttc agctccatca agtcctttaa    10500
gaacttctct gcattggtta ttctagttat ccatttgtct gattttttttt caaagctttt    10560 aacttctttg ccattggttt gaatttccac ctgtagctca gagtagtttg atcatctgaa    10620
gccttcttct ctcaacttgt caaagtcatt ctccatccag ctttgttccg ttgctggtga    10680
ggagctgcat tcctttggag gaggagaggc gctctgatct ttagagtttc cagttttttct   10740 gctctgtttt tttctcatct ttgtggtttc atctatcttt ggtctttgat gatggtgacg    10800
tacagatggg ttttggtgc ggatgtcctt tctgtttgtt agttttccctt ctaacagaca    10860 ggaccctcag ctgcaggtct gttagagttt gctagaggtc cactgcagac cctgtttgcc    10920
tgggtttcag cctcagtggc tgtagaagag cggatattgg tgaaccacaa atgctgctgc    10980
ctgatcgttc ctctggaagt tttgtctcag aggagtaccc gaccgtgtga ggtgtcagtc    11040
cgcccctact gggggggtgcc tcccagttag gctactcggg ggtcagggac ccacttgagg   11100
aggcagtctg cctgttctca gatctcaagc tgcgtgctgg gagaaccact gctctcttca    11160
aagctgtcag agagggacat ttaagtctgc agaggttact gctgtctttt tgtttgtctg    11220
tgccctgccc ccagagatgg agcctacaga ggcaggcagg tgtccttgag ctgtggtggg    11280
ctccacccag ttcgagcttc ccagccgctt tgtttaccta atcaaacaac taactcagca    11340
atggtggccg cccctccccc agcctcgctg ccacccttgca gtttgatctt ggatggctgt    11400
gcttgcaatg agcgagactc tgtgggcata ggaccctcca agccaggtgc aggatataat    11460
ctcctggtgt gctgtttttt aagccggttg gaaaagcaca gtattagggt gggagtgacc    11520
caattttcca ggtgccgtct gtcaccccctt tctctgacta ggaaagggaa ttccctgacc    11580
ccttgtgctt cccgggtgag gcaatgcctc gccctgcttt ggcttgcgca cggtgcgctt    11640
cacccactgt cctgcaccta ctgtctggca ctccccagtg agatgaaccc ggtacctcag    11700
ttggaaatgc agaaatcacc agtcttctgt gttgctcatg ctgggagctg tagaccagag    11760
ctgttcctat ttggccatct tggctcctcc cctcagcaca gttttttagca tgaactaagg    11820 cctcaataaa tattagttcc cttctccaat tcagaaagtt gtctgccttg ataagacaat    11880
tgtttttatt gtgaaagtga ggtggagatg ggggattgtc tctcctataa aaggtctaag    11940
aagttagcaa atgctgtttt tcctttttgc tcctcagttg cataagtaca tggtagaaat    12000
tgggtcactt tgcctaaacc ggttttctat aacctattaa gtattaaaag cttgacacag    12060
ataagtagag gctgataaga ttctgtcctg caccccactc ctatcaaatt tggaagaact    12120
gacctcttcc gggaagaatt gcaatgctaa atccaaatgc ctatggttct atcttataaa    12180
caaatggtgt cctcaaaatt catttatgta aatcatttga aatttaagaa aaaaatatgt    12240
tcagagaaaa atatgttaaa tgtcaaggtg aattagaaag tgtggcatttt agtcaagcat    12300 aaattaatat tccaactttc tagttacttt gtagtaactt atttaacatt ttggtgaaat    12360
gaggaacaaa gtgtccacct ttttttcctg aatatttat ctgaagatct aggagagaga    12420
```

```
tgtgaaatag tattttctg gggaagtagg ggaaatacaa agaaaagtaa tgacttcagg    12480
tatattctcc actggtacag caggatggga gatattatca acaggtggta agtataaaaa    12540
tattgaagag gtacaatttg gatcagcatt acaaccaaga atggagaatg acattcagga    12600
ttgaaagaaa catacaagag ggcagaaagc tttcttcttg ggactgtggt ttcatgtgtc    12660
tgcaggtgct atgggtatat tgagaatggt tctaaaaaca ggggcttggt ttaggttgtg    12720
aagaccatca aatagaaact gtgaattta ttttgtgtcg ttaaagggat ctttgaaaga    12780
ttcttaggat aaatatgata tgcataggat agaaagaaag gtgggagaca ggacaaacag    12840
aagttaatca attgaaataa accaggtttg gagtggtggg acaatagcct tcaagcatc    12900
aagaatattt gttagtagaa agaaaatcga agcctaaaac taaggaaga ctatccacct    12960
tgcaagtcat acagagatat ttgctattat ataattttt taaaaaaga tttcctaata    13020
tttaaattat gaagaaagag atagaaacag atattcatgg aaaaaatggg gtgaaattaa    13080
tcaaagggca gcttattacc ttgagactaa acagccattg actttttct tacctcactg    13140
aacccagaaa cccgacatat ctaggtacag gcatgcataa aacatgtaca cacacaaaat    13200
gtaataattg gagttcactt agaggtacac atgtatgggt ttctgtattc aaccatatgt    13260
tgatatatac tcacatatat gtaagtgata atatcctgtt tgttacttcc acatttatgc    13320
actatccctt aaatatgtat tatatatatt tatattattc agaatccatc agcccttgtt    13380
gaataaatta gtgaataaaa tatagagtcg agtctcatta ttcacagatt ctatataaga    13440
aaatttgtct attcactaaa attcctttgt aacaccaaaa tcaatactgc tggactttca    13500
tgggcattca catgcatgtg caaagtggtg aaaaatttga gctgccatgt tcccaactaa    13560
ggttgaacaa aatgaagctc tgtcttcttg ttctgctca catatgataa agaaatatcc    13620
tttcacact gtatttattg ccacatttt ggcattttg tgttttgtgt ttctgagttg    13680
aatgtttcga atgggcccca agatagtgc tgaagtgctc tccggtgcac aagagtatct    13740
gagggaaaag atacatatgc tgtataagct tcctccaggc ctgaactaca gtgttgttga    13800
caactaattc aatgttaatg aatcaatagt atgtattaaa taaagtgtct ttaaacaaaa    13860
catacataaa acacagttct atattgaaca atttaccaaa atattgtgac cagaggcaga    13920
caggcatata actaaccca catctctcca aggaacaatg gttcaatatt tgctaattca    13980
gtgttcccag caactttata aaacataact actgcaacaa gtatcaactg tacatataat    14040
atatattaga catattgtat aattactgcc ctattaaaaa tcatgtatct atgctgtgtc    14100
tgcttatata gatatcttag atacataaat atgtattgtt tacatacata ggagcaagaa    14160
tgtatttcta aaactccatg aagaacacat tatattctat ataaaagagt cagttgaagt    14220
aaaaagttaa ctcattttac tagtctttaa agtaggactt taatgactct caaaataaca    14280
atttctctca tacattgact ccaaaacttt agttgttgaa tttattctgc agatatggcc    14340
acataaaacc aaaatggcat atgatatatt aagaacatct ttaatatgaa atgattagat    14400
acaacctaaa agctgatgaa tatagaacca gttgcatata ttatggacaa cttaataccc    14460
tgctaccata agaaaaatga gaaagactta ttaagattaa gtatatagag aagataaaaa    14520
ggtagagaat gatgtttaag gtatgctacc atttgcattg aaaaggaaaa tattatgtac    14580
ttaatgaaaa atccatatta tattttctgga taatgggaca agagttagag gaagaatctt    14640
tgttttattt ttttaatttg catttccaac tatatgcatt ttctcttgga aaagaaatga    14700
acaaaatcaa aataaagtaa catcatgatg gtggtaaggt caagcaatac cagagttgct    14760
```

```
ctgagaagta cttggagtac actttgctct ttttaacaaa tccaaattct gtttgctttt    14820
tgagcctgat tccagtggtg tctcctttat aaaactgagg ccattctaat ttaattcttt    14880
atattatttt tgtatctgtt ttgaatatct actctgtgca aggggctaat aggcacattt    14940
taaaactaga aggataaaga aaacatatat ttgcttttat aaattttaca ataggtgt      15000
gtagaaaaga taataattta aatttctata atttaaaatg ttcatgtaat ctggtgtgtg    15060
attctatatt acttacttgt ttcaaatttc tctccacaaa tttattttc tattaaattg     15120
taatctcctt aggctagaat ttgtgtctgt ctttcctact tttgtttcca gcattgacct    15180
agcagagtgg taacgacata gtagaccctg agtgaatgtt agtgaatggt tgattgattg    15240
atgatgatct tgtggctttt cttatttcta aattatatat tgtaaaaata aaataaacta    15300
tactttttct tccttaatag gtgattgttt caaactgagc atcaacaaca aaacatttg     15360
tatgatatct atatttcaat catggaccaa aatcaacatt tgaataaaac agcagaggca    15420
caaccttcag agaataagaa aacaagatac tgcaatggat tgaaggtaga ataagtttta    15480
tgttttgag ctaaaataag taaataggga actttaatgt atagaaaagc aagttgttaa      15540
aaagaacatt atgttccaaa ttataatttt caattgaagc atatattgaa atattaacat    15600
aatgattcat accttgattt aaaccagtct tttaatctga ttaagtattt ctttggcgaa    15660
attttgatg cttaatagtt tatcaatgta gaaaatttag aaatattttg atagcttctc      15720
tttggttttg gattgatcac gacatatttta ggaatgtgat taaaataaaa aatgcataat   15780
gaataatatt ttaaaattct tagaattgac ttataaactt agaatattaa tgtcttgaga    15840
ctcactttgt gatactgact tatttaaaaa ttcttttaaa aaaaaaaaca aaaaacagga    15900
tttaaaaaag ttctgataag taatttaggc tcatggaacg gaggtctatg atagtcaaaa    15960
acttggccaa aagacctgtt tgacgattta gaaaagccat ttaatgtttt catttgccag    16020
ctggtaaaag taataattct gcttttttgct tttggcacaa actgtattaa atgatacagt    16080
tgaggtatta agtgatgctg gcatttttat aaacaggaat gagtactcct aagcacaatg    16140
ctaaatgaga agccaagact cagaaaagtt aagaaatttt cctgaagtca tctacattgt    16200
gaattgaaaa ccctggaacc caagacaaag cctttaaatc cccatatgga agtcttgagg    16260
aaatcaagaa ataagggtca ccttttatca atgttttaac ttttttattt agtcaaattt    16320
gtagtcttat acagctgaat aaaggccacc aagattggag tcaattacaa taatgttata    16380
aaaggttcct tttagctcct tccagggaac ataaaatttg tttgttttct gagattactg    16440
ataaagcctt ctctgatgaa atatttgagt aacatttagg ccaagtggca gtcataagga    16500
aaaagtattg gttaatgcaa gtgaattatg ttctatattc taaggataat ataatgtact    16560
gaattgtttt tatttttaaa tactgagtgt tacagtaatt tcactgacat gtgcatagca    16620
aaatggcagc aaactgcctg aagcaataaa atttccagag tgatccctta tagcatatct    16680
ggagaagctg ggagttaggg aattagcagt gtgtggaaag gacattaact gcagcccaat    16740
aaagaagact agagctagag gaagatactg ggataagact ggcatcccta atgctggtat    16800
ttcagaaaca tcgctaaatt ggttaatcat gtctacaagt gatatttaaa ataatatttt    16860
cactcactta aattgttaac attgatatgt tgttgataaa gaatattaaa ctcaacaatc    16920
attttacaat aattctgtaa agacttgcgt gcctgtagtt gaggtttgtt gcatttctga    16980
gcttactttt tattcatgag aaatgaaaac ataatgggag aaaatttttt aaataaaggg    17040
tatttaatt ttttatgaag tttgggactt caaagtatta acaaaagttg ctgaaaatat      17100
attgacttt actttcatta aattacattt tatcatctaa tttcttaatt ttctgtatt      17160
```

```
gaaatattat gatttagaga tatctctgta gatagaaaga taatgaaaac aatagtaaaa    17220
caaatgtaat tcaggagcat aaaaaaagat gagagaaacc ttaataatag tagctaacat    17280
ttatcaagca tttactatat gccagacatt gatttagtgt tttacttttg ctaacagatt    17340
ttttccttac cataattcta tcaactggat ggtattatct cccctttca gatgaaaaaa    17400 cctagatata gacagggcaa atgtcttctc ctaggtctca aagttggtaa ttggtacact    17460
gaaggtctga actcaggcaa tctgattcca aatcctatgc tctcaactgt attccatatt    17520
gctaaaataa atgtggattt ttgtaatatt agtaccctca agatgttatg gcaagcaggc    17580
ttttataagt ggtgtcttta ataactttcc tcattccata cttctaaaaa attatcttaa    17640
ggttaaatta ttgagtgtca agcaactgtg gattctaaca cttgctaaca tgcatgcaca    17700
cacccaaata tacatgttgt tactgactta catatacaga cacagcaggt ggcaatatat    17760
aagtgcaaat tgataatata tccgtggaaa tacaaacaaa actttgagaa atcaaatact    17820
tgaattcttt tctaccccctt ctcctcaatt tttgtactga actaactaca ttacatagaa    17880
cctgctagta tatgtttcat cattacactt gtcatttctt ctcttcaaat ttaaacccaa    17940
caagatacag gggaagattt aaatgcaatc caaagaaaac aggaaaacaa ttcaagagtt    18000
taaagatgac atagtcattt taagaaagaa ccaaaattaa cttctgaaat taaatatttt    18060
actacaggaa tttcataata caattatagt aattaacaac aaaatagacc aagcttaaga    18120
aagaatctca gagtttgaag attaccccctt tgaatcaaca caagcagaca aaattaaagg    18180
aaaaatatta atgaaaaaaa cctctgagaa atatgggatt atgtaaagag accaagcctg    18240
tgactcattg gcattcctga agaggagaa agagtaagca acttggaaaa tgtctttgag    18300
gataaagtcc atgaaaaatt tcccagtctt gctagagagg tggatatgca agttcaaaaa    18360
attcaaagaa tcccttcaag atactataca agatggtcat ccacaagaca cataatcatc    18420
agattctcca aggtaaacaa gaaagaaaaa aaccttaaag gcagctagag agaagggggca    18480 ggtcacttac aaaaggagcc ccatcagtct aacaatagat ctttcagcag aaagcttaca    18540
agctagaaga gattggggac ctattttcac catccttaaa gaaagaaat tgcaactaag    18600 aattttatat tctgccaaac taagcttcat aagtaaagaa aaaatattat tttcggtcaa    18660
gcaaatgcta acagaatttg ttaccattag acctgcctta ccagagatgc ttaagggagt    18720
cctaaacatg gaaatgaaag aatgataacct gtcaccacaa aaatagactt aactacagag    18780
cccacagaca ttataaagca attatgcaat caagccaaca taataaccag ctaacaacac    18840
tatgacagaa tcaaatcctc acatatcagt attaatcttg aatgtaaatg ggttaaatgc    18900
ctacacttaa aaggcataga atagcaagtt ggataaagaa gcaagaccca accgttttgt    18960
tgtcttcatg actcatgtat catgacatcc ataagataga aaatgaataa attgaaataa    19020
tatttatctc agagttgtca ggatatttat aaggtgctta gcacagtgtt acatagaaac    19080
tcaataaatt ggaaagttcc aacatagtag cattatagtt gctgcacttt ttttgagaca    19140
gggcctctgt cacccaggct ggagtgcagt ggcataatct tggctcactg caaactccac    19200
ctcccaggct caagtgattc tcccaccctcc tgagtagctg aactacagg cacatgccac    19260 ttcacccagc attttttca ttttttttttt tttttttttt tttttttagta gagatgaggt    19320 cttaccttgt tgccaggctg gtcttaaatt cctaggctca agcaatcagc ccgccttggc    19380
ctcctaaagt gctggaatta caggtatgag ccatcacatc tggaagctgt ttcttttta    19440 agtgactaca ttaattact tgatcacgag taatacataa atgaaaattt gagaatacat    19500
```

```
tcactccaat atttggaatt atgtgacttc tagattttg caatttaagt aggcataaaa    19560
tggtactttg ttttagtatt tgtctgtgct ccttgattct tataaatatt atattttgtg    19620
aaatccattg ctgaatgcaa gtggtgctgg ttacatttgc ctatttccaa gttttagtac    19680
atttatttt gaaatatatt ttatcagttt aaggacttac ttgtaatatc tttgtgtggt    19740
cttggtatta ggttaatgtt ggcctcaata aatgagatag gaagtatttt tttctgcttc    19800
taacctctga aaaaaactgt agagaattga tataaaattaa ttcttaggta tttggtagaa    19860
ttcaacagtg aaaccatgta ggcctgtttc tttctgtttt ggaaagttat taaaatcagt    19920
tcaatttctt aaacagaaat agtccttta atattgtcta tttattcttg tacaaaattg    19980
ggtagatcgt gtcttcaat atattggtct attttatata ggttatcata gttgtaggca    20040
gagtgttgct tatagtattt ctttattatc ctttcatgt atattggatc tgtagttatg    20100
tcccgcctt tatttctgtt attagtaatt tgtgccttcc ctcatcttct taggtaacct    20160
ggctgggtca atttattaa tctttctaaa gaattaactt gtggttttgt caatttcctc    20220
tattgatttc ctgtttatga tttaattgat ttcaggtcca attttattc tattttttct    20280
tgtgcttact taaaatttaa tttgcttttc ttttgattt tcccaaggtg gaaacttaga    20340
tattgatttt agcattttct tgttttctaa catatgcatt cagtgcaata aatctctaag    20400
tcttgatttt gctacctttc acaaattttg atcacttgta tgtttaattt tatttttttc    20460
aagatgttt aaaattttc ttcagatttc ttttgactca taagttactt aaaagtgtgg    20520
tagttaatct ccacatattt tggtattttt ccagttatct ttctgttata ttctagctta    20580
atttcattgt catctaagag aagacattat tagtttaaat gtgttaaggt gtgttttatg    20640
gcttaggctg tggtatatat tggtgaatat tccatgtaag cttaagaaga atgtgtattc    20700
tgttgttgtt ggatgaaata acatatagat gtttattata tccagttaat tgatgatgtt    20760
gttaaggtca atcatgttct tcctgttttt acctgctgga tctttccatt tctagagaga    20820
tgtagagtct ccaaatacca tagtgtattc atttatttct ccttgtattt ctactggctt    20880
ttacttcaga tagtttgcag ctctgttgtt tggtgcctct atgttaagaa gtgttatgtt    20940
ttcttaagaa ttgacccctt taacattttg taatgccccg ttttttacctc tgttaatttc    21000
cttgctttag agtctgctgt gtccaaaatt aatttagatt gtcttgcttt gttttggtta    21060
ttgttaccat ggaatgtttt tctccacttc tttacttttt taaaaatta cactttaagt    21120
tctgggatac atgtgcagaa tgtgcacatt tgttacatag gtaaacacat gccatggtgg    21180
tttgctgcac ccatcaaccc gtcatctaca ttaggaattt ctcctaatgc tactccctag    21240
ccccccaacc cccaacaggt gctggtgtgt aatgttcccc tccctgtgtc catgtgttct    21300
cattgttcaa ctcccactta tgagtgggaa catgcagtgt ttggatttct gctcctatgt    21360
tagtttactg agaatgatgg tttccagctt catccatgtc cctgcaaagg acataaactc    21420
attctttctt ttggctgcat agtattccat ggtgtatatg tgccacattt tatttatcca    21480
ttcaattatt gatgggcatt tgggttggtt ccaagtcttt gctattgtga atagtgctgc    21540
aataaacata catgtgcatg tgtcttata gtagaatgat ttataatcct atggatacat    21600
tcaacaatgg ttgaattaat ttacactccc accaacaggg taaaagcatt cctatttctc    21660
cacatcctct ccagcatctg ttgtttcctg acttttaat gatcgcttcc aactggcgtg    21720
agatagtatc tcattgcagt tttgatttgc attctctaat gaccagtgat gatgagcttt    21780
tttaatatgt ttgttggcca cataaatgtc ttatttgag aagtgtctgt tcatatcctt    21840
ggcccacttt ttgatggcat tgtttgtttc tttcttgtaa atttgtttaa gttccttgta    21900
```

```
gattctggat attagctctt tgtcagatgg atagattgta aaaattttct cccattctgt   21960
aggttgcctg ttcactctga tgatagtttc ttttgctatg caggagcttt ttagtttaat   22020
tagatcccat ttgtcaatct gggttttttgt tgccattgct ttttgtgttt tagtcatgaa   22080
gtatttgtcc atgcctatgt cctgaatggt attgcctagg ttttgttcta ggttttttat   22140
ggtgttaggt cttacattta agtctttaat ccatcttgag ttaattttttg aataaggtgt   22200 aagaaagggg tccagtttca attttctgca tatggctagc cagttttccc aacatcatat   22260
atattaagaa gggaatcctt tttccattgc tttttttggt cagacttgtc aaagatcgga   22320
tggttgtaga tatgtggcat tatttctgag gtctctgttc tgttccattg gtctatatat   22380
ctgttttggt aaaagtacca tgctgtgttg gttactggag gcttgtagta tcatttaaag   22440
tcaggaagca tgatgcctcc agctttgttc ttttttgctta ggattgtctt ggctatatgg   22500 gcttttttt ttttttttt ttggttccat atgaaattta aagtagtttt ttccaattct   22560
gtgatgaaag tcaatggtag cttgatgggg atagcattga atctataaat tactttgggc   22620
agtatggcca ttttttacaat attgattctt cctatccatg agcatagaat gttttttccat   22680 ttatttgtgt cctctcttat ttcattgagc agtggtttgt agttctcgtt gaagaggtcc   22740
ctcacacccc ttgtaagttg tattcctagg tattttattc tcattgtagc aattgtgaat   22800
ggaagttcac tcatgatttg gctctctgtt tgtctattat tggtgtatag gaatgcttgt   22860
gatttttaca cattgatttt gtatcctgag actttgctga agttgcttat cagcttaagg   22920
agattttggg ctgagacaat gggggttttct aaatatacaa tcatatcatc tgcaaacaaa   22980
gacaatttga cttcctctct tcttatttga gtatctttta tttatttctc ttgcctgatt   23040
gccctggcca gaacttccaa tactatgttg aataggagtg gtgagagagg gcatccttgt   23100
cttgtgccgg ttttcaaagg gaatgcttcc agctttcacc cattcagtat gatattggct   23160
gtgggtttgt tatagatagc tcttattatt ttgagatata ttccatcaat acctagttta   23220
ttgagagatt ttagcacagc tccagtgtgc agctcccaaa aagatcaacg cagaaggtgg   23280
gtgatttctg catttccaac tgaggtaccc agctcatctc tttgagactg gttagacagt   23340
gggtgcagcc aacaggggc aagccgaagc agggtagggt gtcacctaac ctgggaagtg   23400
caagttgtca ggaaacttcc tcccctagcc aagggaagcc acgagggact gtgccctgag   23460
gaaaagtgca ttctggtcca gatactatgc ttttcccagt ctttgccact ggcagaccag   23520
gagattccct cgggtgccta caccaccagg gccctgggtt gcaagcacaa aactgggtgg   23580
ctgtttgggc agacactgag atagctgcag gattttctttt ttaaacccca gtggtgcctg   23640
ggacaccagc aagacagaac ccttcactcc cctggaaaag gggctgaagc tagggaacca   23700
agtggtctag ctcagtggat cccaccccca tagagcccag caagctgaga tccactggct   23760
tgaaattctc cttgccagcc gagcagtctg aagtcaaccc gggatgctcg agcttggtag   23820
ggggaggggt gtctgccatt actgaggctt gagtaggtgc ttttccctca caatgcaaac   23880
aaagccacta ggaactgggt ggagcccacc gcagctccac aaagcccctg tagccagact   23940
gcctctctag attcctcctc tctgggcagg gcatctctta aagaaaggca gcagccccag   24000
tcacgggctt atatataaaa ttccctctat ctgggacaga gcacctggga gaaggggcag   24060
ctgtgggcgc agcttcagca gacttaaact atcctgcctg ctggctctga agagggcagt   24120
ggatctccta gcaccattct caagctctgc taagggacag actgcctcct taagtgggtc   24180
cctgactccc gtgcctcctg actgggagac acctcacagc agggttcaac agacacctca   24240
```

```
tgcaggagag ttctggctgg catctggtgg gtgcccctct ggaatgaagc ttccagagga   24300
aggaacaggc cgcaatctct gctgttctgc agccactgct ggtgatacct aggcaaacag   24360
ggtctggagt ggacctccag caaactccag cagacctgca gctgaggggc ctgactgtta   24420
gaagaaaaac ctacaaacag aaaggaatag catcaacatc aacaaaaagg atgtccacac   24480
aaaaacccca tctgaaaggc accaacatca aagaccaaag gtagataaat ccacgaagat   24540
gaggaaaaac aagtgcaaaa aggctgaaaa ttccaaaacc cagaatgcct catctcctcc   24600
aaaggatcat gtttactttt aatctatatg tgtttatata tttaaagtgg gtttcatgta   24660
gacaacatat agttggttct tgttacttga tctactgtgt caatttcaat cttttaatta   24720
atacatttag atcatttgcg ttaaaagtga ttactgatat atagtcatgt gtcatttaac   24780
aacaggaatg cattatgaga aatgcattgt tagataattt tgtcattgtg caaacatctt   24840
agcgtgtaca tacataaacc tagatattat agcctactac acacctaagc ttatggtata   24900
ggctattact ttgatgctac caaaacctgt acattattgt agtttactaa atactaatta   24960
caacacagtg atattggtgt atctaaacat atctgagcac agaaaagata aagtaaaaat   25020
atggtattat aatcttatgg gaccatcatt gtatatgctc tccaacattg acttaaatgt   25080
cattatgaca tgtgtgactg tagttagatt agtatctacc atagcggttg ggttgcctgg   25140
gtgtttgcaa gataaattta caaataattc aagtccactt tcacgtgacg tcataccact   25200
tcatgggtag tatgagtacc tgataatagc aaattattta taatactttc cttccatttc   25260
ttgtatcatt attgtcattc atttcaattt tgtgtcagca tacataatca aatacattat   25320
agatattatt ttaaaaacag ttatgtctta gattaagaat aagaaaagta ataatttata   25380
ttttatgctc acttatttct cctccaatgt tttccttgct ttaagtagat ctgagtttct   25440
gatttatatt attttatctt tctgtaaaga actcctttta acaccttgca aggctgatct   25500
aaaggcaaaa catttctttc agtttcattt ctcagaggaa gttttatttc tccttcatgt   25560
tagatggata aatacacagg gtatggggaa ggtattttt cctctgtatt cttttgggat   25620
ttttttcctt tgtctgtgat tttctatagt tttaaaatga catgactagg tgtaacttt   25680 tgggcattta tacaacttgt tattctatgg acttccagga tctgtggttt gttgtctgat   25740
actaatttgg ggaaattctc ggttgttatt gtttcaaata tttctttagt ctctatttct   25800
ccttctagtg attccattat gtatatgcta tacctttttt agttggccca cagttttttg   25860
atactttgtt ctgatttttt tgtctttgtt attttttattt gcttttagt tttgcagatt   25920 ttaattcata tatcctgaat ctcagatatc ctgttttcag tcttgtgcag tatactgatg   25980
tgtttaccaa aggcattctt catttctgct acgatgttgt gacattataa ttttttttaat   26040 gaaattttta tctgtctgct tacattgctc tgttcttgtg tgcttctta ttttaccact   26100 agaacactta gcatattaat cacagttgtt ttaaattctc agtccaataa atccaacatc   26160
ctttctgtat ctgagtttgg ttctgattct tgctctgtct cttcaaaatt atatatattt   26220
tttttctttt agatgactgg taatatattc tggatatcca gacataatgt attgagtttt   26280
gtaaaacctg ctatacatag gccttcaata attgttgcta aggtgtggga gaggagaggc   26340 ttttttttt ttttttttgc ctctggactg taaccttcac aagtgttttt ttagtatttt   26400
ttttccttct tggtcagaat gggtttggta gagtgagatg gattttggta ttttccttct   26460
gtcacatgga agactagaat tggctggagc tgggtatttc cttcccttc ggtcagttag   26520 gctctaataa cacaccatct tatgaggctc tgataaacta gttctgccta agggcaagca   26580
ctaaaagtcc tattaaaaac agagggctct agtctatttc aaaaatgagt cttgtctcct   26640
```

```
catgctactg aaagaacaag ataattttc tccaacattt actataagaa cctggtcaag  26700
ctcctggagg gaaaactcaa aatgtggagg tcaccgactg ggttcccttg gagtgtttag  26760
tgctcagact taaccacact gagtgagact ctagcagttt atcaattata gtgaaggtat  26820
ttctacccttg tcactggttc ctgtgcagtt tctgttcatg agtctctact gctataagct  26880
gtgacacttt gtaatcacct atttgtctct ccaatcttga aggcagtcga ttgccattgg  26940
tcctcacctc ttttacagat ccagaaagag ttgctgcatt taaattggt tcagtgtttt  27000
tcttgttgtt actataaaat ggcaagctcc aagctccttg aaggtttcca gagcctagaa  27060
accagaaata ccagcatata tttttattg tattttctta tctcatgtct tacagttcta  27120
cattttactt aagaattcat tgtgattgct tgattaatat acaagttatt ttaaaataac  27180
attttcttca aatatttgga gattttcgt aataaatttt ttgccagtaa tatttgtcat  27240
aattgcattg tggaagctat gacaactaat tttgaaatt agttgagact tctctatgtc  27300
ctagtacatc attgatgttt gtaagtctcc ctgatgtact taataaaaat gcatattcca  27360
tattctttca attgttggat gtataatttt atatgtgtct gagaggtcag tcttgttaat  27420
tgtgttattc agatcttcta tgtccttgct aatattttaa ctatttcact tatcataatt  27480
gaaagaaaga tgttgaattt ttttcttaca aaagcagttg tattgatttt tgcttatata  27540
tttttgcatct actaagtgca ttattatata accgttttat cttttaggat gatataattc  27600
aatatatgga ggacttctct atccttaatg atgtttctat gtctatttgg gctattattt  27660
atacacctat aaaattttct ctaagtggtt atatttttctt atcatttac tatcacgaag  27720
aatttcttcg tgatttagga atatctctta taaaaagcac agaggtaaat tttgaagaaa  27780
aatccaaact aaaaattatc tatctttaaa ctagcaattt tctacactta tgtttattgt  27840
atctattgat atagttagac ttgcttttac tatcttacat tattatggtg attttcccct  27900
tttttaatgc tcccttaaaa ttcttttctta tacttttga atgtatatgc ctatctctct  27960
cataacaaga caaacattct agcatgattc tatgatctga atgtttgttt ccccccaaat  28020
ttgtatgtcg agtcataatc accaaggtga ttctattaga aggtggagac tttggaaagt  28080
gattagttca tgaaggtaga gtcctcatga acaaaattag tgtccttatg aaagagaccc  28140
aatagagctt ccttgcctct tctaacatgt gaggttacag tgagaagatg gttctcacca  28200
aataccaaat atgttggtgt cttgatctca gacttcccag gctccagagc tgcaaaaagt  28260
aaatttctat tgtttataaa gtacacagtt ttcttatatg ctatattttg ctatatttc  28320
ttacagcacc ccaaacagac tgagacatat gttcacatac tctttatat gcctctttac  28380
cctctataca atatgatgct atctggattt tcaatctaaa attttaaatt ctagacacta  28440
tgactatttt acctccttc ctgttttag ttttttttta agacattgag aaaatttatc  28500
aagtatttta ttcactttgc tttacaaatc tcatgcaaca ccttcagaat tggattcttc  28560
ttttatttaa gcaattcttc caaaattgtt tccagtacgt gtttggttgc agtattttg  28620
aggccttata tgcttgagca tatatctctt tatagctgag aggctgttta tctcaatgta  28680
aaattatggg ttcaatgctc ttttacttca gtacttaaaa aatatatttc tttgtctttt  28740
gtgtacccac ttttgctgtt agaaagtgat atactttctt tcctgaaagg cctcaatttt  28800
ttttcttgtc tttgatattc ataaatttta atatacttct tccaaatatg tctgtgttct  28860
tacttatctc ttgtgttgag cattcaatgg gcactctcaa cctgcatttt tgtttttttt  28920
taatcttagt aaattatttg aaaatttca tttattattt cttaaatat ttctcctctt  28980
```

```
caacttattt tttctcattt taaggcatta ataattaaat tattctcaat tttagttaaa   29040
aattatgtat atcttaacct tttacctata tatgctttca atgttttaaa tgaaataacc   29100
aattttattt tccaattctt tcttgtttta agcccatata ttattttata ctattttaca   29160
tcttgtactc catattttct acttgttctt ttttgttatc ttattttgct tttatttcat   29220
tttgctaata ttcttttctt atatattttg tgtatttgta atgcttaaac tcctgttaag   29280
tgttttgtaa aacaattact ccttatggtg tcttcaaacc agtttacttt tttcttttctc  29340 ttttgaaatg ttttctcaaa gacatcacta ttttgccctg aagtcacatt tacttagtta   29400
tgatagtttc tttttttatag taattgcaca ggggaagagc taaaggatag aactctgtca  29460
ttgtgaaccc tgaaagctca gaaaaagggg agggaaatga gcctcaaggt gatgaccagt   29520
aaccaataaa tcacgtcact ctgcccttg acaaacattt ctttatccat ggctccctca    29580
gtcccctgaa tgcgaaattg ctttgaggag attgttaact agtactgcag aaatactgag   29640
gggattacct gtagaaggga atgctcaagg ctagtcagcc tttcctcctt tgctcagctg   29700
ctctgattca gagctactct gattttactc tggaggacac atgcaaccaa tgtctgaaca   29760
gtcatactca atccctgcat tgaggtagaa agcactgatt cctagaggct gatctgaatc   29820
atgcaactgt attgaaggca acaaaaaata ataaaatagc catgtatttt aatagggaaa   29880
gtatatagta attgaaaaga aaaccaaaa tcaatacaag tagtattgtg accgagagac    29940
aaaggtaaat ttgaagatag gtttgtgatt tcataatgga gacctttgaa tgctagaagc   30000 tacccccctcc ctttgtaaag aacaacatta ggtaaatgat taaaaaatta tgtcaaagtc  30060
tatgattttg aaactctacc atatttgaaa atattatatt aaaataatga tactaaacaa   30120
agaatttatg acaaatgttc atcttttaag taaaagaacc ttaaaatttg taagcagcta   30180
aatctaatga tataggcaac tgctaggata tcacaaaaga atgggatttt aatagtgaac   30240
ttatacaatt tgcctgaaat taatcaaatc agcacagaaa tgcacagatg acaaacactg   30300
taagatgtaa gaggaattaa tcataagagg tttatttggc taaagtgaca attgttaaag   30360
atagaattgc ctaacgttag ttaataacag aaaaaatatc agaaatttta aaaaatgctg   30420
tcttaatcta ttaaaattat ataaagataa agcaaaacaa tgtaggttta taaacaagaa   30480
cctttaaaaa agcataatac tgatgcttat tacaaattta tatcttgagc tggggtacat   30540
catccaattt acgcatgaga aaagtgtttt ataattttc actctgtaat tcatattta    30600 agttcatctg aaatgtattt tacagaggta agaacaagca acttggtgct caactctctt   30660
cctgctcttc gcctagtgct aaaataattt gtgtaaatga actgtgaatg aatttaagtt   30720
tcagaaataa aatttatatt aatagagaga aagaaggata aatcaatagt cttccaaata   30780
tgatacatgt acaatgcaat gatattcaca aacatcttca tgaacacacg aacataattt   30840
cttttgaatc ttaccatgac cttctaaaat aagtaagcta aatattctat attatactac   30900
tatttatgag gaaactacat ttctgtgaat tgtgtaactt tttcatcttt ataaggttag   30960
caagcaaaaa caaacaaata acaaaataaa caaaaaaaca aaaacttggc ccagatctga   31020
ctttaaagta ccttcacttt tattgtatca catacgatct cagtccacag atgggttcct   31080
gatttagcca agaatatagt aaagtgagtg taaagtagaa gaaaaaagaa ggaaaatatt   31140
aggtatagaa acctacatga aataaaatga aataaagaga gcctactctt tctgaaatgc   31200
accagtaaaa tgtactccta tcttgtgtat taagtttata atcatacatt caattcaaaa   31260
tttaactaaa actatggaaa ctgagagcta ataataaaat gatatacaca gcattctaac   31320
cagaaaatct tctaagcaat tgtacaattc agataagaag aaataattac aaatgttcag   31380
```

```
aaattaagat taattaagac tgtaaaattt tttttttttt tttttttgaga cagggtctca  31440
ctctgtcacc caggctggag tgcagtggcg cgatcttggc tcactgcaag ctctgcctcc  31500
caggttcacg ccattctcct gcctcagcct cccaagtagc tgggactaca ggcgcccacc  31560
accacgccca ctaatttttt gtattttttag tagagacggg gtttcatcat gttagccagg  31620
atggtctcga tctcctgacc tcgtgatctg cccacctcgg cctcccacag tgctgggatt  31680
acaggcgtga gccaccgtgc ccggccaaga ctgtataatt tgttcctgaa gggcagggaa  31740
aatgtagtgg taattttttca agatgaattg gaagataaag aaagagaggt cacattattt  31800
gtgttattca actgaaatag ttttgaattt caataaaaca agctaagaaa tgcccttttgt  31860
catcaaattg atgtgaagag taaaaaaatt ttaaaatga aattctctaa gataatatgt  31920
gaaaataaga ctatttaaat ttcaacaaac atttaacaag tgtataccca tcctatgttc  31980
gttttatcca acttcttatc attcctaagt atattaagta aagtaatagc tattaatatg  32040
ttgacgtcat tagcagaaaa ataactttgc aaatgattaa gtgatgacag ttgtatatcc  32100
atgttattag atgtttaaaa ttcaaaaaat aattaattca ataaattttt gaaacaaatc  32160
catagaataa aaacatagtt tttcaaaatg tattttttcaa aggtaaaaat ttctcacatt  32220
aggctaggtg cgtggctcat gcctgtaatc ccagcacttt gggaggccaa ggcgggcaga  32280
tcacgagctc aggagttcaa gatgagcctg gccaacatag tgaaacccca tctctactaa  32340
aaatacaaaa attagccagg tgtggtggtg cctgccttta gtcccagcta ctcaggaggc  32400
tgaggtgaga gaatcgcttg aacccaggag gcagaggttg cagtgagcca agaccacgcc  32460
attgcactcc agccttgggg gaagagtaag agtctgtctc aagaaaaaaa aaattctcac  32520
attattgtaa atactattac aatagctaac ataaattcaa gatttataat tattttttc  32580
tgatgctcat acaaatacac attttactgg atcttgggtg ttgtagtaaa aaacaattta  32640
ctaaaacaaa aaaaagaat gtataccta aatacataga attttatttg tcaatcatac  32700
cttaatatga gaaaataatg ttcttctttt ccaaagtaaa aagaaattaa tagagcaaag  32760
ctatatttta caacaatgta catataatcc ataattctgt ctaatacttg atattctact  32820
aactgaattg aagcagtact tgccaacatt tacatatata tgaataattg aattataaaa  32880
gttatgagat gctgatctga attacaaaag tccctctgtg atagtaaaca catgcataaa  32940
ttaattctat aaagtgttat tgcatttttct caaaatacat tgaagttctg tagtcaaagt  33000
aatcaataga gagccaaaac tgttttttgaa cagtttagca tattttcatt attaaaaaca  33060
aaacttgcca atagatataa gaaaaagagc tgaccaaatt agagtttaaa tagcataaaa  33120
taataatttt gaaattctaa aattgtatt tagaaaatca tgacacgtag aaaaattatt  33180
ttaatacagg tctcatttga attagataaa cttatattct atacctgaat aaaaagtaat  33240
tgaaaatacc tatgactttg cagcaataaa aaatggcaaa tgataaaaaa ttcaaattt  33300
tcttacataa atatttgtga aaagggggaaa ctgaagagag aaaatatgat agtttattta  33360
aagtgaaaca tttacatagt ttgatgtaga taaaagtaaa ttgagaaaat tcctatttgg  33420
cattatttgc tgtgagttta ccaagataat gttttctcc attttaaaaa caatggtcta  33480
tggtcaaaaa gtaagtcaaa ctatccctgt ttgcaggtga catgattcta tatctagaaa  33540
acccccaaag ctccttcagc tgataaacaa cttcagcaaa gttacaggac acaaaatcaa  33600
tgtacaaaaa tcagtagcat tcctatacac caacaacagc caaaccgaga gccaaatcag  33660
gaaggcaatc ccattcacaa ttgacacaaa aagaataaaa tactttgaaa tatagctaac  33720
```

-continued

```
tagggaggtg aaaaatctct acaatgagac ttatgaaaca ctgctcaaag aaattagaga    33780
tgaaacaaac aaagagaaaa acatgcttat agataggaag aatcaatata attaaaatgg    33840
tcatactgcc caaagcaatt tataggttca gtgctattcc tattaaacta ccagcaatat    33900
tcttcacaga actaaaaaaa aaaaaaaaaa aaactatttt gaaattcata cagaaccaaa    33960
atggccaaat agcgaagaca atctaagcaa aaagaataaa gctagagaca tcatgccgtc    34020
tgatttcaaa ctatactaca ggactatagt aaccaaaaca gcatggtact agtagaaaaa    34080
cagacacata aaccaatgga acaaaataga gagcccagaa attaggccgc atgcctatga    34140
acatttgatc ttcaacaaag ctcacaaaaa caagcaatgg ggaaaaaaaa ccctgttcaa    34200
taagtgattc tgggataact agctggtcat acacagaaaa ttgaaattgg acccctteet    34260 tacaccatac ataaaaattc taaaaattca aattataaaa aaggaaaaaa aaaatcaact    34320
ccaggcagac taaagactta aatctaaaac ctcaaactac aaaaaccctg gaagacaacc    34380
taggcaatat catcctggac ataggaatgg caaagatttc atgacaaatg acaccgaaag    34440
caatcaaaac aaaagcaaat attgacaaat gagatataat taaacttaag agcttctgca    34500
cagaaaaaga aactgtcaac agcataaaca gacatcctac agaatgggag aaaatattta    34560
caaatatgca tctaacaaag gtctaatatc cagcatctat aagaaactta aatttacaag    34620
agaaaaacaa acggcctcat taaaatgtag gcaaagggta tgaacagaca cttttcaaaa    34680
gaagacatac acatggccaa caagcacttg aaaaaaaggc caatattact gatcattaga    34740
gaaattcaaa tcaaaaccac aatgagacat tatctcacgc tagtcagatt attattatta    34800
aaaaataaaa aactaacaga tgcctggcaa ggttgtggag aaaagtgaac acttatacac    34860
tgttggtggg agtgtaaatt agttcaacca tgtgcaaagc agtgtggcaa ttcctcaaag    34920
agctaaaacc agaactacca ttcaacccag caacctcatc actgtgtata tacacccaga    34980
ggaatataaa tcattctact ataaagacac aggcatgtga atgttcattg caacattatt    35040
cacaatagca aagaaagaca tggaattaac ctatatgccc atcaatgaca gattggataa    35100
agaaaatgtg gtacatacta tggaatacta tgcagccata aaagaacaag atcatgtctt    35160
ttgtggaaac atggatggag ctggaagcta tcatctttag caaactaaca caggaagaga    35220
aaaccaaata cttcatgttc tcacttataa gtgggagcta aatgatgaga actcataaag    35280
acaaaaaagg gaatgacaaa cactggggtc tagctgaggt tggagggtgg agggtgggaa    35340
gagagagaga agcagaagaa ataactattg agtactaggc ttaatcctg agtgatgaaa     35400 taatctgtac cacaaacccc cgtgacacgt gtttacctgt acaataaacc ttcacatgta    35460
cctctgaaca taaaagttag aaagaaaata ttaacaactt taaatttagt aatcataaat    35520
gtcaaattaa aaaaaaaaga ttttagactc acacttataa tcatagcact ttgggatgcc    35580
gaggtgggcg aatcacttga ggtcggggt ttgagatcag cctggccaac atggtgaaac     35640
cctgtctcta ctgaaaatat aaaaattagc caggtgtgat ggcatgtgcc catagtccta    35700
gctattcagg aggccgaggc aggaaaatct ctggaacctg ggaggcagag gttgcagtga    35760
gccgagatca aacagtgca ctttagcctg ggtgacaaag tgagactctg cctcaaaaaa     35820
tacatataaa ataaaaaga ttttaaataa tattataaat aaactaaaat ttctaggaac     35880
aattttttaa aatcagaaaa ataagtcata tgataataca gatactctta agaaatgcat    35940
aaaatatatg aatatacatg tgtacttatt gatgtgcatg aagatacact aatatatcca    36000
acaagaataa gcacatccat tatttttataa tattaaagta agcaataaaa ggaacactta    36060
aaaatatttt cttcaattta attgactata tttttttatt tggaaaacaa ttttaacaca    36120
```

```
tattttaaat agtttaaata gagaaaaatg taaataaagc tgtattacaa agatattcat    36180
tgataaacac ttcaaaaaat ttttcaactt ccttattttt atcacgtatt ttgctctaga    36240
aaatttccat tccacatgat acatttgttg tataagagat acaaaacaaa ttcctactag    36300
gggaaataaa gcttcagtaa ggaggtggca ttaagctggg ctttaaaatt catgcagaat    36360
tcccgttgct tcaaatggag agaagcagca gtgtaccaca gataaatgaa gtgagacgta    36420
ataagggttt ggctcaagat aataaggaga tgtataatac tttttatgt ataatactt     36480 tgttccaatt ccctttatgc tttacttcag ttttgtttct ctagttaaat aactttgcat    36540
ctctaaactt tattattctt atttgtataa tgaagagagt aacttatgcc aggcaaagat    36600
tttacagaca ctagaaataa tatatacaaa atagttggaa tagttcctga aaaatagtag    36660
gttccacatg ataacaagat ttatgcttgt gctctttctg tattatttgg aaagaaatat    36720
gtgaagtgca ggaaagtggt gtgaagttat ttttgtggga tatctggtgt aatctttctc    36780
ttttatctat gttatcaaat attttttcaaa agctgtattt ctcattagtg cttttgtga   36840 ataaattaac taggaaaatt agaagaatgg caacaatata catcatagaa aggcatagat    36900
tacaaagaga gtatatacac aatacctgtc cagaagatgt ggtataagcc aatattttaa    36960
ttatacttat ttacttcaga tattgcaaat ttttcttatt tttataccTT ctttctttta    37020 atgcatttc ctatattttc attcactatg acattgtttt ctttatatca atacttatga    37080
agagaactaa ctattctaac tagggagtag ttagactagt tattttaaaa tacttcatta    37140
aaggactaca acgtgtgtac catctatgac ttagtattga ttgattgtca tctttcatgt    37200
tcttcataag tgggtaattt tgaacactgt tatattattt caaagggtgt tatttgtttg    37260
ttcagatgtt ttacaaagta attaactttg ttggcttgaa attgcaaact ctgtcttctt    37320
ggtgtcttag tcaattcagg ctgctatgac aaaaatacca cagactgggt agcttaaaca    37380
acaaacattt atttctcaca gttcagtagg ctgggagacc aagatcaggg tgccagtatg    37440
gttagcttct ggtgacagtt ctcttcttgc tttcctgaca tggctaaaag agaaagagaa    37500
tggaagtgag ttctcttctt aaagggtac aaatctcatt catgagggtt ccacagccat    37560
tatctaatca ccccccaaaa gcttcacctc ctgataccat cacattgggt taggatttga    37620
catgcgcatt tgagagggac acaaacattc attctatgac agatggtaat cgaagcaaag    37680
acaatgaatg ggtttgccca gcaagagtat gtagagtaaa aagagaagac ggtatgaaac    37740
aaatcactga aaaaaaaaa atgtaacagc cagaataaca tgatctaagg atacttggga    37800
ggaattatgc aaaaaatagg atttgagtca tgcaggcaaa ctctttaaat ttttactgga    37860
aaagacatga gagacagagt tatggaaaag aaagcatttg gtggaggcag atccattttt    37920
tctaataaaa taaattaata tggatgaatt gtacaatcat tccttagtaa atttcaaaac    37980
tgcatccagg caaatctctt atgcaacagg cctgccttag ttgtgtctac tgggtacttg    38040
tttattttta ggcatgtcaa attcgacttg tgaaaagatg attatattgt ctttaatgct    38100
gtcttctttt tcccaccaaa tgacagttat tcaaaccaga aactataaaa caaacataca    38160
gttatccgaa ctagaaaaca aaatcagaat ttacattttc tattttcccc acctcctgtt    38220
ggttctcctc ttaaacttct ccttgtgtgt ctgtaagctt gttatacact tttcatctct    38280 actcttttt attttctgaa gtcagctttc taacagatct ctttttccta agttcttctt    38340
cttcatggct gccagaatta accatctaaa atttaatttt gttatgtaac attttaaagt    38400
gcatattgac tcctcaatgt tgaacatatt tctatcctta cacttcacct acacaaataa    38460
```

```
tatttctgtt tttcaaataa tccgtgttat ttcacttctt aggggctttt catgtgcttc    38520
ctattttgtt ttaagtattt tgtgtcttca atatctaagc ttctataatc aactgaagac    38580
ttagccccaa tgtcaacaca tctttaagaa ctttaacctg taaggtcaga atagtccctt    38640
tttcctatct gcacataaca ttacaaactt atggcaatta taaaactcaa tacatattat    38700
actgtcatta ttggtttatt gctgctgaag attataattt tcagtgcatt gattatgtct    38760
tatttgtttt tactgcccct gttcctgttc ctctgtacct gcctcaacta catagcttag    38820
cagactaact gctatattac agttgctcaa tgaatgtttc ttgagtaaat cagttgagtt    38880
ccaaagctaa tccaagttgt gcgtttgaca aattagaagc ttggaactgt cttctgactt    38940
taagtttaga actattgcca taataaatta atgaccgatc tgccatgatt gcaggcaagt    39000
agagacttta tttcttatct caatgtcagt tgtctctttc tgccaatgca catttattt    39060 gatgattgtg cacatttata tctctggttt ttatttaaat aaatttagaa catatagctg    39120
gagacggtag ctcaaactga ggatgaaaat agacatttat caaggttatt atgtagctag    39180
cactgcatgt acacagaggt atttagggag ccacacatat gtccaaggca agacatatgc    39240
tcataaaacg tctgagaaga ttgtatcctt ttacctaatg ctaatcccca agcttagaac    39300
aaggcaagtg aaaggtcaaa gggataaaaa aatacaataa acaaataaa aatttacaag    39360 aagttgttat ggactaaata tttgttcccc tctccccaaa attgtgtatt gaatttcaaa    39420
atccaatgta atagtatttg ggagtctttg ggagctaaag agatcatgag aaatttgctc    39480
ttataatgtg agtagtgcct tacaagaaaa tgctggagag ctcactagat tttttcctc    39540 catgtgagaa tacaaagaga agttagctgt ttgcagccta ggagagggcc ctcaccagaa    39600
attgaccatg ctggcaccct tatctcagac ttctcaccct tcagaactgt gagaaataaa    39660
tgtttgttgt ttaagccatc cgttccatca taatttgtga tagcagtctg aactgactta    39720
gacaaaagtt caacagcaaa tttgagcagt tagaacacag aatccgcaaa cttgaagata    39780
agacaattga aatgattagt ctgagaagca gaaagaaaaa aaaacgaag aaaaattaac    39840 aaaacatacg gaactgtggg acactatcag gtgaaccagc ataacaatta cagtagttct    39900
agaaagagaa gagacagaga aagggaaga aataatattt gaaaaaaag tggccgagaa    39960 cgtcccaaat ttgataaaat atatgatctc aatatcgtag aagcataaga aaatccaaat    40020
aaactcagag atccactttg aggcacatta tgatcaaact gtcaaaggcc aaaaaaataa    40080
aaataaattc agaatcttga cagcaacaag agtaggaaat aatcatgggc aagagttcct    40140
taataagatt aacaactgat ttctcatcag agaccagaag acattgaaat gatatatcca    40200
ataaagaact gatattcaaa agtatgcaaa gaacatctaa aactcaataa ttagaaaaat    40260
aacccaatga taaaatgagg atgatatctg aacagatgcc tcactgaaga agatatagag    40320
acaacaaatg agcatgtgga aaaatgctcc acatcccgtc attagggaat tgtaaattaa    40380
acaataagct atgtcactgt atacttgtta aaaggactaa aattccaaac acaaaaatat    40440
accaaatact ggcaagaatg tggagcgaca agaactctta tttactgcca gtgagaatgc    40500
aaaatagtgc agccactttg gaaaatattc taatagtttc ttacaaattt aaagatggc    40560 ttaccataca atcaagcatt tgtagtcctt ggtatttact gaaataagta tcaagtggaa    40620
agcatgtcta cacaacagcc tacaaagagg tgtttatagc agccttattg ataattgcca    40680
taagttagaa gcaaccaagg tgtccttcaa tatgagaata ggtaaagcga ccttggtaca    40740
ttcatgcaat agaataagaa tattttagt gattaacaag aaatgagaca taaccaatga    40800
aaagacatga aacattaaaa gtatatttat aagtaaaaga acgcaatatt aaaatgttac    40860
```

```
ctactatatg attccaacta tatgacaaat tttattttat aaatgcttta ccacaaaagt   40920
taattctaaa aatgtttgcc accaaaaaac aaacaaaaaa catggtagag atcatcttta   40980
tagtttttta taataatcct cttgataaag attatatcat aagaaatctt gacagtttac   41040
attcaaggat atgacatttt atttacaaat taatgaaatc taataaaatg tgacaatgaa   41100
aatttagctg agtataaaag aacctaaatt agtagacagt gagagaggaa tgggggaggg   41160
gatgtttaca agaagttcta catcagtaca gaacttcata aattagtgga taagagcatg   41220
gtgaagagca attgtaaatc aaatgaaaat gttgtggaac tcttattagt atctgcagcc   41280
actctggcac tttaaacata tccagtagga gaggttaatt ctctcagcag gagaccactc   41340
acattacttt tttctcccta taaaataatg catcgttttg tcatgctggt aaaaaacaca   41400
taacattaaa tgtacctttt caaccaattt ttaagtgtac aattaaaaag tgtaaagtac   41460
actcacattg atgaacaaca gatctcttga acttttcat tttccattgc tgaaactttg   41520
tatccactaa actatcttct cctcagttct aagtaagtac ctttccactt tctgtttcta   41580
attttttgac tactttaaat atttcttct ttttctttc ttttctttt ttttttttt   41640 taagatggag tctcgcactg tcacccaggt tggagtgcag tggtgtgatc tcgtctcact   41700
gcaaccgccg cctcctgggt tcaagcgatt ctcctgcctc agcctcccaa gtagctggga   41760
ttacaggtga ctaccaccat gcgcaggtaa tttttttttt tgtatttta gtagagatgg   41820 ggtttcacta tgttggctag gctggtctca aactcctgac ctcgtgatcc gcccaccttg   41880
gcctccaaaa gtgctgggat tacaagtgtg agccactatg cttggactac tttaaatatt   41940
tcatatgata gaatcataca gtatctctcc tttcgtgact ggcttattta gcttagcata   42000
atgtccttga ggttcatcca tattgtagca catgatgtaa tttacttatt ttttaagtct   42060
gcataatatt ccattgtgta tgtataccac attttcttta ttcattcatc agtagacatt   42120
tgggttgctt ctacatcttg gccgttgtta ataatgctgc atgaatatgc atgtacaaat   42180
atctctgcta gatcctgttt tgaattactt tgactatata cccagaagaa taattaatgg   42240
cttgtatggt gattctattg tttagtattt gtggaacctc caaactcttt ttcatgaaag   42300
ctgaaccatt ttatatttcc atcaacaaac atgaagttcc taacttctct tactcgttat   42360
tttctattct tgaaatagtg gcttttctga tggttgtggg gtgatatctc attgtggttt   42420
taatttgcat ttccctgata agtagaaagt tgagcatctt ttaatgtgct tattggctct   42480
ttgtatatct tctttgcaga aatgtctatg taagtccttg acccattttt aaattgggtt   42540
gttctttgtt gttgtttcct tggaaaagtc catatattct agatattaac tcctcatcac   42600
ttatattatt tgcatttatt ctgtgccatt ccataggtta tcttttcacc tgttgttttc   42660
ttttatgtgc agatgattta agtttgatat agtctgattt gtgtatttt aattttgttg   42720 cctgtgcttt ttgtatcaca ttttaaaaat tgccaaattg aatgtcctga agcttttctt   42780 ttatttttt ctggaagttt aaggtcttac atttaggtat ttagttcatt ttgagttaat   42840
ttttgcatat agtatagggt aagggcccaa tttcatttca ttgcatgtgg gtatccagtt   42900
tcccaaacat catttgaaga ggctgtccgc ttccttgtac taaatgaatg gtgttttgct   42960
gcttctttta agagtctctg tttgtgtgta acttttgaca gtttgattat actgtgtctt   43020
ggtatagagt tttttagatt tatcttatt ggaattactt gagcttctta aatgtttagg   43080
ttcctttatc tcttaagatt taaaaaaatg gggtccataa tttacaagtt tcagaccttt   43140
tctcatttac ttctcttctg gtattcccat aatgcatatg ttgccctgct ggatggagtc   43200
```

```
ccataatttc tttaggctct tcttttcttt ttgctcctgt gactctaatt ttagaagttc  43260
tgtctttgat tttcctgatt ttttcttctg cctagccaag ttacctgttg agtcttctta  43320 gtgaatttt cagttcagtt actttataat tcaactccag aatttctgtt tggttcttca   43380
tagtttataa tctgttaata ttgctatttt gtttatttgt tatgttcctc atttcattta  43440
attgtctgtt catattctct tttaattcat tgcactactt gactaatttc aagttctatg  43500
tctggcaatt cctatatctt catttgtttt tggtcagttt ctggagatgt aattttttt   43560 tccttttaat gtgtgagaat ccttcttttc tttttatact ttgtattatt ttgttgttga  43620
gattttaaca tttaaaaaat cagtcaactc tcccagattt tgtgagatga ttttccataa  43680
ggagaactct cctcactaat tctgaataga gattctgtgg cctactcatg ctttttttct  43740
agtatgtttt cctttcttc tcctttaggc ttgtgtgtgt gatctgtttg aaaaggttg    43800 ttggtttcta tagaagaccc tcccctgggg cttgaggtac agtggccttt ctgggctgc   43860 attaaattgt tgtactggtg ctccacctcg tgtctctgtc tggaactgca gttttggtg   43920 tacctttgct tgcaaagacc gcattttat tagtacttga atataggcaa gtcagaagcc   43980
tgtccttggg caacctccct aaaagtcaaa atattgaaca taggagattt aaatgtttcc  44040
ttccaattgc attgcacagg gtggagtgag aaagactcta gtgagagaga ctggaaacaa  44100
tcatgatttt tcttgccagg ttgttttcac gatagcctgg aggtacagaa accttgtaat  44160
tggttctgaa gttctcacag aggcatttag tacatatgtt gttaatattg tgtcttgctg  44220
ttgaggttcc agggctgttc tgctctcttg ctgatgtcac tctcttccac atttcttagt  44280
cctttttaat aaaatgattt tttaatgatt aggacctgaa caattttcat cactattcta  44340
tggcacaaag actgcataca tttttacaag atgttagaat tgactatctt tgaagaaaat  44400
cttcataatt tttgtctaac tctgttgccc ctttctcctg ttttattatt cccatcatca  44460
acttaataca actagttttg atactcttct acatttatg ctgtttctta gataactttt    44520 tacatttat tttaaaactt ttagttatct ctataagttg tatcatttaa taaatctttt    44580
gaattccttt tatcttcatt gatagcatat atcatttgat agtttcttat gcagaaagga  44640
acacacccac attttgtcgg ctatcaaaga gttttgttgg gccttttatc tctgtccccc   44700
aaacatggcc tagggccaga cacagagtag gttttggtta tataaatgtt cactcattat  44760
ttcttaagca tctttgtgac agacactgtc ctaatcactg gggacggagc aatgaacaaa  44820
acagacaaaa acctatgact tgatggggct aatattctgc tgtggcaata taaaataaac  44880
tcataaagga ataaatgtat tgtgagcaga aaggggtgca attttaaaga gattgatcaa  44940
ggaaaacctc actgtgaaag ttccactgag caaaactctt aagggtgtga aggaatgaat  45000
gatagaaata cgactatggg gaagagcctt tcatgtcaag tgaaaagcaa gaacaaaaag  45060
cctggagcaa tataatgaat ctggaatgct caatatacag caacaaggtc taatgtagct  45120
ggagaggaat gaccaaggac aagagtaaca aagtataaga ttagaaagat aaagaggaat  45180
atttgtgggg aggtgggtgt aaaaagagg ataggttgtt tatggtctca taggttattg   45240
gaaaaacttg atatgactat aagttacata ggaaaacaga ggggcagcat gatctatttc  45300
tgatttgtaa aggacttctt tagctacttt gttgagaaga gactgttagg cagatgtgca  45360
cagaagtaga aacatggctc aggaggctct tgcaataatt gaagctaggc atggtggtgg  45420
aaaccactgg gaaatatagg aggtaattag aagaggtcgt ttagtcagtt caggctgaca  45480
gaatagaata gacttggtga cttaaacaac aaatatttgt ctctcacatt tccggaggct  45540
gagaattctg atatcagggt tctggcataa ttgagttctg ataagggccc tattcctggt  45600
```

```
ttccagaagg ccatatcctc attgtgtcat cacttggggg taggggagag agagagagaa    45660
agagagaaat agagggaatc cctaatttct tgtcttataa gggcactgat cttatcaaga    45720
gggctccatt ctcatgacct aatttcctca aaaagaccct atcaccaaac atcaacacac    45780
tggaaattag agtttcaaca tataaatttg aggtagggga tataaagatg taatacataa    45840
cagggtaaat attaatagta gagagcccaa agaaatttgt ttatggatat aaatgtgagc    45900
tgtaatagaa atgattaatc gatacatttt attaacatga aattgacaaa taaaacatct    45960
ataaccactg catcttacac tggatgtcag tcacttgtgt tggtcataga attttttcttt   46020 gcctctgcaa agttctgttt ttcagctggc ttcctggaaa tgctgccttt gagaatgtac    46080
tgccactccc ctcccagtta gccaatgcta ttcatatgga aataaagaat agctcaccat    46140
catggccatc tgagaacatg atgtagcttt ctataaatca gttaatgaga ttaatttaaa    46200
aataacaacc ttaactgtag tgctctaata ttttgatatt ataaccaaat tagaaatgat    46260
gctttatcag tgtagtgata ataacattta aatggctgag tagtagtacc tggtaaaagg    46320
gaaaactaag tatggttttt aagatacaaa taatgttttt aagtaaagaa gaaagctatt    46380
ataattccat gtgcctattg acattatata gtccttcgat taaccatttt ccccctttcc    46440
ttctgatttt tcttagatgt tcttggcagc tctgtcactc agctttattg ctaagacact    46500
aggtgcaatt attatgaaaa gttccatcat tcatatagaa cggagatttg agatatcctc    46560
ttctcttgtt ggttttattg acggaagctt tgaaattggt aacatttatt ttctatttta    46620 ataccaaac ttgcaaagtt aaaaaatata tatgctttac accactggtt atcaactggg     46680
gtaaatttat ctctcacagg caatttggca ataactaaaa acatttgtgg ttgtcataac    46740
tgcacagggg ttgggggcaa tggaagtgct actggtatct aaaggtagag gtcagggta    46800 ctgctaaata ttctataatg cacaaagaat gatgtaactg aaaatgttga tagtgaggat    46860
gttcagaaac cctgattcta cacaaattca ttttttgcaa actaacgcca tgtcatactt    46920
tacctcccct ctctcaagat gaagaaactt tgggagagga ctgttattct taaggagaaa    46980
ggaatctttt cagagcaacc tacgttagac ctctattgtt tcactgagca cacaaaaatc    47040
tttcctttga aatactgaag atattttgtt gtcttcattt tatgttggat ttctccaata    47100
acagctcagg gaaaacattt tctggttcat atttgtgttt ttccctatta gtaattttt    47160 tctagataat ttataagatg aatattaaat tttctgggaa tttttctctt taaatttttt   47220
tcttctaaat ttccattgtt tttctttatg tttcattaat ctttgatgcc atcatccatc   47280
ttaccatatt aagttctaat ttgtatattt aatctgtatt ttatatttac aacagcactt    47340
tattattccc ttattatttt taggctgcca gttctgattt catggatgca atgtgcctt     47400 gtacccgtaa aggtactaaa ttttttataa agtaaaaaaa aaatttactc attcattttg    47460
gtgcttttat tccaaattat ttttatgcta tttttttttca gaagtgctca gttatcctta   47520
actgctattt gttattgtt atgcctgagg ctccagatgg attagaagtg gtcatgactt     47580
tttttttttt ttttttttgag acggagtctc gctctgtcgc ccaggctgta gtgcagtggt   47640
gcgatctccc ctcactgcaa gctctgcctt tctcctgctt catcctcccg agtagctggg    47700
actacaggca cccgccacta tgcccggcta attttttgta tttttagtag agacgggatt    47760
tcactgtgtt agccaagatg gtctcgattt cctgacctcg tgatccaccc acctcagcct    47820
cctaaagtgc tgggattaca ggtgtgagcc accatgcctg gcctctggaa gttcttaatt    47880
aagttccgcc tttctgtggt ttaatagcac ctctgtccat ctatttttat cgttagtatg    47940
```

```
aaacttcttg aagacagatg ccatggttta ttcttttttca agtaactttc ttatttctgg    48000
ctctgagctt catgtcaggt tcatgttaga aatttaaata atattaagaa taaataaaga    48060
aacgcatgaa ggagcacctt accctcatca ggaagattca tctccatttt tcttcattcc    48120
agtataatcc agtcaactcc aaattttttca ataaaatttt acttcactaa tattgccaag    48180
taattcaagt gctttttttt tgtatttaaa acaacttttc aatgagtggt ctaatgtagg    48240
tgaattcacc ttctcaatta aatcacattg tctttgaggg aaggcactat gtcttggact    48300
ctatttgcat ccattctggg gttttcaatt ctagacgcaa aattgaacta agctgtatca    48360
acataatttt gttccctttc taggaaattt gcttgtgatt gtatttgtga gttactttgg    48420
atccaaacta catagaccaa agttaattgg aatcggttgt ttcattatgg gaattggagg    48480
tgttttgact gctttgccac atttcttcat gggatagtaa gtgttaaaaa aaaaaaaaac    48540
ctctgtgcca ctatcagtac cttgtaaatt aggagtagaa ttttattatt atccctttaa    48600
ataggcagtt accttttgag aagataccca ctaagtgtgt acagaaatga aatagtgtct    48660
atttgtctac ataatcattt tatttatcgt agctttcata tactttgaaa taacaaaaag    48720
actaaactgt agagtttcaa atgaaataaa taggctttttt atgaattttt agtataacgt    48780
atatactgta cgtctttgcc tataagattt tgattatttt ttataagacc tcaacactta    48840
cacctatacc cactgaagta tagttgttcc catcatttca ctgaagctgt tattcctaag    48900
gtcactgtgt agtyataatt acagtcagat gctcctgaga gaaagttaa aatggcacat    48960
gggggagaaa cttatttttc acattacagt taatgtagcc agttcaagga tgatatgatt    49020
ctacctcttt ccatcatagt gctatgcctt gcatggtctt ggcttcatga tccaaattgt    49080
ggcaacgtat ttccaggcaa caagatagaa gaagaaaaga ataagaagca acaaacagtc    49140
cacacaggct gaggcttaag aagcattttc agaagcaaaa tatctctact gactttacat    49200
ttaccagatg ttagttacat ttcacacata gatatataaa tgctgaaaaa aatagacatt    49260
attccaagtt accaagttcc cggttaaaaa tcccaagtat aattactgtg aaggaaaga    49320
agagaggata ttaggagaca atgagcagtt tctgttagag acaccaatta cttactcatt    49380
gccaaatcca gcaatgacat catttgctca ccatattaaa tccattcacc caccatattt    49440
ggcccttata ggaagtttct tcttagtggt actgctctag cttgttttca tcatactgca    49500
ctctcttgat tcattttcta tctttgtgtc ttcttcatca tgtccatttt ttttcatctg    49560
cttttggcac cataccgtca gagtcctcta atttccttttt taatctttat ttatgattct    49620
tcatgagttg tatggaaaat aaaccttaaa ggcaagtatc acagcttcat cttccattct    49680
accctaaaat taaggaccac aatctagatc agcattgctc taaatatgcc ataatatgtg    49740
acactttgc acctggtatt tctacagcct tgaatacctt tgtttctttg tctacccttc    49800
tattcatctt ccagattcgt tttacctgtc attctcatgt tgatgtcttc tctgatctat    49860
tcccgcaacc tccaagcaaa gttgatcata tcctttgtct ttgtgacaac tcaggacctt    49920
atatattaaa cttataactt ttatcatcta tgtttatact agtgtgaaat tccctaagta    49980
caaaaactgt gtgttttatt tctagctctt tgaagcttag cataatgcct ggaatacagt    50040
aggctgcctt tagagctcac gtggtaccta attatttatg gatattaaca tctctgttat    50100
tcctatcaag ttttctctca tctagttgaa atggattaga ttttatttttt actacatttt    50160
gaagagtcat acattagagc gtgtgtgtga atatgtgtcc atgaaagaaa atctgacaga    50220
ctgatcatct ttgaagataa ttcaaaagga tgaatggtta cacacaatta ataattcttt    50280
tttaaaaagg tgaaactagg atatttcata tcttgaccaa gatataacca ctcctaggat    50340
```

```
aatagcaagg tgataaccca cttagcctgg ggtgtattga attatctttc ttgctggaca   50400
cttccatttc acttttaccc atcacatctc ttaaaacaca tgctgggaaa ttgacagaaa   50460
gtactctggt aatttgggga agataatggt gcaaataaag gggaatattt ctctgtattt   50520
ctaggaaaag tgaaaatatt cagtagataa gcaaaatgtt taattcagtg atgttcttac   50580
agttacaggt attctaaaga aactaatatc aattcatcag aaaattcaac atcgacctta   50640
tccacttgtt taattaatca aattttatca ctcaatagag catcacctga gatagtggga   50700
aaaggtaaga attaatattg acagtaaaaa gtcttctaaa atgtatacat ttaattacat   50760
ctctaaaaat tgttgtgata ttcattagca aaatttaatt aagaatgaat aggaaaaaca   50820
tttgactctt acagacataa ttatagtgtt aatatacaca gttcgcccat taacaacaca   50880
ggtttaaact acgcgttttc acttctatgc aaattttgtc catctgaact ggatgataaa   50940
cctgccggta agaatatctg acattttcta tatttggatt gaacagggcc aactgcagaa   51000
cttaagtgtg catgaatttg agaacacaca ggcagccctg taacaaattc cttaatatac   51060
caagggatga ctgtattata tgtaaaagca tttagaagta gatcagaaaa gagaatattt   51120
tcaataggaa attgacaaag aatatatgca ttaaagtaaa acagaaggaa atggtataaa   51180
tatgtaaata atataacttt gctttcattg caaaaggcaa actattatat catttaaaga   51240 cttttttgcct attataacac aaattataaa ttataattgc aaattgtact gctaaagatt   51300
tttttaacct attaaataga aaaagactaa aaatacatag agacgaggta gaggcaaaaa   51360
aggatttcac attgtatata ttgctggaag tgtatacgtt tgtaaatctt tctggagatt   51420
cattatcaat atatgttaag aacaaaaata tacttaccta cttagtctga aattctgcta   51480
ttattgatta atcttaagga aataaccagg aaactgcaaa aggacttatt tacagttata   51540
gtcatgataa acctaataga ataaacaac aaaaagaaa ttaaaacata agatactgaa   51600
taaacacatt tggaaactta ttcagcacat tactgtccag tcattaaagt tttgatatta   51660
aagaaatctt aacaacatgg aacaattgtt ataatatggt gttaactgtg tataccattt   51720
aacaatatga actagatttt taaatatata atggatataa tgaatataat gtatatgttt   51780
tgtgcaaatc tagaagatat ataaaaagc ttgaggtgat cttctgtgtg taatgtgatt   51840
acagataatt tttacttgtt tgtgcttttc tgtatgatat ggcttgactg tgtccccact   51900
caaatatcac cttgattgta ataatctcca catgccaaga gtggggccag gtagagataa   51960
ttgaattttg ggggcggttt cccccatact gttctcgtgg taatgaagaa gtctcacaag   52020
atctgatgat tttataaatg agagttcccc tgcaaaagct ctcttgcctg ccaccatgta   52080
agacatggct ttgctcttcc ttcatcttcc gccatgattg tgaggccccc cagccatgag   52140
gaactatgag tccattagac cctttttcctt tataaattac ccagtctcag gtatgtattt   52200
attagcagca taagaatgga ctaatacacc atattgtcaa agtttgcaaa gtgaatataa   52260
attacttgta cttgtaaatt aaaaaaaaat aagtagaata attaagagtt tacaagtagt   52320
taaatttgta atagaaatgc taaaattaat gtttaaaatg aaacactctc ttatctacat   52380
aggttgttta aaggaatctg ggtcatacat gtggatatat gtgttcatgg gtaatatgct   52440
tcgtggaata ggggagactc ccatagtacc attgggcctt tcttacattg atgatttcgc   52500
taaagaagga cattcttctt tgtatttagg taatgtacac aaaatattaa attgtatgat   52560
cactttccct ttgtctactt ttgaaatagt agagttacta aacttattat tttacctatt   52620
agaacatata tttgggtata tgtattgtat catatttctt ttaaaaacat ggtgaataag   52680
```

```
aaccatgcat tcttggcatc tagtaaaatt gctttataat attttcaggt atattgaatg    52740
caatagcaat gattggtcca atcattggct ttaccctggg atctctgttt tctaaaatgt    52800
acgtggatat tggatatgta gatctaagta agtacaacca gaacaaggta ccatgataac    52860
gtctttctaa gcacacatgc gaaaaacatt ttttcaaata actgaattca ctctttcaat    52920
agtcctttgc ttaatataat tagaaagtta caagtaggaa ataaatgtat tactaatcag    52980
aataaatata aaatccagct cctatttata ctatctttat aactaagtgt aaaatgagag    53040
aatgtaaaca aatttatttt catgagcttg gtccaaaata accaaatgta aaatgtctcc    53100
ctcccaaact gactgtccag tcaagtaaat tttattttc agttgatggt ggcttggatg     53160
ttgatgtgta caacttaaag tttgctttgc taaagtcttc ttgtggctgc tgcattgatt    53220
tatggctgga gtcatttgag agacttcact gtgtatttta tggtcatttt ccctggtcct    53280
agcagagggc ttggcgtatg gcaatgttca gtaagtactt gttgaacaaa ggaataaagc    53340
agaggacaca taaataaaat ctatgatttt cttcttcatt ctcagagcat actttccttc    53400
ttatctcata gatgaaagag atgccatgtt ataaaaactg tctcaacttc aggccctttt    53460
ccctaaaaat attcttgcac catatctatc tttatcttct ttttcttttt tgcagctcag    53520
tggaaaatat atacatctgt atccaatgtt gatagatcta gctggagctt agattctccc    53580
ttcccgcttc tttatctcca tcttctcttt tattcagcaa acacacccaa gtatttccca    53640
tctttatatg tagatacagt tttttatacc cccacacaac tttccagctg aatccttttt    53700
ttattcctct ttagaaccaa gcacctagga aaatatcagc taaattagct aagatatctc    53760
accttctcac ctcccatcca cttctaaatc cagtataatc tgcttctgtt attagtgaaa    53820
cacaatcaat ttctacctac tttactatag atttgtaaat gggtatattt ctatcatttg    53880
cgttaattga tatttccagt gcttcttcat ccattttccc tccttagata tcttattagt    53940
acctaaagca caatatgtca aaatctgatc tcatcacctt acctccaacc ccactgtatt    54000
ccctatattc ctccttttga tgaatatcca taccttattc aattattgac tgagttactg    54060
tgccctgtaa tctcacattt tctgcatttt acacttggta aaacttttcc ctcttttca     54120 tttgcatagt tcttgaagcc tcttccaaaa tgtggatcct cttagagaag ccttacttca    54180
ccactttcca ttagtctcaa attaatagcc aagagcatgc ctttattgta acccttctca    54240
caatgagcta ttaatatttg tgtgcttact tgccatctct ttaccacatg acagaatggc    54300
atgttcttag caaataataa ttagttaagt ttgtgaataa ataaatatga ttttccacct    54360
cattaggcct tcaatagatc attccaaaga gatcaaagga ttcatttcca agatgggata    54420
gacatcacag tgggccagca acagccaaaa acttgaaagt gtttgctaat ctaaaactat    54480
aaagaaaata cttgataaaa tgttttacat gttcaatttt agacatatgc cttagagtag    54540
ctacacatta tgtacattat ttctactcat tcaactccag tttcatcact gctttatcac    54600
gaagagtaca gaaatacgtg gtaaatgtcc ttaggttaat tattttataa gctctctaaa    54660
taagaaatta ttacattatt tgagaattca tcaccataca atttctaaca ttgaatgttc    54720
agatatcatt atatcttctc ttattcagtg atgagtatga gcttcactta caaagtatac    54780
tttggcaaac tccaatgcct aaaggagctg aagacataaa aataaatgag taagagtgc     54840 caggaacagg aatttagggt gtgatggtta gaataggaga attctttttgg ttgtgaactg    54900 ctctccccat gcatccaaaa gcacttgtgt tcctcagctc tggcctattc ttttaatgca    54960
caaatttagg ccctgcattg gcaaggactt ctgattggtt tccaagaaaa tccaaacacc    55020 aaaattttg tgtagaattt ttcaattttt aagactgtga gtgagccaag aaaaactttt      55080
```

```
tctcacgtcc tatctagcgc gattatgacc cttagttact atgtgtagaa cagtgaaaga   55140
acagaaaaaa aagtcatcaa aattacattt gtcacaggtg atgaataaat actttgcatg   55200
tagatggagt cactgattta accaatcatt tcctgaagtc tgagttgttg attatgacat   55260
ggtatgatca tataaatcaa atttaaaccc agatctgtgc atacttgaaa ataattattt   55320
ctaggtagtt tgttatcaag tcaatgttat cttatattag tgagttttct tatagattag   55380
agtaatggca ccatttaatc gtgccacaaa cttctgtggt gtgtgtttct gtatgcatat   55440
gcttttttat ttcttattat ttttctttta ttatggtaag aacaattaaa atgacatcta   55500
ccttcttaac aggttttgaa acatacagtg gacccatgaa caataggttt aaattatgct   55560
cgtccactta tgcacagact tttttcaata aatatattga aaaaatttgg ggagatttgt   55620
gaaaatttga gaaaatttat agatgaattg catagtgtag aagtaaagga aaccctaaga   55680
aaaaggtata tcatgagtgc ataaagtatg tttagatact ccactatttt atcatttact   55740
accataaaat atacacaaat ctattataag aaattaaact tattagaggg tacaagatgg   55800
ccaactagac acactcagga agcaccactt ccactgagga agcccaaaat attgaataaa   55860
ctaacatact tcgagcatat cttttgagag aaaacactga aagtcaatag agaggtgaca   55920
cagacactga ggctgaagag agagaaagct ggaaacccag tgcagggttg ttgaacacca   55980
gagatagttt ccagccctga gtggctccta gctaaggggt gagtaaagtg gcagtgggac   56040
agcctactct cactgttgac atctgggatc ctacctacaa gagaacccac gaccccagga   56100
gacattggaa caggcagggg catctgccca gagagtaggc agaaatagaa ctacagccag   56160
ccttgaaccc aggggttttt gcatgttggg tagctgcagc agaacgcagc cataggcgcc   56220
caacatccaa ggctctcttt cttccaccaa gtagctctca actcacctga cttctgagcg   56280
aagagacagc ggggccaact ttcctgtgag ctgggacaca tctgtattgt aggcccttct   56340
gcccgccagt ccctcccagt actcctgcct ggccacacct gcaagaatat gtgcacagca   56400
cagcctccac tgctcagcct gagggttttt tcaaggaccc ccacctgagt acttcctcag   56460
tatccttgga gcacttcaga tccccccagtg tagctactgc ctgaaccaga ggggccagac   56520
agtggagaca caggctagtc ccaaaacccc agggctgcag tgcatagctt gggagtgtga   56580
gctgagattg tgcccagca ctcaagcaga ggaagaattc tgaatctcag aacactgaga   56640
ggggtgagat gcacgggttc atgggccagt gcagaatgag acatgcctca tttcataggc   56700
ccagtccagg aaggctgtgt cctgtctgcc agctgctgcc tctgcctaag ggagctccat   56760
ggctcagaac agtttcctaa caaaagaaat gcaagtgtgg caccagtgac cagagcggga   56820
gattgggggg gtgtcccta tggcccaggc acaggcctgt taaggggtc atctctcttg   56880 cccgctgcca caagcactgt tgtaaacaca ctgaaaaaca aaagagttat gtccccgagt   56940
aacagcttat ctgccagcca ttactcttaa gcaccattta ctggatcaca gctcaattta   57000
aaacatctgc ctatatattt gagactgtac ctcactctgt tacccaggct agagcgcaga   57060
gaagcaatcg tagctcactg cagcctcaag ctcctaggct caagccattc tcccacctca   57120
gccttctgag tagctgggac tacaggcaca caccactaca cttggctaat atgtgttatt   57180
ttctgtaaag acagggtttt ccatgttgcc caggctgatc tcaaacttct ggcctcaagt   57240
gatcctccca ccttagcctg gcaaagtgct ggaattacag gcttgagcca ctgtgcctga   57300
cttcaaaaat agtttgtcag tatacattgc atatgaaact gagagcaaga atctagctat   57360
aaataaaaat attgtgcaga gtcttatccc agaaattaaa ccaactgacc atactcaact   57420
```

```
tataccacag ttaaaggaac accattcctt caagatgaaa agaatcaac aagaaatctg    57480 gcaattcaaa aagtaagaat gtaccttaac cttcaaatgg gtgcatttga gctctccagc    57540
gatggttctt aaccacattg gaatgactaa aatgacagac aggcaattcg gaatctggat    57600
ggcaagaaag ctcattgaga ttcaggaaag tgctgaaaca caatttaagg aattcaataa    57660
ttccagtaga atgatccaaa agctgaaaga cataatagcc attaaaaaaa cactacttct    57720
ggaattaaaa aaaatactac atggatttga taatacatcc agacctttag caacagaaca    57780
taccaaagag agaaaagaat ctcagagctt aaaaaccagt ttttataatc cactccatca    57840
gacaaaaaga aagaaagaaa aaaaaacata aaaatgaaga aaacttctag gaatttggtt    57900
tccttctgta aagaaaccaa gcctatgatt cattggaatt cctgagagag aaaaagagag    57960
agtaaacaac ttgtaaaacg tatttgcaga tatagtccat gaaaatatcc tcaaacttgc    58020
tagagagatt gatatgcaaa ttcctaaatt acagagaacc cctttgagat gctataaaga    58080
tgacaatccc caaggcatct actcattaga ttccccaaag tccacatgaa agaaataaat    58140
attttaagat tttttttgggg ggcagctaga gagatggatc aagtcactgt caaggggaac    58200
cccatcaatc ttgcagaaca cctttgagca aaaaccatac aagccagaag agattgggga    58260
cctattttca gcacccttaa agaaaagaaa tttcaaccaa aaatttaata tcccaccaaa    58320 ttaatttttgt aagtgaaaga gaactaaact ccttctcata caagcaaaca ttgaggaaat    58380
ttcttatcac taaaccagcc ttataacagg tctctagaag agtgctaaac atggaaacaa    58440
aagattaata cttgccacaa caaatactca cttaaatagg tagcccagac acataaagca    58500
actatacaac caagtctatg aaacaaccag ctaacaacat gatgccatga tcaaaatctc    58560
acgtatcaat aataaccctg aatgtaaaca ggctaaatgc cccaagtaaa agacactgag    58620
tgacaagctt cataagtaga caaaacttag ccttctgttg tctttaaaag acacatctta    58680
catgtacaat acccacagga tcaaagtaaa ggaacggaaa gagatctatc catgcaaaca    58740
gaaaacaaaa cagggcagta atcactattc ttatatcaga taaaacagac attaaaccaa    58800
aaaccatcaa gaaggacaaa gaagggtatt acataaggat aaagtgttcc attaaacgag    58860
aagacttaac tattctaaat atatatgcag tcaaagtgg aggacccaga tttacaaaaa    58920
agattcttag agacctaagg aaactaaaaa cagacagcca caccatgata gtggaagact    58980
tcaacaactc actgacagtg ttagatatcg aagcagaaaa ttaaaatgta aattttggac    59040
ttaaactcaa ctctcaacca actggatcca aaaacatcct acagaatact ccacccagca    59100
ctatcagaat atgctttctt ctcatctgca tatagattgt attctaaaat caatcatatg    59160
ctcagtcata aagtctcaat acattcaaaa aattaaaaga ttttgagtac attcttgaac    59220
aaaagtgcaa taaaatagaa atcaatacc aaaagatt cttaaaacca cccaaaagta    59280
tggtaattca acaacttttc ctgaataatt cttggtttaa gaatgaaagt aaaaccgttt    59340
ttgacattaa ataaaataga gacacacctc actaaaatct ttgggatcta tctaaagcag    59400
tgttaagagg aagtttacaa tgctaaaggc cttcatcaag aaggcagaga gatttcaaat    59460
taacaattta acattgcact tacactaact agaaaaaaaa aggacaaccc caaagcaaac    59520
tgaaaataaa taacgaaaat cagaatgaaa ttgtgatgca aatgtatac aaaagataaa    59580 taaaaccaag agtttgttat tcaaaagaat acaaaaagat taatagactg ttaactagat    59640
taacaaggaa aaaaaggaga cccaattaag cacaatcgga aatgacaaag atcacattac    59700
aactcccata gaaatgcatt acaaatgccc ctctgcacac aaattagaaa atctagagga    59760
agtagagtca ttcttggaaa caacctccaa agattaaacc agaaaaaaag tgaaaacctg    59820
```

```
aacagaccga taacaagtta tcaaattgaa ttagtaataa aaaacctact gaccaaaaaa   59880
aaagccctgg accagatgga ttctcagcca aattctacta attctaattt tattctaaca   59940
taaaagttcg cttttttaaa gttaaacttc aaatttaagc acagaaacac atatgtacct   60000
catattatct catctacagt caagagaagt gaaaacaaat gtgaagatgt actattaaag   60060
cataacttta tacaattgac tgtaatatat acgttactgc tgtaataatt tcatagcacc   60120
tcctgtaatt gtagtaataa ggttgtgttg aaagcacctg cttaaaacac catgtgacac   60180
taattatctc cacatgaaca gttcctctct ccaataaatt gcggattgca gcaaaatctg   60240
attgtgattc ttgtgcgttt ttatactgtt tagtgcaata ctgtcaactt tgaataacac   60300
cgttggagcc atatgaattg ccactagtga tgctgaaact gctcctaaga aactgagaaa   60360
agtcacgaca ttcaagaaaa aagttgtatt gcttgatata taatgcagat tgaggtcttc   60420
agctgcccat tgtttcaata caaatgaatc cagcataaag atcattgtaa aaaacaaaaa   60480
aagggaaaaa aaaaggaaat tcatgatggc attgctgagt ctatgccagc aggcacaaaa   60540
tcttgcactt ttagtaatat accgtcttat ctcatattga aaatgaaatt gttatatggc   60600
tgcaaacttt tataagaaag gcataaccac agactttaat gtgatttgag aaaaagtgaa   60660
gttattatat gaccatttaa agcaaaggaa ggtgagggat ctaaaactgg agaaactaat   60720
gcaagcaaag gatggtttga taatttttaga aaatgatttg ggtttaaaaa ttttcaaaat   60780
aacagaagca gcagcttctg ccaaatgaga gaaagtgaac aagttttcag attccactaa   60840
gaaaatcatt gagaaagcat atctgcatga gcaggttttt aatgcagatg aaagtgtcct   60900
atcctgggga aagaaagcc acgaaggacg tttattaata aagaagagaa gtgagcacca   60960
ggatttaagg caggaaggga tgaggtaagt ctactattct gtacaaataa ggtcaggctt   61020
attatcaaaa ctgctagtat ctacaaagtt gataagtccc aaaccttgaa ggcaaaagat   61080
aaaaatcaac tgctagtctt ccagtcatac aaaaggaagg tctgaacaat tagtactctt   61140
tttcagaatt gtttccatca atgccttgtt cctgaagaca ggaagtagct tgacagtaag   61200
ggactgcctt tacagttctt ttcatatcag tcgatgcccc tggtcaccta gaaagcccat   61260
aagttcaaca tcaaaggcat tgtagtgatc tatttcttcc accacaacat ctctaattca   61320
gcctctagat catggagtca taagaaactt taaaggatca ttacagatga tactctaacg   61380
aaaggattat cagtgctatc aaagaaaatc ctgataggca gaacatcata aaagactaga   61440
agaattacac catttaagat gctattgtta tagggaaaaa aaaaagtgaa agtcattaag   61500
tgcaaaacaa tacatttcta ccagagaaaa ttttgttcag atgttgtgca taaattcata   61560
ggattaacaa catggccaat caagaaaatt atgaaagaga ttatggatat ggaagaaaaa   61620
gtgaggagta aagaatttca agatatcggt attggagaaa ttcaagagct aattcatacc   61680
tcatcaggga agttaacaga agatgacctg atggagatga gtgcctgcga actagtgtca   61740
gatgatgggg aaggagacat agaagcagca gtgccagaaa caattgttta ttaggcaatc   61800
tagcagaagg attctgataa ttcaagactg ttttggctt cttttataac agggactctt   61860
gtctaatgtg ggcactgaaa ctaaagcatg tgttggaaga aggattagtt ccatttagaa   61920 aaattttag agaaatgaca aaccacaaa gtcaaataga aattatggcg tatttatgaa   61980
atagttactg aatgtacttg cctctttttgc cttccctcta cctcctccac ctcttccacc   62040
tcttctaccc tagtgaaagc aagaccagtg cctcccattc cttctcctcc tcagcctact   62100
caatgtgaag agatgagaaa gatcttatga tggtccactt caacttaata gtaaatatgt   62160
```

```
tttatcttcc ctgtgatttt ctttataaca ttttttctct agcttacttt atattaagaa    62220
tactatatat aatacatata acatacaaaa catgtgttaa tcaactgttt atgttattgg    62280
taaggattct gatcaacagt agctggtatg atttggatct gtgttcccgc caaagtcatg    62340
tagaattgta atccccaatg acggaggtgg ggcctggtgg gaggtgattg ggtgataaag    62400
gtagtttctc atgaatagtt taacaccatc cccttgatg ctgatctcat gatactgagt     62460
gaattctcat gagatttatt tgctcaaaag tgtgtaatac ctccccctc tcttcttcct     62520 gtagagactg cagaactgca taactgaaac tttatacca ttgactaaca actccctgct     62580
tccccttccc cttaatcact ggcaataacc attctactct ttgcttctgt gagtgttact    62640
gttttatgtt cctcacatga atgtaatcat gtagtatatg tccttctgta actggttcat    62700
tttgcctaat gtcctcaaag ttcatccaag ttatcacata ttgcagaata tccttctttt    62760
taaagactga ataatattcc attgtatgtc tatacaatat tttctttatc catttatccc    62820
tcagcagaca tgaggttgtt tttacagcta gctattatga atagtgctgc aatgaacgtg    62880
caaatgcaaa tggtctcttc aagataatga tttcaattct tttatatatg tacccagaag    62940
tgggattgct gggtcatatg agagttctgt atttaatttt tgaggaatct ttataatacc    63000
ttttatactg gctgtacctt tttgtattct accagcagtg taccgtgttc aaatatctcc    63060
acattcttgc aaacactttc tttcttaaat gatagccatt ctacaggtgt aaggtgtagg    63120
aaaagagtgg agttgtgctt ttgatttgca tttccctgat atgcaatgtt gaaaatcttt    63180
ttattgacct gttgttcatt tgtgtgtctt ctttggagaa atttctattc aggtatgtag    63240
cctaattgtt ttttcaaatt aattttttt ttttgagtca ctctcactct gtcacccagg     63300
ctggagtgca gttgtgtgat ctcagctcac tgcaatctct gcctgccagg ttccagtgat    63360
tatccagcct cagcctccag agtatctggg attacaggtg cctccaccac acctggctaa    63420 ttttttgtatt tttagtagag atgggatttc accatgttgg cctggctggt ctcaaactcc    63480
tgacctcagg tgatccaatt tgtccttggcc tcccaaagtg ctgggattac aggttatcag    63540
ccactgactg acatatataa aattgtattt ttatcatgta cactctaatg ttttgaaata    63600
catatataag tggaatagtt aaatttagct aattaacaaa tgcattatct tacatagtta    63660
cttttgtagt ggaaacactt aacatctact ctctcagcat atttcaaaaa tacaacatat    63720
tgtggttaag aatagtcacc ctgctgcata ataaatctct gcaatttttt cctcctaatt    63780
gtaattatgt atgctttgac cagtatctcc tcatgtggga gatcagtcag agtggtggaa    63840
gaagctatag ggaaggaagc aggcctttag aaaggtcaga aggctctgca aaacttcagg    63900
ggagactaag ctgaagatag ctgttctctt accctgaggc agagcacaag aaataggtat    63960
aaggaagtat aggggaattt atctaaatag gcttgtctac ccatgttgtc cagaaactga    64020
cctttgacca tccgtacacg tgactgttcc cagtaagggg gaacaataat gttaattaca    64080
cacagattgt gttggctcca gcctttcggc attatgtctg tactaaataa aagtgagcag    64140
ctccagcttg ttgggactgc tactcactct ttggcagtcc cctagccact ctttcaccac    64200
atacctgtgt ctgagtactc ctttcatctg ttggtaggcc agggtctacc aggatggacc    64260
aggcatcctc aactccactg ttctcccaac cacctggctt ctggtagcca ccattctact    64320
cactaataac taattaattt ttatttcaat agcttttggg gtagatgttg tttttcgtta    64380
catgggtgaa ttctataatg ataaattttg atattttaca tacctgagta atgtacattg    64440
tacccaatat gtagtttttt tatccctcag tccccttcca tctttcccct tctgagcctc    64500
ctaaatccac cacatcaatc tgtatgtctt tgtatcttca tggcttagct cccaatgata    64560
```

```
agtgagaaca tacagtattt ggttttccat tcctgagtta cttcacttag aataatgtcc    64620
tccagttcca tccaagttcc tgcaaaattt ttcatcgtta ttatttttt gctattgagt    64680 tgtaggattt ccccgtgtgc tttagaaatt aacccctttt catatataaa tgatttataa    64740
tattttattt tattctgcat atttcttttt tacccccattt attgtctctg ttctgttcca    64800
ttggtctata tttctgtctt tatgctggta ccatattata ttaattacta tagctttaaa    64860
atacattttg taattaggaa atatgaggca gctttattct ttctcaatgc ttttttggct    64920
atttgatgtc cttcttggtt ccatatgtat tttagaattg tttgttatat ttttgtaaaa    64980
atactattgg gcttttgata ggtattgtat tgaatcttta catatatttg ggtagtatgg    65040
acatttacta ttaataagtc cttcaattat taacacagaa tgtcttttcta attatttatg    65100 gcttctttat ttcctcagtg tcttgaagta tttcatgcac aagtctttca ccttcttaaa    65160 tttattttttg tgttttattc tttatgattt tagtgtaaat ggaattgctt tcctaatgtc    65220
ttttcaaata gtacttggtt aattcataga aatataagta atatcttata attatttttgt    65280 atcctgcaac tttacagaat gtgtttattc aattctaaca ggtgtgtgtg tgtgtgcatg    65340
tgtcatcttt agggttttct atatacaaaa tcatgccatc tgcaagtaga ggcaatttta    65400 cttcttttctt tcaagtttga atgtctttta tttcttttttc ttggttaatt gctctggcat    65460
aaaatggcag gactgtgttg aatagaagtg atgagaatgg ccattcttcc tttgttcctg    65520
aaagctttct gttttttcact cttgaattta atgctagctg tgagcttttt aaatatgcac    65580
ttcattttgt tgaggcaatt tttatctatt cctagcttgt tgaaagttttt tatcacaaaa    65640 cattgttgga ttttatcaaa tgctgtttaa catctgcata tttgatcatg tagatttttgt    65700 ccttttttttg ttaatgtgtt acattacgct tggtgatatt tgttaaactt agcatttcag    65760
gtataaatcc cccttgaata tagtgtagta tccttttttat atgctattaa atttggttta    65820
ctagtattgt ttgaggattt tctcctctgt cttcatcaga tatattggtt tgtagttttc    65880 ttcctttttgg tgtctttgtc tggctttggt atcagaataa tgctggcctt ataaaattag    65940
tttgaagatg ttctcttctc ttcaattttt ggcaagagat tggaatggat tgccattaat    66000 attttctttta gctatttagt aacacgcacc agtaaagcca tctggtccta agttttttgt    66060
tgagaagtat ttgattatta attcaatatt tttactggtt gtaaatctct ttatattttc    66120
tatattttct gtgtttatg tctccaggaa tttatttttt ctttcttatc taattttga    66180 tgtataattt ctcatagtaa tctcttatga ttgttttatt tttctagcat caattaaatg    66240
tctctacttt cagctcttat tttgtttgtt tgagtctttt ctcttttgct tagtctagtt    66300
taaagtttgt caattttgcc tctctttcaa aaagatcaac acttagttgt gttgatattt    66360
tttctaatgt ttttttttcc atattcttta ttgtatttat ttcttctcta atcttttttt    66420
ctcctgctaa ctttggcctt agtttgtttt tcttttttata attttgtgag gtgtaaaata    66480
ggttgttagt ttaagataat tctttacttt ttactagcat aattatgtga tatttatcag    66540
tgtgtactga gagcaaacaa tgccagatgc tactagtgac cataaattag agaaataacc    66600 tatgttttttt ggatatggaa atgaaattta ccctacaaat gtagatattt tttactgaac    66660
acttcctctt actactgttc ttgctgcatc tcacatttta gaatgttttg ttttttgattc    66720 tcttcgtatc taaatatttt ctaatttccc ttttgatttc tttgacaatt taattattga    66780
aaagtttgtt agtatccata ttttttaaaat tttctacttt tcttttttgat actaatttcc    66840 agttttattc cattgtagtt agaaaagata attggtatga ttttaatttt aaatttatca    66900
```

```
agacctgttg catgatgtaa catgtggtct atcttagaaa atattccatt tctatttgaa    66960
aagaatatac attctgtttt tattgagtga agtattctct atgtgtctgt tacgttcaat    67020
tggtctataa tgttgttgaa gtcctctgtt tcctcattga ttttctctct agtcattcta    67080
tttataattg aaagtgagat attatgaagt cagcctacta tggagggcta actgtaatac    67140 actatttat ataagagact ggagcatcct tggatttggg tatccatagg gagtcctaga    67200
accattgttc acagatacca agagatgatt ttattgtatt tctctatatt tctcttttca    67260
gttctgtcca tgtttgcttt atagcttttg ggtctttgag attgggtgaa tatattgggt    67320
tgtatattct tggtgaatta acttaaaaaa tcattttata atgtcctttt tgcaacttga    67380
gacagttttt tacttaaact cttttttctt ctttgacaaa tagttaggtt gcaaattttc    67440
caaacttgta tgctctgctt cccctttaaa tataactttc aactttaggt catttctttg    67500
ctctcatatc tgagcattgc atgttagaag cagccaacct atatccttaa tgctttactg    67560
cttagaaatt tcttccatca gatgttctaa gtcattgctc ttttttttta ttttggagac    67620
agagtctcac tctgtggccc aggctggagt gcagtggtgc gatctcggct cactacaagc    67680
tccacctccc aggttcacac tattctcctg tttctgcctc ccaagtagct gggactacag    67740
gtgcccacca cgatgcctgg ctaatttttt tgtattttta gtagagatgg ggtttcaccg    67800
tgttagccag gttggtctcg atctcctgac cttgtgatcc acccaccttg gcctcccaaa    67860
gtgctgggat tacaggcgtg agccaccgtg cccggccaag tcatcaccct ttatttcaga    67920
cttccacaga tcccctaggg tatgaacaaa atgcagccaa gtactttgcc cgacaccatg    67980
cccggcttat tttgtacttt attagtggag acggggtttc tccatgttgg tcaggctggt    68040
ctcaaactcc cgacctcaga tgatccaccc gtctcagcct cccaaagtgc tgggatgaca    68100
ggcgtgagcc accgcgcctg gcctatttta ttttctatag cctcataaca gaggtgagac    68160
tagtgatttt agagccacac ttcctggctt ctgtttttat tattttaatt atttattatt    68220
attattatta attttgtttt tttgggggggg tgttttgtt ttgctaaggc ataacaagag    68280
tgacttttgc tctagctccc aataactgtc atttctattt gagacctttt cagcatgaac    68340
ttcattgtcc atgtcacgat ctgcattttg gtcataatca tttatcagtt tccaagaagt    68400
ttcaaacttt ccttcatttt cttatcttct tctgagtcct ccaagctctt gtaagctctg    68460
ctcattacct agttccaaag tcaagtccac attttcaggt atccttatag caatgtccca    68520
cttcttggta acaattttct gtgttaggcc attctggcat tcttacacaa gaatgcatga    68580
gactggctaa tttatcaagt aaagaggttt aattggctta tgattctgca agctgtacag    68640
gcatggcact ggcattatct cagattctga ggagaccccca aggagctttt actcctggca    68700
gaagttaaag caggagcagg cacatcacat gttgagagaa agagcaaggg ggaggcaagg    68760
tgccacacac ttttaagca atcagatctt ctcctgagaa ctcatacact attgcaagga    68820
cagcaccaag caatgaagga tcaaccccca tgacccaaac acctcccacc aggccctacc    68880
tccaacattg gatattacat ttcagcagga gatttgaaca agacaaatac ccaaaccata    68940
tcagcctcca agtcttcatg gactggtatt gtataggaga aaactttctt cattcaaccc    69000
cagcagagcg tctgtgggcc tctcaaattt tgattctttt ttaaactgct atcttttgt    69060 taggaacttt cagaatctag agtatgtagg gtctcatgag cactttaga cagtggacag    69120 agaagcccgt cacttggtca actcccagaa aattttgaat atttcacatg ctatccaatt    69180
ttttccttcc caaggagaat ttgaaaactg aggtgttttc tttgttttt gtttgttgt    69240 ttgttttct tttctttttt acctcctcac tctgcataga tctgggagca gggaggagct    69300
```

```
gtagcaagtg ctcatgtgct aatttaagcc accatttttg tgctctttgt agcccattgg   69360
aagcaagcat atgcctagcc ccaagatagg caagacaatg accagctgct ggagttggac   69420
acagaaaaga tgaaatgtta ggtttgtggt cgaaatattt ccctccccat agagaagctg   69480
gagttaagtt tttgtttcta attttttta acttggtcat tctgccctaa gctatgggcc   69540
aggagctatg ggaatgctta catactagtt caagctgcct tctttatttt ccgtagcctc   69600
caaaggtctg gtatatgctg agtcctgtca acacttcaag ataggtgata tagaagacag   69660
tcgcaagggt agtacctgaa aagttacagt tttggatgtg cagtctcact ctgtctctcc   69720
acagggataa gctggagatg cagttttctt acattcagtc tatgttgagc caggaaatag   69780
agctattgca agtgttcata ggcacttgca aatttctagt tcctcttgaa tgcatggtat   69840
tataatgagg agaggaacag caaagaggtg tctccaattt tcttaaaagt gtcaatgtag   69900
ctaatattgc acttccctgg ggtacaatgg cctgtcaact agcttctgga ttttccacta   69960
atggaattga tcgctgtata attgttgaat aaaatattgt tgaaagaaaa aagggtccag   70020
tccttcctat taggctatct tgctgataac tcatattggc ttttttttatt acttagattg   70080 tttattttat acctgttaaa agagtgcatt tacacttgag atatagcatt tacataatac   70140
tcttattcat gatttaaaga aaaatatgac tgaaataaaa tggttaaatt atccttaact   70200
tttagagtct aactcttcag ggttactttt aaactcatat tttcactgta ttttcttatc   70260
ctctgtgctg tcaggagagt tggaaatgct tatttcaggc atggtgggaa gccccttttat  70320 tgactcagta gatttcttgc aaactgctaa aatttcattg ctgaccctt cttgattta    70380 ttagcttgtg ccaatagaca ttttcagaca acaatgagac gtcatagttc ttccacaggt   70440
agtaattaaa cagtctgcaa gcttaaatgt ccagtgatag aaactgtcca gtcatgtaat   70500
cagaaaagcc atcaagtgca cacaagctca ggcaatgaca acaatatcat gactgattcc   70560
tagacagtat ctgttgcatt atgtcatcaa atgttagact gatcctagtc tcagagatga   70620
caaaaaatta aagaaaaaa atcgtgtctt ggaattgagg aaatgtagtt tactttcttc   70680
ataccattat ttccctgaac ctattgtatt tcaaaatgat ttttgactgg cttctataat   70740
tatttattct aggcactatc aggataactc ctactgattc tcgatgggtt ggagcttggt   70800
ggcttaattt ccttgtgtct ggactattct ccattatttc ttccatacca ttctttttct   70860
tgccccaaac tccaaataaa ccacaaaaag aaagaaaagc ttcactgtct ttgcatgtgc   70920
tggaaacaaa tgatgaaaag gatcaaacag ctaatttgac caatcaagga aaaaatatta   70980
ccaaaaatgt gactggtaag tatttaacat tcattgtcaa tttggagttg ttaatctcaa   71040 tgaaaggaa gaatgagtat tccaaaataa taaagcatac ccaactcatc tggagttggc   71100
tttcttttgc actaaattta gataaattat ttttctaaaa ctcctattaa agttaacata   71160
tatgtcttga gcacataaca agtggaagag aattaggttt gtacttttta gcagggagaa   71220
accaacaaaa gtttacaaac atccattttt tatgagccaa atagtaaata ttaattttag   71280
tattatatgg tctaaactgg gagagttcaa agaattataa tatttcattc cttcatttat   71340
tcaacaagta gtaccaggaa ctgtactatg ccctggtaat aaaacattac ctctattttt   71400
caagaaccta gtgggtgatg ctgagaaata tatagacaat agcaatatag tgccttaagt   71460
attatggtga aattaaactt aactattatc aggtgtagag atggattaag gagaaggaag   71520
tcgggagaag tttctcccta tgtaattaga gtaatattta ttttggtaat tatctatcta   71580
tctatcttat ctaaatattc aaaataaagt ggaagcaaag gtggtagtta agataattag   71640
```

```
actaagtaat gtaaattagg atgcatcagc atttgacagt gcctcctctt ttgaatataa    71700
accctgggac taatggagaa ccattgagag tcaataaaca aagagaatga cttggcagta    71760
gccagagcaa gatatgtgaa tcagtgaggt gttgacagca gttttcagat ttgggagaaa    71820
tggtgaaata gccaaagcaa tgcaacactt aaaccctcag catcttttc aagttttctt     71880 taaagtaaga tgacaaattc tccagtgtag cctaggttct tcctttcatc aggtctttta    71940
cttattactt tattgctatt ttctcctttc tatcacacta acccaagagc agtggtgttc    72000
tggtactctt tatattggct catagcagag gactgttaag tttcagctac attggtaggt    72060
tgaaattgtt catggcaaga gaattaccat gatttattac catggaaatt gggatatact    72120
acaagtagaa gtttgttttc ctaagaatca gatgttaaac atttatgttt ttaaaattta    72180
acattcacac taaaagtact ataccaataa ttttcatttt gtatatgatg tttctactgt    72240
accaaatcaa atctttaaaa aatagtagat tgtctaaacc tataaggagc ggggttgact    72300
gtgatccaaa cagaacagag aggataatga agttgtaaaa ataggacaat tgtagacata    72360
atctctatta tgaacagttt ttgtaggtgt gaccctaaga aagaggatct taagtatgta    72420
tctattagga atggataaaa taagaatata tagtcagaaa aaatattgaa tttattccat    72480
atgctcttga atagaactaa aactgattag aatgaaaaga tgatttcagt tcattacaaa    72540
aacagtgtgt aaacaatgag aacttttcaa aagtggagga aattgcttcc taaggtactt    72600
agtttaatgc cacttaagtt gtttattgat ccacttatta atgatatata gtagatcatg    72660
actatacaga agtttacact ggatgacatt gaatttctca tcctcaaaaa tgcaacgctt    72720
gtgtgaatgt atatactcca tttctgttga agaaaggcca caactcactt ataatactta    72780
caaatcaggg atggttttc atgactgggg agacctgtgg agagaaatgt ggcacttttg     72840
cccaagaatt ttaaatgttg tttattccca ctatacattt tcttatctct tctttttttc    72900
ttttctgttt cttttctcta actccttcta ctccttattt caagcagatg caactgtttc    72960
gtagctgaca ttaaatggat gtcttagttc tgaccatatc taatgaaaat ctttagagat    73020
ttaaatagag aaaaatattt caaagtccgt atcatccaac tctcagtaac catatcttgg    73080
ctctgtcttg atgaactctg atacttccta ctgtttttct aagtagttcc ttctacttt      73140 aagtcctatt acagctagtt gacctggtga tcacagatcc aaatgacata atttctacca    73200
tgaacagaag ttagaagttt gttaccacag ctgtttgtag ggataggtgg ttgtattatt    73260
actattataa tactacttgg gacacaatat tatcccctgg ctgctttcct tgtatcttaa    73320
gacagagggt taataatatt gccaaattta ctgagaaagt atgttatggt agaagagctg    73380
tatactagag aaacaggagg tctgagtcct catactaaat taatctttaa gaattttgaa    73440
cctcaatggt cttatttctg tgagttttga attatgctgt cttttacattt ccatttaata    73500 gttatatttt taatataata cttatatcat taagtactaa taaataagaa acatcatatg    73560
tcttattcac tttttgtttg tttgtttttg ggttttttg tttgtttgtt tgtttgtttg      73620
tttgagatgg agtcttgttg ctctattgcc taggctggag tgcagtgtca ccatctcagc    73680
tcactgcaac cttcgcctcc ctaattcaag caattctcct gcctcagcct cccaagtagc    73740
taagattaca ggtgtgtgcc atcgtgctgg ccaatgtttg tatttttagt agagttgggg    73800
tttcaccatg ttggccaggc tggtctcgaa ttcctgaccc caggtgatcc atctgcctcg    73860
gcctcccaaa gtgctaggat tacaggagtg agccactgtg cccggccttc acttttgttt    73920
tttgaacaat tagcatattg tctggtaccc agttgaaaac ctaacatttg ctgaatgaat    73980
gaataagtga attaatatgt ttgcaatagt attgtaaagt acccaggata accaaatatt    74040
```

```
aagtgaagaa agcaagttac aaaacagcac ttacgtatga ccctatttga gggtaaaata   74100
aactaaacta ataaatatta atattcgtat ggaaaatatt gaaagaatat atttaaaagc   74160
tgtgaacagc ctgtggtatt gcaggctatt ctcactcttt gtgttatgtg tttatagaat   74220
tttaaatctt acatgactta cgttcacaaa ttttagatat aaatgtatat ttaagttgca   74280
ttcaaatatt ttctttattt ttacaatttt acaggttttt tccagtcttt taaaagcatc   74340
cttactaatc ccctgtatgt tatgtttgtg cttttgacgt tgttacaagt aagcagctat   74400
attggtgctt ttacttatgt cttcaaatac gtagagcaac agtatggtca gccttcatct   74460
aaggctaaca tcttattggg taagacatat tttttacttg tgtgcttaat aagtgaaata   74520
atactaaata ctgtattcca agtggtattt tattgtgaaa gtgattttgt attttagtaa   74580
tacaggataa gtataatttt cttgtattct ttctcaaatg ttattaaaca tataaaactt   74640
gtgatgtcac tattgctctg catttgaagt tgcatcttat tttagatgag ttcctgaaaa   74700
aaatgttgca aataaatgga caatttagag gtagtatctg tataattgga tcttataatt   74760
tagtgctaag atctgagaca aacccttttg taattataat cattataatt ctataattta   74820
tggactttga aatcaagact cagttactta caaaaatatg acactaatag ttccaaaaag   74880
agtatcgatt taaatacatc aaaatatgca taattcaaaa caaatatatt ttacagagta   74940 tttttttgcta caatatctat tttcaatggc acatttagat gtgcttatta aggaaagttt   75000
ccttgtatta ttcttcccac aactctagta ttgtagacac attatagaaa ttcaatataa   75060
atatatgatg aattaaacaa cttatcatgt ggtatgtaac taggtcataa gtaaacaaga   75120
aaatgaatgt actgaagcag gagaccaagc ttccagataa tctctttgtt gatcttaaga   75180
taaaagttta aaatcgaaaa ataatgtttt gactcccagt aacctagcct gagcttttc    75240 ctagagaaga cttcatcttt gttaactctt attagacaaa gatatggaaa agttatagga   75300
gggattaaac attattaatc ctgtatgtag agcgatttgt cagttcaggt tctgtatgtt   75360
ttttaataaa tgacaaagat atattaattt ttatgttgtt aagctctggg cagatttagt   75420
gtgagttact gagggttaga actctatctg agagaggcaa aaggctttag atgaagttcc   75480
ataggcagaa agatggtgtt ttgttgttgt ttatttccag aaaaacaaaa ttgcctcata   75540
gaaattatct gctccaacaa atatcctcag ccacactgcc ttttgctatt gaggaaacca   75600
aactgtcatc attggcagga acaaattaca cagatcccct accaccatac tgctatatca   75660
ttcttctttt taaaaagtaa taagattggc attctactat aaagatacat gcacacatat   75720
gtttattgca gcactatttg caatagcaaa gacttggaac caacccaaat gaccaccaat   75780
catagactgg ataagaaaa tgtggcacat gtgtaccatg gaatactatg cagccataaa    75840
aaagaatgag tttatgtcct ttgcaggac atggatgaag ctggaaacca tcattctcag    75900
caaactaaca caggaacaga aaaccaaaca ctgcatgttc ccactcataa gtgggagttg   75960
aacaatgaga acacatggac acagggaggg gaacatcaca caccggggac tgttgagggg   76020
tgggaagcaa ggggaggaag aacattagga caaatacccta atgcattcag gggttaaaac   76080
ctagatgaca gtttgatagg tgcagcaaac caccatggca catgtatatg tatgtaacaa   76140
acatgcacat tctgcacatg tatcccagaa cttaaagtaa aattttaaaa agaagcaata   76200
atattgaata aatttgattg acatacattg tgtttcatct ataagacat atcagaaaac     76260 tcatatatga ttcaactttt ttttcttttt tttctaggag tcataaccat acctatttt     76320 gcaagtggaa tgttttagg aggatatatc attaaaaaat tcaaactgaa caccgttgga    76380
```

```
attgccaaat tctcatgttt tactgctgtg atgtcattgt ccttttacct attatatttt    76440
ttcatactct gtgaaaacaa atcagttgcc ggactaacca tgacctatga tgggtttgta    76500
tatatcacta tatcaattgc ataatatgtt aaccatcaaa ttaagagtct ctgtataagt    76560
aatataaggc agaaaacaat tttaactaaa cttttctttaa gttaagagaa atttcaattt    76620 taaaatttt aaaatatctg tttcttaaga cctcaaacac attcttttat tcctccacta    76680
aagagaagca acataggttg taataataat aactattatt tatgtggtac ttacaattag    76740
tagtgggtac ttttatcatt atttatgaa tgggaaaagt aaggcttaga gaaatacatg    76800
gattacacag ctagcattat taagattcta actcaaattt gagttttta agtccaaaac    76860 tcttagtctt aaccaccact gtaatcttgg atggatcata agagttacat aaatggcatt    76920
agccaaaagt gactaaacaa cttttatcta cagttcatat cgatgttcaa caactatctt    76980
aacaaaagaa cacttttaat gttgtactga attttctttt ttgcaagcta atattgtttt    77040
tttctgatat tatctacatt ggaagtagca ttaagaaata ttctatatat aattgcatat    77100
tagacattga agaatctta cttttccatg attaccatg atagcaaagt attttagtg    77160 caacagtctc cacctcaaat caagggcaag aatcctatgc agttttctga taatttcctg    77220
aatatagcca acaatttaag cttaggaagg ttcacattca agcaacaagc agagatgctc    77280
agatcacaat tcagtaacca tgttctttag tgctgcttac tactggtgct gagcttcaa    77340 agtctggatc ccatgaggtg ttggttttaa cttgtcaaat attcccacat tttcttctat    77400
aaacattgtg ctattcttgg aggcttgcca aggttatctg aaattgtttc cctgcacact    77460
gctaattctg aactgttatt ggtatctcct atccaccatc aactactgta gtaaattaaa    77520
atacattgtc ctagaatact gaattttaga ggtaaaagaa ccttagagat gatgcaatcc    77580
aacccttgta ttatactttc ctttattatt gaagagtcag aaaaaatgta acatgttgaa    77640
gtcacacaat gtctttagac tctagactga tcctatgtca cacccttagt tcaaaagcct    77700
tcttggttgt aaggacaggc cagtttcttg acaacaaggt tagtcactgt acaaagtata    77760
caaaagatgg cagcagagtt aaacagaatt tgtttcattt aataaaattt tattaagcct    77820
ttccttaaag gtaaatatta aggatatttg taggatacat cagttccctc atgggactca    77880
taatctaatg ataaataata taattaatgg attcaacatt cataaaatcc tgcgactggg    77940
ataagttttt ttttaagtat gaattattgc agaggtctcg gaatgtgttc tgaatatctc    78000
taaggatccc tgagacttta tcaaggggtg cacaacttca aaactatttt tataataata    78060
ctaagacatt atttgccttt ttattctcat gctatcctga cagtatagtg atattttcta    78120
atgctccaag gtatgttatt aattcattaa tctgactgct aaaatatgtg tgcttatgta    78180
cttttgtgta ttaaaatttt cttagtatta ctttctaata tagtacatgt caagaggtac    78240 aacttaatttt aacaaaatcc ctttggaaca agccctcaat cttttataag agtgtgaagg    78300
acttctgaga accaattttt tttccaaaaa aaaaaaaac cctgtgaggt tggcattatt    78360
atctatgact tacaaatggc aaaactgatt ttagaaagaa gtgccagaat taatataaac    78420
acagatgtga ctgattgcaa tatctggact gggtcattgt cttagtccat tcaggctgca    78480
aagttctagg tagcttatta atacacagaa attaattttt caagattcta aaggctgaa    78540 catgtaagac caaggtgatg gcacttttgg tgtctaggaa gggcccattt cttaatttat    78600
agacggtacc ttctcattgt gtccaggcat ggtggatggg gcaggcaaag ggtcagtaat    78660
tccattcatg agtactcatc ctcatgacct tatcactttc tagaggcctg acttcataaa    78720
gtcttcatat acgagattag ttttcaatct atgaatttgg gggccacaaa cattctgact    78780
```

```
atagtagtca taaaccattc tacttaacca ctccaagtag tatttcctca agcagaatat   78840 gcttttaat aaaattattg ataatgtagt ttctgaagta tgaatcttag tttttcattt    78900
aaattatgtg ctcattcaaa gataacacat caatcctcaa ttattatcaa attaaacatt   78960
tgaaagaaaa taatttttta aatgtttaag cagaaatgaa ttatacaaaa aatatatttt   79020
ataattttag ctatgttata atcatatttt ataatttata accatttcat aaaggaaatc   79080
agtataaagt atactatagt tttatttcaa aaatatactg agcttttcta gccttttca    79140 actgattcta ttcttgattt ttcattttgt agaggttctg ctttaagcat gtctgttttt   79200
ttcttacata ttaaaataga gattttaaa ttcaacctag ttaaatagca ttcgtagact    79260
cacaagactt tacagtgagc tgaaaggaat gtcagtctaa tgtcatcacc ttactgaaga   79320
gaaactcagt ctcagaaaaa agatgtaact tatctaatgt gaagtttctt catgaaatta   79380
taacaacttc ttgtctaagt cctacttaac atctttggtt tatttttaca ttttgctttt   79440
tctaggtcac aagtcatgta ttggcaaaga tggagagcgt aaaataaata agcattaaaa   79500
aaaactttgc catttcgtca tcatcaaagc aaatttcttc atataaagaa aaattcttta   79560 tctactttt ttccctcttt ctctgcttc actttacttc ttccttctcc tccccttctt    79620 tgtcttttc ttctctctct ctcttttga tatatgtcta tcatatattt ccagaaataa    79680
tccagtgaca tctcatagag atgtaccact ttcttattgc aactcagact gcaattgtga   79740
tgaaagtcaa tgggaaccag tctgtggaaa caatggaata acttacatct caccctgtct   79800
agcaggttgc aaatcttcaa gtggcaataa aaagcctata gtgagtatta gttttactt    79860 tcctctcctt attcaaaagc acagattaga ttgaacaatt ttttaccaaa tatttctgta   79920
actaaggact ccattaaaaa gataaaagag aaagtttcca gtattatctg ttattgtgat   79980
gggtgtgatg tataaacaaa gttttatata aaagtctgct tagggcacaa tcaggttttt   80040
ctgttacttg aattctaatt ggagatcacc ccactttttt cctttgagat tgtaagacta   80100
tgacctttta gaatttgaat gcatttagaa tatctaagaa gcacctcatt tgactaaagc   80160
ctataatttt cattaagttg gaattacttt atccctcaga attcaggaaa atgagttaac   80220
ccattgtcag cacttcctat cttactaaga caacagtcaa tatgcaatgt tatatacaga   80280
ttctgatctg tttagctctg ggatcactac ccttttttact ttttaagaaa ttaatcaagg  80340
cttcatgctc acttgactgc cctattcttg attttctatt ttgattttc caaagctggc    80400 acttctaccc aagataatgt agtatcctgc tcacctaatg tcaatatgtc ccatagaaat   80460
gtcatttatt ccgtcctgca aaaccttct ttccatgtga actacagttt ttctctaatc    80520
tcctgggtag ctacctgtca ctgggaatgg gttatggtgt ttcccatacc tacaatccac   80580
tcaacatctc acaaagttgt gtaatgtttt cctaggaact tttactatta ccaacattac   80640
taaaacagtc aactataatt attgctctct gccacaccct tctgtgtttg atttttaaac   80700
attctccatc tactcttgcc catggatcta cctaccaatt ataataagga atggcatgta   80760
gaattttaaa gaataaagca tcctggactt tttgaagaaa ggccacaact ttaataaact   80820
tgcacaaata tggcccaaag actacttaaa agcccacatc ttagtcatgg caacaatgaa   80880
tcttttgtgc agttgtttcc ttttcctttg ctgtttattt ttatttgct gttttttaaa    80940 aaaataattt aactcttatt ttaggtaaag gggatacaaa tgaatttgtg ttagatgggt   81000
atattgtgat aagctaaagt ttagggtaca atcattccca tccccaggt agtgagcata    81060 atacccaata agtggctttt tagtacttgc tgttttttat ctctccactc tagtagtctg   81120
```

```
taatatgtat ttttcctgtc cttatattcg tgtggaccca gtgattagct tccacttata  81180
agtgagaaca tgtggcatct ggttttctgt tcctatgtta attcacttaa gataatgacc  81240
tccagctgca tccaggttgc tgcaagggac attatttcat ccttcttttg gccatgtagt  81300
attccattgt ctatatgtac cacatttctt tatctaattc actgttgacg ggcacccagg  81360
ttgagaccgt gtctttgcta ttgtgaatag agctgtgatg accatagaag tatataagta  81420
gatgtgtttt tggtagaaga atttattttc ctttgggtat atacccggta gtgggattgc  81480
tgagttgaat ggtagttctg tttaagttct ttgggaaatc tcgaaactac tttacacagt  81540
gactgaacta atttacattc ctaccaacat aggataagca ttcccttct tctgcagcct   81600 tgccagcgtc tgttttttta atgttttgaa ccagtcagcc cttctgactg gtgtgagatg  81660
gtatctcctt gggattttga tttgcatttt tttgatgatt agtgatgtta aacatttta   81720 tgtgtttgtt agctgcttgt atgtcttctt ttgagaagtg tctgttcatg tcctttgtct  81780
actttttaat attgttttg tttttgctt gttgaattgt tcaagtttct tatagattct    81840
ggatattagt cctgtgttag atgcatggtt tgcaaaggtt ttctcccatt ccatagattg  81900
tcttttcact ctgttgatta tttttgttgt gcagaagctc attagtttaa ttatatccca  81960
cttgtccatt ttttttgttg caattgcttt tgagaactta gtcacaaatt ttttgccaag  82020
gccaatatcc agaatctttt cttggttttc ttcagtggtt tttatagttt taggttttac  82080
atttcagtct gtaatacatt ttgattaaat tttttatatg aaaagaaggg gtccagtttc  82140
atttctctgc atagttagcc agttattcca gcaccattta ctgaataatg agtactttcc  82200
ccattgcatt ctttttgcta acttcattga agatcagatg gttttaggtg tgtggctttg  82260
cttctgggtt ctctattctg ttcctttagt ctaggtgtct gttttttgaac cagtactatg  82320 ctgtttggtt actgtggcct tgcagtatag tttgatatca ggtaatggga tgcctctcac  82380
tttgttcttt atgcttagga ttgctttgac tattcagtct ctttttttcct atggaatttt  82440 acaatagttt tattctaatt cagtgaaaaa tcatgccggt tgtttgataa gaataccatt  82500
gaatctgtag attgctttgg gcagtataga cagtttaatg ataattttc taccaatcca   82560 tgagagtaga atgttttcc acttgtttgt gtcacctata atttctttca tcagggtttg   82620
tatttatcct agtagagatc tttcacttcc ttggtttaaa tgtattccta ggtatttaat  82680
ttattgtagt tattctaaat ggaattgcat tattgatttg ggtatcagtt taactgttat  82740
cggtgtatag aaatgctact aattttttc cattgatttt gtattctgaa actttattag   82800
agtatgttgt cagttctagg aggcttttgg cagagtattt aggggttttt tttaattaat  82860
taatttattt atttttaatt atactttaag ttttaggta catgtgcaca ttgtgcaggt   82920
tagttacata tgtatacatg tgccatgctg gtgcactgaa cccactaact cgtcatctag  82980
cattaggtat atctcccaat gctatccctc cccctcctc ccaccccaca acagtcccca   83040
gagtgtgata ttcccttcc tgtgtccatg tgatctcatt gttcaattcc cacctatgag   83100
tgagaatatg cggtgtttgg ttttttgttc ttgcaacagt ttactgagaa tgatgttttc  83160
cagtttcatc catgtcccta caaaggacat gaactcatca ttttttatgg ctgcatagta  83220
ttccatggtg tatatgtgcc acattttctt aatccagtct atcactgttg gacatttggg  83280
tgggttccaa gtctttgcta ttgtgaataa tgccacaata aacatacgtg tgcatgtgtc  83340
tttatagcag catgatttac agtcatttgg gtatatacc agtaatggga tggctgggtc   83400
aaatggtatt tccagttcta gatctctgag ggaatcgccac actgacttcc acaatggtta  83460
aactagttta cagtcccacc aacagtgtaa aagtgttcct atttctccac atcctctcca  83520
```

```
gcacctgttg tttcctgact ttttaatgat tgccattcta actggtgtga gatggtatct   83580
cattgtggtt ttgatttgca tttctctgat ggccagtgat gatgagcatt ttttcatgtg   83640
ttttttggct gcataagtgt cttcttttga gaagtgtctg ttcatgtcct tcgcccactt   83700
tttgatgggg tttttttgttt ttttcttgta aatctgttgg agttaattgt agattctgga  83760
tattagccct ttgtcagatg agtaggttgt gaaaattttc tcccatttg taggttgcct    83820 gttcactctg atggtagttt tttttgctgt gcagaagctc tttagtttaa ttagatccca   83880
tttgtcaatt ttgtcttttg ttgccattgc ttttggtgtt ttagacatga attccttgcc   83940
catgcctatg tcctgaatgg taatgcctag gttttcttct agggttttta tggttttagg   84000
tctaacgttt aagtctttaa tccatcttga attgattttt gtataaggtg taaggaaggg   84060
atccagtttc agctttctac atatggctag ccagttttcc cagcaccatt tattaaatag   84120
ggaatccttt ccccattgct tgttttctc aggtttgtca aagatcagat agttgtagat    84180
atgcggcatt atttctgagg gctctgttct gttccattga tctatatctc tgttttggta   84240
ccagtaccat gctgttttgg ttactgtagc cttgtagtat agtttgaagt caggtagtgt   84300
gatgatgcct ccagctttgt tcttttggct taggattgac ttggcgatgt gggctctttt   84360
ttggttccat atgaacttta aagtattttc caattctgtg aagaaagtca ttggtagctt   84420
gatggggatg acattgaatc tgtaaattac cttgggcagt atggccattt tcacgatatt   84480
gattcttcct acccatgagc atggaatgtt cttccatttg tttgtatcct cttttatttc   84540
cttgagcagt ggtttgtagt tctccttgaa gaggtccttc acatcgcttg taagttggat   84600
tcctaggtat tttattctct ttaaagcaat tgtgaatggg agttcactca tgatttggct   84660
ctctgtttgt ctgttgttgg tgtataggaa tgcttgtgat ttttgtacat tgattttgta   84720
tcctgagact ttgctgaagt tgcttatcag tttaaggaga ttttgggctg agacaatggg   84780
gttttctaga tatacaatca tgtcatctgc aaacagggac aatttgactt cctcttttcc   84840
taattgaata ccatttatt ccttctcctg cctaattgcc ctggcagaa cttccaacac     84900 tctgttgaat aggagtggtg agagagggca tccctgtttt gtgccagttt tcaaacggaa   84960
tgcttccagt ttttgcccat tcagtatgat attggctgtg ggtttgtcat agatagctct   85020
tattattttg aaatacgtcc catcaatacc taatttattg agagttttta gcatgaagtg   85080
ttgttgcatt ttgtcaaagg cttttttctgc atctattgag ataatcatgt ggttttgtc    85140 tttggctctg tttatatgct ggattacatt tattgatttg tgtatattga accagccttg   85200
catcccaggg atgaagccca cttgatcatg gtggataagc ttttggatgt gctgctggat   85260
tcattttgcc agtattttat tgaggatttt tgcatcaatg ttcatcaagg atattggtct   85320
aagattctct tttttgttg tgtctctgcc tggcttggt atcagaatga tgctggcctc     85380
ataaaatgag ttagggagga ttccctcttt ttctattgac tggaatagtt tcagaaggaa   85440
tggtaccagt tcctccttgt acctctggta gaattcagct gtgaatccat ctggtcctgg   85500 actcttttg gttggtaagc tactgattat tgccacaatt tcagatcctg ttattggtct   85560
attcagagat tcaacatctt cctgatttag tcttcggaga gtgtatatgt caaggaattt   85620
atccatttct tctagatttt ctagtttatt tgcgtagagg tgtttgtagt attctctgat   85680
ggtagtttgt atttctgtgg gatcggtggt gatatcccct ttatcgtttt ttattgtgtc   85740
tattagattc ttctctcttt ttttcttat tagtcttgct agcggtctat caattttgtt    85800
gatcctttca aaaaaccagc tcctggattc actaattttt tgaaggtttt tttttgtgtc  85860
```

```
tctatttcct tcagttctgc tctgatttta gttatttctt gccttctgct agcttttgaa   85920
tgtgtttgct cttgcttttc tagttctttt aattgtgatg ttagggtgtc aattttggat   85980 cttttcctgct ttctcttgtg ggcatttagt gctataaatt tccctctaca cactgctttg   86040
aatgcgtccc agagattctg gtatgtcgtg tcttttgttct cgttggtttc aaagaacatc   86100
tttatttctg ccttcatttc gttatgtacc cagtagtcat tcaggagcag gttgttcagt   86160
ttccatgtag ttgagcggtt ttgagtgaga ttcttaatcc tgagttctag tttgattgca   86220
ctgtggtctg agagatagtt tgttataatt tctgttcttt tccatttgct gaggagagct   86280
ttacttccca gtatgtggtc agttttggaa taggtgtggt gtggtgctga aaaaaatgta   86340
tattctgttg atttggggtg gagagttctg tagatgtcta ttaggtccgc ttggtgcaga   86400
gctgagttca attcctgggt atccttgttg actttctgtc tcattgatct gtctaatgtt   86460
gacagtgggg tgttaaagtc tcccattatt aatgtgtggg agtctaagtc tctttgtagg   86520
tcactcagga cttgctttat gaatcttggt gctcctgtat tgggtgcata tatatttagg   86580
atagttagct cttcttgttg aattgatccc tttaccatta tgtaatgcc ttctttgtct   86640 cttttgatct ttgttgtttt aaagtctgtt ttatcagaga ctaggattgc aacccctaac   86700 ttttttttgtt ttccatttgc ttggtagatc ttcctccatc cttttatttt gagcctatgt   86760
gtgtctctgc acgtgagatg ggtctcctga atacagcaca ctgatgggtc ttgactcttt   86820
atccaatttg ccagtctgtg tcttttaatt ggagcattta gtccatttac atttaaagtt   86880
aatattgtta tgtgtgaatt tgatcctgtc tttatgatgt tagctggtta ttttgctctt   86940
tagttgacgc agtttcttcc tagtcttgat ggtctttaca ttttgccatg attttgcagt   87000
ggctggtacc agttgttcct ttccatgttt agcgcttcct tcaggagctc ttgtagggca   87060
ggcctggtgg tgacagaatc tctcagcatt tgcttgtctg taaagtattt tatttctcct   87120
tcgcttatga agcttagttt ggctggatat gaaattctgg gttgaaaatt cttgtcttta   87180
agaatgttga atattggccc ccactctctt ctggcttata gggtttctgc cgagagatcc   87240
gctgttagtc tgatgggctt cccctttgagg gtaacccgac cttctctct ggctgccctt   87300 aacattttt ccttcatttc aactttggtg aatctgacaa ttatgtgtct tggagttgct   87360
cttctcaagg agtatctttg tggcattctc tgtatttcct gaatctgaac gttggcctgc   87420
cttgctagat tggggaagtt ctcctggata atatcctgca gagtgttttc caacttggtt   87480
ccattctccc catcactttc aggtacacca atcagacgta gatttggtct tttcacatag   87540
tcccatattt cttggaggct ttgctcgttt cttttttattc ttttttctct aaacttccct   87600
tctcacttca tttcattcat ttcatcttcc attgctgata ccctttcttc cagttgatcg   87660
catcggctcc tgaggcttct gcattctcca cgtagttctc gagccttggt tttcagctcc   87720
atcagctcct ttaagcactt ctctgtattg gttattctag ttatacattc ttctaaattt   87780
ttttcaaagt tttcaacttc tttgcctttg gtttgaatgt cctcctgtag ctcagagtaa   87840
tttgatcgtc tgaagccttc tctcagctcg tcaaagtcat tctccatcca gctttgttcc   87900
attgctggtg aggaactgca ttcctttgga ggaggagagg tgctctgctt tctatagttt   87960
ccagtttttc tgttctgttt tttccccatc tttgtggttt tatgtacttt tggtctttga   88020
tgatggtgat gtacagatgg gttttcggtg tggatgtcgt ttctgtttgt tagttttcct   88080
tctaacagac aggaccctca gctgcaggtc tgttggaata ccctgccgtg tgaggtgtca   88140
gtgtgcccct gctgggcgt gcctcccagt taggctgctc aggggtcagg ggtcaggac   88200 ccacttgagg aggcagtgtg cccgttctca gatctccagc tgcgtgccgg gagaaccact   88260
```

```
gctctcttca aagctgtcag acagggacat ttaagtctgc agaggttact gctgtctttt    88320
tgtttgtctg tgccctgccc ccagaggtgg agcctacaga ggcaggcagg cctccttgag    88380
ctgtggtggg ctccgcccac ttcgagcttc caggccgctt tgttttttcct aatcaagcct   88440 gggcaatggc gggcgcccct cccccagcct cgctgccgcc ttgcagtttg atctcagact    88500
gctgtgctag caatcagcga gactccatgg gcgtaggacc ctccaagaca ggtgcgggat    88560
gtaatctcgt ggtgcgccgt tttttaagcc cctcggaaaa gcgcagtatt cgggtgggag    88620
tgacccgatt ttccaggtgc tgtccgtcac ccctttcttt gactgggaaa gggaactccc    88680 tgacccttg cgcttcccaa gccaggcaat gcctcgccct gcttcggctc acgcacggtg     88740
cgcgcaccca ctgacctgcg cccactgtct ggcactccct agtgagatga acccggtacc    88800
tcagatggaa atgcagaaat cacccgtctt ctgcgtcgct cacgctggga gctgtagacc    88860
ggagctgttc ctattcggcc atcttggctc ctccaaccag ggttttgag atatagaatc     88920 atatcatagt gcagagagat aatgtgagtt catttcctat ttgtcagtgt tttatttctg    88980
tctctttcct gattgatctg tctaggattt ccagtactat gttgaatagg agtggtgaga    89040
gtgggcattc atgctttgct cctgttctta agaagaatgc ttccagcttt tgcacattat    89100
atatgaagtt ggctgtggtt ttatcataga tggctcttat tattttgagc tatgttcctt    89160
caatgcccag tttgttgaag aactttatca taaaaggatg gtggatttta ttgaaagctt    89220
tttctgcatc tggtgaaatg ctcatatact gtttatccta aattccattt atgtagtgaa    89280
tcacatttat tgattgtgta tactggacca tccttacatc tcaaaaataa agcctacttg    89340
gtcatgatga attcacttt tgatgtgctg ctggattcag tttgctagtg ttttgttgag     89400
gaattttgca cctatatgca tctatattca tctatattca ccaggatat tggcctgttg     89460 gtttgttttt gatgttgttg ttgttttttgt gtcttgctat attttggtac caggatgatt   89520
ctggcttcaa aaaaatcagt taagaaagag tccttctttc tcaattttttc agaataattt   89580 agtacagtgg gtactcactc ttttttgtat ttccagtaga atttggctat gaatgcattt    89640
ggtctagggc ttttattgat aggcaggttt tttcagtact gattcaaatt tggaactcta    89700
tattagtgtt cagggtttca attactcttt gttcgtcttg gatggttgtt ggatggttca    89760
ttttggatgg ttggataaga atgacccagt taatacatgc tccctctttg cacactagcg    89820
aaggcctgaa agtgatagaa tattagaacc ctaaaaagaa ttgtgtctac cacaagacat    89880
aatcttcatt atactggcaa tgactatgcc atttggggac tattgcaaag tttttattat    89940
ttatttattt gtgtatttat ttatttatta ctaaatcctc aataatgaac catcacttct    90000
taaaatagtg ttctttgtac caaagcttag ttttattgac caatacactt gttccataaa    90060
aaattcctct atattattcc tagtgaaaaa aaatagtaag aactgtaagt ttggcagaac    90120
tgtagatgta tagatttaaa ttcttctaca attcttcctt caataattga tctttagcat    90180
taatagattc aacgtgaggt tcccttaaac tttagcctag atttagaaca gaatttatta    90240
aagccacctg tctatataaa ctgttcaact gattaaaaat ctgaaatcac ttgtttctac    90300
attttccact tctgtgctct aaacactagt ggggcattct gttgtgttta acctctctgg    90360
taataatatc atcgtgtcatt gtatccttgg attttgttta tgcctgctaa attaaaattt   90420
tagcatctct acctgtctct attttttcctg gactcagtgc cattttcatg ggtgactcca    90480
gttaaatttt gattactccc aaactgctaa attatctgaa ttctttggat aattcctcct    90540
cagggcatgt ctctgaaact tagagattgt ccaaaagagt atgtgctctg cagagggtaa    90600
```

```
aagggaatgg aaaataatta ttaaagagaa tctatagtga tgagaaaatt gtatacagag    90660
ttctaggcac taatttcttt gtttcttagt tttaaaatta agaatgaact aaatgtcaat    90720
catgaattac attgtcttat atagaaagaa atccacaaaa ctatttttacc ttttatctct   90780 taagcaactg tattttttaga atcttcttaa actgtaaata tattagtttg aacaagtgag   90840
acttcactaa atataatgca atgtatttgc agcactgtta ggtcttgcaa atttcttatg    90900
tcatatttta tacacaacgc ttaaggtgtt ttacaactgc agttgtttgg aagtaactgg    90960
tctccagaac agaaattact cagcccattt gggtgaatgc ccaagagatg atgcttgtac    91020
aaggaaattt tactttttg ttgcaataca agtcttgaat ttattttct ctgcacttgg      91080 aggcacctca catgtcatgc tgattgttaa gtaagtatga ctttttaaaaa cattttcata   91140 tgcatgagac tataaacaca cctaatgata tgcatatttt tacataatat actgggaatt    91200
caaattcata tttcatcaaa ttttaatttt ctgagaattc attttattaa aattactatg    91260
aactctcaag gctgtaatta ataattttgc ctctaattct tccattaaaa gtccagattc    91320
catacgtttc ttctcttact aagaatctga agacacagac tgacaattct ctcagttgta    91380
aaagaatcgc cctaggatcc taaaagaact tgttgaattt tgagttgcct tacatcctaa    91440
tgagagatgc cttgcatctc tcagggtaaa tctattgatt tcactaaaat aaagcatttg    91500
aaaactagat ataaaatatg ctccatttga taacattcca aaacttttaa tcgactcaca    91560
gcatgacttt tataataccc ttgtagaaaa ataaaaaaat acacaggaag aattagttcc    91620
tttcttggct cattagaaaa gatacaatgc ttggtgaata ttacatggta aatgaaacca    91680
ataagatact tgttgtcata cagctttcaa aattacagga aagactggtg tgagataaat    91740
aatcttaaaa tcaaagcaca tatttataaa ttgttctgag tcctcatcag gaaaaagatt    91800
tccctaaaaa gaaagattca aaaggaaagt taatttagga ttgaggtggg gggctgtgaa    91860
gaagaggatt cagagtacat ctcaaaataa gtaacattta ttctaaaggt ctaaagaaaa    91920
agccaaatga aagggtttcc aggagagggt cttggtgctg acgccttaat acaggaaaga    91980
gctggtgtgt ttgagaaatg aaaagaagct ggcagattga aacatactga atgagaggtt    92040
gtgacacatg ataagattgg agagttagga agggtgcagg taatgcatgc cctactggcc    92100
aagttgattc aatcacctaa aacttgtaac atgtaaataa ttgcttttag atcttaaaaa    92160
tatacatgtg taagtatagt gacctgggtt aacattcaat tgtacttttta aaacttacat   92220 tgttgatcat aagttcactg tcagccaaca gcatgacatg gtagagatga aaaaaaaaag   92280 cattttttaac atttgttaac attagtatca acctgtaaat tgaatttaca gttgtttaat   92340
tttgaccctg actgcaaatc ttatcaaatt atttatacta aatatgccac agatatagct    92400
ccatcttaat ataaaatgtt gtctactcaa aaggagaagt cttcatatt tgccaaatta    92460 aattcattaa catattaaaa ataaccttaa aattaaataa tagtctgcat atcaacaggt    92520
tttagctttt tattttaaac tcatgagttt gaaaaaacac tgttccatca tcgatgataa    92580
caatatcata tctgtttcag aaattgatta aatcagcatt acaacttgtc aaaaatattt    92640
aactcttgct agcctttgat tttattgaaa taagcatttt gtgaatatga ctacagaata    92700
aaaatataaa tttcagtttg ttaatagttt tctaatgctt aacactatga agctatttt    92760 taaacttgat taagtaggca gaaggacatc catttattca atatgtattc atttttttatg   92820 tcaggcatag ttgtatgcac tgaggatgca actgtgaaca aaagtgatag aactttataa    92880
gcttttagta tgggtgggga atgaaggaat gaatgtgtgt agcagaaaac acagtaaaca    92940
aataagtgag taaacatcta aaatagagta agtgtgaagc actagaaaga taaataaatc    93000
```

```
acagttaaga aaatagaaaa aaatgagaaa ataggcaaga gatactagtt cagatatggt    93060
gctttggaag tcctttgagt aaagacctga atgaagagat agaaaataaa ggtacaagcc    93120
atgctaaatg gagacatagg aggaacaatc caggcaaggt agaagaaagg tcagcgtcct    93180
ggtgtgaagt atagttgaca tgtacaaggt ccaaaaacgt gtgtaaggag gagagaggtg    93240
acaagtgcag caagagagct agcctagttc agatcctatg ggtcacagga aagactttga    93300
aatatattct aaatgtgttg aaagcccaag gggatttaag cattagtatt tgcaaagatg    93360
ccttacataa ctagaagatc actctggctg tgggtagaaa gtgtgttttg tgaaaacaat    93420
agtgaagtca gggaaaacag aaggcttgaa ttgttcttct caagatggaa gcttgattga    93480
gaatgctgat aataggaaaa tatgaagtaa atgaaatgag taaatgaaac aaatatgagt    93540
ctcagttgtt ttgctttatt ttattatatt tatttattta tttttgagag acagtcttgc    93600
tctgtcaccc aggctggagt gcagtagcac aaccttggat tgctgcaacc ctccgcctcc    93660
caggttcaaa cgatgctcct gcctcaacct cctaagtagc tggaattaca ggtgcacgcc    93720
accgtgcctg actaattttt gtattttttag taggacctgg ttttaccacg ttggccaggc    93780
tggtctcaaa ctcctgacct caagtgatct gctagcctct gcctctcaaa gtgctgggat    93840
tacaggcctg agccacagca cctggccttt gttttatttt ttaatgcaaa gccagtaggg    93900
tttgctgaga cattgaatgt ggcatgtgag aaagataatt taaggataat cccaaagttc    93960
tggcttgagt tctggaagga tggtggtact attgaacaaa atgggaaaga ctaagaaagg    94020
gtagattggg aaagtgaaaa agcaagaatt tgttctatct ctataaagct gagcagcctg    94080
ttcaatatct agcaatgtca tatatgcaat ccaacaggag aaaccttgat gccagagcca    94140
taaattttag agtcagcaac gtacagatgg tatttatttt tattttttact tatttattta    94200 tttagagaca aggtctcatt ttgttgtcca ggctgaagta taatggcatg attatagctc    94260
actgtaacct tgaatgcctg tattcaagca atcccccaag gcggtattaa aatccatgga    94320
actaatgaga tcttctaggg actgagtaca gatagaaaca agatcctagg atcagttctc    94380
aatcactcta atttaaagat cactaatagg agaaaccaat aaagaaaact gaggaggttt    94440
catgagaaaa actaggaaag agcgttgtcc tcaaactaat aaagcatatg tcaaaaagag    94500
cataagtaac tgtgtcaagg gctgctgaga gttcacagga gttgaacctg ggaggcggag    94560
gctgcagtga gccaagatcg ctccactgca ctccagcctg ggagacagag caagactggt    94620
ctaaaaaaaa aaaaaagaa aagaaaacca caaaccaata tccctgatga acatatgaaa    94680
aaattatcaa taaacacta gcaaatcaaa tccgatggca cataagaaaa attttataac    94740
atgatcaagt tgtttttatt ctagggatga agggttggtt caacatatat aaatcaataa    94800
atgtgatttg ccacatagaa taaactaaaa accaaaacca tttgataaga caaaattaaa    94860
aacaaaaacc atatgatcat ctcaatagat gcagaaaaat tatttgataa aatttaacat    94920
ctttcatgac aaaaatcctc aacaatctgg gcatcaaagg aacataacctc aaaataataa    94980 aagctatgta tgacaaaccc actgccaact tcatactgaa aggaaaaaag ttgaaagcat    95040
tctcctgaga cctgaaacaa gacaagtgtg tctattttca ctactcttac tgcacatagt    95100
atgggaagtc ctagctagag caatcaggca atagaaagaa agaaaggta tccaaattag    95160 aaaagaggaa ctcaaataaa ctctgttcac tgatgatatg caacaataac aacaaaaata    95220
gactaatggg acttaaacta aaatttcct gcacagcaat ggaaataatc aacagagtaa    95280
acagacaacc tacaggaagg gaaaaaatat ttacaaacaa tacatctgac aaagggctaa    95340
```

```
tatccttaat ctataagaaa tacaaaaaaa ctcatcaaga aaaaaattat taaaaatagg    95400
gtaaatgata cgaccagcat gtttcaaaag acaaacagtc aacaaacaac aaacatatga    95460
caaaatgctc aatatcacta atcatcagag aaatgaaaat taaagctaca gtgagattcc    95520
attttatacc agtcagaacg gccattacta aaaagtcaaa aagcaagata ctggtaagaa    95580
tgttgaggaa aaggaatgct tatatactgt tgagaatata aattagtaca acctttatga    95640
aaaacaatgt ggagattttt caagtatctg aaaatagaag taccatttga cccagcaatc    95700
caactattgg atatctacca aaaggaaagt aaatcatttt atgaaaaaga ctcatgctct    95760
ttcacactta ttataacact gactagacca caaaaaatca gtatcttcag aggcataata    95820
aagtctgttc taaccacttc ctcataggat tttcataagt accatgagag aaaatatttt    95880
aagccatctt gaaatcatga tgcattgaat aaataaggga ataattatta ttattgctca    95940
agtgtttgcc ttttaaaaca attaaaatat aattttatat aatggggcca ttcaactgtg    96000
agcttaattc tatcatggag aaaaacaaca caggagaagg tttaatgttg tttcgttttg    96060
atattttaat gatatttaat gtttctttgc ctttgtcttg tttcagaatt gttcaacctg    96120
aattgaaatc acttgcactg ggtttccact caatggttat acgagcacta ggtatgatga    96180
aaaaaaaaaa aaaaaaaaa aaaaatatat atatatatat atatatatat atatacacac    96240
acacatacat atattaaatt taagttataa atattaatgt caaggattaa agactgtaat    96300
gaatctttaa ttatgatagt aaataaaatt agtatccttt ctatttctgt gataaataaa    96360
aacaataaga gacagagtaa aattgagtga tggacctaaa ggagaattcg attgttaatt    96420
atacataaag tcaatctgtt aagactaagg aattattgta tttgtattac actctttcaa    96480
acacaaagat agatggtcct ccaaattttt cttttttttc agaaaaataa gaatatttcc    96540
tcccagtagg cagagtgaag ggcctaactt ctaaactgtg gcatgattta ggcaaggcct    96600
aaagctagct tgggaagcgt gggaatctgg tcagagaatc tggccaggct atggccaaat    96660
tacaatgaag aaaattgtcta agaagcgtat ttgatgataa agtcacaaat cctcaaagtt    96720 aaaaagaag aaatataaag ggaatagaag agaggaaatg agatgctata gtattctgtt    96780
ggttttcttc cctccgttcc gttttgtgtg tctctaatct cccagactct gtacattctg    96840
gcaggtttct accttcagtt tcaatggaga tacctctctg ctagaacctg ggtgacaaaa    96900
gcttaaagta acatctgggt tgttagtact ccttctcata tgtagaaatg agactatgag    96960
aatggagtaa aattttttt agcaatagaa aataggaaaa aaaatgagtt tcaccattct    97020
aattctgagt atcctatttc gatgtatcca atctgtggca cgatggaacc taaatgcacc    97080
tatggaaaaa atacacattt agtacaaaac tttcaattca taaacaattg tcttgaatac    97140
aataaacgtg taaattgtgg aaggcctata tatttacctg aaaaagtcat ttagaaaata    97200
ggttatgagt tttaaaattg tagtgattag gacaaagttt attacttaaa acaatccatt    97260
acgtttgttc aaatcagtgg cattatgtgg ggaaaataaa ctgttagcat atattttca    97320 tttttcaaag ggtggctgtg attttttgaaa cctgaaaatt tctcactcat ttcctcagta    97380
ccgggttttc tcagatacat tggcctcagt cccttgtcat tttaatattt ctcactctca    97440
aaaaattgag actgaggaaa actaaatgga attagtaaaa ttgtgatata tcaatcacta    97500
tcattttatc catggcaaaa taaattctga aaattattca ccacaataca aaaaaaaaca    97560
aagtaaagtt atgaacactt tagttgcacc atcttaagga cagttctcta ctggcgtgtc    97620
cctaaaattc ttcatcaaat tacctttgcc tagaaccagg agtgaatctc agagttcatt    97680
aaaacagcag tggaagcaga tggacactta ttatataaac aacatatctg tctgtgaaaa    97740
```

```
gccttgcatt ctgctaaatc atgagctaca aataaaaatt aactaagaaa aagaccactg   97800
aaaacttatc attgtgatca gaacactaac acaaacaaaa ttcagtacca caagccctaa   97860
cttagcctaa gctgcttcag gaggtattta caaatgcaca aaatcaattg tagaaaatca   97920
ctggactgtg agctctaatg acatcaataa gtgggaagta gatgtctgag cccagaaaaa   97980
agtacaacct gccaaaagct aagcactctc tgaagctcag cctatactta tctggggagg   98040
gagttctgat gaagcactca cttttaaatt ctcttaaaat aatgttaaaa aaaaaaaag    98100 tctgctttta cagcaattga gccaagatct ttttcctttc cccataaaat tgtaattcta   98160
ctccatttca ggtttctttg cctaagaaaa atcccatatt aaccaacata acttccaagt   98220
tttactaaca acattctcct ttttaccatt caggcttaag ttaattgtta tcataagaag   98280
aacagagtat atatgcatgt atgtagggag ggtacgagta ggtaaaaggt gtcaatgaca   98340
ttactacatg atttgggtct ttgagatttc taataatctt tattattggg tagatgcaga   98400
acaaaataat aaacgaatcc tccaaatttt tgaacttta tttaatcaaa atatatcaat    98460
gtggaatatc atgcagttac atttaaaata tgttccctaa actgacatct tctcttctcc   98520
tattacagga ggaattctag ctccaatata ttttggggct ctgattgata caacgtgtat   98580
aaagtggtcc accaacaact gtggcacacg tgggtcatgt aggacatata attccacatc   98640
attttcgtaa gttgtcataa atatatttca ttattttttc tttgactata ttaattccta   98700
aaaaatatca ttttcattat ataataatat taataatgat agccaccatt taatgaaaac   98760
tgactttgca tgcagtatgg tatcaagcaa tctcgtatct cattttagta ctcatagaaa   98820
ctataggaaa tggatatttt cttctattct gttatatacg aagaaactgt gattcaagga   98880
taataaccaa cttgtcaaaa atcagagata atagaaaatg ctaggatttt gtatgtgaat   98940
cttttttgtt tccaaaactc tcctcatgtc agtatatata aggataaata tacacatgta   99000
aatatagaca cagacatata tatatgcatg tgtgtgtatt cgattgcctc tgacttctct   99060
agaaagaaac agaatgacta gctggggctc tggtcatatg tcaattaaga aaaacggga    99120 aaatatgttt ctatattact ctattcgtgg ggagagatat tccgtaagtg acatgaagat   99180
aactgcatgg gcatctggaa aaacaaaaag ctacaattat actttacctc tttaaaaaaa   99240
aactaatttc aaattcatat attgacaaat tatacacttt gaaatgtgaa actacatgta   99300
ttaaaactca tagtataatt tctttcaatt atctacgaag cagaaactaa gtatgaccca   99360
aatgcccaaa accataatag aaaaaaagac aaaatattta taaaatctgc atcattaaac   99420
tttgaaaagg aaatttcaaa gtgaaagtat aaattaggag aataatttgc aacttgtaac   99480
acagacacag gcaaatatcc cgaatatata cggaactctt aaacatcagc aaaaaaacca   99540
tccaatgctg gcaaggatgc aaaacaacag gaatttcctt taattttct ttcattgctg    99600 gtggatatgt aaaaaatagt acagccatgg tagaagacag tctggaagtt tcttacaaag   99660
aaaaacacag gcttatgata ctgttaagta atcatgcacc taggtattta cctaagttag   99720
atgaaaacat gaccccacaa aaacctgcac ttgcatatga aaaatggaa gcaaacaaga    99780 tgtctttcaa taggtgaatg gatagccaaa ctggggtata ttcatacaat agaaaattat   99840
tcagcaataa aaagaagtga cctatcaact cacaaaaaga caagaagaa attaaatgca    99900 tgtagctaag tgaaagaagg cagtctaaag aagcttctgg gcctggtgca gtggcccatg   99960
cctgtaatct aggcactttg ggaggccaag gtgggaggat tcatgaggcc aggatttcaa  100020
gaccagcctg gacaacatga caaaaccctg tctctactaa aaatacaaaa attagccagt  100080
```

```
cacggtggtg cacatctgta atttcagcta cttgggaggc taaagcacaa gaatcccttg    100140
aacccaggag gcggaggttg cagtaagcca agctcatggc actgctctcc ggcctggctg    100200
acagagcgag actctgtctc aaaaaaagaa aaaaaaagaa cattaaaaaa aattaaagaa    100260
gcttctgact gtattattct aactgtatga ccttttgtaa aagggccaaa ctatgaagac    100320
aatgaaacat cagtggttgc taggagctca gtggggagaa gataaggatg agtaggtgga    100380
gcacagggca ttttaagggt ggtgaaatga ttttatatga tattatcatg ttggatacat    100440
gatgttatgt atttgtcaaa cctatggacc cataccata caacatacaa accacataaa    100500
aagcaaactc taatctaaaa tatgaattta ataataatgc attcatattg gttcatcaat    100560
tgtaacaaag ttacacacta atacaaactg ttaatgatag gggaaactgt atgtgtgggg    100620
cggggagtat atgggacttc atactttctg tacagttttt ctgtaaatct aaaatttctg    100680 taaaagtat gttctattaa aaaaaatcaa gtatctccca agaaaaaat cacgaatggc    100740 tattaaatat ataaaaagat gctcaaatta attgataatg acaggattgc aattaaaact    100800
cacccaaatt gtcaaccatc aaaaatgtta agtagacatt gtcttggcaa aagtacagaa    100860
ctttgagcca gcagcaaact tctagaaatt tatcctacag ataactatac tcccaaatag    100920
ataaaatggc acatatataa gattacatac atgtgtatgg caacattgtt tatgatgca    100980 aaatattgga agcaacttaa atatctcttg ataagggagt aattagataa atagttctac    101040
ctgcaggaaa atgaatagtc tgatgtcttg aaaaagaag aaaaaattat ttgtttacta    101100
atatggaacc ttcttcaaga catattttta tatgaaaaaa aagaaccatg aagaatgtgt    101160
atggagcatg ctatcattta tatgaaagtg gaggtttatt agttcaggat acatctctgg    101220
agtaaagacc taggatcaaa tttaccaaac agactctctt ccatttaatg tgtaaattca    101280
ctatctaaaa tccccagcag ataaaatgat ccaacttttt ccagaattgt accccacaga    101340
cattctcaca aatttattta aatattaatg acagaaaatg tctcacaaaa tgggagaaag    101400
aaatgaaaag aaattacaaa tgaaaacttc ataaatttat cttaatgact ttatttaaga    101460
atgtgttcat tttttattga aatcatcatg tatttccagg acacctggca agatgctcct    101520
cagaatttcc ccaaagcaat gaccacaact tcaagtatta atgtaacatt ttgagatggc    101580
tttataatgg tttgagtata aaaagaccct aaaactattt tttaagccat actagttcct    101640
ttttgttcag tgaaggttta gttagaacta aaatggaatt taaaaatatt ttatgttaat    101700
tgatttatta atgcattctt cttgttgaac aactggtata gtatccaaat ttttaatata    101760
ctgcaaagac cattgtgata acattatata gtgtatatgt gtactatata tatttaatat    101820
gcatatatat gcatatataa gacagacata ttatatatat gttattcttg tgtacttaa    101880 tttatgctca tcccaagact ttaagattta aagggtcggt ctttgtacat ccccacatat    101940
ttatcatttt cttttctctg atttcttctt gcatgtcaga ttctatctag ggtcattttc    102000
cttctgatta aagtcgattt ttaaaatgt ctttcagtga gctctttagt ggcaaattgc    102060
caatttaaat ttctctggaa ggaactttag ttcaactgta tacttaaag aaatgtacaa    102120 ggtatagaat tctaaattga caactatttt ctcttgtcag attgaagata ttactctatt    102180
gtcttctaag ttccatttta ctcttgataa gtaagctgtt gtctgttttc ttgttccttt    102240 aaggtaaccct cactcctctg tggattcttt aaatatcttg tcttaatccc tggaatctgt    102300
aattacacta tgttcaggtt gcagatggaa taagtttgct aattagctga actcaagata    102360
agaaaattat ttggttgggc ccaatataac cacaaatatc ctaaaaaata aaagaggag    102420 gtcagaagga tgtgatgtga gaaagactca gtctattgtt gctgggtttg aagatggaag    102480
```

```
aaagggycca ggagccgagg aatgtaggtg gcctctagaa gtgagaaaaa gcgaaggaac 102540
agcttatttc ctggaggtcc cagaaaggaa tacagccctg ctgataccct gattttagcc 102600
aactaagaca agtattaggc ttctaactgc caggaaatgc tccgggctta gctcacacac 102660
ccttttcttt cataaagttc acaccattcc aaccagctgg aaatgaccaa ccctctttgg 102720
gacttaccac attgtagcta actcatggcc cttatcactt tccttttggt cacttgtgtt 102780
ctttgcttga ttgtgtaaag tggaatttaa aaaaaaaaa agagcagtgc atttaccaat 102840
gaatacataa aaagttaaat tgttaccttta agaatttttt aaataaactc aattttagag 102900
agttttagga tcacagtaaa attgaggaga aattacagag atttcccaca taccacctgc 102960
cccacacatg catagcctat cctaccatca atgtctccca acaaagggtg atacagttgt 103020
tacaaatgat gaaacaacat taacacatct ttatctccca gagtccacag tttacattag 103080
gtttcactct tgacattgta cttttatggg tttggacaaa tgcataatga catatatcca 103140
ccattacagt attatacaaa gtagtttctc taccctaaaa atcctctgct ctgcctattc 103200
attccttcct cctctaaaac ccctggagac cactgtgctt tttactgttt tcatagtttt 103260
gcgttttcca gaatcataca gtatgtagca ttttagact agcttattta acttaatcac 103320
atgcatttaa atttcctcca ggtgtttcaa ttgcttgata gctcatttct ttttattgct 103380
gaataatatt ccattgtcta gatgtataac agattattta tatattcacc tactgagggc 103440
atcttgatgg cttccaagtt tcatgtttct ttgatgatat atatgaagat gtttgattct 103500
gttatattaa ccctggatcc tgtgtcctga aaccttgcaa taattgctta ttagttccaa 103560
gtgtgttttt gtctgttatt ttaaactttc tacttagaca attatgtcat attgcaaaca 103620
aagacaattt ctttcttttc aatctatata catttcattt tcttttcttt ttaaaaatta 103680
cattaattac gactcccagt accatgttga aaaacagtgg tgagagggga cgttttgac 103740
ttgttcctga ccttagtggg aagactttga gtttctcact attaagtatg aagttagatg 103800
tagggttttg gcagatattt ttgatcaagt tgaggaggtt ctcccctatt ccaagtttaa 103860
tgggagtttt tattataaat gagtgttga ttttgcaaat tcactttttct agatctattg 103920
atgtgatcat gtcattttat tattcttctt tagcctgtta atgtaatgaa ctgtaagaat 103980
tcattttgaa tgttgaacca gtcttggaaa cctgagggaa atcccactta gtcatgatgt 104040
atactatatt tatacattgt tggattcaat ctgatatttt tgagaatttt ttgcgtctat 104100
gttcatgaga gaagttgctc tgtagtattc tttttttttt ttttttttttt ttgggagaca 104160
tagttttgct cttgttaccc aggctggagg gcaatggtgc gatcatggct caccgcaacc 104220
tccgcttccc aggttcaagc gattctcctg cctcagcctc ccgagtagct gggattacag 104280
gcatgcacca ccatacccgg ctaatttgt acttttagta gagacaaggt ttctccacgt 104340
tggtcaggct ggtctcgaac tcctgacctc aggtgatccg cccacctcgg cctctcaaag 104400
tgctggcatt gcaggtgtga gtcaccatgc ccagccctct gtagtattct tttcttgtaa 104460
tgtctttgtc tgatttgtt attaggataa tgctagcctc acagaatgaa ataggaagta 104520
cttctgctgc tgctatcatc tgaagaagat tgtaatgatt tggtataatt tcttacttaa 104580
gtgtttgata gaattcacca atgaacctat cttaatttga tgctttctt tttattatta 104640
ttattatact ttaagttcta gggtacatgt gcacaatgtg ctggtttgtt acataggtat 104700
acatgtgcca tgtggtgta ctgcacccat taactactca tttacattag gtatatctct 104760
cagtgctatc cctcccccct ccccccaccc cacgacaggc cccagtgtgt gatgttcccc 104820
```

```
ttcctgtgtc caagtgttct cactgttcaa ttcccaccta tgagtgaaaa catgtggcat   104880
ttggtttttt tgtccttgtg atagtttgct gagaatgatg gtttccagct tcatccatgt   104940
ccctacaaag gacatgaact catccttttt tatggctgca tagtattcca tggtttatat   105000
gtgctacatt ttcttaatcc agtctatcac tgatggacat ttgggttggt tccaagtctt   105060
tgctattgtg aatagtgcag caataaacaa acttggcttt ttggctaata tcaagtatag   105120
tatctgttct tttcagttta gtttgatgct ttctgtttta gaaggttatt aaatatggat   105180 tcattttttag agagttctat cctccttcaa tgcctggggt tccatgagga aatcagagct   105240 tttttcccaaa aatggtacct cctatttttc ccaaggactc ctcgtctgtt agaaatgaac   105300
ttagttcctt tcatgtggtc atcaagaggg gcaaaaagac agactgagga aataattcac   105360
tcaagtgaga aaaataaata aataaaaact tctcaaaaaa acaagatcca agaagagaaa   105420
aagcacaaag gtcttgtata tagatatata cacacacaga cacacacaca tatatataca   105480
tatatgtata tatgtgtgta tatatgtata tgctatatat acatgtatat atgtgtatgt   105540
atatatacac acaaacgtat atgtgtgtct gtaaagagag agggagagcg agagagagta   105600
tgggagagca cttggatatc cattttttaat taagctgact tttagctata gtgcccttta   105660
aaaaaaatcc tttatatctc ttattatctg actttagcaa ggccaaacag ccagtatttc   105720
tggcttttga acttctttag aaatagtaat ctcctaggtg aaataaataa gccttaactg   105780
aggttgtaac ttaccatga gtgtatgagg tattttcaaa taggtggtaa gcagttttta   105840
caagatctag aatcttcaaa ggtaactcac agaaacgaaa attcaagaag ggaagccaga   105900
agttggtcat ggaggagcag agaatcaaca aatggaaaaa gccacaagaa tatcaaatca   105960
gaaagcattc attccctggg ccaagaattg agtcccaggc caccattgtg aaaagacaaa   106020
ctcttagctt ctgagctata gcattggata gtcttcatta cctttcccag aaggattcca   106080
gtgcaaccga tttcaagctt gcaaaggctt ttaactgctc gagataattt ttagagctaa   106140
ctatgacatt aactacaaaa ttcctgtcct ctagatggca gagaccaaga gtaagtactg   106200
ccacatagtt acaagatcaa gctcccacgg acataaaaca agatgagagg gaaacctcat   106260
ccagtatagg tttcaggaac acacagcaaa gtttgtaacc gaccagccca agaggctggc   106320
ttaaaaagta ggcttatagg aatcctaagc ctactttcta cattctttcc tatgacaccc   106380
ctctccatta cagaacaaca ctaaaagaca aattcttagc acaaagtaca ccagatttgc   106440
taaagcctaa gactagtctc aaaaattcat ttttctatta atcagaccac acacacacag   106500
agagagagag agagagacag aaagacagag acagagagag acagaaaag acagagacag   106560 agacagagag acagagacca gaagcttggc tggtaacaaa ttcttacccc ttttgccagc   106620
ataccacgtt tctgggttcc ctttctctgc agcttccaga agaatgaagt ggcttttgat   106680
gaccctgctc attgcaccat agctttgggg gccaagccac tttacaaaag aaaattatcc   106740
ttttctgttt tataaaacta taggcaaaag cttctcattt ttgcaagatg ctgcccaatg   106800
ggctgcatga ggaaccaaat taacattttc caccccagcc tagcaaaata cacataacaa   106860
aacagacatt tgtcacctca ttcagcaccc aatattgacc tggcgaggct caaactttct   106920
ttcattggtc cctatcatct ctgatccact caagatgtgg agggctaaac tccaactgag   106980
aattcaggtc tctgggcaag atgaagaagt ggacagtcac cccgactcag gccttttga   107040 gcttccttca ggactcactg aatgtgacca gacaaataat gagggttttc tgagttaggt   107100
gtcctagact tccatcagta gttcctttag aggtctcctc cacatataca aatacacaca   107160
acaaagacaa gacagacaga aggccttcca aaccacgact tctaaccaag aattccgagt   107220
```

```
cttcctccca aacgaacctt ctattctcca cctgagaatt ctccctaaaa tcttcttgat  107280
tgaagagaaa tctcctgaac caagacttcc tactaattag agctaaccaa cacctccaaa  107340
ggagctgaac tgagacctca aaaaaaaaac aaacaaacaa aaaaaaaaa acaagagccc  107400 caaaggagcc aaaccaaggc ccctaaagaa gccaaatcat gatccccaaa ggagccaaac  107460
caactgggag aagaaaggag gagttggcag tgcctagaat actcaccaaa ttagtttgga  107520
gacagacatc atttccagga actatttctc cattgcaatt aaatccatgc acattgggtc  107580
agcagcaccc tgccagtaga gacagtgcca gagtcagccc acagtccaag agaactaggc  107640
agccacttgg gctggcctct ggatccatca ccagagcagg gctactgaac catgggcagg  107700
taggcacaaa ggcaatccca gatgagaccc ctagtgtgta accacctaac gggttcacct  107760
tgcccactgc ctagacagag cttatttatc aagaaagatc ttacttatca aaacagaaa  107820 attgcaataa agagtaattc atgcagagcc agctgtgcag tacaccagag ttttgttatt  107880
attcaaatca gtctctctga gaatttgagg actggagttt ttaaagataa tttggtgggt  107940 agggggggcca gtgagtcaag agttctgatt ggtcaggtga gagatgaaat catagggagt  108000
tgatactgtc ctctcgtgct gagtcacttc ctgggagggg gccacaggat gagataggcc  108060
agtttatcaa tctgggtggt gtgagctcat ctgtgaagtt caggatctgc aaaatatatc  108120
aagtattgat cttaggtttt acaatagtgc tgttatcctc aggagcaatt tggttagagt  108180
cagaatcttg tagcctccag atgcattact cctaaatcat aatttctaat cttttggcta  108240
attcgttagt cctacaaagg tagtctgttt cccaggcaag aagctggttt gttttgggaa  108300
aggactgtta ctgtcttggt tttaaactcg aagctataaa ctaaatttct cccagaatta  108360
gttcggctta cacccagaaa tcaacaagaa cagcttggag gatagaagca agatggagtt  108420
ggttaggtca gctctctttc agtctcggtt atagttttgc agtgaaaatt tcataagcat  108480
ttagtgcaat aaactttcca ctttatgctg ttgaagctat atcctagagg ttttaaaata  108540
ctttgtctcg attttcattt gtttaaaaca aaaaaattgt gttctgctct aattttgtta  108600
tttacccaaa agtaattcag gaccaagtta tacagatttc ttgtaattgt gtagtttcaa  108660
gagttgctct tgatactgat ttctattttt attctgctgt ggttcatgaa gatgtttgtt  108720
ataactctga ttttttaaaa aatttattgt gacttatgac ttagaatgtg gttagtttta  108780
gagaatgttt tatgaacaga taaaaaatgc attttctctg attttgggt gaagtattct  108840 ctagatatct attagatcca cttggtaaag agtctacttc aagtcgaatt ttttttttt  108900 tttttagct tttggccttg atgatgtgcc tgcctagtgc tgtcagtctg gtgtcgaagc  108960
ttattactca ttgtattact ttctatctct ttgcttaggt ctggtagtat ttattttata  109020
aatatgattg cttcagtatt gagtgtgtat atatttagat tagttaaatc ttgttgaatt  109080
aaatgcttta tcattatgta atgcacttac ttggtttttt ttaaactgtt gtttgtttaa  109140
ggtctgtttt atttgataca aagagaggaa tttcagctta ttttttgcttt ccatttgaaa  109200 gatagatctt tcttcattct tttactttaa gtctatgggt gtccttacat acgagatgga  109260
ttccttaagg gcagcagaag gttgccttt ttttttttaat ccactttgct actctatgtc  109320
ttttatatga agcatttagg caatttacat tcaaagttaa tattgatatg tgagattttg  109380
tacctctcat actgttgtta gctagttgct ttatagttgc aattgtgtag ttacttaata  109440
ggatctgtag gcttttgtaat tatgggtgct tttatagtag caagtattgg tctgtttttt  109500
cctgttttga actcctttga gcatttttc taaaactgat ctggtggtga catatttcct  109560
```

```
tagtgtttac tggtctggga aatattttat ttctacttta ttcacaaatc ttcatttggg    109620
aagttatgaa gttcttggct gtcattatta tttttctttt gtaagtctaa caataggccc    109680
ccagtctctt ctagcttgta atgtatctgc tgggaagttc acctttagtc taatggtatt    109740
tccttcataa ataatttggc ccttttctct agctgccgtt aggatttgtt ttttcatgtt    109800
gaacttaggc aatctgatga ctatattcat atagtatctg aatggttgtt ttgtatagta    109860
tctcatacta tagtatgttt tgtatagtat ctcatacact gttgcaccca caacagtgta    109920
cagtggagag agtgggaaat taccctctat ccagattcat tcctgagtgt tggtactgcc    109980
tccttcagta attggtgctg tgcccatgtt ctctttgtcc caggggaagc tatagtgggc    110040
tacagtcccc actctttag gggaagaaca cattgagggt tagatctcca gaggtcctgc    110100
tgtctcccca aagtccactg accctgtgc ctaccaaagt cagagcagtt tgttggacat    110160
gtttgccagg aattgggtgg catggtgact caaagatgga gaatcctcag gcagggcggt    110220
ggcataccat agatgcacca acagtatggc acatctttcc tttagataga aaggtggtgc    110280
agctgtacct gtgcaggctg gccacctagt tgtctatccc tggggagttc ccaaattgcc    110340
accaatagca ttaccctgca tcaagagggc agaggaaatt cctaacaatt tggtggtcag    110400
cagattatca gagatgtgag gggagcagag aagcactttc agctaaattt tcacagggtt    110460 ctctggggt tgattattac caggctttta ccgcttttct ttactacacc acagctgctt    110520
cttatgggca ctataacagt tcctggctct ctttctcagt tttttatttg gtacttcttt    110580
attcaccagt aactttgatc ttcttcgta ggagaactgt aatttgatgt ccctggtcag    110640
ccatcttgaa aagaacttga cttatttttt tatcagtggc agcatgatat atcttcctcc    110700
atctaattac tttttaatcta tacatctata agtagatctc ttagagacta catatagttt    110760
gtttcttctt tttaatcctt taacaaactc agtcttttaa ttggtggatt tagatcattg    110820
acattaaaag tgactactga tgttgtgaga ccaatgttga ttataattt actattgtct    110880 atttgttata cttgttcttt gatcctattt ttgtcttcta ttctttttc ttctgttgtg    110940 ttcttaacta aatagtctat atgactctga ttttatatga ctatataatc ataacttttt    111000
atgttacctt tctttatgta tatcaagttt ctgacctata tgagtctctc taaaaagctt    111060
ctcttaacat ttcttacaag gaagatgtac tggaaaaaca tttcttcaat tgttgtttgt    111120
ctgagaatgt gtttatttct actttacttt taaaagaatt tcacagagta cagaattta    111180 agttggtgat ttttttctct taagactttta aatatttcac tccactctct tcttgcttgc    111240
atggtttctg aagagaagtc tattttctcc cctatagata aaatttgttt ttccttctgg    111300
ttagtttcag gataaagttt tctttatctt tgactttctg taatttgaaa ataacacacc    111360
tacacgtagt ttttctggtc aataataact tatttgtata tttaaaaata acttaggaag    111420
tgtagttgaa ttgtttgtaa ctcaaaggac aaatccttag catttttctga gtttcctgaa    111480 tctgtgatat agtgtctgac attaatttaa gagaaattct tagtaatttt tttttttttg    111540
agatggagtc tcactctgtt gcccaggctg gagtgcaatg gcatgatctt ggctcactgc    111600
aacccccgcc tcccgagttc aagtgattct cctgcctcag cctcctgagt agctgggata    111660
acaggcaccc gccaccacgc ccagctagtt tttgtatttt tggtatagac ggggtttcac    111720
catgttggtc aggctggtct ctaactcctg acctcgtgat ctgcctgcct cagtctccca    111780
aagtgctggg attacaggca tgatccactg cacctggcca gtaattattt tttaaaaatg    111840
tttcttttgc tccttttctc tttgtttcc ttctaacctt tccattacac ccactttatt    111900
aattgtctca aaattttat atgatttcaa ttgatttact ttttagtctt gtttctcttt    111960
```

```
gcttttcagt tttggaggtt ttcattgata tatcctcaaa ttagagagtc ttcatcagtt    112020
gtgttctatc tactaataag cccatcaaag gcattcttta tttctgctac agaattttt    112080 attttagca ttttcttggg ttcttaaaat ttttattttt atacttacat tgtccatctg    112140
ttattgaatg ctgtctacct tattgattag aacacttaac atattaatca tagttgtttt    112200
aaattccatt tgaaaattt ccacgtcccg gacatatcta ggtctggttt aaagcttact    112260
tattcctttc aatctatgtt tttttttttca cttttggtat gactggcaat tttttttcatt    112320 acagttaagc ataatgcatt aggtaaaagg aactgctttg ataagccttt attaatatgg    112380
tgtaaggtgc tggagaaggg gtagcattct acaggcctac atttaggttt tattattta    112440 gttataatcc agtaacctct ggattataaa tttcaaacat acttctcagt ttctcctccc    112500
agctgtaggt ggggcaggat ggcttaacag ggcttgagtt gtatattttt ctcgttttat    112560
gaagaaggcc agaggcaact agagtatagt ttctatggct tcataaccct attacaataa    112620
taaaatatct atcgttatgc cccaataaaa agaattatta gaattattgt cttaatattt    112680
tatttataat ttttttttctt taggatctgg atactggaga aaatgtttta agttattaca    112740 cacaattta actgatttat tgttttattt tctctatttc tacagaaggg tctacttggg    112800
cttgtcttca atgttaagag tctcatcact tgttttatat attatattaa tttatgccat    112860
gaagaaaaaa tatcaagaga aagatatcaa tgcatcagaa aatggaagtg tcatggatga    112920
agcaaactta gaatccttaa ataaaaataa acattttgtc ccttctgctg gggcagatag    112980
tgaaacacat tgttaagggg agaaaaaaag ccacttctgc ttctgtgttt ccaaacagca    113040
ttgcattgat tcagtaagat gttattttg aggagttcct ggtcctttca ctaagaattt    113100
ccacatcttt tatggtggaa gtaaaataa gcctatgaac ttataataaa acaaactgta    113160
ggtagaaaaa atgagagtac tcattgttac attatagcta catatttgtg gttaaggtta    113220
gactatatga tccatacaaa ttaaagtgag agacatggtt actgtgtaat aaaagaaaaa    113280
atacttgttc aggtaattct aattcttaat aaaacaaatg agtatcatac aggtagaggt    113340
taaaaaggag gagctagatt catatcctaa gtaaagagaa atgcctagtg tctattttat    113400
taaacaaaca aacacagagt ttgaactata atactaaggc ctgaagtcta gcttggatat    113460
atgctacaat aatatctgtt actcacataa aattatatat ttcacagact ttatcaatgt    113520
ataattaaca attatcttgt ttaagtaaat ttagaataca tttaagtatt gtggaagaaa    113580
taaagacatt ccaatatttg caagctgtga ttgtcaaaca acatattaca ttatgtgtta    113640
agtttccagt gggcccacgg taatgtatta ggaaaaattg actttgacta atgtagccac    113700
tctcatactt atcttagcta gatttcctag atcatttgcc gcaccttcta cgtcagcact    113760
tgcttcttca ctttgtactt agataatgaa accagcttct tttttaaac cccgtgaaac    113820 aaattctaca gcttttttc tttgcagct ttcccacgtc tcttagtcat catagaatga    113880
cagagagtta tgtccttgct ctagattaga tttggcctaa gggaacattg tggctgcttt    113940
gttcttcaat ccaggctact gaagttttct ccatgttagc cataagtctg tttcactttg    114000
ttattatttg tgtgttcact gaagtaggac tcttaattat cttcaagtac tttattttg    114060 cattcacaac ttggctaact gctgaatgca agatgctag ttttgactta ccttggctct    114120
tgatatgcct tcctcactaa acttaatcat ttctaaaatt tgacttaaaa tgagagatat    114180
gtgactcttt ctttcactca aacacctaga ggtcattgta aggttattat ttggcttaat    114240
ttctatgttg ttctgtctca ggacatagga aggcccaagg ggatggagag agatgtagca    114300
```

```
atagctggtt ggtggagcat tcagaacaca cacaacttta ttgattaagt tccacgtatt    114360
atatgggtat ggatagtggc aagtcaaatc aattacaata gtaacatcaa agatcactaa    114420
ccacaggtca ctatcacaga tacaataaca atgaataagt ctgaaatatt gtgagaatta    114480
gtaaaatgtg acacagagac ataaagtgag cacatatttt tgaaaaaatg atgtcaatag    114540
acttgtttga tgcaggattg ccacaaactt ccaatttgaa aacaaaaaac aaacaaaaaa    114600
aacaccaaaa tatgtgaagt gcaataaagt gaagttcaat aaaatgaagt atgccaggaa    114660
taaaaactag caggatcaca ggatcaacct ctacttaaaa gtattagaaa tatggaggta    114720
aatagaagaa atagctaaaa agagttgtaa atgcttgcct ctggaaagca gtaataataa    114780
gcagagaaaa actcattttc aatatgagat ttttgatata atcttatttt tacaactttg    114840
tgcataaatg gctttggtaa aaattaaaaa tcaatcatca gactggtatg tctcttatta    114900
atcaacaata aacaataata ttgataccca ggtactacac tgagagcctt gggtgagcct    114960
ccaagtcttg ctggcttcag ataccagaaa gatcacaggg gttaatgcac taagcagact    115020
cttgaggtcc ctgattccag gacttgactc tgggatagca tttctgaacc tgccctcggc    115080
cagaggggag cccattgttc tgaagtttga atcccacctc aggcagaatt caatagaagc    115140
tgattaaagt gcccttgggc cttaaggaaa cattggcagt agtctagcag tactcccgtt    115200
gggcctgaag tgttgtggct atgggttgag gctcctttgt atttggaaat gcgagggaag    115260
agtgggaaag acggtcttgt ggtttgcgtg ccacctcagc cacaatatga tagaacacca    115320
ggtagacttt acgagttttg gctctagtct ctgactcctg gatggcatct ctggacccac    115380
atgggacctg ggggacctcg ccaccctgaa aggaaggaca caggccttgc tggcttttct    115440
gcctgctgat tgtagagccc catggccttg agcaaacatt ggcagtagtc agggagtaat    115500
tacagcagac cttgggcaag actcataaat gtgctggctt caggtgtaac ccaatgtagt    115560
catagttctg gatgccacag aggtgcttac gccactccaa acc                     115603
```

<210> SEQ ID NO 73
<211> LENGTH: 691
<212> TYPE: PRT
<213> ORGANISM: Homo sapiens

<400> SEQUENCE: 73

```
Met Asp Gln Asn Gln His Leu Asn Lys Thr Ala Glu Ala Gln Pro Ser
1               5                   10                  15

Glu Asn Lys Lys Thr Arg Tyr Cys Asn Gly Leu Lys Met Phe Leu Ala
            20                  25                  30

Ala Leu Ser Leu Ser Phe Ile Ala Lys Thr Leu Gly Ala Ile Ile Met
        35                  40                  45

Lys Ser Ser Ile Ile His Ile Glu Arg Arg Phe Glu Ile Ser Ser Ser
    50                  55                  60

Leu Val Gly Phe Ile Asp Gly Ser Phe Glu Ile Gly Asn Leu Leu Val
65                  70                  75                  80

Ile Val Phe Val Ser Tyr Phe Gly Ser Lys Leu His Arg Pro Lys Leu
                85                  90                  95

Ile Gly Ile Gly Cys Phe Ile Met Gly Ile Gly Gly Val Leu Thr Ala
            100                 105                 110

Leu Pro His Phe Phe Met Gly Tyr Tyr Arg Tyr Ser Lys Glu Thr Asn
        115                 120                 125

Ile Asn Ser Ser Glu Asn Ser Thr Ser Thr Leu Ser Thr Cys Leu Ile
    130                 135                 140
```

```
Asn Gln Ile Leu Ser Leu Asn Arg Ala Ser Pro Glu Ile Val Gly Lys
145                 150                 155                 160

Gly Cys Leu Lys Glu Ser Gly Ser Tyr Met Trp Ile Tyr Val Phe Met
                165                 170                 175

Gly Asn Met Leu Arg Gly Ile Gly Glu Thr Pro Ile Val Pro Leu Gly
            180                 185                 190

Leu Ser Tyr Ile Asp Asp Phe Ala Lys Glu Gly His Ser Ser Leu Tyr
        195                 200                 205

Leu Gly Ile Leu Asn Ala Ile Ala Met Ile Gly Pro Ile Ile Gly Phe
    210                 215                 220

Thr Leu Gly Ser Leu Phe Ser Lys Met Tyr Val Asp Ile Gly Tyr Val
225                 230                 235                 240

Asp Leu Ser Thr Ile Arg Ile Thr Pro Thr Asp Ser Arg Trp Val Gly
                245                 250                 255

Ala Trp Trp Leu Asn Phe Leu Val Ser Gly Leu Phe Ser Ile Ile Ser
                260                 265                 270

Ser Ile Pro Phe Phe Phe Leu Pro Gln Thr Pro Asn Lys Pro Gln Lys
        275                 280                 285

Glu Arg Lys Ala Ser Leu Ser Leu His Val Leu Glu Thr Asn Asp Glu
    290                 295                 300

Lys Asp Gln Thr Ala Asn Leu Thr Asn Gln Gly Lys Asn Ile Thr Lys
305                 310                 315                 320

Asn Val Thr Gly Phe Phe Gln Ser Phe Lys Ser Ile Leu Thr Asn Pro
                325                 330                 335

Leu Tyr Val Met Phe Val Leu Leu Thr Leu Leu Gln Val Ser Ser Tyr
            340                 345                 350

Ile Gly Ala Phe Thr Tyr Val Phe Lys Tyr Val Glu Gln Gln Tyr Gly
        355                 360                 365

Gln Pro Ser Ser Lys Ala Asn Ile Leu Leu Gly Val Ile Thr Ile Pro
    370                 375                 380

Ile Phe Ala Ser Gly Met Phe Leu Gly Gly Tyr Ile Ile Lys Lys Phe
385                 390                 395                 400

Lys Leu Asn Thr Val Gly Ile Ala Lys Phe Ser Cys Phe Thr Ala Val
                405                 410                 415

Met Ser Leu Ser Phe Tyr Leu Leu Tyr Phe Phe Ile Leu Cys Glu Asn
            420                 425                 430

Lys Ser Val Ala Gly Leu Thr Met Thr Tyr Asp Gly Asn Asn Pro Val
        435                 440                 445

Thr Ser His Arg Asp Val Pro Leu Ser Tyr Cys Asn Ser Asp Cys Asn
    450                 455                 460

Cys Asp Glu Ser Gln Trp Glu Pro Val Cys Gly Asn Asn Gly Ile Thr
465                 470                 475                 480

Tyr Ile Ser Pro Cys Leu Ala Gly Cys Lys Ser Ser Gly Asn Lys
                485                 490                 495

Lys Pro Ile Val Phe Tyr Asn Cys Ser Cys Leu Glu Val Thr Gly Leu
            500                 505                 510

Gln Asn Arg Asn Tyr Ser Ala His Leu Gly Glu Cys Pro Arg Asp Asp
        515                 520                 525

Ala Cys Thr Arg Lys Phe Tyr Phe Phe Val Ala Ile Gln Val Leu Asn
    530                 535                 540

Leu Phe Phe Ser Ala Leu Gly Gly Thr Ser His Val Met Leu Ile Val
545                 550                 555                 560

Lys Ile Val Gln Pro Glu Leu Lys Ser Leu Ala Leu Gly Phe His Ser
```

-continued

```
                565                 570                 575
Met Val Ile Arg Ala Leu Gly Gly Ile Leu Ala Pro Ile Tyr Phe Gly
            580                 585                 590

Ala Leu Ile Asp Thr Thr Cys Ile Lys Trp Ser Thr Asn Asn Cys Gly
            595                 600                 605

Thr Arg Gly Ser Cys Arg Thr Tyr Asn Ser Thr Ser Phe Ser Arg Val
    610                 615                 620

Tyr Leu Gly Leu Ser Ser Met Leu Arg Val Ser Ser Leu Val Leu Tyr
625                 630                 635                 640

Ile Ile Leu Ile Tyr Ala Met Lys Lys Lys Tyr Gln Glu Lys Asp Ile
                645                 650                 655

Asn Ala Ser Glu Asn Gly Ser Val Met Asp Glu Ala Asn Leu Glu Ser
            660                 665                 670

Leu Asn Lys Asn Lys His Phe Val Pro Ser Ala Gly Ala Asp Ser Glu
        675                 680                 685

Thr His Cys
    690
```